US011390675B2

(12) United States Patent
Liu et al.

(10) Patent No.: US 11,390,675 B2
(45) Date of Patent: Jul. 19, 2022

(54) ANTIBODIES FOR SIGLEC-15 AND METHODS OF USE THEREOF

(71) Applicant: NEXTCURE, INC., Beltsville, MD (US)

(72) Inventors: Linda Liu, Clarksville, MD (US); Benjamin Dallas Flies, Rockville, MD (US); Solomon Langermann, Baltimore, MD (US)

(73) Assignee: NEXTCURE, INC., Beltsville, MD (US)

( * ) Notice: Subject to any disclaimer, the term of this patent is extended or adjusted under 35 U.S.C. 154(b) by 118 days.

(21) Appl. No.: 16/334,409

(22) PCT Filed: Sep. 21, 2017

(86) PCT No.: PCT/US2017/052714
§ 371 (c)(1),
(2) Date: Mar. 19, 2019

(87) PCT Pub. No.: WO2018/057735
PCT Pub. Date: Mar. 29, 2018

(65) Prior Publication Data
US 2019/0202912 A1    Jul. 4, 2019

Related U.S. Application Data

(60) Provisional application No. 62/500,578, filed on May 3, 2017, provisional application No. 62/451,271, filed on Jan. 27, 2017, provisional application No. 62/397,794, filed on Sep. 21, 2016.

(51) Int. Cl.
    *A61K 39/00* (2006.01)
    *A61K 39/395* (2006.01)
    *C07K 16/28* (2006.01)
    *A61P 35/00* (2006.01)

(52) U.S. Cl.
    CPC ...... *C07K 16/2803* (2013.01); *A61K 39/0011* (2013.01); *A61P 35/00* (2018.01); *A61K 39/001111* (2018.08); *A61K 39/395* (2013.01); *A61K 2039/505* (2013.01); *C07K 2317/24* (2013.01); *C07K 2317/33* (2013.01); *C07K 2317/70* (2013.01); *C07K 2317/74* (2013.01); *C07K 2317/75* (2013.01); *C07K 2317/76* (2013.01); *C07K 2317/92* (2013.01)

(58) Field of Classification Search
    None
    See application file for complete search history.

(56) References Cited

U.S. PATENT DOCUMENTS

| 4,012,112 A | 3/1977 | Masterson |
| 4,063,083 A | 12/1977 | Cathey et al. |
| 4,179,337 A | 12/1979 | Davis et al. |
| 4,444,887 A | 4/1984 | Hoffmann |
| 4,528,364 A | 7/1985 | Prier |
| 4,676,980 A | 6/1987 | Segal et al. |
| 4,716,111 A | 12/1987 | Osband et al. |
| 4,725,661 A | 2/1988 | Miyabayashi |
| 4,741,900 A | 5/1988 | Alvarez et al. |
| 4,816,397 A | 3/1989 | Boss et al. |
| 4,816,567 A | 3/1989 | Cabilly et al. |
| 5,066,762 A | 11/1991 | Ohbuchi et al. |
| 5,120,727 A | 6/1992 | Kao et al. |
| 5,162,333 A | 11/1992 | Failli et al. |
| 5,190,929 A | 3/1993 | Borch et al. |
| 5,202,332 A | 4/1993 | Hughes et al. |
| 5,225,539 A | 7/1993 | Winter |
| 5,385,908 A | 1/1995 | Nelson et al. |
| 5,413,923 A | 5/1995 | Kucherlapati et al. |
| 5,484,790 A | 1/1996 | Failli et al. |
| 5,530,006 A | 6/1996 | Waranis et al. |
| 5,530,101 A | 6/1996 | Queen et al. |
| 5,545,806 A | 8/1996 | Lonberg et al. |
| 5,559,112 A | 9/1996 | Skotnicki et al. |
| 5,565,332 A | 10/1996 | Hoogenboom et al. |
| 5,567,709 A | 10/1996 | Skotnicki et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,642,821 A | 7/1997 | Hafliger |
| 5,659,421 A | 8/1997 | Rahmel et al. |

(Continued)

FOREIGN PATENT DOCUMENTS

| CN | 1349096 A | 5/2002 |
| CN | 101633731 A | 1/2010 |

(Continued)

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Orentas et al. (2012, Frontiers in Oncology 2(194)1-16; doi.org/10.3389/fonc.2012.00194).*
Stanculeanu et al. (2016, Journal of Medicine and Life 9(3):240248).*
Anatelli, F. et al., "Macrophage-Targeted Photosensitizer Conjugate Delivered by Inlratumoral Injection," Mol Pharm. 3(6):654-664, (2006).

(Continued)

*Primary Examiner* — Elizabeth C. Kemmerer
(74) *Attorney, Agent, or Firm* — Smith, Gambrell & Russell; Judy Jarecki-Black

(57) ABSTRACT

Siglec-15 binding molecules are provides. The molecules are typically an antibody or antigen binding fragment thereof that immunospecifically binds to Siglec-15. Siglec-15 ligand-binding molecules are also provided. The molecules are typically Siglec-15 polypeptide or fusion protein. Methods of using the molecules to reduce Siglec-15 mediated immunosuppression in a subject in need thereof are also provided.

3 Claims, 48 Drawing Sheets
Specification includes a Sequence Listing.

(56) References Cited

U.S. PATENT DOCUMENTS

| | | |
|---|---|---|
| 5,661,016 A | 8/1997 | Lonberg et al. |
| 5,691,841 A | 11/1997 | Ohsaki et al. |
| 5,693,761 A | 12/1997 | Queen et al. |
| 5,693,762 A | 12/1997 | Queen et al. |
| 5,759,808 A | 6/1998 | Lee et al. |
| 5,766,886 A | 6/1998 | Studnicka et al. |
| 5,779,203 A | 7/1998 | Edlinger |
| 5,780,462 A | 7/1998 | Lee et al. |
| 5,807,715 A | 9/1998 | Morrison et al. |
| 5,814,318 A | 9/1998 | Lonberg et al. |
| 5,843,597 A | 12/1998 | Getz |
| 5,856,372 A | 1/1999 | Ho et al. |
| 5,916,771 A | 6/1999 | Hori et al. |
| 5,929,212 A | 7/1999 | Jolliffe et al. |
| 5,936,047 A | 8/1999 | De et al. |
| 5,939,598 A | 8/1999 | Kucherlapati et al. |
| 5,952,450 A | 9/1999 | Ishihara et al. |
| 5,973,099 A | 10/1999 | Nodelman et al. |
| 5,989,591 A | 11/1999 | Nagi |
| 6,005,079 A | 12/1999 | Casterman et al. |
| 6,015,809 A | 1/2000 | Zhu et al. |
| 6,046,301 A | 4/2000 | Bolton et al. |
| 6,180,370 B1 | 1/2001 | Queen et al. |
| 6,194,551 B1 | 2/2001 | Idusogie et al. |
| 6,235,883 B1 | 5/2001 | Jakobovits et al. |
| 6,277,375 B1 | 8/2001 | Ward |
| 6,311,415 B1 | 11/2001 | Lind |
| 6,350,861 B1 | 2/2002 | Co et al. |
| 6,395,554 B1 | 5/2002 | Regan et al. |
| 6,407,213 B1 | 6/2002 | Carter et al. |
| 6,534,620 B1 | 3/2003 | Hovestadt et al. |
| 6,624,278 B2 | 9/2003 | Mueller et al. |
| 6,646,100 B2 | 11/2003 | Hofmann et al. |
| 6,838,254 B1 | 1/2005 | Hamers et al. |
| 6,982,323 B1 | 1/2006 | Wang et al. |
| 7,052,694 B2 | 5/2006 | Pease et al. |
| 7,064,244 B2 | 6/2006 | Jakobovits et al. |
| 7,098,274 B2 | 8/2006 | Wu et al. |
| 7,140,738 B2 | 11/2006 | Guiney et al. |
| 7,227,002 B1 | 6/2007 | Kufer et al. |
| 7,241,504 B2 | 7/2007 | Verborgt et al. |
| 7,250,483 B2 | 7/2007 | Heuer et al. |
| 7,300,163 B2 | 11/2007 | Scampini |
| 7,332,582 B2 | 2/2008 | Hardy et al. |
| 7,355,008 B2 | 4/2008 | Stavenhagen et al. |
| 7,371,826 B2 | 5/2008 | Presta |
| 7,390,888 B2 | 6/2008 | Pease et al. |
| 7,403,330 B2 | 7/2008 | Henderson et al. |
| 7,411,051 B2 | 8/2008 | Rosen et al. |
| 7,488,802 B2 | 2/2009 | Collins et al. |
| 7,521,051 B2 | 4/2009 | Collins et al. |
| 7,521,521 B2 | 4/2009 | Bruchmann et al. |
| 7,524,498 B2 | 4/2009 | Hardy et al. |
| 7,534,423 B2 | 5/2009 | Jalkanen |
| 7,563,869 B2 | 7/2009 | Honjo et al. |
| 7,597,889 B1 | 10/2009 | Armour et al. |
| 7,649,074 B2 | 1/2010 | Bruchmann et al. |
| 7,858,732 B2 | 12/2010 | Bruchmann et al. |
| 7,859,667 B2 | 12/2010 | Scampini |
| 7,928,182 B2 | 4/2011 | Dinh et al. |
| 7,928,183 B2 | 4/2011 | Truong et al. |
| 7,948,676 B2 | 5/2011 | Virag et al. |
| 7,956,285 B2 | 6/2011 | Tally et al. |
| 7,960,512 B2 | 6/2011 | Stavenhagen et al. |
| 7,964,202 B2 | 6/2011 | Orsoni et al. |
| 7,981,416 B2 | 7/2011 | Hardy et al. |
| 7,989,160 B2 | 8/2011 | Sooknanan et al. |
| 7,990,454 B2 | 8/2011 | Notsu et al. |
| 8,020,249 B2 | 9/2011 | Masuda et al. |
| 8,044,170 B2 | 10/2011 | Bruchmann et al. |
| 8,088,905 B2 | 1/2012 | Collins et al. |
| 8,110,710 B2 | 2/2012 | Dai et al. |
| 8,114,845 B2 | 2/2012 | Langermann et al. |
| 8,159,199 B2 | 4/2012 | Arnold |
| 8,168,181 B2 | 5/2012 | Sooknanan et al. |
| 8,188,238 B2 | 5/2012 | Pease et al. |
| 8,197,715 B2 | 6/2012 | Weber et al. |
| 8,247,520 B2 | 8/2012 | Allen et al. |
| 8,273,846 B2 | 9/2012 | Nefzger et al. |
| 8,282,851 B2 | 10/2012 | Duwenhorst et al. |
| 8,287,856 B2 | 10/2012 | Li et al. |
| 8,309,646 B2 | 11/2012 | Terrenoire et al. |
| 8,362,146 B2 | 1/2013 | Eipper et al. |
| 8,383,796 B2 | 2/2013 | Korman et al. |
| 8,399,554 B2 | 3/2013 | Roller et al. |
| 8,410,227 B2 | 4/2013 | Eipper et al. |
| 8,428,268 B2 | 4/2013 | Konagai et al. |
| 8,431,126 B2 | 4/2013 | Sooknanan et al. |
| 8,445,576 B2 | 5/2013 | Eipper et al. |
| 8,446,125 B2 | 5/2013 | Mkhitarian |
| 8,470,956 B2 | 6/2013 | Allen et al. |
| 8,501,280 B2 | 8/2013 | Bruchmann et al. |
| 8,530,567 B2 | 9/2013 | Roller et al. |
| 8,540,988 B2 | 9/2013 | Sooknanan et al. |
| 8,546,540 B2 | 9/2013 | Sooknanan et al. |
| 8,575,316 B2 | 11/2013 | Hiruma et al. |
| 8,580,247 B2 | 11/2013 | Li et al. |
| 8,593,730 B2 | 11/2013 | Yamamoto et al. |
| 8,604,155 B2 | 12/2013 | Allen et al. |
| 8,609,089 B2 | 12/2013 | Langermann et al. |
| 8,625,930 B2 | 1/2014 | Tatke et al. |
| 8,709,416 B2 | 4/2014 | Langermann et al. |
| 8,728,474 B2 | 5/2014 | Honjo et al. |
| 8,741,289 B2 | 6/2014 | Tremblay et al. |
| 8,779,105 B2 | 7/2014 | Korman et al. |
| 8,822,622 B2 | 9/2014 | Huybrechts et al. |
| 8,853,319 B2 | 10/2014 | Weber et al. |
| 8,900,579 B2 | 12/2014 | Tremblay et al. |
| 8,902,501 B2 | 12/2014 | Suzuki et al. |
| 8,921,508 B2 | 12/2014 | Allen et al. |
| 8,933,192 B2 | 1/2015 | Gurtler et al. |
| 9,005,616 B2 | 4/2015 | Langermann et al. |
| 9,018,334 B2 | 4/2015 | Montgomery et al. |
| 9,029,498 B2 | 5/2015 | Allen et al. |
| 9,040,246 B2 | 5/2015 | Sooknanan et al. |
| 9,067,984 B2 | 6/2015 | Sooknanan et al. |
| 9,067,999 B1 | 6/2015 | Honjo et al. |
| 9,073,994 B2 | 7/2015 | Honjo et al. |
| 9,079,959 B2 | 7/2015 | Hiruma et al. |
| 9,084,776 B2 | 7/2015 | Korman et al. |
| 9,090,692 B2 | 7/2015 | Hiruma et al. |
| 9,102,725 B2 | 8/2015 | Korman et al. |
| 9,114,131 B2 | 8/2015 | Watanabe et al. |
| 9,120,894 B2 | 9/2015 | Muller et al. |
| 9,155,479 B2 | 10/2015 | Solem |
| 9,205,148 B2 | 12/2015 | Langermann et al. |
| 9,249,259 B2 | 2/2016 | Muller et al. |
| 9,255,147 B2 | 2/2016 | Pease et al. |
| 9,273,135 B2 | 3/2016 | Korman et al. |
| 9,334,331 B2 * | 5/2016 | Igawa .................. C07K 16/40 |
| 9,376,531 B2 | 6/2016 | Allen et al. |
| 9,358,289 B2 | 7/2016 | Korman et al. |
| 9,387,247 B2 | 7/2016 | Korman et al. |
| 9,388,242 B2 | 7/2016 | Tremblay et al. |
| 9,393,301 B2 | 7/2016 | Honjo et al. |
| 9,447,192 B2 | 9/2016 | Elvin et al. |
| 9,492,539 B2 | 11/2016 | Korman et al. |
| 9,492,540 B2 | 11/2016 | Korman et al. |
| 9,493,562 B2 | 11/2016 | Stuible et al. |
| 9,522,976 B2 | 12/2016 | Tabor et al. |
| 9,580,507 B2 | 2/2017 | Korman et al. |
| 9,617,337 B2 | 4/2017 | Tremblay et al. |
| 9,695,419 B2 | 7/2017 | Sooknanan et al. |
| 9,751,944 B2 | 9/2017 | Hiruma et al. |
| 9,809,678 B2 | 11/2017 | Allen et al. |
| 9,815,899 B2 | 11/2017 | Hiruma et al. |
| 9,857,580 B2 | 1/2018 | Quarre et al. |
| 9,896,540 B2 | 2/2018 | Tabor et al. |
| 9,994,636 B2 | 6/2018 | Elvin et al. |
| 10,053,533 B1 | 8/2018 | Blumsom et al. |
| 10,421,807 B2 * | 9/2019 | Gonzales ................ A61P 43/00 |
| 2003/0229208 A1 | 12/2003 | Queen et al. |
| 2004/0049014 A1 | 3/2004 | Queen et al. |
| 2005/0271652 A1 | 12/2005 | De Romeuf et al. |

(56) References Cited

U.S. PATENT DOCUMENTS

| | | |
|---|---|---|
| 2005/0281661 A1 | 12/2005 | Kesil et al. |
| 2005/0288407 A1 | 12/2005 | Heuer et al. |
| 2006/0033894 A1 | 2/2006 | Binnard |
| 2006/0116055 A1 | 6/2006 | Oyu et al. |
| 2006/0127392 A1 | 6/2006 | De Romeuf et al. |
| 2006/0164611 A1 | 7/2006 | Scampini |
| 2007/0147979 A1 | 6/2007 | Rice et al. |
| 2007/0202077 A1 | 8/2007 | Brodsky et al. |
| 2007/0243184 A1 | 10/2007 | Fischkoff et al. |
| 2007/0244227 A1 | 10/2007 | Eipper et al. |
| 2007/0257240 A1 | 11/2007 | Engelmann et al. |
| 2007/0260015 A1 | 11/2007 | Stork et al. |
| 2007/0290150 A1 | 12/2007 | Krupyshev et al. |
| 2008/0015303 A1 | 1/2008 | Eibeck et al. |
| 2008/0020194 A1 | 1/2008 | Younes et al. |
| 2008/0045668 A1 | 2/2008 | Eibeck et al. |
| 2008/0064827 A1 | 3/2008 | Eipper et al. |
| 2008/0076859 A1 | 3/2008 | Eipper et al. |
| 2008/0097033 A1 | 4/2008 | Rosenau et al. |
| 2008/0139715 A1 | 6/2008 | Scherzer et al. |
| 2008/0167419 A1 | 7/2008 | Eipper et al. |
| 2008/0180895 A1 | 7/2008 | Jin et al. |
| 2008/0194741 A1 | 8/2008 | Engelmann et al. |
| 2008/0198450 A1 | 8/2008 | Guo et al. |
| 2008/0207812 A1 | 8/2008 | Mettlach et al. |
| 2008/0211135 A1 | 9/2008 | Eipper et al. |
| 2008/0214701 A1 | 9/2008 | Wilms et al. |
| 2008/0226084 A1 | 9/2008 | Konagai et al. |
| 2008/0260733 A1 | 10/2008 | Watkins et al. |
| 2008/0266560 A1 | 10/2008 | Kok |
| 2008/0309787 A1 | 12/2008 | Notsu et al. |
| 2009/0011916 A1 | 1/2009 | Steidl |
| 2009/0047717 A1 | 2/2009 | Gross et al. |
| 2009/0057137 A1 | 3/2009 | Pitts et al. |
| 2009/0064442 A1 | 3/2009 | Masuda et al. |
| 2009/0091149 A1 | 4/2009 | Chevassu et al. |
| 2009/0149637 A1 | 6/2009 | Kucherlapati et al. |
| 2009/0169855 A1 | 7/2009 | Tunis |
| 2009/0171408 A1 | 7/2009 | Solem |
| 2009/0180090 A1 | 7/2009 | Hara |
| 2009/0209701 A1 | 8/2009 | Steinmeiz et al. |
| 2009/0247658 A1 | 10/2009 | Kobayashi et al. |
| 2009/0275680 A1 | 11/2009 | Bruchmann et al. |
| 2009/0281271 A1 | 11/2009 | Bruchmann et al. |
| 2009/0315513 A1 | 12/2009 | Mkhitarian |
| 2010/0000783 A1 | 1/2010 | Tally et al. |
| 2010/0032611 A1 | 2/2010 | Fukuhara et al. |
| 2010/0040439 A1 | 2/2010 | Temple et al. |
| 2010/0048935 A1 | 2/2010 | Mijolovic et al. |
| 2010/0178299 A1 | 7/2010 | Sitkovsky et al. |
| 2010/0222524 A1 | 9/2010 | Lawrey et al. |
| 2010/0249311 A1 | 9/2010 | Eipper et al. |
| 2010/0280165 A1 | 11/2010 | Terrenoire et al. |
| 2011/0196098 A1 | 8/2011 | Mettlach et al. |
| 2011/0201745 A1 | 8/2011 | Roller et al. |
| 2011/0243932 A1 | 10/2011 | Barrett et al. |
| 2011/0274932 A1 | 11/2011 | Benten et al. |
| 2012/0003454 A1 | 1/2012 | Younes et al. |
| 2012/0085961 A1 | 4/2012 | Rogunova et al. |
| 2012/0201982 A1 | 8/2012 | Stewart et al. |
| 2012/0230988 A1 | 9/2012 | Hiruma et al. |
| 2013/0273062 A1 | 10/2013 | Bensussan et al. |
| 2014/0240824 A1 | 8/2014 | Taylor et al. |
| 2014/0362436 A1 | 12/2014 | Forget |
| 2014/0371363 A1 | 12/2014 | Nakamura et al. |
| 2015/0044722 A1 | 2/2015 | Tremblay et al. |
| 2015/0125470 A1 | 5/2015 | Hiruma et al. |
| 2015/0138632 A1 | 5/2015 | Mikhailov |
| 2015/0299372 A1 | 10/2015 | Allen et al. |
| 2015/0299374 A1 | 10/2015 | Hofmann et al. |
| 2015/0357213 A1 | 12/2015 | Yokoyama et al. |
| 2016/0003065 A1 | 1/2016 | Stratton et al. |
| 2016/0229955 A1 | 8/2016 | Muller et al. |
| 2016/0272756 A1 | 9/2016 | Tabor et al. |
| 2016/0297919 A1 | 10/2016 | Klesczewski et al. |
| 2016/0362518 A1 | 12/2016 | Muller et al. |
| 2017/0051103 A1 | 2/2017 | Tabor et al. |
| 2017/0129956 A1 | 5/2017 | Filion et al. |
| 2017/0261735 A1 | 9/2017 | Quarre et al. |
| 2017/0315340 A1 | 11/2017 | Quarre et al. |
| 2017/0322407 A1 | 11/2017 | Quarre et al. |
| 2017/0363850 A1 | 12/2017 | Quarre et al. |
| 2018/0003939 A1 | 1/2018 | Quarre et al. |
| 2018/0003940 A1 | 1/2018 | Quarre et al. |
| 2018/0037656 A1 | 2/2018 | Hiruma et al. |
| 2018/0134841 A1 | 5/2018 | Share et al. |
| 2018/0155481 A1 | 6/2018 | Share et al. |
| 2018/0318419 A1 | 11/2018 | Chen |
| 2018/0355097 A1 | 12/2018 | Blumson et al. |
| 2019/0040184 A1 | 2/2019 | Blumson et al. |
| 2019/0055345 A1 | 2/2019 | Blumsom et al. |
| 2019/0055346 A1 | 2/2019 | Blumsom et al. |
| 2019/0241699 A1 | 8/2019 | Blumsom et al. |

FOREIGN PATENT DOCUMENTS

| | | |
|---|---|---|
| CN | 101775129 A | 7/2010 |
| CN | 102206333 A | 10/2011 |
| CN | 102313978 A | 1/2012 |
| CN | 102382441 A | 3/2012 |
| CN | 102540441 A | 7/2012 |
| CN | 102911636 A | 2/2013 |
| CN | 104004179 A | 8/2014 |
| CN | 104119486 A | 10/2014 |
| CN | 104163976 A | 11/2014 |
| CN | 104356634 A | 2/2015 |
| CN | 104610872 A | 5/2015 |
| CN | 105174822 A | 12/2015 |
| CN | 106008948 A | 10/2016 |
| CN | 106415356 A | 2/2017 |
| CN | 108070067 A | 5/2018 |
| CN | 110035769 A | 7/2019 |
| CN | 110218257 | 9/2019 |
| CZ | 2011336 A3 | 1/2013 |
| EP | 0224769 A2 | 6/1987 |
| EP | 0239400 | 4/1989 |
| EP | 0519596 | 12/1992 |
| EP | 0519596 | 11/2004 |
| EP | 1609818 A2 | 12/2005 |
| EP | 1612231 A1 | 1/2006 |
| EP | 2299281 A2 | 3/2011 |
| EP | 2548906 A1 | 1/2013 |
| EP | 2548907 A1 | 1/2013 |
| EP | 3149533 A1 | 4/2017 |
| EP | 3515478 A1 | 7/2019 |
| FR | 2874217 A1 | 2/2006 |
| FR | 2880025 A1 | 6/2006 |
| GB | 2188638 | 10/1987 |
| GB | 2441594 A | 3/2008 |
| JP | 60-210674 A | 10/1985 |
| JP | 03-152181 A | 6/1991 |
| JP | 08-080672 A | 3/1996 |
| JP | 10-036474 A | 2/1998 |
| JP | 2002-284976 A | 10/2002 |
| JP | 2002-293869 A | 10/2002 |
| JP | 2003-147070 A | 5/2003 |
| JP | 2003-147185 A | 5/2003 |
| JP | 2003-183405 A | 7/2003 |
| JP | 2003-192761 A | 7/2003 |
| JP | 2003-246852 A | 9/2003 |
| JP | 2004-035738 A | 2/2004 |
| JP | 2006-160871 A | 6/2006 |
| JP | 2010-013523 A | 1/2010 |
| JP | 2013-224850 A | 10/2013 |
| JP | 2017-014413 A | 1/2017 |
| JP | 2018-044431 A | 3/2018 |
| JP | 2018-047011 A | 3/2018 |
| JP | 2019-536470 A | 12/2019 |
| KR | 2019-0050816 A | 5/2019 |
| RU | 2139731 C1 | 10/1999 |
| RU | 2297430 C2 | 4/2007 |
| WO | 8807089 | 9/1988 |
| WO | 8907142 | 8/1989 |
| WO | 9317105 | 9/1993 |

(56) References Cited

FOREIGN PATENT DOCUMENTS

| | | |
|---|---|---|
| WO | 9634096 | 10/1996 |
| WO | 9823289 | 6/1998 |
| WO | 9951642 | 10/1999 |
| WO | 02/75425 A1 | 9/2002 |
| WO | 03/91137 A2 | 11/2003 |
| WO | 04029207 | 4/2004 |
| WO | 2007/009897 A1 | 1/2007 |
| WO | 2011/035743 A1 | 3/2011 |
| WO | 2011/041894 A1 | 4/2011 |
| WO | 2011/089120 A1 | 7/2011 |
| WO | 2011/129940 A1 | 10/2011 |
| WO | 2013/011014 A1 | 1/2013 |
| WO | 2013/011015 A1 | 1/2013 |
| WO | 2013/034660 A1 | 3/2013 |
| WO | 2014/072336 A1 | 5/2014 |
| WO | 2014/093995 A1 | 6/2014 |
| WO | 2014/153046 A2 | 9/2014 |
| WO | 2014/203173 A1 | 12/2014 |
| WO | 2015/078801 A1 | 6/2015 |
| WO | 2015/128277 A1 | 9/2015 |
| WO | 2015/132080 A1 | 9/2015 |
| WO | 2015/183691 A1 | 12/2015 |
| WO | 2015/197742 A1 | 12/2015 |
| WO | 2015192214 | 12/2015 |
| WO | 2016/001164 A1 | 1/2016 |
| WO | 2016/025421 A1 | 2/2016 |
| WO | 2016/025423 A1 | 2/2016 |
| WO | 2016/069622 A1 | 5/2016 |
| WO | 2016/186727 A1 | 11/2016 |
| WO | 2017/083354 A1 | 5/2017 |
| WO | 2018/057735 A1 | 3/2018 |
| WO | 2018/140073 A1 | 8/2018 |
| WO | 2018/140074 A1 | 8/2018 |
| WO | 2018/190891 A1 | 10/2018 |

OTHER PUBLICATIONS

Angal, S. et al., "A Single Amino Acid Substitution Abolishes the Heterogeneity of Chimeric Mouse/Human (Igg4) Antibody," Molec. Immunol. 30(1):105-108 (1993).

Angata, et al., "Siglec-15: an immune system Siglec conserved throughout vertebrate evolution," Glycobiology, 17(8):838-46 (2007).

Bansal, P. et al., "MHC Class I-Restricted Presentation of Maleylated Protein Binding to Scavenger Receptors," J. Immunol. 162(8):4430-4437, (1999).

Bass, et al., "Immunopotentiation with low-dose cyclophosphamide in the active specific immunotherapy of cancer," Cancer Immunol. Immunother. 47:1-12 (1998).

Berger et al., "Phase I Safety and Pharmacokinetic Study of CT-011, a Humanized Antibody Interacting with PD1, in Patients with Advanced Hematologic Malignancies," Clin. Cancer Res., 14:3044_3051 (2008).

Brode, et al., "Immune-potentiating effects of the chemotherapeutic drug cyclophosphamide," Crit Rev. Immunol. 28:109-126 (2008).

Butte et al., "PD-L1 interacts specifically with By-1 to inhibit T cell proliferation," Immunity, vol. 27, pp. 111-122, (2007).

Crocker, et al., "Siglecs and their roles in the immune system," Nat. Rev. Immunol., 7:255 266 (2007).

Crocker et al., "Siglecs as positive and negative regulators of the immune system," Biochemical Society Transactions, 36 (6):1467-1471 (2008).

Cubillos-Ruiz et al., "Polyethylenimine-based siRNA nanocomplexes reprogram tumor-associated dendritic cells via TLR5 to elicit therapeutic antitumor immunity," J. Clin. Invest. 119(8): 2231-2244 (2009).

Dave, S.S. et al., "Prediction of survival in Follicular Lymphoma Based on Molecular Features of Tumor-Infiltrating Immune Cells," N. Engl. J. Med. 351:2159-2169, (2004).

Elliott, S. et al., "Enhancement of Therapeutic Protein In Vivo Activities Through Glycoengineering," Nature Biotechnol. 21:414-21, (2003).

Erbe et al., "Small Molecule Ligands Define a Binding Site on the Immune Regultaory Protein B7.1," J. Biol. Chem., 277:7363-7368 (2002).

Farinha, P. et al., Analysis of multiple biomarkers shows that lymphoma-associated macrophage (LAM) content is an Independent predictor of survival in follicular lymphoma (FL), Blood 106:2169-2174, (2005).

Flavell, et al., "The polarization of immune cells in the tumour environment by TGFB," Nat Rev Immunol, 10:554-567 (2010).

Freeman, "Structures of PD-1 with its ligands: Sideways and dancing cheek to cheek," Proc. Natl. Acad. Sci. U. S. A, 105:10275-10276 (2008).

Ishida-Kitagawa, "Siglec-15 Protein Regulates Formation of Functional Osteoclasts in Concert with DNAX-activating Protein of 12 kDa (DAP12)," J. Biol. Chem., 287, 17493-17502 (2012).

Li et al., "Vascular Endothelial Growth Factor Blockade Reduces Intratumoral Regulatory T Cells and Enhances the Efficacy of a GM-CSF-Secreting Cancer Immunotherapy," Clin Cancer Res., 12(22):6808-16, (2006).

Lin, J.Y. et al., "Clinical Significance of tumor-associated macrophage infiltration in supraglottic laryngeal carcinoma," Chin. J. Cancer 30(4):280-286; (2011).

Liu, J. et al., "Tumor-Associated Macrophages Recruit CCR6 Regulatory T Cells and Promote the Development of Colorectal Cancer via Enhancing CCL20 Production in Mice," PLoS One. 6(4):e19495; (2011).

McMillan, et al., "CD33-related sialic-acid-binding immunoglobulin-like lectins in health and disease," Carbohydr. Res., 343:2050-2056 (2008).

Morea et al., "Antibody modeling: implications for engineering and design," Methods 20:267-79, (2000) (abstract).

Mukhopadhyay, A. et al., "Intracellular Delivery of Drugs to Macrophages," Adv. Biochem. Eng. Biotechnol. 84:183-209, (2003).

Muyldermans et al., "Recognition of antigens by single-domain antibody fragments: the superfluous luxury of paired domains," Trends Biochem. Sci. 26:230, (2001).

Nucera, S. et al., "The interplay between macrophages and angiogenesis in development, tissue injury and regeneration," Int. J. Dev. Biol, doi: 10.1387/ijdb.103227sn; (2011).

Nuttall et al., "Immunoglobulin V11 Domains and Beyond: Design and Selection of Single-Domain Binding and Targeting Reagents," Cur. Pharm. Biotech. 1:253, (2000).

Padlan, A possible procedure for reducing the immunogenicity of antibody variable domains while preserving heir ligand-binding properties, Molecular Immunology 28(4/5):489 498, (1991).

Pollard, J.W., "Trophic macrophages in development and disease," Nat. Rev. Immunol. 9:259-270, (2009).

Rigo, A. et al., "Macrophages may promote cancer growth via a GM-CSF/HB-EGF paracrine loop that is enhanced by CXCL12," Molec. Cancer 9(273):1-13; (2010).

Shields, R.L. et al., "Lack of Fucose on Human IgG N-Linked Oligosaccharide Improves Binding to Human Fcgamma RIII and Antibody-Dependent Cellular Toxicity.," J. Biol. Chem. 277(30): 26733-26740, (2002).

Solinas, G. et al., "Tumor-associated macrophages (TAM) as major players of the cancer-related inflammation," J. Leukoc. Biol. 86(5):1065-1073, (2009).

Stavenhagen, J.B. et al., "Fc Optimization of Therapeutic Antibodies Enhances Their Ability to Kill Tumor Cells In Vitro and Controls Tumor Expansion In Vivo Via Low-Affinity Activating Fcgamma Receptors," Cancer Res. 57(18):8882-8890, (2007).

Stuible, et al., "Mechanism and Function of Monoclonal Antibodies Targeting Siglec-15 for Therapeutic Inhibition of Osteoclastic Bone Resorption," J. Biol Chem., 289(10): 6498-6512 (2014).

Takamiya, et al., The interation between Siglec-15 and tumor-associated sialyl-Tn antigen enhances TGF-B section from monocytes/macrophages through the DAP12-Sky pathway, Glycobiology, 23(2):178-87 (2013).

Tan et al., ""Superhumanized" Antibodies: Reduction of Immunogenic Potential by Complementarity-Determining Region Grafting with Human Germline Sequences: Application to an Anti-CD281", J. Immunol. 169:1119-1125, (2002).

(56) References Cited

OTHER PUBLICATIONS

Van der Most et al., "Cyclophosphamide Chemotherapy Sensitizes Tumor Cells to TRAIL-Dependent CD8 T Cell-Medicated Immune Attack Resulting in Suppression of Tumor Growth," Cancer Immunol. Immunother. 58:1219-1228 (2009).
Vergati, M., "The Consequence of Immune Suppressive Cells in the Use of Therapeutic Cancer Vaccines and Their Importance in Immune Monitoring," J. Biomed. Biotechnol. 2011:182413, (2011).
Wu, F. et al., "Galactosylated LDL Nanoparticles: A Novel Targeting Delivery System to Deliver Antigen to Macrophages and Enhance Antigen Specific T Cell Responses," Molec. Pharm. 6(5):1506-1517, (2009).
Zamarron, B.F. et al., "Dual Roles of Immune Cells and Their Factors in Cancer Development and Progression," Int. J. Biol. Sci. 7(5):651-658; (2011).
Office Action received for Russian Patent Application No. 2019111722, dated Dec. 21, 2020, 7 pages (3 pages of English Translation and 4 pages of Original Document).
Search Report received for Russian Patent Application No. 2019111722, dated Dec. 20, 2020, 4 pages (2 pages of English Translation and 2 pages of Original Document).
Achaya et al., "The Component Fatty Acids and Glycerides of Castor Oil" The Journal of the American Oil Chemist's Society, vol. 41, Issue 12, pp. 783-784 (1964).
Appendix A Supplementary material. Available at HYPERLINK "http://dx.doi.org/10.1016/j" \hhttp://dx.doi.org10.1016/j .eurpolymj .2016.11.030 cited at the end of the article. Benes et al., "Medium Chain Glycerides of Coconut Oil for Microwave-Enhanced Conversion of Polycarbonate into Polyols" European Polymer Journal, vol. 86, pp. 173-187 (2017).
Benes et al., "Medium chain glycerides of coconut oil for microwave-enhanced conversion of polycarbonate into polyols" European Polymer Journal, 86, pp. 173-187, 2016.
Benes et al., "Polyurethane foams based entirely on recycled polyols derived from natural oils" Polimery, vol. 60, Issue 9, pp. 579-585 (2015).
Chao-Hsing et al., "Novel Chemical Recycling of Polycarbonate (PC) Waste Into Bis-Hydroxyalkyl Ethers of Bisphenol A for Use as PU Raw Materials," Green Chemistry, Issue 1, pp. 38-43, Jan. 2007.
Final Rejection dated Apr. 3, 2020 for U.S. Appl. No. 15/602,789.
Final Rejection dated Mar. 5, 2019 for U.S. Appl. No. 15/708,937.
Final Rejection dated Oct. 7, 2019 for U.S. Appl. No. 15/601,687.
Iannone et al., "Ionic liquids/ZnO nanoparticles as recyclable catalyst for polycarbonate depolymerization," Journal of Molecular Catalysis A: Chemical, 426(Part A), pp. 107-116, 2017.
International Preliminary Report on Patentability received for PCT Patent Application No. PCT/US15/031969, dated Dec. 8, 2016, 6 pages.
International Preliminary Report on Patentability received for PCT Patent Application No. PCT/US17/032614, dated Aug. 5, 2019, 12 pages.
International Preliminary Report on Patentability received for PCT Patent Application No. PCT/US17/034044, dated Aug. 8, 2019, 8 pages.
International Preliminary Report on Patentability received for PCT Patent Application No. PCT/US17/034205, dated Aug. 8, 2019, 9 pages.
International Preliminary Report on Patentability received for PCT Patent Application No. PCT/US17/052714, dated Apr. 4, 2019, 8 pages.
International Search Report and Written Opinion received for PCT Patent Application No. PCT/US15/031969, dated Aug. 28, 2015, 12 pages.
International Search Report and Written Opinion received for PCT Patent Application No. PCT/US17/032614, dated Dec. 14, 2017, 10 pages.
International Search Report and Written Opinion received for PCT Patent Application No. PCT/US17/034044, dated Aug. 29, 2017, 8 pages.
International Search Report and Written Opinion received for PCT Patent Application No. PCT/US17/034205, dated Aug. 7, 2017, 9 pages.
International Search Report and Written Opinion received for PCT Patent Application No. PCT/US17/052714, dated Feb. 13, 2018, 11 pages.
Lin et al., "Identification and Quantification of the Molecular Species of Acylglycerols in Castor Oil by HPLC Using ELSD" Journal of Liquid Chromatography & Related Technologies, vol. 26, Issue 5, pp. 773-780 (2003).
Liu et al., "Fully degradable brush polymers with polycarbonate backbones and polylactide side chains," Science China: Chemistry, 58(6), pp. 999-1004, 2015.
Nikj e et al., "Chemical recycling of polycarbonate wastes into bisphenol A by using green solvent composition," Dolimery, 58(4), pp. 292-294, Warsaw, Poland, 2013.
Non-Final Rejection dated Feb. 7, 2020 for U.S. Appl. No. 15/708,769.
Non-Final Rejection dated Feb. 20, 2019 for U.S. Appl. No. 15/601,687.
Non-Final Rejection dated Feb. 21, 2019 for U.S. Appl. No. 15/602,789.
Non-Final Rejection dated Jan. 14, 2020 for U.S. Appl. No. 15/601,687.
Non-Final Rejection dated Jul. 2, 2018 for U.S. Appl. No. 15/708,937.
Non-Final Rejection dated Jun. 15, 2020 for U.S. Appl. No. 15/603,716.
Non-Final Rejection dated Jun. 24, 2020 for U.S. Appl. No. 16/105,089.
Non-Final Rejection dated Jun. 24, 2020 for U.S. Appl. No. 16/105,106.
Non-Final Rejection dated Jun. 24, 2020 for U.S. Appl. No. 16/105,126.
Non-Final Rejection dated Jun. 24, 2020 for U.S. Appl. No. 16/105,148.
Non-Final Rejection dated Jun. 24, 2020 for U.S. Appl. No. 16/105,161.
Non-Final Rejection dated May 15, 2020 for U.S. Appl. No. 15/601,267.
Non-Final Rejection dated Sep. 19, 2019 for U.S. Appl. No. 15/602,789.
Notice of Allowance and Fees Due (PTOL-85) dated May 1, 2020 for U.S. Appl. No. 15/601,687.
Office Action received for European Patent Application No. 17853889, dated Mar. 27, 2020, 4 pages.
Pant, "Polycarbonate Waste Management using Gylcerol," Process Safety and Environmental Protection, 100, pp. 281-287, 2016.
Ray et al., "Polycarbonate and Poly(carbonate-ester)s Synthesized from Biocompatible Building Blocks of Glycerol and Lactic Acid," Macromolecules, 36(10), pp. 3557-3562, 2003.
Requirement for Restriction/Election dated Dec. 4, 2019 for U.S. Appl. No. 15/601,267.
Requirement for Restriction/Election dated Jan. 3, 2020 for U.S. Appl. No. 15/603,716.
Search Report received for U.S. Patent Application No. 201580028007, dated Jul. 13, 2018, 1 page.
Supplementary European Search Report and Search Opinion Received for EP Application No. 15799175, dated May 10, 2017, 6 pages.
UniProtKB G0U045TRYVY (Oct. 19, 2011) [downloaded from the internet on Feb. 5, 2018, http://www.uniprot.org/uniprot/G0U045], amino acids 173-180.
Wang, Jun, et al., "Siglec-15 as an immune suppressor and potential target for normalization cancer immunotherapy," Nature Medicine, 25:656-666 (2019).
Extended European Search Report issued by the European Patent Office dated Jun. 16, 2020; 9 pages.
First Office Action received for Chinese Application No. 201580028007, dated Jul. 23, 2018, 8 pages (5 pages of English Translation and 3 pages of Original Document).
Intention to grant received for European Application No. 15799175, dated Nov. 7, 2018, 1 page.
Notification to Grant Patent Right for Invention received for Chinese Application No. 201580028007, dated Feb. 2, 2019, 3 pages (2 pages of English Translation and 1 page of Original Document).

\* cited by examiner

| | L#36 | L#37 | L#38 | L#39 | L#40 | L#41 | L#42 | L#43 | L#44 | L#45 | L#46 | L#47 | L#48 | L#49 | L#50 | L#51 | L#52 | L#53 | L#54 | L#55 | L#56 | L#57 | L#58 | L#59 | L#60 | L#61 | L#62 | L#63 | L#64 | L#65 | L#66 | L#67 | L#68 | L#69 | L#70 | SEQ ID NO: |
|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | CDR2 | CDR2 | CDR2 | CDR2 | CDR2 | CDR2 | CDR2 | | | | | | | | | | | | | | | |
| 1B2 | Y | L | Q | K | P | G | Q | S | P | K | L | L | I | Y | K | V | S | N | R | F | S | G | V | P | D | R | F | S | G | S | G | S | G | T | D | 237 |
| 1C3 | F | L | Q | R | P | G | Q | S | P | K | L | L | I | Y | R | W | N | L | A | S | G | V | P | D | R | F | G | G | S | G | S | G | T | A | 238 |
| 1H3 | Y | L | Q | K | P | G | Q | A | P | K | L | L | I | Y | S | G | S | T | L | E | G | V | P | S | R | F | S | G | S | G | S | G | K | D | 239 |
| 1C12 | Y | L | Q | K | P | G | Q | S | P | R | L | L | I | Y | K | V | S | N | R | F | S | G | V | P | D | R | F | S | G | S | G | S | G | T | D | 237 |
| 3H10 | Y | L | Q | K | P | G | Q | S | P | K | R | W | I | Y | D | T | S | K | L | V | D | V | P | G | R | F | S | G | S | G | S | G | T | T | S | 240 |
| 5G12 | F | L | Q | R | P | G | Q | S | P | K | L | L | I | Y | R | A | N | R | L | A | S | G | V | P | G | R | F | S | G | S | G | S | G | T | Q | 241 |
| 6F8 | F | L | Q | K | P | G | Q | S | P | Q | L | L | I | Y | A | W | S | N | R | A | S | G | V | P | D | R | F | S | G | S | G | S | G | T | A | 238 |
| 8C3 | Y | L | Q | K | P | G | Q | S | P | K | L | L | I | Y | R | R | N | N | K | A | G | G | V | P | D | R | F | G | G | S | G | S | G | T | A | 238 |
| 8H8 | F | L | Q | R | P | G | Q | L | P | K | G | L | I | Y | G | T | S | K | L | Q | P | G | V | P | A | R | F | S | I | S | G | I | G | D | K | 242 |
| 9A5 | V | L | E | K | P | D | H | L | P | K | R | L | I | Y | K | V | N | N | R | A | S | G | V | P | D | R | F | T | G | S | G | S | G | T | D | 243 |
| 10G9 | Y | L | Q | R | P | G | Q | S | P | K | L | L | I | Y | G | T | S | K | L | Q | P | G | V | P | A | R | F | S | I | S | G | I | G | D | K | 242 |
| #6 | V | L | E | K | P | D | H | L | P | K | R | L | I | Y | K | V | N | N | R | F | S | G | V | P | D | R | F | T | G | S | G | S | G | T | D | 237 |
| #28 | Y | L | Q | R | P | G | Q | S | P | K | L | L | I | Y | L | V | S | E | L | D | S | G | V | P | D | R | F | S | G | S | G | S | G | T | D | 244 |
| #63 | L | L | Q | K | P | G | Q | S | P | K | L | L | I | Y | K | V | S | K | L | D | S | G | V | P | D | R | F | S | G | S | G | S | G | T | D | 243 |
| #77 | Y | L | Q | K | P | G | Q | S | P | K | L | L | I | Y | K | V | S | N | R | F | S | G | V | P | D | R | F | S | G | S | G | S | G | T | D | 245 |
| #80 | Y | L | Q | K | P | G | Q | S | P | K | L | L | I | Y | W | A | S | T | R | E | S | G | V | P | D | R | F | S | G | S | G | S | G | T | D | 246 |
| #82 | Y | L | Q | R | P | G | Q | S | P | K | F | L | I | Y | Y | A | S | N | L | A | S | G | V | P | S | R | F | S | G | S | G | S | G | T | D | 244 |
| #83 | Y | L | Q | K | P | G | K | S | P | K | L | L | I | Y | W | T | S | I | R | E | G | G | V | P | S | R | F | S | G | S | G | S | G | T | F | 247 |
| #92 | Y | L | Q | K | P | G | T | S | P | K | L | L | I | Y | L | V | S | N | L | A | S | G | V | P | D | R | F | T | G | S | G | S | G | T | D | 248 |
| #93 | Y | L | Q | R | P | G | Q | S | P | K | L | L | I | Y | Y | A | S | I | R | E | S | G | V | P | S | R | F | T | G | S | G | S | G | T | D | 246 |
| #99 | Y | L | Q | K | P | G | Q | S | P | K | L | L | I | Y | L | V | S | K | L | D | S | G | V | P | D | R | F | S | G | S | G | S | G | T | D | 243 |
| #104 | L | L | Q | R | P | G | Q | S | P | K | R | L | I | Y | L | V | S | K | L | D | S | G | V | P | D | R | F | T | G | S | G | S | G | T | D | 243 |
| #105 | Y | L | Q | K | P | G | Q | S | P | K | L | L | I | Y | K | V | S | N | R | F | S | G | V | P | D | R | F | S | G | S | G | S | G | T | D | 237 |

Direct Binding to S15

Blocking Analysis

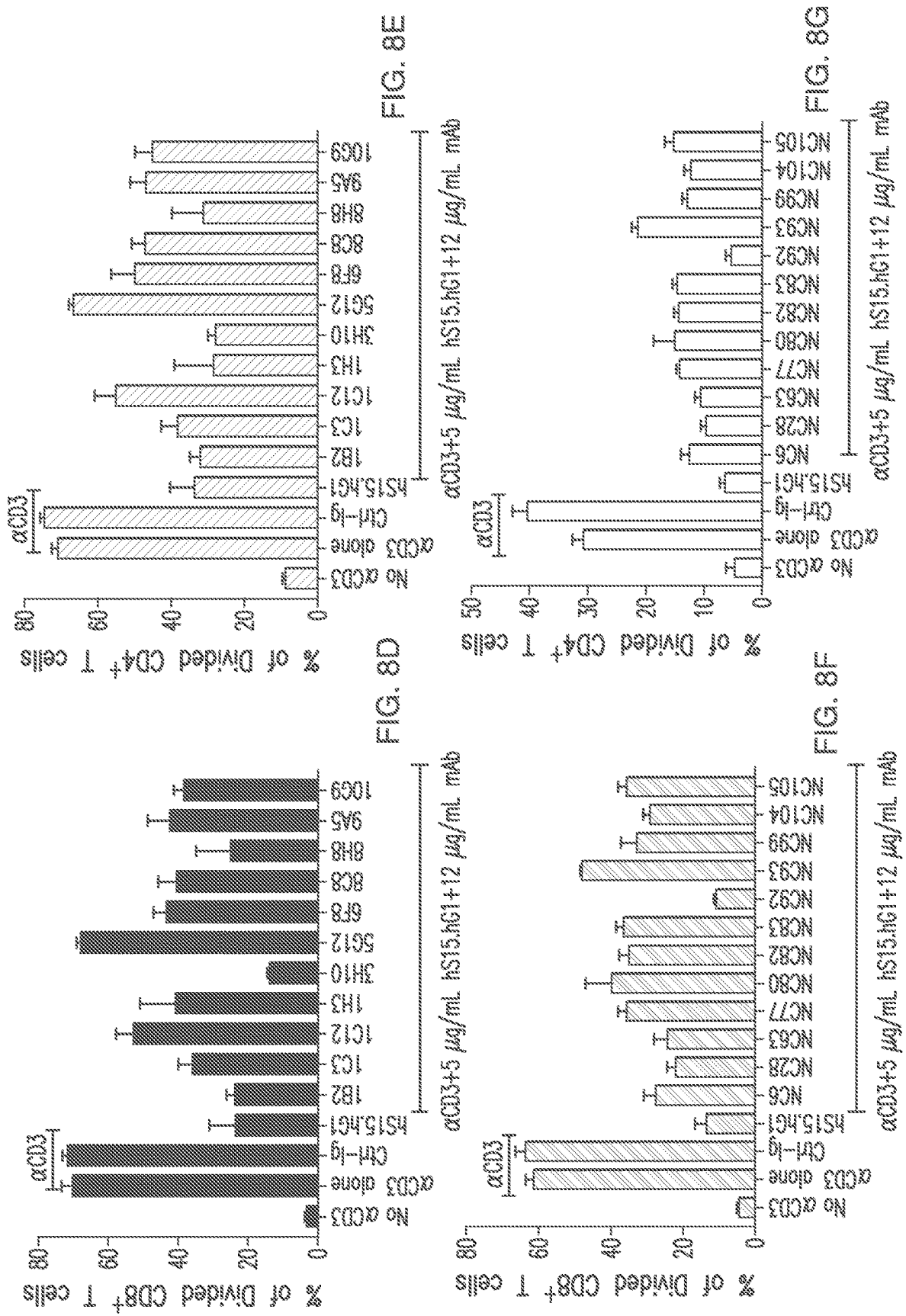

Alignment: Global Protein alignment against reference molecule
Parameters: Scoring matrix: BLOSUM 62

Reference molecule: 5G12_VL, Region 1 to 107
Number of sequences to align: 6
Total length of aligned sequences with gaps: 107 aas
Settings: Similarity significance value cutoff: >=60%

Summary of Percent Matches:

| Ref: | 5G12_VL  | 1 to 107 | (107 aa) | —   |
|------|----------|----------|----------|-----|
| 2:   | 5G12_VL1 | 1 to 107 | (107 aa) | 86% |
| 3:   | 5G12_VL2 | 1 to 107 | (107 aa) | 85% |
| 4:   | 5G12_VL3 | 1 to 107 | (107 aa) | 85% |
| 5:   | 5G12_VL4 | 1 to 107 | (107 aa) | 85% |
| 6:   | 5G12_VL5 | 1 to 107 | (107 aa) | 84% |

SEQ ID NO:

| 5G12_VL  | 1 | dikmtqspssmyaslgervtitckasqdinsylswfqqkpgkspktliyranrlvdgvps | 344 |
| 5G12_VL1 | 1 | diqmtqspsslsasvgdrvtitckasqdinsylswfqqkpgkdpktliyranrlvdgvps | 345 |
| 5G12_VL2 | 1 | diqmtqspsslsasvgdrvtitckasqdintylswfqqkpgkdpktliyranrlvdgvps | 346 |
| 5G12_VL3 | 1 | diqmtqspsslsasvgdrvtitckasqdinvylswfqqkpgkdpktliyranrlvdgvps | 347 |
| 5G12_VL4 | 1 | diqmtqspsslsasvgdrvtitckasqdiqsylswfqqkpgkdpktliyranrlvdgvps | 348 |
| 5G12_VL5 | 1 | diqmtqspsslsasvgdrvtitckasqdinvylswfqqkpgkdpktliyranrltsgvps | 349 |

SEQ ID NO:

| 5G12_VL  | 61 | rfsgsgsgqdysltissleyedmgiyyclqydefpytfgggtkleik | 350 |
| 5G12_VL1 | 61 | rfsgsgsgtdytltisslqpedfatyyclqydefpytfgggtkveik | 351 |
| 5G12_VL2 | 61 | rfsgsgsgtdytltisslqpedfatyyclqydefpytfgggtkveik | 351 |
| 5G12_VL3 | 61 | rfsgsgsgtdytltisslqpedfatyyclqydefpytfgggtkveik | 351 |
| 5G12_VL4 | 61 | rfsgsgsgtdytltisslqpedfatyyclqydefpytfgggtkveik | 351 |
| 5G12_VL5 | 61 | rfsgsgsgtdytltisslqpedfatyyclqydefpytfgggtkveik | 351 |

FIG. 13A

Alignment: Global Protein alignment against reference molecule
Parameters: Scoring matrix: BLOSUM 62

Reference molecule: 5G12_VL, Region 1 to 122
Number of sequences to align: 4
Total length of aligned sequences with gaps: 122 aas
Settings: Similarity significance value cutoff: >=60%

Summary of Percent Matches:
```
Ref:   5G12 VH      1 to  122   ( 122 aa)  —
  2:   5G12 VH1     1 to  122   ( 122 aa)  83%
  3:   5G12 VH2     1 to  122   ( 122 aa)  82%
  4:   5G12_VH3     1 to  122   ( 122 aa)  81%
```

| | | | SEQ ID NO: |
|---|---|---|---|
| 5G12_VH  | 1 | qvqlqqpgaelvkpgasvkmsckasgytftsywitwviqrpgqglewigdiycgsdtmhy | 352 |
| 5G12_VH1 | 1 | qvqlvqsgaevkkpgasvkvsckasgytftsywitwvrqapgqglewmgdiysgsdtmhy | 353 |
| 5G12_VH2 | 1 | qvqlvqsgaevkkpgasvkvsckasgytftsywitwvrqapgqglewmgdiysgsdtthy | 354 |
| 5G12_VH3 | 1 | qvqlvqsgaevkkpgasvkvsckasgytftsywiswvrqapgqglewmgdiysgsdtthy | 355 |

| | | | SEQ ID NO: |
|---|---|---|---|
| 5G12_VH  | 61 | nekfknkatltvdtssstaymqlssltsedsavyycarwwdygssydyfdywgqgtltlv | 356 |
| 5G12_VH1 | 61 | dekfqgrvtltvdtststaymelsslrsedtavyycarwwdygssydyfdywgqgtltvtv | 357 |
| 5G12_VH2 | 61 | dekfqgrvtltvdtststaymelsslrsedtavyycarwwdygssydyfdywgqgtltvtv | 357 |
| 5G12_VH3 | 61 | dekfqgrvtltvdtststaymelsslrsedtavyycarwwdygssydyfdywgqgtltvtv | 357 |

| | | |
|---|---|---|
| 5G12_VH  | 121 | ss |
| 5G12_VH1 | 121 | ss |
| 5G12_VH2 | 121 | ss |
| 5G12_VH3 | 121 | ss |

| | H#1 | H#2 | H#3 | H#4 | H#5 | H#6 | H#7 | H#8 | H#9 | H#10 | H#11 | H#12 | H#13 | H#14 | H#15 | H#16 | H#17 | H#18 | H#19 | H#20 | H#21 | H#22 | H#23 | H#24 | H#25 | H#26 | H#27 | H#28 | H#29 | H#30 | H#31 | H#32 | H#33 | H#34 | H#35 | H#36 | H#37 | H#38 | H#39 | H#40 | H#41 | H#42 | H#43 | H#44 | H#45 | H#46 | H#47 | H#48 | H#49 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | CDR1 | CDR1 | CDR1 | CDR1 | CDR1 | | | | | | | | | | | | | | | |
| Parent | Q | V | Q | L | K | E | S | G | P | G | L | V | A | P | S | Q | S | L | S | I | T | C | T | V | S | G | F | S | L | S | N | Y | G | V | H | W | V | R | Q | P | P | G | K | G | L | E | W | L | V | 364 |
| VH1 | Q | V | Q | L | Q | E | S | G | P | G | L | V | K | P | S | E | T | L | S | L | T | C | T | V | S | G | F | S | L | S | N | Y | G | V | H | W | V | R | Q | P | P | G | K | G | L | E | W | I | G | 365 |
| VH2 | Q | V | Q | L | Q | E | S | G | P | G | L | V | K | P | S | E | T | L | S | L | T | C | T | V | S | G | F | S | L | S | N | Y | G | V | H | W | V | R | Q | P | P | G | K | G | L | E | W | I | G | 366 |
| VH3 | Q | V | Q | L | Q | E | S | G | P | G | L | V | K | P | S | E | T | L | S | L | T | C | T | V | S | G | F | S | L | S | N | Y | G | V | H | W | V | R | Q | P | P | G | K | G | L | E | W | I | G | 366 |
| VH4 | Q | V | Q | L | Q | E | S | G | P | G | L | V | K | P | S | E | T | L | S | L | T | C | T | V | S | G | F | S | L | S | N | Y | G | V | H | W | V | R | Q | P | P | G | K | G | L | E | W | I | G | 366 |

| | H#50 | H#51 | H#52 | H#53 | H#54 | H#55 | H#56 | H#57 | H#58 | H#59 | H#60 | H#61 | H#62 | H#63 | H#64 | H#65 | H#66 | H#67 | H#68 | H#69 | H#70 | H#71 | H#72 | H#73 | H#74 | H#75 | H#76 | H#77 | H#78 | H#79 | H#80 | H#81 | H#82 | H#82A | H#82B | H#82C | H#83 | H#84 | H#85 | H#86 | H#87 | H#88 | H#89 | H#90 | H#91 | H#92 | H#93 | H#94 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | CDR2 | CDR2 | CDR2 | CDR2 | CDR2 | CDR2 | CDR2 | CDR2 | CDR2 | CDR2 | CDR2 | CDR2 | CDR2 | CDR2 | CDR2 | CDR2 | | | | | | | | | | | | | | | | | | | | | | | | | | | | | | | | | |
| Parent | L | I | W | S | D | G | S | T | T | Y | N | S | A | L | K | S | R | L | S | I | S | K | D | N | S | K | S | Q | V | F | L | K | M | N | S | L | Q | T | G | D | T | A | M | Y | Y | C | A | R | 367 |
| VH1 | L | I | W | S | D | G | S | T | T | Y | N | S | A | L | K | S | R | V | T | I | S | K | D | T | S | K | N | Q | V | S | L | K | L | S | S | V | T | A | A | D | T | A | V | Y | Y | C | A | R | 368 |
| VH2 | L | I | W | S | D | G | S | T | T | Y | A | S | A | L | K | S | R | V | T | I | S | K | D | T | S | K | N | Q | V | S | L | K | L | S | S | V | T | A | A | D | T | A | V | Y | Y | C | A | R | 369 |
| VH3 | L | I | W | S | D | G | S | T | T | Y | N | P | S | L | K | S | R | V | T | I | S | K | D | T | S | K | N | Q | V | S | L | K | L | S | S | V | T | A | A | D | T | A | V | Y | Y | C | A | R | 370 |
| VH4 | L | I | W | S | E | G | S | T | T | Y | A | S | A | L | K | S | R | V | T | I | S | K | D | T | S | K | N | Q | V | S | L | K | L | S | S | V | T | A | A | D | T | A | V | Y | Y | C | A | R | 371 |

| | H#95 | H#96 | H#97 | H#98 | H#99 | H#100 | H#100A | H#100B | H#100C | H#100D | H#100E | H#100F | H#100G | H#101 | H#102 | H#103 | H#104 | H#105 | H#106 | H#107 | H#108 | H#109 | H#110 | H#111 | H#112 | SEQ ID NO: |
|---|---|---|---|---|---|---|---|---|---|---|---|---|---|---|---|---|---|---|---|---|---|---|---|---|---|---|
| | CDR3 | CDR3 | CDR3 | CDR3 | CDR3 | CDR3 | CDR3 | CDR3 | CDR3 | CDR3 | CDR3 | CDR3 | CDR3 | | | | | | | | | | | | | |
| Parent | H | P | Y | D | D | Y | S | G | Y | Y | Y | T | M | D | Y | W | G | Q | G | T | S | V | T | V | S | S | 372 |
| VH1 | H | P | Y | D | D | Y | S | G | Y | Y | Y | T | M | D | Y | W | G | Q | G | T | L | V | T | V | S | S | 373 |
| VH2 | H | P | Y | D | D | Y | S | G | Y | Y | Y | T | M | D | Y | W | G | Q | G | T | L | V | T | V | S | S | 373 |
| VH3 | H | P | Y | D | D | Y | S | G | Y | Y | Y | T | M | D | Y | W | G | Q | G | T | L | V | T | V | S | S | 373 |
| VH4 | H | P | Y | D | D | Y | S | G | Y | Y | Y | T | M | D | Y | W | G | Q | G | T | L | V | T | V | S | S | 373 |

- Tumor cells or M2 macrophages ($\varphi$) express S15
  +
- S15 tumors or M2$\varphi$ may directly suppress T cell function, reducing IFN-$\gamma$
  +
- S15 tumors or M2$\varphi$ directly affects myeloid cells, increase TNF-$\alpha$, IL-6 & IL-1$\beta$ in

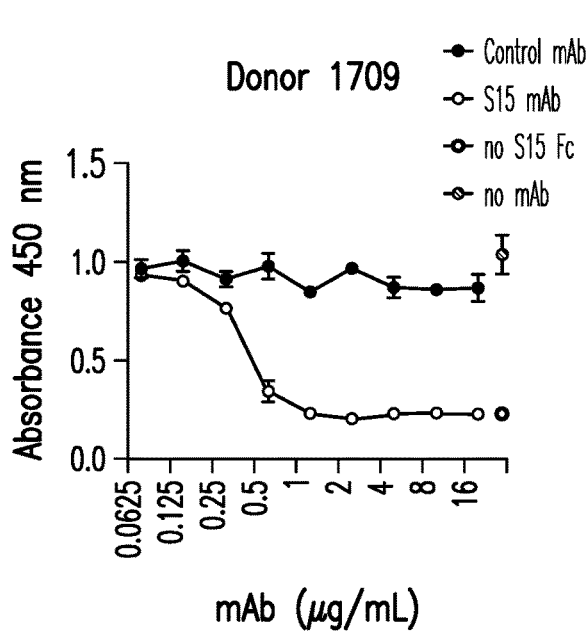
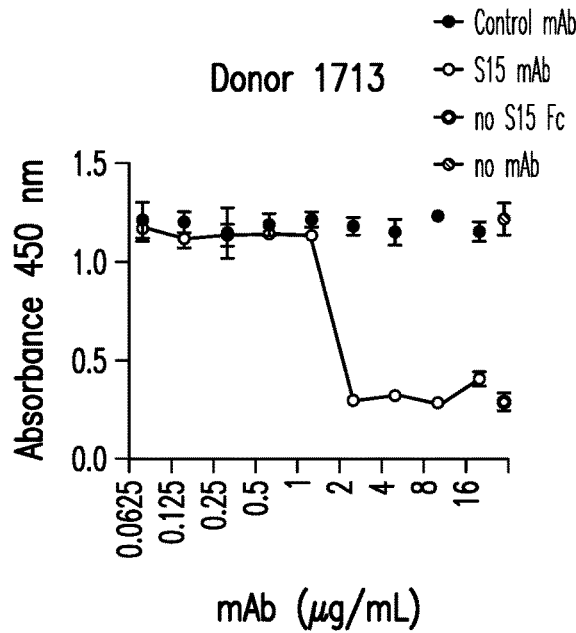
FIG. 28A          FIG. 28B
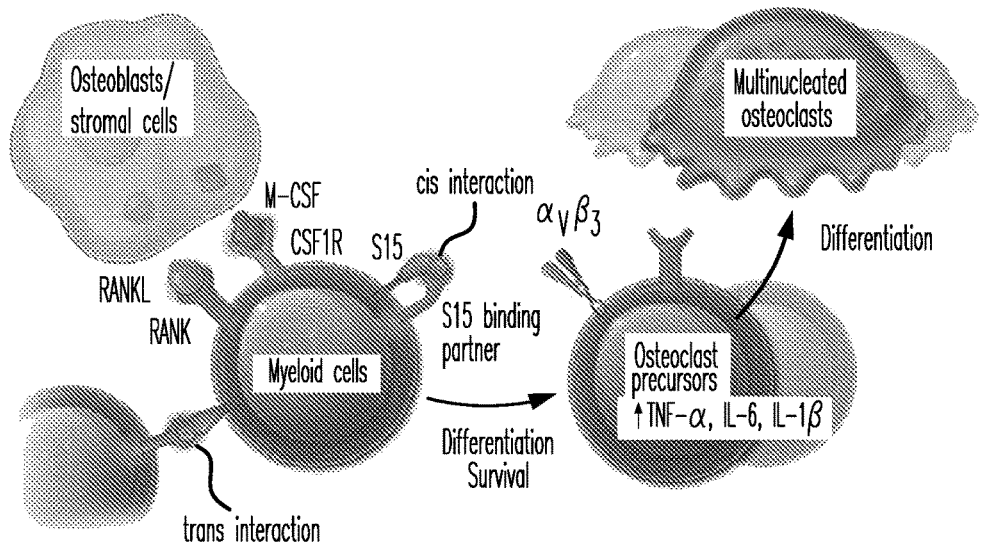
FIG. 29

SEQUENCE LISTING

```
<160> NUMBER OF SEQ ID NOS: 374

<210> SEQ ID NO 1
<211> LENGTH: 328
<212> TYPE: PRT
<213> ORGANISM: Homo sapiens

<400> SEQUENCE: 1

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125
```

-continued

```
Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Ala Ser Thr Val Ala Leu Leu Leu Gly Ala Leu Gly
            260                 265                 270

Phe Lys Ala Leu Leu Leu Gly Val Leu Ala Ala Arg Ala Ala Arg
    275                 280                 285

Arg Arg Pro Glu His Leu Asp Thr Pro Asp Thr Pro Pro Arg Ser Gln
    290                 295                 300

Ala Gln Glu Ser Asn Tyr Glu Asn Leu Ser Gln Met Asn Pro Arg Ser
305                 310                 315                 320

Pro Pro Ala Thr Met Cys Ser Pro
                325

<210> SEQ ID NO 2
<211> LENGTH: 342
<212> TYPE: PRT
<213> ORGANISM: Mus musculus

<400> SEQUENCE: 2

Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
                20                  25                  30

Asn Thr Glu Ala His Ser Ala Pro Ala Gln Arg Trp Ser Met Gln Val
            35                  40                  45

Pro Ala Glu Val Asn Ala Glu Ala Gly Asp Ala Ala Val Leu Pro Cys
        50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Ser Gly Arg Tyr Phe Cys Arg Val
    130                 135                 140

Glu Phe Thr Gly Asp Ala His Asp Arg Tyr Glu Ser Arg His Gly Val
145                 150                 155                 160

Arg Leu Arg Val Thr Ala Ala Pro Arg Ile Val Asn Ile Ser Val
                165                 170                 175
```

```
Leu Pro Gly Pro Ala His Ala Phe Arg Ala Leu Cys Thr Ala Glu Gly
            180                 185                 190

Glu Pro Pro Pro Ala Leu Ala Trp Ser Gly Pro Ala Pro Gly Asn Ser
            195                 200                 205

Ser Ala Ala Leu Gln Gly Gln Gly His Gly Tyr Gln Val Thr Ala Glu
            210                 215                 220

Leu Pro Ala Leu Thr Arg Asp Gly Arg Tyr Thr Cys Thr Ala Ala Asn
225                 230                 235                 240

Ser Leu Gly Arg Ala Glu Ala Ser Val Tyr Leu Phe Arg Phe His Gly
                245                 250                 255

Ala Pro Gly Thr Ser Thr Leu Ala Leu Leu Gly Ala Leu Gly Leu
            260                 265                 270

Lys Ala Leu Leu Leu Leu Gly Ile Leu Gly Ala Arg Ala Thr Arg Arg
            275                 280                 285

Arg Leu Asp His Leu Val Pro Gln Asp Thr Pro Pro Arg Ser Gln Ala
            290                 295                 300

Gln Glu Ser Asn Tyr Glu Asn Leu Ser Gln Met Ser Pro Gly His
305                 310                 315                 320

Gln Leu Pro Arg Val Cys Cys Glu Glu Leu Ser His His His Leu
                325                 330                 335

Val Ile His His Glu Lys
            340

<210> SEQ ID NO 3
<211> LENGTH: 112
<212> TYPE: PRT
<213> ORGANISM: Artificial Sequence
<220> FEATURE:
<223> OTHER INFORMATION: Synthetic construct

<400> SEQUENCE: 3

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 4
<211> LENGTH: 112
<212> TYPE: PRT
<213> ORGANISM: Artificial Sequence
<220> FEATURE:
<223> OTHER INFORMATION: Synthetic construct

<400> SEQUENCE: 4

Asp Ile Val Met Thr Gln Ala Ala Pro Ser Val Pro Val Thr Pro Gly
1               5                   10                  15
```

```
Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Gly Gly Ser Gly Ser Gly Thr Ala Phe Thr Leu Arg Ile
65                  70                  75                  80

Ser Arg Val Glu Ala Glu Asp Val Gly Phe Tyr Tyr Cys Met Gln His
                85                  90                  95

Leu Glu Tyr Pro Tyr Thr Phe Gly Gly Gly Thr Arg Leu Glu Ile Lys
                100                 105                 110

<210> SEQ ID NO 5
<211> LENGTH: 107
<212> TYPE: PRT
<213> ORGANISM: Artificial Sequence
<220> FEATURE:
<223> OTHER INFORMATION: Synthetic construct

<400> SEQUENCE: 5

Asp Ile Gln Met Thr Gln Ala Ser Ser Leu Ser Val Ser Leu Gly
1               5                   10                  15

Gly Arg Val Thr Ile Thr Cys Lys Ala Ser Asp His Ile Asn Asn Trp
                20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Ser Pro Leu
                85                  90                  95

Thr Phe Gly Ala Gly Thr Lys Leu Glu Leu Lys
                100                 105

<210> SEQ ID NO 6
<211> LENGTH: 106
<212> TYPE: PRT
<213> ORGANISM: Artificial Sequence
<220> FEATURE:
<223> OTHER INFORMATION: Synthetic construct

<400> SEQUENCE: 6

Gln Ile Ile Leu Thr Gln Ser Pro Ala Ile Met Ser Ala Ser Pro Gly
1               5                   10                  15

Glu Lys Val Thr Met Thr Cys Ser Ala Ser Ser Ser Thr Ser Phe Met
                20                  25                  30

His Trp Tyr Gln Gln Lys Pro Gly Thr Ser Pro Lys Arg Trp Ile Phe
            35                  40                  45

Asp Thr Ser Lys Leu Ala Ser Gly Val Pro Gly Arg Phe Ile Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys His Gln Arg Ser Ala Tyr Pro Trp Thr
                85                  90                  95
```

Phe Gly Gly Gly Thr Lys Leu Glu Ile Lys
            100                 105

<210> SEQ ID NO 7
<211> LENGTH: 108
<212> TYPE: PRT
<213> ORGANISM: Artificial Sequence
<220> FEATURE:
<223> OTHER INFORMATION: Synthetic construct

<400> SEQUENCE: 7

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg
            100                 105

<210> SEQ ID NO 8
<211> LENGTH: 113
<212> TYPE: PRT
<213> ORGANISM: Artificial Sequence
<220> FEATURE:
<223> OTHER INFORMATION: Synthetic construct

<400> SEQUENCE: 8

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Gly Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

Arg

<210> SEQ ID NO 9
<211> LENGTH: 112
<212> TYPE: PRT
<213> ORGANISM: Artificial Sequence
<220> FEATURE:
<223> OTHER INFORMATION: Synthetic construct

<400> SEQUENCE: 9

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Gly Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 10
<211> LENGTH: 109
<212> TYPE: PRT
<213> ORGANISM: Artificial Sequence
<220> FEATURE:
<223> OTHER INFORMATION: Synthetic construct

<400> SEQUENCE: 10

Gln Ala Val Val Thr Gln Glu Ser Ala Leu Thr Thr Ser Pro Gly Glu
1               5                   10                  15

Thr Val Thr Leu Thr Cys Arg Ser Ser Gly Ala Val Thr Thr Gly
            20                  25                  30

Asn Phe Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 11
<211> LENGTH: 112
<212> TYPE: PRT
<213> ORGANISM: Artificial Sequence
<220> FEATURE:
<223> OTHER INFORMATION: Synthetic construct

<400> SEQUENCE: 11

Asp Val Val Met Thr Gln Thr Pro Leu Thr Leu Ser Val Thr Ile Gly
1               5                   10                  15

Gln Ser Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

```
Ser Arg Val Glu Ala Glu Asp Leu Gly Val Tyr Tyr Cys Trp Gln Gly
                85                  90                  95

Thr His Phe Pro Phe Thr Phe Gly Ser Gly Thr Lys Leu Glu Ile Lys
            100                 105                 110
```

<210> SEQ ID NO 12
<211> LENGTH: 109
<212> TYPE: PRT
<213> ORGANISM: Artificial Sequence
<220> FEATURE:
<223> OTHER INFORMATION: Synthetic construct

<400> SEQUENCE: 12

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105
```

<210> SEQ ID NO 13
<211> LENGTH: 119
<212> TYPE: PRT
<213> ORGANISM: Artificial Sequence
<220> FEATURE:
<223> OTHER INFORMATION: Synthetic construct

<400> SEQUENCE: 13

```
Glu Val Gln Leu Val Glu Ser Gly Gly Phe Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ile Ile Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Asp His Tyr His Gly Asn Gly Ser Asp Tyr Trp Gly Gln Gly
            100                 105                 110

Thr Thr Leu Thr Val Ser Ser
        115
```

<210> SEQ ID NO 14
<211> LENGTH: 116
<212> TYPE: PRT
<213> ORGANISM: Artificial Sequence
<220> FEATURE:
<223> OTHER INFORMATION: Synthetic construct

<400> SEQUENCE: 14

Gln Val Gln Leu Lys Gln Ser Gly Ala Glu Leu Val Lys Pro Gly Ala
1               5                   10                  15

Ser Val Lys Ile Ser Cys Lys Ala Ser Gly Tyr Ile Phe Thr Asp Tyr
            20                  25                  30

Tyr Val Asn Trp Val Lys Gln Arg Pro Gly Gln Gly Leu Glu Trp Ile
        35                  40                  45

Gly Lys Ile Gly Pro Gly Ser Val Ser Ile Tyr Tyr Asn Glu Lys Phe
50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
            85                  90                  95

Ala Ser Tyr Tyr Tyr Gly Phe Ala Tyr Trp Gly Gln Gly Thr Leu Val
        100                 105                 110

Thr Val Ser Ala
        115

<210> SEQ ID NO 15
<211> LENGTH: 123
<212> TYPE: PRT
<213> ORGANISM: Artificial Sequence
<220> FEATURE:
<223> OTHER INFORMATION: Synthetic construct

<400> SEQUENCE: 15

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Asn Tyr
            20                  25                  30

Gly Val His Trp Val Arg Gln Pro Pro Gly Lys Gly Leu Glu Trp Leu
        35                  40                  45

Val Leu Ile Trp Ser Asp Gly Ser Thr Thr Tyr Asn Ser Ala Leu Lys
50                  55                  60

Ser Arg Leu Ser Ile Ser Lys Asp Asn Ser Lys Ser Gln Val Phe Leu
65                  70                  75                  80

Lys Met Asn Ser Leu Gln Thr Gly Asp Thr Ala Met Tyr Tyr Cys Ala
            85                  90                  95

Arg His Pro Tyr Asp Asp Tyr Ser Gly Tyr Tyr Tyr Thr Met Asp Tyr
        100                 105                 110

Trp Gly Gln Gly Thr Ser Val Thr Val Ser Ser
        115                 120

<210> SEQ ID NO 16
<211> LENGTH: 119
<212> TYPE: PRT
<213> ORGANISM: Artificial Sequence
<220> FEATURE:
<223> OTHER INFORMATION: Synthetic construct

<400> SEQUENCE: 16

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Asp Tyr
            20                  25                  30

Gly Met His Trp Val Arg Gln Ala Pro Glu Lys Gly Leu Glu Trp Val
        35                  40                  45

```
Ala Tyr Ile Ser Ser Gly Ser Ser Ile Leu Tyr Tyr Ala Asp Ile Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Asp His Tyr His Gly Asn Gly Ser Asp Tyr Trp Gly Gln Gly
            100                 105                 110

Thr Thr Leu Thr Val Ser Ser
        115

<210> SEQ ID NO 17
<211> LENGTH: 120
<212> TYPE: PRT
<213> ORGANISM: Artificial Sequence
<220> FEATURE:
<223> OTHER INFORMATION: Synthetic construct

<400> SEQUENCE: 17

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Glu Arg Pro Glu Gln Gly Leu Glu Trp Ile
        35                  40                  45

Gly Arg Ile Asp Pro Glu Asp Gly Asp Ile Glu Tyr Asp Pro Lys Phe
    50                  55                  60

Gln Gly Lys Ala Thr Met Thr Ala Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Val Thr Asp Tyr Asp Tyr Asp Gly Gly Trp Phe Ala Tyr Trp Gly Gln
            100                 105                 110

Gly Thr Leu Val Thr Val Ser Ala
        115                 120

<210> SEQ ID NO 18
<211> LENGTH: 122
<212> TYPE: PRT
<213> ORGANISM: Artificial Sequence
<220> FEATURE:
<223> OTHER INFORMATION: Synthetic construct

<400> SEQUENCE: 18

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Ile Gln Arg Pro Gly Gln Gly Leu Glu Trp Ile
        35                  40                  45

Gly Asp Ile Tyr Cys Gly Ser Asp Thr Met His Tyr Asn Glu Lys Phe
    50                  55                  60

Lys Asn Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

```
Ala Arg Trp Trp Asp Tyr Gly Ser Ser Tyr Asp Tyr Phe Asp Tyr Trp
            100                 105                 110

Gly Gln Gly Thr Thr Leu Thr Val Ser Ser
        115                 120

<210> SEQ ID NO 19
<211> LENGTH: 116
<212> TYPE: PRT
<213> ORGANISM: Artificial Sequence
<220> FEATURE:
<223> OTHER INFORMATION: Synthetic construct

<400> SEQUENCE: 19

Gln Val Gln Leu Lys Gln Ser Gly Pro Glu Leu Val Arg Pro Gly Ala
1               5                   10                  15

Ser Val Lys Ile Ser Cys Glu Ala Ser Gly Tyr Thr Phe Thr Asp Tyr
            20                  25                  30

Tyr Val Asn Trp Val Lys Gln Arg Pro Gly Arg Gly Leu Glu Trp Ile
        35                  40                  45

Gly Lys Ile Gly Pro Gly Ser Val Ser Ile Tyr Tyr Asn Glu Lys Phe
    50                  55                  60

Lys Asp Lys Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Ser Tyr Tyr Tyr Gly Phe Ala Tyr Trp Gly Gln Gly Thr Leu Val
            100                 105                 110

Thr Val Ser Ala
        115

<210> SEQ ID NO 20
<211> LENGTH: 116
<212> TYPE: PRT
<213> ORGANISM: Artificial Sequence
<220> FEATURE:
<223> OTHER INFORMATION: Synthetic construct

<400> SEQUENCE: 20

Gln Val Gln Leu Lys Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Val Asn Trp Val Lys Gln Arg Pro Gly Gln Gly Leu Glu Trp Ile
        35                  40                  45

Gly Lys Ile Gly Pro Glu Ser Val Ser Ile Tyr Tyr Ser Glu Lys Phe
    50                  55                  60

Lys Ala Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Tyr Tyr Tyr Gly Phe Ala Tyr Trp Gly Gln Gly Thr Leu Val
            100                 105                 110

Thr Val Ser Ala
        115

<210> SEQ ID NO 21
<211> LENGTH: 118
<212> TYPE: PRT
```

<213> ORGANISM: Artificial Sequence
<220> FEATURE:
<223> OTHER INFORMATION: Synthetic construct

<400> SEQUENCE: 21

```
Glu Val Gln Leu Leu Glu Thr Gly Gly Gly Leu Val Gln Pro Gly Gly
1               5                   10                  15

Ser Arg Gly Leu Ser Cys Glu Gly Ser Gly Phe Thr Phe Ser Gly Phe
            20                  25                  30

Trp Met Ser Trp Val Arg Gln Thr Pro Gly Lys Thr Leu Glu Trp Ile
        35                  40                  45

Gly Asp Ile Asn Ser Asp Gly Ser Ala Ile Asn Tyr Ala Pro Ser Ile
    50                  55                  60

Lys Asp Arg Phe Thr Ile Phe Arg Asp Asn Asp Lys Asn Thr Leu Tyr
65                  70                  75                  80

Leu Gln Met Asn Asn Val Arg Ser Glu Asp Thr Ala Thr Tyr Phe Cys
                85                  90                  95

Val Arg Tyr Asp Asp Tyr Gly Tyr Phe Asp Val Trp Gly Thr Gly Thr
            100                 105                 110

Thr Val Thr Val Ser Ser
        115
```

<210> SEQ ID NO 22
<211> LENGTH: 116
<212> TYPE: PRT
<213> ORGANISM: Artificial Sequence
<220> FEATURE:
<223> OTHER INFORMATION: Synthetic construct

<400> SEQUENCE: 22

```
His Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Leu Ile Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Lys Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Ser Ser Pro His Gly Asp Tyr Trp Gly Gln Gly Thr Thr Leu
            100                 105                 110

Thr Val Ser Ser
        115
```

<210> SEQ ID NO 23
<211> LENGTH: 118
<212> TYPE: PRT
<213> ORGANISM: Artificial Sequence
<220> FEATURE:
<223> OTHER INFORMATION: Synthetic construct

<400> SEQUENCE: 23

```
Glu Val Gln Leu Leu Glu Thr Gly Gly Gly Leu Val Gln Pro Gly Gly
1               5                   10                  15

Ser Arg Gly Leu Ser Cys Glu Gly Ser Gly Phe Thr Phe Ser Asp Phe
            20                  25                  30
```

Trp Met Ser Trp Val Arg Gln Thr Pro Gly Lys Thr Leu Glu Trp Ile
            35                  40                  45

Gly Asp Ile Asn Ser Asp Gly Ser Ala Val Asn Tyr Ala Pro Ser Ile
    50                  55                  60

Lys Asp Gln Phe Thr Ile Phe Arg Asp Asn Lys Arg Thr Leu His
65                  70                  75                  80

Leu Gln Met Ile Asn Val Arg Ser Glu Asp Thr Ala Thr Tyr Phe Cys
                85                  90                  95

Val Arg Tyr Asp Asp Tyr Gly Tyr Phe Asp Val Trp Gly Thr Gly Thr
                100                 105                 110

Thr Val Thr Val Ser Ser
        115

<210> SEQ ID NO 24
<211> LENGTH: 16
<212> TYPE: PRT
<213> ORGANISM: Artificial Sequence
<220> FEATURE:
<223> OTHER INFORMATION: Synthetic construct

<400> SEQUENCE: 24

Arg Ser Ser Gln Ser Ile Val His Ser Asn Gly Asn Thr Tyr Leu Glu
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Stnthetic construct

<400> SEQUENCE: 25

Arg Ser Ser Lys Ser Leu Leu His Ser Asn Gly Asn Thr Tyr Leu Tyr
1               5                   10                  15

<210> SEQ ID NO 26
<211> LENGTH: 11
<212> TYPE: PRT
<213> ORGANISM: Artificial Sequence
<220> FEATURE:
<223> OTHER INFORMATION: Synthetic construct

<400> SEQUENCE: 26

Lys Ala Ser Asp His Ile Asn Asn Trp Leu Ala
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic construct

<400> SEQUENCE: 27

Ser Ala Ser Ser Ser Thr Ser Phe Met His
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic construct

```
<400> SEQUENCE: 28

Lys Ala Ser Gln Asp Ile Asn Ser Tyr Leu Ser
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic construct

<400> SEQUENCE: 29

Arg Ser Ser Ser Gly Ala Val Thr Thr Gly Asn Phe Ala Asn
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Synthetic construct

<400> SEQUENCE: 30

Lys Ser Ser Gln Ser Leu Leu Asp Ser Asp Gly Lys Thr Tyr Leu Asn
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Synthetic construct

<400> SEQUENCE: 31

Arg Ser Ser Thr Gly Ala Val Thr Thr Ser Asn Tyr Ala Asn
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Synthetic construct

<400> SEQUENCE: 32

Lys Val Ser Asn Arg Phe Ser
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic construct

<400> SEQUENCE: 33

Arg Met Ser Asn Leu Ala Ser
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 34

Gly Ala Thr Ser Leu Glu Thr
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic construct

<400> SEQUENCE: 35

Asp Thr Ser Lys Leu Ala
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic construct

<400> SEQUENCE: 36

Arg Ala Asn Arg Leu Val Asp
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic construct

<400> SEQUENCE: 37

Gly Thr Asn Asn Arg Ala Pro
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic construct

<400> SEQUENCE: 38

Leu Val Ser Lys Leu Asp Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic construct

<400> SEQUENCE: 39

Phe Gln Gly Ser His Val Pro Trp Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic construct
```

```
<400> SEQUENCE: 40

Met Gln His Leu Glu Tyr Pro Tyr Thr
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic construct

<400> SEQUENCE: 41

Gln Gln Tyr Trp Ser Ser Pro Leu Thr
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic construct

<400> SEQUENCE: 42

His Gln Arg Ser Ala Tyr Pro Trp Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic construct

<400> SEQUENCE: 43

Leu Gln Tyr Asp Glu Phe Pro Tyr Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic construct

<400> SEQUENCE: 44

Ala Leu Trp Tyr Ser Asn His Trp Val
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic construct

<400> SEQUENCE: 45

Trp Gln Gly Thr His Phe Pro Phe Thr
1               5

<210> SEQ ID NO 46
<211> LENGTH: 10
<212> TYPE: PRT
<213> ORGANISM: Artificial Sequence
<220> FEATURE:
<223> OTHER INFORMATION: Synthetic construct
```

```
<400> SEQUENCE: 46

Gly Phe Thr Phe Ser Asp Tyr Gly Met His
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic construct

<400> SEQUENCE: 47

Gly Tyr Ile Phe Thr Asp Tyr Tyr Val Asn
1               5                   10

<210> SEQ ID NO 48
<211> LENGTH: 5
<212> TYPE: PRT
<213> ORGANISM: Artificial Sequence
<220> FEATURE:
<223> OTHER INFORMATION: Synthetic construct

<400> SEQUENCE: 48

Asn Tyr Gly Val His
1               5

<210> SEQ ID NO 49
<211> LENGTH: 10
<212> TYPE: PRT
<213> ORGANISM: Artificial Sequence
<220> FEATURE:
<223> OTHER INFORMATION: Synthetic construct

<400> SEQUENCE: 49

Gly Phe Ser Phe Ser Asp Tyr Gly Met His
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic construct

<400> SEQUENCE: 50

Gly Phe Asn Ile Lys Asp Tyr Tyr Met His
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic construct

<400> SEQUENCE: 51

Gly Tyr Thr Phe Thr Ser Tyr Trp Ile Thr
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic construct
```

```
<400> SEQUENCE: 52

Gly Tyr Thr Phe Thr Asp Tyr Tyr Val Asn
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic construct

<400> SEQUENCE: 53

Gly Phe Thr Phe Ser Gly Phe Trp Met Ser
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic construct

<400> SEQUENCE: 54

Gly Tyr Thr Phe Thr Ser Tyr Gly Leu Ile
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic construct

<400> SEQUENCE: 55

Gly Phe Thr Phe Ser Asp Phe Trp Met Ser
1               5                   10

<210> SEQ ID NO 56
<211> LENGTH: 17
<212> TYPE: PRT
<213> ORGANISM: Artificial Sequence
<220> FEATURE:
<223> OTHER INFORMATION: Synthetic construct

<400> SEQUENCE: 56

Tyr Ile Ser Ser Gly Ser Ser Ile Ile Tyr Tyr Ala Asp Thr Val Lys
1               5                   10                  15

Gly

<210> SEQ ID NO 57
<211> LENGTH: 17
<212> TYPE: PRT
<213> ORGANISM: Artificial Sequence
<220> FEATURE:
<223> OTHER INFORMATION: Synthetic construct

<400> SEQUENCE: 57

Lys Ile Gly Pro Gly Ser Val Ser Ile Tyr Tyr Asn Glu Lys Phe Lys
1               5                   10                  15

Gly

<210> SEQ ID NO 58
<211> LENGTH: 16
<212> TYPE: PRT
<213> ORGANISM: Artificial Sequence
```

```
<220> FEATURE:
<223> OTHER INFORMATION: Synthetic construct

<400> SEQUENCE: 58

Leu Ile Trp Ser Asp Gly Ser Thr Thr Tyr Asn Ser Ala Leu Lys Ser
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Synthetic construct

<400> SEQUENCE: 59

Tyr Ile Ser Ser Gly Ser Ser Ile Leu Tyr Tyr Ala Asp Ile Val Lys
1               5                   10                  15

<210> SEQ ID NO 60
<211> LENGTH: 17
<212> TYPE: PRT
<213> ORGANISM: Artificial Sequence
<220> FEATURE:
<223> OTHER INFORMATION: Synthetic construct

<400> SEQUENCE: 60

Arg Ile Asp Pro Glu Asp Gly Asp Ile Glu Tyr Asp Pro Lys Phe Gln
1               5                   10                  15

Gly

<210> SEQ ID NO 61
<211> LENGTH: 17
<212> TYPE: PRT
<213> ORGANISM: Artificial Sequence
<220> FEATURE:
<223> OTHER INFORMATION: Synthetic construct

<400> SEQUENCE: 61

Asp Ile Tyr Cys Gly Ser Asp Thr Met His Tyr Asn Glu Lys Phe Lys
1               5                   10                  15

Asn

<210> SEQ ID NO 62
<211> LENGTH: 17
<212> TYPE: PRT
<213> ORGANISM: Artificial Sequence
<220> FEATURE:
<223> OTHER INFORMATION: Synthetic construct

<400> SEQUENCE: 62

Lys Ile Gly Pro Gly Ser Val Ser Ile Tyr Tyr Asn Glu Lys Phe Lys
1               5                   10                  15

Asp

<210> SEQ ID NO 63
<211> LENGTH: 17
<212> TYPE: PRT
<213> ORGANISM: Artificial Sequence
<220> FEATURE:
<223> OTHER INFORMATION: Synthetic construct
```

```
<400> SEQUENCE: 63

Lys Ile Gly Pro Glu Ser Val Ser Ile Tyr Tyr Ser Glu Lys Phe Lys
1               5                   10                  15
Ala

<210> SEQ ID NO 64
<211> LENGTH: 17
<212> TYPE: PRT
<213> ORGANISM: Artificial Sequence
<220> FEATURE:
<223> OTHER INFORMATION: Synthetic construct

<400> SEQUENCE: 64

Asp Ile Asn Ser Asp Gly Ser Ala Ile Asn Tyr Ala Pro Ser Ile Lys
1               5                   10                  15
Asp

<210> SEQ ID NO 65
<211> LENGTH: 17
<212> TYPE: PRT
<213> ORGANISM: Artificial Sequence
<220> FEATURE:
<223> OTHER INFORMATION: Synthetic construct

<400> SEQUENCE: 65

Glu Ile Tyr Pro Arg Ser Gly Asn Thr Tyr Tyr Asn Glu Lys Phe Lys
1               5                   10                  15
Gly

<210> SEQ ID NO 66
<211> LENGTH: 17
<212> TYPE: PRT
<213> ORGANISM: Artificial Sequence
<220> FEATURE:
<223> OTHER INFORMATION: Synthetic construct

<400> SEQUENCE: 66

Asp Ile Asn Ser Asp Gly Ser Ala Val Asn Tyr Ala Pro Ser Ile Lys
1               5                   10                  15
Asp

<210> SEQ ID NO 67
<211> LENGTH: 10
<212> TYPE: PRT
<213> ORGANISM: Artificial Sequence
<220> FEATURE:
<223> OTHER INFORMATION: Synthetic construct

<400> SEQUENCE: 67

Asp His Tyr His Gly Asn Gly Ser Asp Tyr
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Synthetic construct

<400> SEQUENCE: 68

Tyr Tyr Tyr Gly Phe Ala Tyr
1               5
```

<210> SEQ ID NO 69
<211> LENGTH: 15
<212> TYPE: PRT
<213> ORGANISM: Artificial Sequence
<220> FEATURE:
<223> OTHER INFORMATION: Synthetic construct

<400> SEQUENCE: 69

His Pro Tyr Asp Asp Tyr Ser Gly Tyr Tyr Tyr Thr Met Asp Tyr
1               5                   10                  15

<210> SEQ ID NO 70
<211> LENGTH: 11
<212> TYPE: PRT
<213> ORGANISM: Artificial Sequence
<220> FEATURE:
<223> OTHER INFORMATION: Synthetic construct

<400> SEQUENCE: 70

Asp Tyr Asp Tyr Asp Gly Gly Trp Phe Ala Tyr
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Synthetic construct

<400> SEQUENCE: 71

Trp Trp Asp Tyr Gly Ser Ser Tyr Asp Tyr Phe Asp Tyr
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Synthetic construct

<400> SEQUENCE: 72

Tyr Asp Asp Tyr Gly Tyr Phe Asp Val
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic construct

<400> SEQUENCE: 73

Ser Ser Pro His Gly Asp Tyr
1               5

<210> SEQ ID NO 74
<211> LENGTH: 336
<212> TYPE: DNA
<213> ORGANISM: Artificial Sequence
<220> FEATURE:
<223> OTHER INFORMATION: Synthetic construct

<400> SEQUENCE: 74
gatgttttga tgacccaaac tccactctcc ctgcctgtca gtcttggaga tcaagcctcc      60
atctcttgca gatctagtca gagcattgta catagtaatg gaaacaccta tttagaatgg     120

```
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
tggacgttcg gtggaggcac caagctggaa atcaag                              336

<210> SEQ ID NO 75
<211> LENGTH: 336
<212> TYPE: DNA
<213> ORGANISM: Artificial Sequence
<220> FEATURE:
<223> OTHER INFORMATION: Synthetic construct

<400> SEQUENCE: 75
gatattgtga tgactcaggc tgcaccctct gtacctgtca ctcctggaga gtcagtatcc     60
atctcctgca ggtctagtaa gagtctcctg catagtaatg gcaacactta cttatattgg    120
ttcctgcaga ggccaggcca gtctcctcag ctcctgatat atcggatgtc caaccttgcc    180
tcaggagtcc cagacaggtt cggtggcagt gggtcaggaa ctgctttcac actgagaatc    240
agtagagtgg aggctgagga tgtgggtttt tattactgta tgcaacatct agaatatccg    300
tacacgttcg gagggggac caggctggaa ataaaa                               336

<210> SEQ ID NO 76
<211> LENGTH: 321
<212> TYPE: DNA
<213> ORGANISM: Artificial Sequence
<220> FEATURE:
<223> OTHER INFORMATION: Synthetic construct

<400> SEQUENCE: 76
gacatccaga tgacacaggc ttcatcctcc ttgtctgtat ctctaggagg cagagtcacc     60
attacttgca aggcaagtga ccacattaat aattggttgg cctggtatca gcagaaacca    120
ggaaatgctc ctaggctctt aatatctggt gcaaccagtt tggaaactgg ggttccttca    180
agattcagtg gcagtggatc tggaaaggat tacactctca gcattaccag tcttcagact    240
gaagatgttg ctacttatta ctgtcaacag tattggagtt ctcctctcac gttcggtgct    300
gggaccaagc tggagctgaa a                                              321

<210> SEQ ID NO 77
<211> LENGTH: 335
<212> TYPE: DNA
<213> ORGANISM: Artificial Sequence
<220> FEATURE:
<223> OTHER INFORMATION: Synthetic construct

<400> SEQUENCE: 77
gatgttttga tgacccaaac tccactctcc ctgcctgtca gtcttggaga tcaagcctcc     60
atctcttgca gatctagtca gagcattgta catagtaatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
tggacgttcg gtggaggcac caagctggaa atcaa                               335

<210> SEQ ID NO 78
<211> LENGTH: 318
<212> TYPE: DNA
<213> ORGANISM: Artificial Sequence
```

```
<220> FEATURE:
<223> OTHER INFORMATION: Synthetic construct

<400> SEQUENCE: 78
caaattattc tcacccagtc tccagcaatc atgtctgcat ctccagggga gaaggtcacc      60
atgacctgca gtgccagctc aagtacaagt tcatgcact ggtaccagca gaagccaggc     120
acctccccca aaagatggat ttttgacaca tccaaactgg cttctggagt ccctggtcgc    180
ttcattggta gtgggtctgg gacctcttat tctctcacaa tcagcaccat ggaggctgaa    240
gatgctgcca cttattactg ccatcagcgg agtgcttacc catggacgtt cggtggaggc    300
accaagctgg aaatcaaa                                                   318

<210> SEQ ID NO 79
<211> LENGTH: 321
<212> TYPE: DNA
<213> ORGANISM: Artificial Sequence
<220> FEATURE:
<223> OTHER INFORMATION: Synthetic construct

<400> SEQUENCE: 79
gacatcaaga tgacccagtc tccatcttcc atgtatgcat ctctaggaga gagagtcact     60
atcacttgca aggcgagtca ggacattaat agctatttaa gctggttcca gcagaaacca    120
gggaaatctc ctaagaccct gatctatcgt gcaaacagat tggtagatgg ggtcccatca    180
aggttcagtg gcagtggatc tgggcaagat tattctctca ccatcagcag cctggagtat    240
gaagatatgg gaatttatta ttgtctacag tatgatgagt ttccgtacac gttcggaggg    300
gggaccaagc tggaaataaa a                                               321

<210> SEQ ID NO 80
<211> LENGTH: 336
<212> TYPE: DNA
<213> ORGANISM: Artificial Sequence
<220> FEATURE:
<223> OTHER INFORMATION: Synthetic construct

<400> SEQUENCE: 80
gatattgtga tgactcaggc tgcaccctct gtacctgtca ctcctggaga gtcagtatcc     60
atctcctgca ggtctagtaa gagtctcctg catagtaatg gcaacactta cttgtattgg    120
ttcctgcaga ggccaggcca gtctcctcag ctcctgatat atcggatgtc caaccttgcc    180
tcaggagtcc cagacaggtt cggtggcagt gggtcaggaa ctgctttcac actgagaatc    240
agtagagtgg aggctgagga tgtgggtgtt tattattgta tgcaacatct agaatatccg    300
tacacgttcg gaggggggac caagctggaa ataaaa                               336

<210> SEQ ID NO 81
<211> LENGTH: 336
<212> TYPE: DNA
<213> ORGANISM: Artificial Sequence
<220> FEATURE:
<223> OTHER INFORMATION: Synthetic construct

<400> SEQUENCE: 81
gatattgtga tgactcaggc tgcaccctct gtacctgtca ctcctggaga gtcagtatcc     60
atctcctgca ggtctagtaa gagtctcctg catagtaatg gcaacactta cttgtattgg    120
ttcctgcaga ggccaggcca gtctcctcag ctcctgatat atcggatgtc caaccttgcc    180
tcaggagtcc cagacaggtt cggtggcagt gggtcaggaa ctgctttcac actgagaatc    240
```

```
agtagagtgg aggctgagga tgtgggtgtt tattactgta tgcaacatct agaatatccg    300
tacacgttcg gagggggggac caagctggaa ataaaa                             336
```

<210> SEQ ID NO 82
<211> LENGTH: 327
<212> TYPE: DNA
<213> ORGANISM: Artificial Sequence
<220> FEATURE:
<223> OTHER INFORMATION: Synthetic construct

<400> SEQUENCE: 82

```
caggctgttg tgactcagga atctgcactc accacatcac ctggtgaaac agtcacactc    60
acttgtcgct caagttctgg ggctgttaca actggtaact ttgccaactg ggtccaagaa    120
aaaccagatc atttattcac tggtctaata ggtggtacca caaccgagc tccaggtgtt     180 cctgccagat tctcaggctc cctgattgga gacaaggctg ccctcaccat cacagggggca   240 cagactgagg atgaggcaat atatttctgt gctctatggt acagcaacca ctgggtgttc    300
ggtggaggaa ccaaactgac tgtccta                                        327
```

<210> SEQ ID NO 83
<211> LENGTH: 336
<212> TYPE: DNA
<213> ORGANISM: Artificial Sequence
<220> FEATURE:
<223> OTHER INFORMATION: Synthetic construct

<400> SEQUENCE: 83

```
gatgttgtga tgacccagac tccactcact ttgtcggtta ccattggaca gtcagcctcc    60
atctcttgca gtcaagtca gagcctctta gatagtgatg gaaagacata tttgaattgg     120
ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttcca    300
ttcacgttcg gctcggggac aaagttggaa ataaaa                             336
```

<210> SEQ ID NO 84
<211> LENGTH: 327
<212> TYPE: DNA
<213> ORGANISM: Artificial Sequence
<220> FEATURE:
<223> OTHER INFORMATION: Synthetic construct

<400> SEQUENCE: 84

```
caggctgttg tgactcagga atctgcactc accacatcac ctggtgaaac agtcacactc    60
acttgtcgct caagtactgg ggctgttaca actagtaact atgccaactg ggtccaagaa    120
aaaccagatc atttattcac tggtctaata ggtggtacca caaccgagc tccaggtgtt     180 cctgccagat tctcaggctc cctgattgga gacaaggctg ccctcaccat cacagggggca   240 cagactgagg atgaggcaat atatttctgt gctctatggt acagcaacca ctgggtgttc    300
ggtggaggaa ccaaactgac tgtccta                                        327
```

<210> SEQ ID NO 85
<211> LENGTH: 357
<212> TYPE: DNA
<213> ORGANISM: Artificial Sequence
<220> FEATURE:
<223> OTHER INFORMATION: Synthetic construct

<400> SEQUENCE: 85

| | |
|---|---|
| gaggtgcagc tggtggagtc tgggggaggc ttcgtgaagc ctggagggtc cctgaaactc | 60 |
| tcctgtgcag cctctggatt cactttcagt gactatggaa tgcactgggt tcgtcaggct | 120 |
| ccagagaagg ggctggagtg ggttgcatac attagtagtg gcagtagtat catctactat | 180 |
| gcagacacag tgaagggccg attcaccatc tccagagaca atgccaagaa caccctgttc | 240 |
| ctgcaaatga ccagtctgag gtctgaggac acggccatgt attactgtgc aagggaccac | 300 |
| taccatggta acgggtccga ctactgggggc caaggcacca ctctcacagt ctcctca | 357 |

<210> SEQ ID NO 86
<211> LENGTH: 348
<212> TYPE: DNA
<213> ORGANISM: Artificial Sequence
<220> FEATURE:
<223> OTHER INFORMATION: Synthetic construct

<400> SEQUENCE: 86

| | |
|---|---|
| caggtccagc tgaagcagtc tggagctgag ctggtgaagc ctggggcttc agtgaagata | 60 |
| tcctgcaagg cttctggcta catcttcact gactattatg taaactgggt gaagcagagg | 120 |
| cctggacagg gccttgagtg gattggaaag attggtcctg aagtgttag tatttactac | 180 |
| aatgagaagt tcaagggcaa ggccacactg actgcagaca atcctccag cacagcctac | 240 |
| atgcagctca gcagcctgac atctgaggac tctgcagtct atttctgtgc aagttattac | 300 |
| tacgggtttg cttactgggg ccaagggact ctggtcactg tctctgca | 348 |

<210> SEQ ID NO 87
<211> LENGTH: 369
<212> TYPE: DNA
<213> ORGANISM: Artificial Sequence
<220> FEATURE:
<223> OTHER INFORMATION: Synthetic construct

<400> SEQUENCE: 87

| | |
|---|---|
| caggtgcagc tgaaggagtc aggacctggc ctggtggcgc cctcacagag cctgtccatc | 60 |
| acatgcaccg tctcagggtt ctcattaagc aattatggtg tacactgggt tcgccagcct | 120 |
| ccaggaaagg gtctggagtg gctggtactg atatggagtg atggaagcac aacctataat | 180 |
| tcagctctca aatccagact gagcatcagc aaggacaact ccaagagcca gttttctta | 240 |
| aaaatgaaca gtctccaaac tgatgacaca gccatgtact actgtgccag acatccctat | 300 |
| gatgattatt ccggctatta ctatactatg gactactggg gtcaaggaac ctcagtcacc | 360 |
| gtctcctca | 369 |

<210> SEQ ID NO 88
<211> LENGTH: 357
<212> TYPE: DNA
<213> ORGANISM: Artificial Sequence
<220> FEATURE:
<223> OTHER INFORMATION: Synthetic construct

<400> SEQUENCE: 88

| | |
|---|---|
| gaggtgcagc tggtggagtc tgggggaggc ttagtgaagc ctggagggtc cctgaaactc | 60 |
| tcctgtgcag cctctggttt tctttcagt gactatggaa tgcactgggt tcgtcaggct | 120 |
| ccagagaagg ggctggagtg ggttgcatac attagtagtg gcagtagtat cctctactat | 180 |
| gcagacatag tgaagggccg attcaccatc tccagagaca atgccaagaa caccctgttc | 240 | ctgcaaatga ccagtctgag gtctgaggac acggccatgt attactgtgc aagggaccac    300 taccatggta acgggtccga ctactggggc caaggcacca ctctcacagt ctcctca       357

<210> SEQ ID NO 89
<211> LENGTH: 360
<212> TYPE: DNA
<213> ORGANISM: Artificial Sequence
<220> FEATURE:
<223> OTHER INFORMATION: Synthetic construct

<400> SEQUENCE: 89
gaggttcagc tgcagcagtc tggggcagag cttgtgaggc caggggcctc agtcaagttg    60
tcctgcacag cttctggctt caacattaaa gactactata tgcactgggt gaaagagagg    120
cctgaacagg gcctgagtg gattggaagg attgatcctg aggatggtga tattgaatat    180
gacccgaagt tccagggcaa ggccactatg actgcagata catcctccaa cacagcctac    240
ctgcagttca gcagcctgac atctgaggac actgccgtct attattgtgt cacggactat    300
gattacgacg gaggctggtt tgcttactgg ggccaaggga ctctggtcac tgtctctgca    360

<210> SEQ ID NO 90
<211> LENGTH: 366
<212> TYPE: DNA
<213> ORGANISM: Artificial Sequence
<220> FEATURE:
<223> OTHER INFORMATION: Synthetic construct

<400> SEQUENCE: 90
caggtccaac tgcagcagcc tggggctgag cttgtgaagc ctggggcttc agtgaagatg    60
tcctgcaagg cttctggcta caccttcacc agctactgga taacctgggt gatacagagg    120
ccgggacaag gccttgagtg gattggagat atttattgtg gtagtgatac tatgcactac    180
aatgagaagt tcaagaacaa ggccacactg actgtagaca catcctccag cacagcctac    240
atgcagctca gcagcctgac atctgaggac tctgcggtct attactgtgc aagatggtgg    300
gactacggta gtagctacga ctactttgac tactggggcc aaggcaccac tctcacagtc    360
tcctca                                                              366

<210> SEQ ID NO 91
<211> LENGTH: 348
<212> TYPE: DNA
<213> ORGANISM: Artificial Sequence
<220> FEATURE:
<223> OTHER INFORMATION: Synthetic construct

<400> SEQUENCE: 91
caggtccagc tgaagcagtc tggacctgaa ctggtgaggc ctggggcttc agtgaagata    60
tcctgcgagg cttctggcta caccttcact gactattatg taaactgggt gaagcagagg    120
cctggacggg gccttgagtg gattggaaag attggtcctg aagtgttag tatttactac    180 aatgagaagt tcaaggacaa ggccacactg actgcagaca aatcctccag cacagcctac    240
atgcagctca gcggcctgac atctgaggac tctgcagtct atttctgtgc aagttattac    300
tacggttttg cttactgggg ccaagggact ctggtcactg tctctgca                348

<210> SEQ ID NO 92
<211> LENGTH: 348
<212> TYPE: DNA
<213> ORGANISM: Artificial Sequence
<220> FEATURE:
<223> OTHER INFORMATION: Synthetic construct

<400> SEQUENCE: 92

| | | | | | |
|---|---|---|---|---|---|
| caggtccagc | tgaagcagtc | tggagctgag | ctggtgaagc | tggggcttc | agtgaagata | 60 |
| tcctgcaagg | cttctggcta | caccttcact | gactattatg | taaactgggt | gaagcagagg | 120 |
| cctggacagg | gccttgagtg | gattggaaag | attggtcctg | aaagtgttag | tatttattac | 180 |
| agtgagaagt | tcaaggccaa | ggccacactg | actgcagaca | atcctccag | cacagcctac | 240 |
| atgcaactca | gcagcctgac | atctgaggac | tctgcagtct | atttctgtgc | aagttattac | 300 |
| tacgggtttg | cttactgggg | ccaagggact | ctggtcactg | tctctgca | | 348 |

<210> SEQ ID NO 93
<211> LENGTH: 354
<212> TYPE: DNA
<213> ORGANISM: Artificial Sequence
<220> FEATURE:
<223> OTHER INFORMATION: Synthetic construct

<400> SEQUENCE: 93

| | | | | | |
|---|---|---|---|---|---|
| gaagtgcagc | tgttggagac | tgaggaggc | ttggtgcaac | cggggggggtc | acggggactc | 60 |
| tcttgtgaag | gctcagggtt | cactttagt | ggcttctgga | tgagctgggt | tcgacagaca | 120 |
| cctgggaaga | ccctggagtg | gattggagac | attaattctg | atggcagtgc | aataaactac | 180 |
| gcaccatcca | taaggatcg | attcactatc | ttcagagaca | atgacaagaa | caccctgtac | 240 |
| ctgcagatga | acaatgtgcg | atcggaggac | acagccacgt | atttctgtgt | gagatatgat | 300 |
| gattacgggt | acttcgatgt | ctggggcaca | gggaccacgg | tcaccgtctc | ctca | 354 |

<210> SEQ ID NO 94
<211> LENGTH: 348
<212> TYPE: DNA
<213> ORGANISM: Artificial Sequence
<220> FEATURE:
<223> OTHER INFORMATION: Synthetic construct

<400> SEQUENCE: 94

| | | | | | |
|---|---|---|---|---|---|
| cacgttcagc | tgcagcagtc | tggagctgag | ttggcgaggc | ctggggcttc | agtgaagctg | 60 |
| tcctgcaagg | cttctggcta | caccttcaca | agctatggtt | taatctgggt | gaagcagaga | 120 |
| actggacagg | gccttgagtg | gattggagag | atttatccta | gaagtggtaa | tacttactac | 180 |
| aatgagaagt | tcaagggcaa | ggccacactg | actgcagaca | tatcctccag | cacagcgtac | 240 |
| atggagctcc | gcagcctgac | atctgaggac | tctgcggtct | atttctgtgc | aagttcctct | 300 |
| cctcacgggg | actactgggg | ccaaggcacc | actctcacag | tctcctca | | 348 |

<210> SEQ ID NO 95
<211> LENGTH: 354
<212> TYPE: DNA
<213> ORGANISM: Artificial Sequence
<220> FEATURE:
<223> OTHER INFORMATION: Synthetic construct

<400> SEQUENCE: 95

| | | | | | |
|---|---|---|---|---|---|
| gaagtgcagc | tgttggagac | tgaggaggc | ttagtgcaac | ctgggggggtc | acggggactc | 60 |
| tcttgtgaag | gctcagggtt | cactttagt | gacttctgga | tgagctgggt | tcgacagaca | 120 |
| cctgggaaga | ccctggagtg | gattggagac | attaattctg | atggcagtgc | agttaactac | 180 |
| gcaccatcca | taaggatca | attcactatc | ttcagagaca | atgacaagag | gaccctgcac | 240 |

```
ctgcagatga tcaatgttcg atcggaggac acagccacgt atttctgtgt gagatatgat      300
gattacgggt acttcgatgt ctggggcaca gggaccacgg tcaccgtctc ctca            354
```

<210> SEQ ID NO 96
<211> LENGTH: 112
<212> TYPE: PRT
<213> ORGANISM: Artificial Sequence
<220> FEATURE:
<223> OTHER INFORMATION: Synthetic construct

<400> SEQUENCE: 96

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110
```

<210> SEQ ID NO 97
<211> LENGTH: 112
<212> TYPE: PRT
<213> ORGANISM: Artificial Sequence
<220> FEATURE:
<223> OTHER INFORMATION: Synthetic construct

<400> SEQUENCE: 97

```
Asp Val Val Met Thr Gln Thr Pro Leu Thr Leu Ser Ile Pro Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Phe Thr Phe Gly Ser Gly Thr Lys Leu Glu Ile Lys
            100                 105                 110
```

<210> SEQ ID NO 98
<211> LENGTH: 112
<212> TYPE: PRT
<213> ORGANISM: Artificial Sequence
<220> FEATURE:
<223> OTHER INFORMATION: Synthetic construct

<400> SEQUENCE: 98

```
Asp Val Val Met Thr Gln Thr Pro Leu Thr Leu Ser Val Thr Ile Gly
1               5                   10                  15
```

```
Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Phe Thr Phe Gly Ser Gly Thr Lys Leu Glu Ile Lys
            100                 105                 110
```

<210> SEQ ID NO 99
<211> LENGTH: 112
<212> TYPE: PRT
<213> ORGANISM: Artificial Sequence
<220> FEATURE:
<223> OTHER INFORMATION: Synthetic construct

<400> SEQUENCE: 99

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110
```

<210> SEQ ID NO 100
<211> LENGTH: 112
<212> TYPE: PRT
<213> ORGANISM: Artificial Sequence
<220> FEATURE:
<223> OTHER INFORMATION: Synthetic construct

<400> SEQUENCE: 100

```
Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Lys Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Met Tyr Tyr Cys Phe Gln Gly
                85                  90                  95
```

Ser His Val Pro Leu Thr Phe Gly Ala Gly Thr Lys Leu Glu Leu Lys
                100                 105                 110

<210> SEQ ID NO 101
<211> LENGTH: 113
<212> TYPE: PRT
<213> ORGANISM: Artificial Sequence
<220> FEATURE:
<223> OTHER INFORMATION: Synthetic construct

<400> SEQUENCE: 101

Asp Ile Val Met Thr Gln Ser Pro Ser Ser Leu Thr Val Thr Ala Gly
1               5                   10                  15

Glu Lys Val Thr Met Ser Cys Lys Ser Asn Gln Ser Leu Leu Asn Ser
            20                  25                  30

Gly Asp Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 102
<211> LENGTH: 112
<212> TYPE: PRT
<213> ORGANISM: Artificial Sequence
<220> FEATURE:
<223> OTHER INFORMATION: Synthetic construct

<400> SEQUENCE: 102

Asp Val Val Met Thr Gln Thr Pro Leu Thr Leu Ser Val Thr Ile Gly
1               5                   10                  15

Gln Ser Ala Ser Ile Ser Cys Lys Ser Ser Gln Ser Leu Leu Asp Ser
            20                  25                  30

Asp Gly Asn Thr Tyr Leu Asn Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Phe Thr Phe Gly Ser Gly Thr Lys Leu Glu Ile Lys
            100                 105                 110

<210> SEQ ID NO 103
<211> LENGTH: 107
<212> TYPE: PRT
<213> ORGANISM: Artificial Sequence
<220> FEATURE:
<223> OTHER INFORMATION: Synthetic construct

<400> SEQUENCE: 103

Glu Ile Gln Met Thr Gln Ser Pro Ser Ser Met Ser Ala Ser Leu Gly
1               5                   10                  15

Asp Arg Ile Thr Ile Thr Cys Gln Ala Thr Gln Asp Ile Val Lys Asn
            20                  25                  30

Leu Asn Trp Tyr Gln Gln Lys Pro Gly Lys Pro Ser Phe Leu Ile
        35                  40                  45

Tyr Tyr Ala Thr Glu Leu Ala Glu Gly Val Pro Ser Arg Phe Ser Gly
50                  55                  60

Ser Gly Ser Gly Ser Asp Tyr Ser Leu Thr Ile Ser Asn Leu Glu Ser
65                  70                  75                  80

Glu Asp Phe Ala Asp Tyr Tyr Cys Leu Gln Phe Tyr Glu Phe Pro Tyr
                85                  90                  95

Thr Phe Gly Gly Gly Thr Lys Leu Glu Ile Lys
            100                 105

<210> SEQ ID NO 104
<211> LENGTH: 104
<212> TYPE: PRT
<213> ORGANISM: Artificial Sequence
<220> FEATURE:
<223> OTHER INFORMATION: Synthetic construct

<400> SEQUENCE: 104

Gln Ile Val Leu Thr Gln Ser Pro Ala Ile Met Ser Ala Ser Leu Gly
1               5                   10                  15

Glu Glu Ile Thr Leu Ile Cys Ser Ala Ser Ser Val Ser Tyr Met
            20                  25                  30

His Trp Tyr Gln Gln Lys Ser Gly Thr Ser Pro Lys Leu Leu Ile Tyr
        35                  40                  45

Arg Thr Ser Asn Leu Ala Ser Gly Val Pro Ser Arg Phe Ser Gly Ser
50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Ser Trp Thr Phe Gly
                85                  90                  95

Gly Gly Thr Gln Leu Glu Ile Lys
            100

<210> SEQ ID NO 105
<211> LENGTH: 113
<212> TYPE: PRT
<213> ORGANISM: Artificial Sequence
<220> FEATURE:
<223> OTHER INFORMATION: Synthetic construct

<400> SEQUENCE: 105

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

-continued

Ile Ser Asn Val Gln Pro Glu Asp Leu Ala Val Tyr Tyr Cys Gln Asn
                85                  90                  95

Asp Tyr Ser Phe Pro Phe Thr Phe Gly Ser Gly Thr Glu Leu Glu Met
            100                 105                 110

Lys

<210> SEQ ID NO 106
<211> LENGTH: 112
<212> TYPE: PRT
<213> ORGANISM: Artificial Sequence
<220> FEATURE:
<223> OTHER INFORMATION: Synthetic construct

<400> SEQUENCE: 106

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Phe Thr Phe Gly Ser Gly Thr Lys Leu Glu Ile Lys
            100                 105                 110

<210> SEQ ID NO 107
<211> LENGTH: 112
<212> TYPE: PRT
<213> ORGANISM: Artificial Sequence
<220> FEATURE:
<223> OTHER INFORMATION: Synthetic construct

<400> SEQUENCE: 107

Asp Val Val Met Thr Gln Thr Pro Leu Thr Leu Ser Val Thr Ile Gly
1               5                   10                  15

Gln Pro Ala Ser Ile Ser Cys Lys Ser Ser Leu Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ile Arg Val Glu Ala Glu Asp Leu Gly Ile Tyr Tyr Cys Trp Gln Gly
                85                  90                  95

Thr His Phe Pro Phe Thr Phe Gly Ser Gly Thr Lys Leu Glu Val Lys
            100                 105                 110

<210> SEQ ID NO 108
<211> LENGTH: 115
<212> TYPE: PRT
<213> ORGANISM: Artificial Sequence
<220> FEATURE:
<223> OTHER INFORMATION: Synethetic construct -continued

<400> SEQUENCE: 108

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Cys Ile Asp Pro Glu Asn Gly Asp Thr Glu Tyr Ala Ser Lys Phe
    50                  55                  60

Gln Asp Lys Ala Thr Ile Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Tyr Val Gly Phe Ala Tyr Trp Gly Gln Gly Thr Leu Val Thr
            100                 105                 110

Val Ser Thr
        115

<210> SEQ ID NO 109
<211> LENGTH: 115
<212> TYPE: PRT
<213> ORGANISM: Artificial Sequence
<220> FEATURE:
<223> OTHER INFORMATION: Synthetic construct

<400> SEQUENCE: 109

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Ile Ser Tyr
            20                  25                  30

Gly Ile Thr Trp Val Lys Gln Arg Thr Gly Gln Gly Leu Glu Trp Ile
        35                  40                  45

Gly Glu Ile His Pro Arg Ser Gly Asn Thr Tyr Tyr Asn Glu Asn Phe
    50                  55                  60

Lys Asp Arg Ala Ser Leu Thr Ala Asp Lys Ser Ser Ser Thr Ala Tyr
65                  70                  75                  80

Met Glu Val Arg Ser Leu Thr Ser Glu Asp Ser Ala Val Tyr Phe Cys
                85                  90                  95

Ala Arg Gly Gly Pro Gly Asp Tyr Trp Gly Gln Gly Thr Thr Leu Thr
            100                 105                 110

Val Ser Ser
        115

<210> SEQ ID NO 110
<211> LENGTH: 115
<212> TYPE: PRT
<213> ORGANISM: Artificial Sequence
<220> FEATURE:
<223> OTHER INFORMATION: Synthetic construct

<400> SEQUENCE: 110

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

```
Gly Gln Ile Tyr Pro Arg Ser Asp Asn Thr Tyr Tyr Asn Glu Arg Phe
        50                  55                  60

Lys Gly Lys Ala Thr Leu Thr Ala Asp Lys Ser Ser Thr Ala Tyr
65                  70                  75                  80

Met Ala Leu Arg Ser Leu Thr Ser Glu Asp Ser Ala Val Tyr Phe Cys
                85                  90                  95

Ala Arg Glu Gly Gly Pro Asp Tyr Trp Gly Gln Gly Thr Thr Leu Thr
                100                 105                 110

Val Ser Ser
        115

<210> SEQ ID NO 111
<211> LENGTH: 115
<212> TYPE: PRT
<213> ORGANISM: Artificial Sequence
<220> FEATURE:
<223> OTHER INFORMATION: Synthetic construct

<400> SEQUENCE: 111

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
                20                  25                  30

Tyr Met His Trp Val Lys Gln Arg Pro Glu Gln Gly Leu Glu Trp Ile
            35                  40                  45

Gly Cys Ile Asp Pro Glu Asn Gly Asp Ile Glu Tyr Ala Ser Arg Phe
        50                  55                  60

Gln Gly Lys Ala Thr Met Thr Ala Asp Thr Ser Asn Thr Ala Tyr
65                  70                  75                  80

Leu Gln Leu Thr Ser Leu Thr Ser Ala Asp Thr Ala Val Tyr Tyr Cys
                85                  90                  95

Thr Thr Tyr Val Gly Phe Gly Tyr Trp Gly Gln Gly Thr Leu Val Thr
                100                 105                 110

Val Ser Ala
        115

<210> SEQ ID NO 112
<211> LENGTH: 115
<212> TYPE: PRT
<213> ORGANISM: Artificial Sequence
<220> FEATURE:
<223> OTHER INFORMATION: Synthetic construct

<400> SEQUENCE: 112

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
                20                  25                  30

Tyr Met His Trp Val Lys Gln Arg Pro Glu Gln Gly Leu Glu Trp Ile
            35                  40                  45

Gly Cys Ile Asp Pro Glu Asn Gly Asp Thr Glu Tyr Ala Ser Lys Phe
        50                  55                  60

Gln Gly Lys Ala Thr Ile Thr Ala Asp Thr Ser Ser Asn Thr Val Tyr
65                  70                  75                  80

Leu Gln Leu Ser Ser Leu Thr Ser Glu Asp Thr Ala Val Tyr Tyr Cys
                85                  90                  95

Thr Thr Tyr Val Gly Phe Gly Tyr Trp Gly Gln Gly Thr Leu Val Thr
                100                 105                 110
```

```
Val Ser Ala
        115

<210> SEQ ID NO 113
<211> LENGTH: 114
<212> TYPE: PRT
<213> ORGANISM: Artificial Sequence
<220> FEATURE:
<223> OTHER INFORMATION: Synthetic construct

<400> SEQUENCE: 113

Gln Val Gln Leu Lys Gln Ser Gly Ala Glu Leu Val Arg Pro Gly Ala
1               5                   10                  15

Ser Val Lys Leu Ser Cys Arg Ala Ser Gly Tyr Thr Phe Thr Asp Phe
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Asp Glu Thr Tyr Tyr Asn Glu Lys Phe
    50                  55                  60

Lys Asp Lys Val Thr Leu Thr Ala Glu Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Leu Trp Phe Phe Asp Val Trp Gly Thr Gly Thr Thr Val Thr Val
            100                 105                 110

Ser Ser

<210> SEQ ID NO 114
<211> LENGTH: 115
<212> TYPE: PRT
<213> ORGANISM: Artificial Sequence
<220> FEATURE:
<223> OTHER INFORMATION: Synthetic construct

<400> SEQUENCE: 114

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Asp
            20                  25                  30

Gly Ile Thr Trp Val Lys Gln Arg Thr Gly Gln Gly Leu Glu Trp Ile
        35                  40                  45

Gly Gln Ile His Pro Arg Ser Gly Asn Thr Tyr Tyr Asn Gly Lys Phe
    50                  55                  60

Lys Gly Lys Ala Thr Leu Thr Ala Asp Arg Ser Ser Thr Thr Tyr
65                  70                  75                  80

Met Glu Leu Arg Ser Leu Thr Ser Glu Asp Ser Ala Val Tyr Phe Cys
                85                  90                  95

Ala Lys Thr Gly Thr Gly Asp Tyr Trp Gly Gln Gly Thr Thr Leu Thr
            100                 105                 110

Val Ser Ser
        115

<210> SEQ ID NO 115
<211> LENGTH: 115
<212> TYPE: PRT
<213> ORGANISM: Artificial Sequence
<220> FEATURE:
<223> OTHER INFORMATION: Synthetic construct
```

```
<400> SEQUENCE: 115

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Ser Tyr Asn Gln Lys Phe
    50                  55                  60

Lys Asp Lys Ala Thr Leu Thr Val Asn Lys Ser Ser Ser Thr Ala Phe
65                  70                  75                  80

Met Glu Leu Arg Ser Leu Ala Ser Glu Asp Ser Ala Val Tyr Tyr Cys
                85                  90                  95

Ala Arg Ser Asp Trp Glu Asp Cys Trp Gly Gln Gly Thr Thr Leu Thr
            100                 105                 110

Val Ser Ser
        115

<210> SEQ ID NO 116
<211> LENGTH: 121
<212> TYPE: PRT
<213> ORGANISM: Artificial Sequence
<220> FEATURE:
<223> OTHER INFORMATION: Synthetic construct

<400> SEQUENCE: 116

Asp Val Gln Leu Gln Glu Ser Gly Pro Gly Leu Val Lys Phe Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Arg His Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Ile Thr Glu Asp Thr Ala Thr Tyr Tyr Cys
                85                  90                  95

Val Arg Glu Ile Tyr Asp Gly Ser Ser Gly Tyr Phe Asp Val Trp Gly
            100                 105                 110

Thr Gly Thr Thr Val Thr Val Ser Ser
        115                 120

<210> SEQ ID NO 117
<211> LENGTH: 114
<212> TYPE: PRT
<213> ORGANISM: Artificial Sequence
<220> FEATURE:
<223> OTHER INFORMATION: Synthetic construct

<400> SEQUENCE: 117

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45
```

```
Ala Arg Ile Tyr Pro Gly Asn Gly Asn Thr Asp Tyr Asn Glu Lys Phe
 50                  55                  60

Lys Asp Lys Ala Thr Leu Thr Ala Glu Lys Ser Ser Thr Thr Ala Tyr
 65                  70                  75                  80

Ile Gln Leu Ser Ser Leu Thr Ser Glu Asp Ser Ala Val Tyr Phe Cys
                 85                  90                  95

Cys Leu Trp Tyr Phe Asp Val Trp Gly Thr Gly Thr Thr Val Thr Val
             100                 105                 110

Ser Ser

<210> SEQ ID NO 118
<211> LENGTH: 115
<212> TYPE: PRT
<213> ORGANISM: Artificial Sequence
<220> FEATURE:
<223> OTHER INFORMATION: Synthetic construct

<400> SEQUENCE: 118

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Ser Asp
                 20                  25                  30

Gly Ile Thr Trp Leu Lys Gln Arg Thr Gly Gln Gly Leu Glu Trp Ile
             35                  40                  45

Gly Gln Ile His Pro Arg Ser Gly Asn Thr Tyr Tyr Asn Glu Lys Phe
 50                  55                  60

Lys Gly Lys Ala Thr Leu Thr Ala Asp Lys Ser Ser Ser Thr Ala Tyr
 65                  70                  75                  80

Met Glu Leu Arg Ser Leu Thr Ser Glu Asp Ser Ala Val Tyr Phe Cys
                 85                  90                  95

Ala Lys Thr Gly Thr Gly Asp Tyr Trp Gly Gln Gly Thr Thr Leu Thr
             100                 105                 110

Val Ser Ser
         115

<210> SEQ ID NO 119
<211> LENGTH: 115
<212> TYPE: PRT
<213> ORGANISM: Artificial Sequence
<220> FEATURE:
<223> OTHER INFORMATION: Synthetic construct

<400> SEQUENCE: 119

Gln Val Gln Leu Gln Gln Ser Gly Pro Glu Leu Ala Arg Pro Gly Ala
 1               5                  10                  15

Ser Val Lys Leu Ser Cys Lys Ala Ser Gly Tyr Thr Phe Thr Ser Tyr
                 20                  25                  30

Gly Ile Ser Trp Val Lys Gln Arg Thr Gly Gln Gly Leu Glu Trp Ile
             35                  40                  45

Gly Gln Ile His Pro Arg Ser Gly Asn Thr Tyr Tyr Asn Glu Asn Phe
 50                  55                  60

Lys Gly Lys Ala Thr Leu Thr Ala Ala Lys Ser Ser Ser Thr Ala Tyr
 65                  70                  75                  80

Leu Glu Leu Arg Ser Leu Thr Ser Glu Asp Ser Ala Val Tyr Phe Cys
                 85                  90                  95

Ala Arg Glu Gly Gly Pro Asp Tyr Trp Gly Gln Gly Thr Thr Leu Thr
             100                 105                 110
```

Val Ser Ser
        115

<210> SEQ ID NO 120
<211> LENGTH: 336
<212> TYPE: DNA
<213> ORGANISM: Artificial Sequence
<220> FEATURE:
<223> OTHER INFORMATION: Synthetic construct

<400> SEQUENCE: 120
gatgttttga tgacccaaac tccactctcc ctgcctgtca gtcttggaga tcaagcctcc    60
atctcttgca gatctagtca gagtattgta catagtaatg aaacaccta tttagaatgg    120 tacctgcaga agccaggcca gtctccaaag ctcctgatct acaaagtttc caaccgattt    180
tctggggtcc cagacaggtt cagtggcagt ggatcaggga cagatttcac actcaggatc    240
agcagagtgg aggctgagga tctgggagtt tattactgct ttcaaggttc acatgttccg    300
ctcacgttcg gtgctgggac caagctggag ctgaaa                              336

<210> SEQ ID NO 121
<211> LENGTH: 336
<212> TYPE: DNA
<213> ORGANISM: Artificial Sequence
<220> FEATURE:
<223> OTHER INFORMATION: Synthetic construct

<400> SEQUENCE: 121
gatgttgtga tgacccagac tccactcact ttgtcgattc ccattggaca accagcctcc    60
atctcttgta agtcaagtca gagcctctta gatagtgatg gaaagacata tttgaattgg    120
ttgttacaga ggccaggcca gtctccaaag cgcctcatct atctggtgtc tgaactggac    180
tctggagtcc ctgacaggtt cactggcagt ggatcaggga cagatttcac actgaaaatc    240
agcagagtgg aggctgaaga tttgggagtt tattattgtt ggcaaggtac acatttttcca   300 ttcacgttcg gctcggggac aaagttggaa ataaaa                              336

<210> SEQ ID NO 122
<211> LENGTH: 336
<212> TYPE: DNA
<213> ORGANISM: Artificial Sequence
<220> FEATURE:
<223> OTHER INFORMATION: Synthetic construct

<400> SEQUENCE: 122
gatgttgtga tgacccagac tccactcact ttgtcggtta ccattggaca accagcctcc    60
atctcttgca agtcaagtca gagcctctta gatagtgatg gaaagacata tttgaattgg    120
ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgtt ggcaaggtac acatttttcca   300 ttcacgttcg gctcggggac aaagttggaa ataaaa                              336

<210> SEQ ID NO 123
<211> LENGTH: 336
<212> TYPE: DNA
<213> ORGANISM: Artificial Sequence
<220> FEATURE:
<223> OTHER INFORMATION: Synthetic construct

<400> SEQUENCE: 123

```
gacgttttga tgacccaaac tccactctcc ctgcctgtca gtcttggaga tcaagcctcc    60
atctcttgca gatctagtca gagtattgta catagtaatg aaacaccta tttagaatgg   120 tacctacaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttccg   300
ctcacgttcg gtgctgggac caagctggag ctgaaa                             336
```

<210> SEQ ID NO 124
<211> LENGTH: 336
<212> TYPE: DNA
<213> ORGANISM: Artificial Sequence
<220> FEATURE:
<223> OTHER INFORMATION: Synthetic construct

<400> SEQUENCE: 124

```
gatgttttga tgacccaaag tccactctcc ctgcctgtca gtcttggaga tcaagcctcc    60
atctcttgca gatctagtca gaacatagta catagtaatg gtaacaccta tttagaatgg   120
tacctgaaga aaccaggcca gtctccaaag ctcctgatct acaaagtctc caaccgatttt  180 tctggggtcc cagacaggtt cagtggcagt ggatcaggga cagatttcac actcaagatc   240
agcagagtgg aggctgagga tctgggaatg tattactgct ttcaaggttc acatgttccg   300
ctcacgttcg gagctgggac caagctggag ctgaaa                             336
```

<210> SEQ ID NO 125
<211> LENGTH: 339
<212> TYPE: DNA
<213> ORGANISM: Artificial Sequence
<220> FEATURE:
<223> OTHER INFORMATION: Synthetic construct

<400> SEQUENCE: 125

```
gacattgtga tgacacagtc tccatcctcc ctgactgtga cagcaggaga gaaggtcact    60
atgagctgca agtccaatca gagtctgtta aacagtggag atcaaaagaa ctacttgacc   120
tggtaccagc agaaaccagg gcagcctcct aaactattga tctactgggc atccactagg   180
gaatctgggg tccctgatcg cttcacaggc agtggatctg gaacagattt cactctcacc   240
atcagcagtg tgcaggctga agacctggca atttattact gtcagaatga ttatagttat   300
ccactcacgt tcggtgctgg gaccaagctg gagctgaaa                          339
```

<210> SEQ ID NO 126
<211> LENGTH: 336
<212> TYPE: DNA
<213> ORGANISM: Artificial Sequence
<220> FEATURE:
<223> OTHER INFORMATION: Synthetic construct

<400> SEQUENCE: 126

```
gatgttgtga tgacccagac tccactcact ttgtcggtta ctattggaca atcagcctcc    60
atctcttgca agtcaagtca gagcctccta gatagtgatg gaaacacata tttgaattgg   120
ttgttacaga ggccaggcca gtctccaaag cgcctaatct atttggtgtc tgaactggac   180
tctggagtcc ctgacaggtt cactggcagt ggatcaggga cagatttcac actgaaaatc   240
```
agcagagtgg aggctgagga tttgggagtt tattattgct ggcaaggtac acattttcca    300
ttcacgttcg gctcggggac aaagttggaa ataaaa    336

<210> SEQ ID NO 127
<211> LENGTH: 321
<212> TYPE: DNA
<213> ORGANISM: Artificial Sequence
<220> FEATURE:
<223> OTHER INFORMATION: Synthetic construct

<400> SEQUENCE: 127
gaaatccaga tgacccagtc tccatcctct atgtctgcat ctctgggaga cagaataacc    60
atcacttgcc aggcaactca agacattgtt aagaatttaa actggtatca gcagaaacca    120
gggaaacccc cttcattcct gatctattat gcaactgaac tggcagaagg ggtcccatca    180
aggttcagtg gcagtgggtc tgggtcagac tattctctga caatcagcaa cctggagtct    240
gaagattttg cagactatta ctgtctacag ttttatgaat ttccgtacac gttcggaggg    300
gggaccaagc tggaaataaa a    321

<210> SEQ ID NO 128
<211> LENGTH: 312
<212> TYPE: DNA
<213> ORGANISM: Artificial Sequence
<220> FEATURE:
<223> OTHER INFORMATION: Synthetic construct

<400> SEQUENCE: 128
caaattgttc tcacccagtc tccagcaatc atgtctgcat ctctagggga ggagatcacc    60
ctaatttgca gtgccagctc gagtgtaagt tacatgcact ggtaccagca gaagtcaggc    120
acttctccca aactcttgat ttatcgcaca tccaacctgg cttctggagt cccttctcgc    180
ttcagtggca gtgggtctgg gacctttat tctcttacaa tcagcagtgt ggaggctgaa    240
gatgctgccg attattactg ccatcagtgg agtagttgga cgttcggtgg aggcacccag    300
ctggaaatca aa    312

<210> SEQ ID NO 129
<211> LENGTH: 339
<212> TYPE: DNA
<213> ORGANISM: Artificial Sequence
<220> FEATURE:
<223> OTHER INFORMATION: Synthetic construct

<400> SEQUENCE: 129
gacattgtga tgacacagtc tccatcctcc ctgactgtga cagcaggaga gaaggtcact    60
atgagctgca gtccagtca gagtctgtta acagtggaa atcaaaagaa ttacttgacc    120
tggtaccagc agaaaccagg acagcctcct aaactgttga tctactgggc atccactagg    180
gaatctgggg tccctgatcg cttcacaggc agtggatctg gaacagattt cactctcacc    240
attagcaatg tgcagcctga agacctggca gtttattact gtcagaatga ttatagtttt    300
ccattcacgt tcggctcggg gacagagttg gaaatgaaa    339

<210> SEQ ID NO 130
<211> LENGTH: 336
<212> TYPE: DNA
<213> ORGANISM: Artificial Sequence
<220> FEATURE:
<223> OTHER INFORMATION: Synthetic construct

```
<400> SEQUENCE: 130
gatgttgtga tgacccagac tccactcact tgtcggtta ccattggaca accagcctcc      60
atctcttgca agtcaagtca gagcctctta gatagtgatg aaagacata tttgaattgg     120 ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggaatt tattattgct ggcaaggtac acattttcca    300
ttcacgttcg gctcggggac aaagttggaa ataaaa                              336

<210> SEQ ID NO 131
<211> LENGTH: 336
<212> TYPE: DNA
<213> ORGANISM: Artificial Sequence
<220> FEATURE:
<223> OTHER INFORMATION: Synthetic construct

<400> SEQUENCE: 131
gatgttgtga tgacccagac tccactcact tgtcggtta ccattggaca accagcctcc      60
atctcttgca agtcaagtct gagcctctta gatagtgatg aaagacata tttgaattgg     120 ttgttacaga ggccaggcca gtctccaaag cgcctaatct atctggtgtc taaactggac    180
tctggagtcc ctgacaggtt cactggcagt ggatcaggga cagatttcac actgaaaatc    240
atcagagtgg aggctgagga tttgggaatt tattattgct ggcaaggtac acattttcca    300
ttcacgttcg gctcggggac aaagttggaa gtaaaa                              336

<210> SEQ ID NO 132
<211> LENGTH: 336
<212> TYPE: DNA
<213> ORGANISM: Artificial Sequence
<220> FEATURE:
<223> OTHER INFORMATION: Synthetic construct

<400> SEQUENCE: 132
gatgttttga tgacccaaac tccactctcc ctgcctgtca gtcttggaga tcaagcctcc     60
atctcttgca gatctagtca gagtattgta catagtaatg aaacaccta tttagaatgg    120 tacctacaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
ctcacgttcg gtgctgggac caagctggag ctgaaa                              336

<210> SEQ ID NO 133
<211> LENGTH: 345
<212> TYPE: DNA
<213> ORGANISM: Artificial Sequence
<220> FEATURE:
<223> OTHER INFORMATION: Synthetic construct

<400> SEQUENCE: 133
gaggttcagc tgcagcagtc tggggctgaa cttgtgaggc caggggcctc agtcaagttg      60
tcctgcacag cttctggctt aacattaaa gacgactata tgcactgggt gaaacagagg    120
cctgaacagg gcctggagtg gattggatgc attgatcctg agaatggtga tactgaatat    180
gcctcgaaat tccaggacaa ggccactata caacagaca catcctccaa cacagcctac    240
ctgcagctca gcagcctgac atctgaggac actgccgtct attactgtac tacatacgtt    300
ggatttgctt actggggcca agggactctg gtcactgtct ctaca                    345
```

<210> SEQ ID NO 134
<211> LENGTH: 345
<212> TYPE: DNA
<213> ORGANISM: Artificial Sequence
<220> FEATURE:
<223> OTHER INFORMATION: Synthetic construct

<400> SEQUENCE: 134
caggttcagc tgcagcagtc tggagctgag ctggcgaggc ctggggcttc agtgaagctg    60
tcctgcaagg cttctggcta caccttcata agctatggta aacctgggt gaagcagaga   120 actggacagg gccttgagtg gattggagag attcatccta gaagtggtaa tacttactac   180
aatgagaatt tcaaggacag ggcctcactg actgcagaca atcctccag cacagcgtac   240 atggaggtcc gcagcctgac atctgaggac tctgcggtct atttctgtgc aagggggtggg   300 ccggggggact actggggcca aggcaccact ctcacagtct cctca                 345

<210> SEQ ID NO 135
<211> LENGTH: 345
<212> TYPE: DNA
<213> ORGANISM: Artificial Sequence
<220> FEATURE:
<223> OTHER INFORMATION: Synthetic construct

<400> SEQUENCE: 135
caggttcagc tgcagcagtc tggagctgag ctggcgaggc ctggggcttc agtgaagctg    60
tcctgcaagg cttctggcta caccttcaca agctatggta taagctgggt gaagcagaga   120
actggacagg gccttgagtg gattggacag atttatccta gaagtgacaa tacttactac   180
aatgagaggt tcaagggcaa ggccacactg actgcagaca atcctccag cacagcgtac   240 atggcgctcc gcagcctgac atctgaggac tctgcggtct atttctgtgc aagagagggg   300 ggtccccgact actggggcca aggcaccact ctcacagtct cctca                 345

<210> SEQ ID NO 136
<211> LENGTH: 345
<212> TYPE: DNA
<213> ORGANISM: Artificial Sequence
<220> FEATURE:
<223> OTHER INFORMATION: Synthetic construct

<400> SEQUENCE: 136
gaggttcagc tgcagcagtc tggggctgag cttgtgaggc caggggcctc agtcaagttg    60
tcctgcacag cttctggctt taacattaaa gacgactata tgcactgggt gaaacagagg   120
cctgaacagg gcctggagtg gattggatgc attgatcctg agaatggtga tattgaatat   180
gcctcgaggt tccagggcaa ggccactatg acagcagaca catcctccaa cacagcctac   240
ctgcagctca ccagcctgac atctgcggac actgccgtct attactgtac tacatacgtt   300
ggatttggtt actggggcca agggactctg gtcactgtct ctgca                  345

<210> SEQ ID NO 137
<211> LENGTH: 345
<212> TYPE: DNA
<213> ORGANISM: Artificial Sequence
<220> FEATURE:
<223> OTHER INFORMATION: Synthetic construct

<400> SEQUENCE: 137

```
gaggttcagc tgcagcagtc tggggctgag cttgtgaggc caggggcctc agtcaagttg      60
tcctgcacag cttctggctt taacattaaa gacgactata tgcactgggt gaaacagagg     120
cctgaacagg gcctggagtg gattggatgt attgatcctg agaatggtga tactgaatat     180
gcctcgaagt tccagggcaa ggccactata acagcagaca catcctccaa cacagtctac     240
ctgcagctca gcagcctgac atctgaggac actgccgtct attactgtac tacatacgtt     300
ggatttggtt actggggcca ggggactctg gtcactgtct ctgca                    345
```

<210> SEQ ID NO 138
<211> LENGTH: 342
<212> TYPE: DNA
<213> ORGANISM: Artificial Sequence
<220> FEATURE:
<223> OTHER INFORMATION: Synthetic construct

<400> SEQUENCE: 138

```
caggtccaac tgaagcagtc tggggctgaa ctggtgaggc ctggggcttc agtgaagctg      60
tcctgcaggg cttctggcta cactttcact gacttctaca taaactgggt gaagcagagg     120
cctggacagg gacttgagtg gattgcaagg atttatcctg aagtgatga gacttactac     180
aatgagaagt ttaaggacaa ggtcacactg actgcagaaa atcctccag cactgcctac     240
atgcagctca gcagcctgac atctgaggac tctgctgtct atttctgtgc cctctggttc     300
ttcgatgtct ggggcacagg gaccacggtc accgtctcct ca                       342
```

<210> SEQ ID NO 139
<211> LENGTH: 345
<212> TYPE: DNA
<213> ORGANISM: Artificial Sequence
<220> FEATURE:
<223> OTHER INFORMATION: Synthetic construct

<400> SEQUENCE: 139

```
caggttcagc tgcagcagtc tggagctgag ttggcgaggc ctggggcttc agtgaagctg      60
tcctgcaagg cttcgggcta caccttcaca agcgatggta ttacctgggt gaagcagaga     120
actggacagg gccttgagtg gattggacag attcatccta gaagtggtaa tacctactac     180
aatgggaagt tcaagggcaa ggccacactg actgcagaca gatcctccag cacaacgtac     240
atggaactcc gcagcctgac atctgaggac tctgcggtct atttctgtgc aaaaactggg     300
acggggggact actggggcca aggcaccact ctcacagtct cctca                   345
```

<210> SEQ ID NO 140
<211> LENGTH: 345
<212> TYPE: DNA
<213> ORGANISM: Artificial Sequence
<220> FEATURE:
<223> OTHER INFORMATION: Synthetic construct

<400> SEQUENCE: 140

```
gaggtccagc tgcaacagtc tggacctgag ctggtgaagc ctggggcttc agtgaagatg      60
tcctgcaagg cttctggata cacattcact gactacaaca tgcactgggt gaagcagagc     120
catggaaaga gccttgagtg gattggatat attaaccctt acaatggtgg tactagctac     180
aaccagaagt tcaaggacaa ggccacattg actgtaaaca gtcctccag cacagccttc     240
```

```
atggagctcc gcagcctggc atcggaggat tctgcagtct attactgtgc aaggtctgac    300
tgggaagact gctggggcca aggcaccact ctcacagtct cctca                    345
```

<210> SEQ ID NO 141
<211> LENGTH: 363
<212> TYPE: DNA
<213> ORGANISM: Artificial Sequence
<220> FEATURE:
<223> OTHER INFORMATION: Synthetic construct

<400> SEQUENCE: 141

```
gatgtacagc ttcaggagtc aggacctggc ctcgtgaaat tttctcagtc tctgtctctc    60
acctgctctg tcactggcta ctccatcacc agtggttatt actggaactg gatccggcag   120
tttccaggaa acaaactgga atggatgggc tacataagac acgatggtag caataactac   180
aacccgtctc tcaaaaatcg aatctccatc actcgtgaca catctaagaa ccagtttttc   240
ctgaagttga attctgtgat tactgaggac acagccacat attactgtgt aagagagatc   300
tatgatggtt cctccgggta cttcgatgtc tggggcacag ggaccacggt caccgtctcc   360
tca                                                                  363
```

<210> SEQ ID NO 142
<211> LENGTH: 342
<212> TYPE: DNA
<213> ORGANISM: Artificial Sequence
<220> FEATURE:
<223> OTHER INFORMATION: Synthetic construct

<400> SEQUENCE: 142

```
caggtccagc tgaagcagtc tggggctgaa ctggtgaggc ctggggcttc agtgaagctg    60
tcctgcaagg cttctggcta cactttcact gactactata aaactgggt gaagcagagg    120 cctggacagg gacttgagtg gattgcaagg atttatcctg gaaatggtaa tactgactac   180
aatgagaagt tcaaggacaa ggccacactg actgcagaaa atcctccac cactgcctac    240 atacaactca gcagtctgac atctgaggac tctgctgtct atttctgttg cctctggtac   300
ttcgatgtct ggggcacagg aaccacggtc accgtctcct ca                      342
```

<210> SEQ ID NO 143
<211> LENGTH: 345
<212> TYPE: DNA
<213> ORGANISM: Artificial Sequence
<220> FEATURE:
<223> OTHER INFORMATION: Synthetic construct

<400> SEQUENCE: 143

```
caggttcagc tgcagcagtc tggagctgag ctggcgaggc ctggggcttc agtgaagctg    60
tcctgcaagg cttcgggcta caccttcaca agcgacggta taacctggct gaaacagaga   120
actggacagg gccttgagtg gattggacag attcatccta gaagtggtaa tacctactac   180
aatgagaagt tcaagggcaa ggccacactg actgcagaca atcctccag cacagcgtac   240 atggaactcc gcagcctgac atctgaggac tctgcggtct atttctgtgc aaaaactggg   300 acggggact actggggcca aggcaccact ctcacagtct cctca                    345
```

<210> SEQ ID NO 144
<211> LENGTH: 345
<212> TYPE: DNA
<213> ORGANISM: Artificial Sequence
<220> FEATURE:

<223> OTHER INFORMATION: Synthetic construct

<400> SEQUENCE: 144

```
caggttcagc tgcagcagtc tgggcctgag ctggcgaggc tggggcctc  agtgaagctg     60
tcctgcaagg cttctggcta caccttcaca agctatggta taagctgggt gaagcaaaga    120
actggacagg gccttgagtg gattggacag attcatccta gaagtggtaa tacttactac    180
aatgagaact tcaagggcaa ggccacactg actgcagcca atcctccag  cacagcgtac    240
ctggagctcc gcagcctgac atctgaggac tctgcggtct atttctgtgc aagagagggg    300
ggtcccgact actggggcca aggcaccact ctcacagtct cctca                    345
```

<210> SEQ ID NO 145
<211> LENGTH: 345
<212> TYPE: DNA
<213> ORGANISM: Artificial Sequence
<220> FEATURE:
<223> OTHER INFORMATION: Synthetic construct

<400> SEQUENCE: 145

```
gaggttcagc tgcagcagtc tggggctgag cttgtgaggc caggggcctc  agtcaagttg     60
tcctgcacag cttctggctt taacattaaa gacgactata tgcactgggt gaaacagagg    120
cctgaacagg gcctggagtg gattggatgc attgatcctg agaatggtga tattgaatat    180
gcctcgaggt tccagggcaa ggccactatg acagcagaca catcctccaa cacagcctac    240
ctgcagctca ccagcctgac atctgcggac actgccgtct attactgtac tacatacgtt    300
ggatttggtt actggggcca agggactctg gtcactgtct ctgca                    345
```

<210> SEQ ID NO 146
<211> LENGTH: 16
<212> TYPE: PRT
<213> ORGANISM: Artificial Sequence
<220> FEATURE:
<223> OTHER INFORMATION: Synthetic construct

<400> SEQUENCE: 146

Arg Ser Ser Gln Asn Ile Val His Ser Asn Gly Asn Thr Tyr Leu Glu
1               5                   10                  15

<210> SEQ ID NO 147
<211> LENGTH: 17
<212> TYPE: PRT
<213> ORGANISM: Artificial Sequence
<220> FEATURE:
<223> OTHER INFORMATION: Synthetic construct

<400> SEQUENCE: 147

Lys Ser Asn Gln Ser Leu Leu Asn Ser Gly Asp Gln Lys Asn Tyr Leu
1               5                   10                  15
Thr

<210> SEQ ID NO 148
<211> LENGTH: 16
<212> TYPE: PRT
<213> ORGANISM: Artificial Sequence
<220> FEATURE:
<223> OTHER INFORMATION: Synthetic construct

<400> SEQUENCE: 148

Lys Ser Ser Gln Ser Leu Leu Asp Ser Asp Gly Asn Thr Tyr Leu Asn
1               5                   10                  15

<210> SEQ ID NO 149
<211> LENGTH: 11
<212> TYPE: PRT
<213> ORGANISM: Artificial Sequence
<220> FEATURE:
<223> OTHER INFORMATION: Synthetic construct

<400> SEQUENCE: 149

Gln Ala Thr Gln Asp Ile Val Lys Asn Leu Asn
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Synthetic construct

<400> SEQUENCE: 150

Ser Ala Ser Ser Ser Val Ser Tyr Met His
1               5                   10

<210> SEQ ID NO 151
<211> LENGTH: 17
<212> TYPE: PRT
<213> ORGANISM: Artificial Sequence
<220> FEATURE:
<223> OTHER INFORMATION: Synthetic construct

<400> SEQUENCE: 151

Lys Ser Ser Gln Ser Leu Leu Asn Ser Gly Asn Gln Lys Asn Tyr Leu
1               5                   10                  15

Thr

<210> SEQ ID NO 152
<211> LENGTH: 16
<212> TYPE: PRT
<213> ORGANISM: Artificial Sequence
<220> FEATURE:
<223> OTHER INFORMATION: Synthetic construct

<400> SEQUENCE: 152

Lys Ser Ser Leu Ser Leu Leu Asp Ser Asp Gly Lys Thr Tyr Leu Asn
1               5                   10                  15

<210> SEQ ID NO 153
<211> LENGTH: 7
<212> TYPE: PRT
<213> ORGANISM: Artificial Sequence
<220> FEATURE:
<223> OTHER INFORMATION: Synthetic construct

<400> SEQUENCE: 153

Leu Val Ser Glu Leu Asp Ser
1               5

<210> SEQ ID NO 154
<211> LENGTH: 7
<212> TYPE: PRT
<213> ORGANISM: Artificial Sequence
<220> FEATURE:
<223> OTHER INFORMATION: Synthetic construct

<400> SEQUENCE: 154

Trp Ala Ser Thr Arg Glu Ser
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic construct

<400> SEQUENCE: 155

Tyr Ala Thr Glu Leu Ala Glu
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic construct

<400> SEQUENCE: 156

Arg Thr Ser Asn Leu Ala Ser
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic construct

<400> SEQUENCE: 157

Phe Gln Gly Ser His Val Pro Leu Thr
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic construct

<400> SEQUENCE: 158

Gln Asn Asp Tyr Ser Tyr Pro Leu Thr
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic construct

<400> SEQUENCE: 159

Leu Gln Phe Tyr Glu Phe Pro Tyr Thr
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic construct

<400> SEQUENCE: 160

His Gln Trp Ser Ser Trp Thr
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic construct

<400> SEQUENCE: 161

Gln Asn Asp Tyr Ser Phe Pro Phe Thr
1               5

<210> SEQ ID NO 162
<211> LENGTH: 5
<212> TYPE: PRT
<213> ORGANISM: Artificial Sequence
<220> FEATURE:
<223> OTHER INFORMATION: Synthetic construct

<400> SEQUENCE: 162

Asp Asp Tyr Met His
1               5

<210> SEQ ID NO 163
<211> LENGTH: 5
<212> TYPE: PRT
<213> ORGANISM: Artificial Sequence
<220> FEATURE:
<223> OTHER INFORMATION: Synthetic construct

<400> SEQUENCE: 163

Ser Tyr Gly Ile Thr
1               5

<210> SEQ ID NO 164
<211> LENGTH: 5
<212> TYPE: PRT
<213> ORGANISM: Artificial Sequence
<220> FEATURE:
<223> OTHER INFORMATION: Synthetic construct

<400> SEQUENCE: 164

Ser Tyr Gly Ile Ser
1               5

<210> SEQ ID NO 165
<211> LENGTH: 5
<212> TYPE: PRT
<213> ORGANISM: Artificial Sequence
<220> FEATURE:
<223> OTHER INFORMATION: Synthetic construct

<400> SEQUENCE: 165

Asp Phe Tyr Ile Asn
1               5

<210> SEQ ID NO 166
<211> LENGTH: 5
<212> TYPE: PRT
<213> ORGANISM: Artificial Sequence
<220> FEATURE:
<223> OTHER INFORMATION: Synthetic construct

<400> SEQUENCE: 166

Ser Asp Gly Ile Thr
1               5

```
<210> SEQ ID NO 167
<211> LENGTH: 5
<212> TYPE: PRT
<213> ORGANISM: Artificial Sequence
<220> FEATURE:
<223> OTHER INFORMATION: Synthetic construct

<400> SEQUENCE: 167

Asp Tyr Asn Met His
1               5

<210> SEQ ID NO 168
<211> LENGTH: 6
<212> TYPE: PRT
<213> ORGANISM: Artificial Sequence
<220> FEATURE:
<223> OTHER INFORMATION: Synthetic construct

<400> SEQUENCE: 168

Ser Gly Tyr Tyr Trp Asn
1               5

<210> SEQ ID NO 169
<211> LENGTH: 5
<212> TYPE: PRT
<213> ORGANISM: Artificial Sequence
<220> FEATURE:
<223> OTHER INFORMATION: Synthetic construct

<400> SEQUENCE: 169

Asp Tyr Tyr Ile Asn
1               5

<210> SEQ ID NO 170
<211> LENGTH: 17
<212> TYPE: PRT
<213> ORGANISM: Artificial Sequence
<220> FEATURE:
<223> OTHER INFORMATION: Synthetic construct

<400> SEQUENCE: 170

Cys Ile Asp Pro Glu Asn Gly Asp Thr Glu Tyr Ala Ser Lys Phe Gln
1               5                   10                  15

Asp

<210> SEQ ID NO 171
<211> LENGTH: 17
<212> TYPE: PRT
<213> ORGANISM: Artificial Sequence
<220> FEATURE:
<223> OTHER INFORMATION: Synthetic construct

<400> SEQUENCE: 171

Glu Ile His Pro Arg Ser Gly Asn Thr Tyr Tyr Asn Glu Asn Phe Lys
1               5                   10                  15

Asp

<210> SEQ ID NO 172
<211> LENGTH: 18
<212> TYPE: PRT
<213> ORGANISM: Artificial Sequence
<220> FEATURE:
<223> OTHER INFORMATION: Synthetic construct
```

<400> SEQUENCE: 172

Gln Ile Tyr Pro Arg Ser Asp Asn Thr Tyr Tyr Asn Glu Arg Phe Lys
1               5                   10                  15

Gly Lys

<210> SEQ ID NO 173
<211> LENGTH: 17
<212> TYPE: PRT
<213> ORGANISM: Artificial Sequence
<220> FEATURE:
<223> OTHER INFORMATION: Synthetic construct

<400> SEQUENCE: 173

Cys Ile Asp Pro Glu Asn Gly Asp Ile Glu Tyr Ala Ser Arg Phe Gln
1               5                   10                  15

Gly

<210> SEQ ID NO 174
<211> LENGTH: 17
<212> TYPE: PRT
<213> ORGANISM: Artificial Sequence
<220> FEATURE:
<223> OTHER INFORMATION: Synthetic construct

<400> SEQUENCE: 174

Cys Ile Asp Pro Glu Asn Gly Asp Thr Glu Tyr Ala Ser Lys Phe Gln
1               5                   10                  15

Gly

<210> SEQ ID NO 175
<211> LENGTH: 17
<212> TYPE: PRT
<213> ORGANISM: Artificial Sequence
<220> FEATURE:
<223> OTHER INFORMATION: Synthetic construct

<400> SEQUENCE: 175

Arg Ile Tyr Pro Gly Ser Asp Glu Thr Tyr Tyr Asn Glu Lys Phe Lys
1               5                   10                  15

Asp

<210> SEQ ID NO 176
<211> LENGTH: 17
<212> TYPE: PRT
<213> ORGANISM: Artificial Sequence
<220> FEATURE:
<223> OTHER INFORMATION: Synthetic construct

<400> SEQUENCE: 176

Gln Ile His Pro Arg Ser Gly Asn Thr Tyr Tyr Asn Gly Lys Phe Lys
1               5                   10                  15

Gly

<210> SEQ ID NO 177
<211> LENGTH: 17
<212> TYPE: PRT
<213> ORGANISM: Artificial Sequence
<220> FEATURE:
<223> OTHER INFORMATION: Synthetic construct

<400> SEQUENCE: 177

Tyr Ile Asn Pro Asn Asn Gly Gly Thr Ser Tyr Asn Gln Lys Phe Lys
1               5                   10                  15

Asp

<210> SEQ ID NO 178
<211> LENGTH: 16
<212> TYPE: PRT
<213> ORGANISM: Artificial Sequence
<220> FEATURE:
<223> OTHER INFORMATION: Synthetic construct

<400> SEQUENCE: 178

Tyr Ile Arg His Asp Gly Ser Asn Asn Tyr Asn Pro Ser Leu Lys Asn
1               5                   10                  15

<210> SEQ ID NO 179
<211> LENGTH: 17
<212> TYPE: PRT
<213> ORGANISM: Artificial Sequence
<220> FEATURE:
<223> OTHER INFORMATION: Synthetic construct

<400> SEQUENCE: 179

Arg Ile Tyr Pro Gly Asn Gly Asn Thr Asp Tyr Asn Glu Lys Phe Lys
1               5                   10                  15

Asp

<210> SEQ ID NO 180
<211> LENGTH: 17
<212> TYPE: PRT
<213> ORGANISM: Artificial Sequence
<220> FEATURE:
<223> OTHER INFORMATION: Synthetic construct

<400> SEQUENCE: 180

Gln Ile His Pro Arg Ser Gly Asn Thr Tyr Tyr Asn Glu Lys Phe Lys
1               5                   10                  15

Gly

<210> SEQ ID NO 181
<211> LENGTH: 17
<212> TYPE: PRT
<213> ORGANISM: Artificial Sequence
<220> FEATURE:
<223> OTHER INFORMATION: Synthetic construct

<400> SEQUENCE: 181

Gln Ile His Pro Arg Ser Gly Asn Thr Tyr Tyr Asn Glu Asn Phe Lys
1               5                   10                  15

Gly

<210> SEQ ID NO 182
<211> LENGTH: 6
<212> TYPE: PRT
<213> ORGANISM: Artificial Sequence
<220> FEATURE:
<223> OTHER INFORMATION: Synthetic construct

<400> SEQUENCE: 182

Tyr Val Gly Phe Ala Tyr
1               5

```
<210> SEQ ID NO 183
<211> LENGTH: 6
<212> TYPE: PRT
<213> ORGANISM: Artificial Sequence
<220> FEATURE:
<223> OTHER INFORMATION: Synthetic construct

<400> SEQUENCE: 183

Gly Gly Pro Gly Asp Tyr
1               5

<210> SEQ ID NO 184
<211> LENGTH: 6
<212> TYPE: PRT
<213> ORGANISM: Artificial Sequence
<220> FEATURE:
<223> OTHER INFORMATION: Synthetic construct

<400> SEQUENCE: 184

Glu Gly Gly Pro Asp Tyr
1               5

<210> SEQ ID NO 185
<211> LENGTH: 6
<212> TYPE: PRT
<213> ORGANISM: Artificial Sequence
<220> FEATURE:
<223> OTHER INFORMATION: Synthetic construct

<400> SEQUENCE: 185

Tyr Val Gly Phe Gly Tyr
1               5

<210> SEQ ID NO 186
<211> LENGTH: 5
<212> TYPE: PRT
<213> ORGANISM: Artificial Sequence
<220> FEATURE:
<223> OTHER INFORMATION: Synthetic construct

<400> SEQUENCE: 186

Trp Phe Phe Asp Val
1               5

<210> SEQ ID NO 187
<211> LENGTH: 6
<212> TYPE: PRT
<213> ORGANISM: Artificial Sequence
<220> FEATURE:
<223> OTHER INFORMATION: Synthetic construct

<400> SEQUENCE: 187

Thr Gly Thr Gly Asp Tyr
1               5

<210> SEQ ID NO 188
<211> LENGTH: 6
<212> TYPE: PRT
<213> ORGANISM: Artificial Sequence
<220> FEATURE:
<223> OTHER INFORMATION: Synthetic construct

<400> SEQUENCE: 188

Ser Asp Trp Glu Asp Cys
1               5
```

```
<210> SEQ ID NO 189
<211> LENGTH: 15
<212> TYPE: PRT
<213> ORGANISM: Artificial Sequence
<220> FEATURE:
<223> OTHER INFORMATION: Synthetic construct

<400> SEQUENCE: 189

Glu Ile Tyr Asp Gly Ser Ser Gly Tyr Phe Asp Val Trp Gly Thr
1               5                   10                  15

<210> SEQ ID NO 190
<211> LENGTH: 5
<212> TYPE: PRT
<213> ORGANISM: Artificial Sequence
<220> FEATURE:
<223> OTHER INFORMATION: Synthetic construct

<400> SEQUENCE: 190

Trp Tyr Phe Asp Val
1               5

<210> SEQ ID NO 191
<211> LENGTH: 6
<212> TYPE: PRT
<213> ORGANISM: Homo sapiens

<400> SEQUENCE: 191

Ser Asn Tyr Glu Asn Leu
1               5

<210> SEQ ID NO 192
<211> LENGTH: 640
<212> TYPE: PRT
<213> ORGANISM: Homo sapiens

<400> SEQUENCE: 192

Met Leu Asn Lys Met Thr Leu His Pro Gln Gln Ile Met Ile Gly Pro
1               5                   10                  15

Arg Phe Asn Arg Ala Leu Phe Asp Pro Leu Leu Val Val Leu Leu Ala
                20                  25                  30

Leu Gln Leu Leu Val Val Ala Gly Leu Val Arg Ala Gln Thr Cys Pro
            35                  40                  45

Ser Val Cys Ser Cys Ser Asn Gln Phe Ser Lys Val Ile Cys Val Arg
        50                  55                  60

Lys Asn Leu Arg Glu Val Pro Asp Gly Ile Ser Thr Asn Thr Arg Leu
65                  70                  75                  80

Leu Asn Leu His Glu Asn Gln Ile Gln Ile Ile Lys Val Asn Ser Phe
                85                  90                  95

Lys His Leu Arg His Leu Glu Ile Leu Gln Leu Ser Arg Asn His Ile
                100                 105                 110

Arg Thr Ile Glu Ile Gly Ala Phe Asn Gly Leu Ala Asn Leu Asn Thr
            115                 120                 125

Leu Glu Leu Phe Asp Asn Arg Leu Thr Thr Ile Pro Asn Gly Ala Phe
        130                 135                 140

Val Tyr Leu Ser Lys Leu Lys Glu Leu Trp Leu Arg Asn Asn Pro Ile
145                 150                 155                 160

Glu Ser Ile Pro Ser Tyr Ala Phe Asn Arg Ile Pro Ser Leu Arg Arg
                165                 170                 175

Leu Asp Leu Gly Glu Leu Lys Arg Leu Ser Tyr Ile Ser Glu Gly Ala
            180                 185                 190
```

```
Phe Glu Gly Leu Ser Asn Leu Arg Tyr Leu Asn Leu Ala Met Cys Asn
            195                 200                 205

Leu Arg Glu Ile Pro Asn Leu Thr Pro Leu Ile Lys Leu Asp Glu Leu
210                 215                 220

Asp Leu Ser Gly Asn His Leu Ser Ala Ile Arg Pro Gly Ser Phe Gln
225                 230                 235                 240

Gly Leu Met His Leu Gln Lys Leu Trp Met Ile Gln Ser Gln Ile Gln
            245                 250                 255

Val Ile Glu Arg Asn Ala Phe Asp Asn Leu Gln Ser Leu Val Glu Ile
            260                 265                 270

Asn Leu Ala His Asn Asn Leu Thr Leu Leu Pro His Asp Leu Phe Thr
            275                 280                 285

Pro Leu His His Leu Glu Arg Ile His Leu His His Asn Pro Trp Asn
            290                 295                 300

Cys Asn Cys Asp Ile Leu Trp Leu Ser Trp Trp Ile Lys Asp Met Ala
305                 310                 315                 320

Pro Ser Asn Thr Ala Cys Cys Ala Arg Cys Asn Thr Pro Pro Asn Leu
            325                 330                 335

Lys Gly Arg Tyr Ile Gly Glu Leu Asp Gln Asn Tyr Phe Thr Cys Tyr
            340                 345                 350

Ala Pro Val Ile Val Glu Pro Pro Ala Asp Leu Asn Val Thr Glu Gly
            355                 360                 365

Met Ala Ala Glu Leu Lys Cys Arg Ala Ser Thr Ser Leu Thr Ser Val
            370                 375                 380

Ser Trp Ile Thr Pro Asn Gly Thr Val Met Thr His Gly Ala Tyr Lys
385                 390                 395                 400

Val Arg Ile Ala Val Leu Ser Asp Gly Thr Leu Asn Phe Thr Asn Val
            405                 410                 415

Thr Val Gln Asp Thr Gly Met Tyr Thr Cys Met Val Ser Asn Ser Val
            420                 425                 430

Gly Asn Thr Thr Ala Ser Ala Thr Leu Asn Val Thr Ala Ala Thr Thr
            435                 440                 445

Thr Pro Phe Ser Tyr Phe Ser Thr Val Thr Val Glu Thr Met Glu Pro
            450                 455                 460

Ser Gln Asp Glu Ala Arg Thr Thr Asp Asn Asn Val Gly Pro Thr Pro
465                 470                 475                 480

Val Val Asp Trp Glu Thr Thr Asn Val Thr Thr Ser Leu Thr Pro Gln
            485                 490                 495

Ser Thr Arg Ser Thr Glu Lys Thr Phe Thr Ile Pro Val Thr Asp Ile
            500                 505                 510

Asn Ser Gly Ile Pro Gly Ile Asp Glu Val Met Lys Thr Thr Lys Ile
            515                 520                 525

Ile Ile Gly Cys Phe Val Ala Ile Thr Leu Met Ala Ala Val Met Leu
            530                 535                 540

Val Ile Phe Tyr Lys Met Arg Lys Gln His His Arg Gln Asn His His
545                 550                 555                 560

Ala Pro Thr Arg Thr Val Glu Ile Ile Asn Val Asp Asp Glu Ile Thr
            565                 570                 575

Gly Asp Thr Pro Met Glu Ser His Leu Pro Met Pro Ala Ile Glu His
            580                 585                 590

Glu His Leu Asn His Tyr Asn Ser Tyr Lys Ser Pro Phe Asn His Thr
            595                 600                 605
```

Thr Thr Val Asn Thr Ile Asn Ser Ile His Ser Ser Val His Glu Pro
    610                 615                 620

Leu Leu Ile Arg Met Asn Ser Lys Asp Asn Val Gln Glu Thr Gln Ile
625                 630                 635                 640

<210> SEQ ID NO 193
<211> LENGTH: 486
<212> TYPE: PRT
<213> ORGANISM: Artificial Sequence
<220> FEATURE:
<223> OTHER INFORMATION: Synthetic construct

<400> SEQUENCE: 193

Met Glu Trp Ser Trp Val Phe Leu Phe Phe Leu Ser Val Thr Thr Gly
1               5                   10                  15

Val His Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Asp Lys Thr His Thr Cys Pro Pro Cys Pro Ala Pro
            260                 265                 270

Glu Phe Glu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

Pro Ala Ser Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
        435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly
                485

<210> SEQ ID NO 194
<211> LENGTH: 467
<212> TYPE: PRT
<213> ORGANISM: Artificial Sequence
<220> FEATURE:
<223> OTHER INFORMATION: Synthetic construct

<400> SEQUENCE: 194

Phe Val Arg Thr Lys Ile Asp Thr Thr Glu Asn Leu Leu Asn Thr Glu
1               5                   10                  15

Val His Ser Ser Pro Ala Gln Arg Trp Ser Met Gln Val Pro Pro Glu
            20                  25                  30

Val Ser Ala Glu Ala Gly Asp Ala Ala Val Leu Pro Cys Thr Phe Thr
        35                  40                  45

His Pro His Arg His Tyr Asp Gly Pro Leu Thr Ala Ile Trp Arg Ala
    50                  55                  60

Gly Glu Pro Tyr Ala Gly Pro Gln Val Phe Arg Cys Ala Ala Ala Arg
65                  70                  75                  80

Gly Ser Glu Leu Cys Gln Thr Ala Leu Ser Leu His Gly Arg Phe Arg
                85                  90                  95

Leu Leu Gly Asn Pro Arg Arg Asn Asp Leu Ser Leu Arg Val Glu Arg
            100                 105                 110

Leu Ala Leu Ala Asp Asp Arg Arg Tyr Phe Cys Arg Val Glu Phe Ala
        115                 120                 125

Gly Asp Val His Asp Arg Tyr Glu Ser Arg His Gly Val Arg Leu His
    130                 135                 140

Val Thr Ala Ala Pro Arg Ile Val Asn Ile Ser Val Leu Pro Ser Pro
145                 150                 155                 160

Ala His Ala Phe Arg Ala Leu Cys Thr Ala Glu Gly Glu Pro Pro Pro
                165                 170                 175

Ala Leu Ala Trp Ser Gly Pro Ala Leu Gly Asn Ser Leu Ala Ala Val
            180                 185                 190

Arg Ser Pro Arg Glu Gly His Gly His Leu Val Thr Ala Glu Leu Pro
        195                 200                 205

Ala Leu Thr His Asp Gly Arg Tyr Thr Cys Thr Ala Ala Asn Ser Leu
        210                 215                 220

Gly Arg Ser Glu Ala Ser Val Tyr Leu Phe Arg Phe His Gly Ala Ser
225                 230                 235                 240

Gly Asp Lys Thr His Thr Cys Pro Pro Cys Pro Ala Pro Glu Phe Glu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Ser
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly
465

<210> SEQ ID NO 195
<211> LENGTH: 107
<212> TYPE: PRT
<213> ORGANISM: Artificial Sequence
<220> FEATURE:
<223> OTHER INFORMATION: Synthetic construct

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Thr Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 196
<211> LENGTH: 11
<212> TYPE: PRT
<213> ORGANISM: Artificial Sequence
<220> FEATURE:
<223> OTHER INFORMATION: Synthetic construct

<400> SEQUENCE: 196

Lys Ala Ser Gln Asp Ile Asn Thr Tyr Leu Ser
1               5                   10

<210> SEQ ID NO 197
<211> LENGTH: 107
<212> TYPE: PRT
<213> ORGANISM: Artificial Sequence
<220> FEATURE:
<223> OTHER INFORMATION: Synthetic construct

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Val Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 198
<211> LENGTH: 11
<212> TYPE: PRT
<213> ORGANISM: Artificial Sequence
<220> FEATURE:
<223> OTHER INFORMATION: Synthetic construct

<400> SEQUENCE: 198

Lys Ala Ser Gln Asp Ile Asn Val Tyr Leu Ser
1               5                   10

<210> SEQ ID NO 199
<211> LENGTH: 107
<212> TYPE: PRT
<213> ORGANISM: Artificial Sequence
<220> FEATURE:
<223> OTHER INFORMATION: Synthetic construct

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Gln Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
            50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                    85                  90                  95

Thr Phe Gly Gly Gly Thr Lys Val Glu Ile Lys
                100                 105

<210> SEQ ID NO 200
<211> LENGTH: 11
<212> TYPE: PRT
<213> ORGANISM: Artificial Sequence
<220> FEATURE:
<223> OTHER INFORMATION: Synthetic construct

<400> SEQUENCE: 200

Lys Ala Ser Gln Asp Ile Gln Ser Tyr Leu Ser
 1               5                  10

<210> SEQ ID NO 201
<211> LENGTH: 107
<212> TYPE: PRT
<213> ORGANISM: Artificial Sequence
<220> FEATURE:
<223> OTHER INFORMATION: Synthetic construct

<400> SEQUENCE: 201

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Val Tyr
                20                  25                  30

Leu Ser Trp Phe Gln Gln Lys Pro Gly Lys Ala Pro Lys Thr Leu Ile
            35                  40                  45

Tyr Arg Ala Asn Arg Leu Thr Ser Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                    85                  90                  95

Thr Phe Gly Gly Gly Thr Lys Val Glu Ile Lys
                100                 105

<210> SEQ ID NO 202
<211> LENGTH: 7
<212> TYPE: PRT
<213> ORGANISM: Artificial Sequence
<220> FEATURE:
<223> OTHER INFORMATION: Synthetic construct

<400> SEQUENCE: 202

Arg Ala Asn Arg Leu Thr Ser
 1               5

<210> SEQ ID NO 203
<211> LENGTH: 122
<212> TYPE: PRT
<213> ORGANISM: Artificial Sequence
<220> FEATURE:
<223> OTHER INFORMATION: Synthetic construct -continued

<400> SEQUENCE: 203

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Gly Leu Glu Trp Met
        35                  40                  45

Gly Asp Ile Tyr Ser Gly Ser Asp Thr Met His Tyr Ala Glu Lys Phe
    50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Trp Asp Tyr Gly Ser Ser Tyr Asp Tyr Phe Asp Tyr Trp
            100                 105                 110

Gly Gln Gly Thr Leu Val Thr Val Ser Ser
        115                 120

<210> SEQ ID NO 204
<211> LENGTH: 5
<212> TYPE: PRT
<213> ORGANISM: Artificial Sequence
<220> FEATURE:
<223> OTHER INFORMATION: Synthetic construct

<400> SEQUENCE: 204

Ser Tyr Trp Ile Thr
1               5

<210> SEQ ID NO 205
<211> LENGTH: 17
<212> TYPE: PRT
<213> ORGANISM: Artificial Sequence
<220> FEATURE:
<223> OTHER INFORMATION: Synthetic construct

<400> SEQUENCE: 205

Asp Ile Tyr Ser Gly Ser Asp Thr Met His Tyr Ala Glu Lys Phe Gln
1               5                   10                  15

Gly

<210> SEQ ID NO 206
<211> LENGTH: 122
<212> TYPE: PRT
<213> ORGANISM: Artificial Sequence
<220> FEATURE:
<223> OTHER INFORMATION: Synthetic construct

<400> SEQUENCE: 206

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Gly Leu Glu Trp Met
        35                  40                  45

Gly Asp Ile Tyr Ser Gly Ser Asp Thr Thr His Tyr Ala Glu Lys Phe
    50                  55                  60

Gln Gly Arg Val Thr Leu Thr Val Asp Thr Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Trp Trp Asp Tyr Gly Ser Ser Tyr Asp Tyr Phe Asp Tyr Trp
            100                 105                 110

Gly Gln Gly Thr Leu Val Thr Val Ser Ser
        115                 120

<210> SEQ ID NO 207
<211> LENGTH: 122
<212> TYPE: PRT
<213> ORGANISM: Artificial Sequence
<220> FEATURE:
<223> OTHER INFORMATION: Synthetic construct

<400> SEQUENCE: 207

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Ser Trp Val Arg Gln Ala Pro Gly Gln Gly Leu Glu Trp Met
        35                  40                  45

Gly Asp Ile Tyr Ser Gly Ser Asp Thr Thr His Tyr Ala Glu Lys Phe
    50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Trp Asp Tyr Gly Ser Ser Tyr Asp Tyr Phe Asp Tyr Trp
            100                 105                 110

Gly Gln Gly Thr Leu Val Thr Val Ser Ser
        115                 120

<210> SEQ ID NO 208
<211> LENGTH: 5
<212> TYPE: PRT
<213> ORGANISM: Artificial Sequence
<220> FEATURE:
<223> OTHER INFORMATION: Synthetic construct

<400> SEQUENCE: 208

Ser Tyr Trp Ile Ser
1               5

<210> SEQ ID NO 209
<211> LENGTH: 107
<212> TYPE: PRT
<213> ORGANISM: Artificial Sequence
<220> FEATURE:
<223> OTHER INFORMATION: Synthetic construct

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60
```

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Trp Ser Ser Pro Leu
                85                  90                  95

Thr Phe Gly Gly Gly Thr Lys Val Glu Ile Lys
                100                 105

<210> SEQ ID NO 210
<211> LENGTH: 107
<212> TYPE: PRT
<213> ORGANISM: Artificial Sequence
<220> FEATURE:
<223> OTHER INFORMATION: Synthetic construct

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Val Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Tyr Trp Ser Ser Pro Leu
                85                  90                  95

Thr Phe Gly Gly Gly Thr Lys Val Glu Ile Lys
                100                 105

<210> SEQ ID NO 211
<211> LENGTH: 107
<212> TYPE: PRT
<213> ORGANISM: Artificial Sequence
<220> FEATURE:
<223> OTHER INFORMATION: Synthetic construct

<400> SEQUENCE: 211

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Tyr Trp Ser Ser Pro Leu
                85                  90                  95

Thr Phe Gly Gly Gly Thr Lys Val Glu Ile Lys
                100                 105

<210> SEQ ID NO 212
<211> LENGTH: 123
<212> TYPE: PRT
<213> ORGANISM: Artificial Sequence
<220> FEATURE:
<223> OTHER INFORMATION: Synthetic construct

<400> SEQUENCE: 212

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asn Tyr
            20                  25                  30

Gly Val His Trp Val Arg Gln Pro Pro Gly Lys Gly Leu Glu Trp Ile
        35                  40                  45

Val Leu Ile Trp Ser Asp Gly Ser Thr Thr Tyr Asn Ser Ala Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg His Pro Tyr Asp Asp Tyr Ser Gly Tyr Tyr Tyr Thr Met Asp Tyr
            100                 105                 110

Trp Gly Gln Gly Thr Leu Val Thr Val Ser Ser
        115                 120

<210> SEQ ID NO 213
<211> LENGTH: 122
<212> TYPE: PRT
<213> ORGANISM: Artificial Sequence
<220> FEATURE:
<223> OTHER INFORMATION: Synthetic construct

<400> SEQUENCE: 213

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asn Tyr
            20                  25                  30

Gly Val His Trp Val Arg Gln Pro Pro Gly Lys Gly Leu Glu Trp Ile
        35                  40                  45

Gly Leu Ile Trp Ser Asp Gly Ser Thr Thr Tyr Ala Ser Ala Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg His Pro Tyr Asp Asp Tyr Ser Gly Tyr Tyr Tyr Thr Met Asp Tyr
            100                 105                 110

Trp Gly Gln Gly Thr Leu Val Thr Val Ser
        115                 120

<210> SEQ ID NO 214
<211> LENGTH: 16
<212> TYPE: PRT
<213> ORGANISM: Artificial Sequence
<220> FEATURE:
<223> OTHER INFORMATION: Synthetic construct

<400> SEQUENCE: 214

Leu Ile Trp Ser Asp Gly Ser Thr Thr Tyr Ala Ser Ala Leu Lys Ser
1               5                   10                  15

<210> SEQ ID NO 215
<211> LENGTH: 122
<212> TYPE: PRT
<213> ORGANISM: Artificial Sequence
<220> FEATURE:

<223> OTHER INFORMATION: Synthetic construct

<400> SEQUENCE: 215

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asn Tyr
            20                  25                  30

Gly Val His Trp Val Arg Gln Pro Pro Gly Lys Gly Leu Glu Trp Ile
        35                  40                  45

Gly Leu Ile Trp Ser Asp Gly Ser Thr Thr Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg His Pro Tyr Asp Asp Tyr Ser Gly Tyr Tyr Tyr Thr Met Asp Tyr
            100                 105                 110

Trp Gly Gln Gly Thr Leu Val Thr Val Ser
        115                 120

<210> SEQ ID NO 216
<211> LENGTH: 122
<212> TYPE: PRT
<213> ORGANISM: Artificial Sequence
<220> FEATURE:
<223> OTHER INFORMATION: Synthetic construct

<400> SEQUENCE: 216

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asn Tyr
            20                  25                  30

Gly Val His Trp Val Arg Gln Pro Pro Gly Lys Gly Leu Glu Trp Ile
        35                  40                  45

Gly Leu Ile Trp Ser Glu Gly Ser Thr Thr Tyr Ala Ser Ala Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg His Pro Tyr Asp Asp Tyr Ser Gly Tyr Tyr Tyr Thr Met Asp Tyr
            100                 105                 110

Trp Gly Gln Gly Thr Leu Val Thr Val Ser
        115                 120

<210> SEQ ID NO 217
<211> LENGTH: 16
<212> TYPE: PRT
<213> ORGANISM: Artificial Sequence
<220> FEATURE:
<223> OTHER INFORMATION: Synthetic construct

<400> SEQUENCE: 217

Leu Ile Trp Ser Glu Gly Ser Thr Thr Tyr Ala Ser Ala Leu Lys Ser
1               5                   10                  15

<210> SEQ ID NO 218
<211> LENGTH: 16
<212> TYPE: PRT

<213> ORGANISM: Artificial Sequence
<220> FEATURE:
<223> OTHER INFORMATION: Synthetic construct

<400> SEQUENCE: 218

Leu Ile Trp Ser Asp Gly Ser Thr Thr Tyr Asn Pro Ser Leu Lys Ser
1               5                   10                  15

<210> SEQ ID NO 219
<211> LENGTH: 107
<212> TYPE: PRT
<213> ORGANISM: Artificial Sequence
<220> FEATURE:
<223> OTHER INFORMATION: Synthetic construct

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 220
<211> LENGTH: 40
<212> TYPE: PRT
<213> ORGANISM: Artificial Sequence
<220> FEATURE:
<223> OTHER INFORMATION: Synthetic construct

<400> SEQUENCE: 220

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp
        35                  40

<210> SEQ ID NO 221
<211> LENGTH: 40
<212> TYPE: PRT
<213> ORGANISM: Artificial Sequence
<220> FEATURE:
<223> OTHER INFORMATION: Synthetic construct

<400> SEQUENCE: 221

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp
        35                  40

<210> SEQ ID NO 222
<211> LENGTH: 35
<212> TYPE: PRT
<213> ORGANISM: Artificial Sequence
<220> FEATURE:
<223> OTHER INFORMATION: Synthetic construct

<400> SEQUENCE: 222

Asp Ile Gln Met Thr Gln Ala Ser Ser Ser Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp
        35

<210> SEQ ID NO 223
<211> LENGTH: 34
<212> TYPE: PRT
<213> ORGANISM: Artificial Sequence
<220> FEATURE:
<223> OTHER INFORMATION: Synthetic construct

<400> SEQUENCE: 223

Gln Ile Ile Leu Thr Gln Ser Pro Ala Ile Met Ser Ala Ser Pro Gly
1               5                   10                  15

Glu Lys Val Thr Met Thr Cys Ser Ala Ser Ser Ser Thr Ser Phe Met
            20                  25                  30

His Trp

<210> SEQ ID NO 224
<211> LENGTH: 35
<212> TYPE: PRT
<213> ORGANISM: Artificial Sequence
<220> FEATURE:
<223> OTHER INFORMATION: Synthetic construct

<400> SEQUENCE: 224

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp
        35

<210> SEQ ID NO 225
<211> LENGTH: 37
<212> TYPE: PRT
<213> ORGANISM: Artificial Sequence
<220> FEATURE:
<223> OTHER INFORMATION: Synthetic construct

<400> SEQUENCE: 225

Gln Ala Val Val Thr Gln Glu Ser Ala Leu Thr Thr Ser Pro Gly Glu
1               5                   10                  15

Thr Val Thr Leu Thr Cys Arg Ser Ser Ser Gly Ala Val Thr Thr Gly
            20                  25                  30

Asn Phe Ala Asn Trp
        35

<210> SEQ ID NO 226
<211> LENGTH: 40
<212> TYPE: PRT
<213> ORGANISM: Artificial Sequence
<220> FEATURE:
<223> OTHER INFORMATION: Synthetic construct

<400> SEQUENCE: 226

Asp Val Val Met Thr Gln Thr Pro Leu Thr Leu Ser Val Thr Ile Gly
1               5                   10                  15

Gln Ser Ala Ser Ile Ser Cys Lys Ser Ser Gln Ser Leu Leu Asp Ser
            20                  25                  30

Asp Gly Lys Thr Tyr Leu Asn Trp
        35                  40

<210> SEQ ID NO 227
<211> LENGTH: 37
<212> TYPE: PRT
<213> ORGANISM: Artificial Sequence
<220> FEATURE:
<223> OTHER INFORMATION: Synthetic construct

<400> SEQUENCE: 227

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp
        35

<210> SEQ ID NO 228
<211> LENGTH: 40
<212> TYPE: PRT
<213> ORGANISM: Artificial Sequence
<220> FEATURE:
<223> OTHER INFORMATION: Synthetic construct

<400> SEQUENCE: 228

Asp Val Val Met Thr Gln Thr Pro Leu Thr Leu Ser Ile Pro Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp
        35                  40

<210> SEQ ID NO 229
<211> LENGTH: 40
<212> TYPE: PRT
<213> ORGANISM: Artificial Sequence
<220> FEATURE:
<223> OTHER INFORMATION: Synthetic construct

<400> SEQUENCE: 229

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp
        35                  40

<210> SEQ ID NO 230
<211> LENGTH: 40
<212> TYPE: PRT
<213> ORGANISM: Artificial Sequence
<220> FEATURE:
<223> OTHER INFORMATION: Synthetic construct

```
<400> SEQUENCE: 230

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp
        35                  40

<210> SEQ ID NO 231
<211> LENGTH: 41
<212> TYPE: PRT
<213> ORGANISM: Artificial Sequence
<220> FEATURE:
<223> OTHER INFORMATION: Synthetic construct

<400> SEQUENCE: 231

Asp Ile Val Met Thr Gln Ser Pro Ser Ser Leu Thr Val Thr Ala Gly
1               5                   10                  15

Glu Lys Val Thr Met Ser Cys Lys Ser Asn Gln Ser Leu Leu Asn Ser
            20                  25                  30

Gly Asp Gln Lys Asn Tyr Leu Thr Trp
        35                  40

<210> SEQ ID NO 232
<211> LENGTH: 40
<212> TYPE: PRT
<213> ORGANISM: Artificial Sequence
<220> FEATURE:
<223> OTHER INFORMATION: Synthetic construct

<400> SEQUENCE: 232

Asp Val Val Met Thr Gln Thr Pro Leu Thr Leu Ser Val Thr Ile Gly
1               5                   10                  15

Gln Ser Ala Ser Ile Ser Cys Lys Ser Ser Gln Ser Leu Leu Asp Ser
            20                  25                  30

Asp Gly Asn Thr Tyr Leu Asn Trp
        35                  40

<210> SEQ ID NO 233
<211> LENGTH: 35
<212> TYPE: PRT
<213> ORGANISM: Artificial Sequence
<220> FEATURE:
<223> OTHER INFORMATION: Synthetic construct

<400> SEQUENCE: 233

Glu Ile Gln Met Thr Gln Ser Pro Ser Ser Met Ser Ala Ser Leu Gly
1               5                   10                  15

Asp Arg Ile Thr Ile Thr Cys Gln Ala Thr Gln Asp Ile Val Lys Asn
            20                  25                  30

Leu Asn Trp
        35

<210> SEQ ID NO 234
<211> LENGTH: 34
<212> TYPE: PRT
<213> ORGANISM: Artificial Sequence
<220> FEATURE:
<223> OTHER INFORMATION: Synthetic construct
```

<400> SEQUENCE: 234

Gln Ile Val Leu Thr Gln Ser Pro Ala Ile Met Ser Ala Ser Leu Gly
1               5                   10                  15

Glu Glu Ile Thr Leu Ile Cys Ser Ala Ser Ser Ser Val Ser Tyr Met
            20                  25                  30

His Trp

<210> SEQ ID NO 235
<211> LENGTH: 41
<212> TYPE: PRT
<213> ORGANISM: Artificial Sequence
<220> FEATURE:
<223> OTHER INFORMATION: Synthetic construct

<400> SEQUENCE: 235

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp
        35                  40

<210> SEQ ID NO 236
<211> LENGTH: 40
<212> TYPE: PRT
<213> ORGANISM: Artificial Sequence
<220> FEATURE:
<223> OTHER INFORMATION: Synthetic construct

<400> SEQUENCE: 236

Asp Val Val Met Thr Gln Thr Pro Leu Thr Leu Ser Val Thr Ile Gly
1               5                   10                  15

Gln Pro Ala Ser Ile Ser Cys Lys Ser Ser Leu Ser Leu Leu Asp Ser
            20                  25                  30

Asp Gly Lys Thr Tyr Leu Asn Trp
        35                  40

<210> SEQ ID NO 237
<211> LENGTH: 35
<212> TYPE: PRT
<213> ORGANISM: Artificial Sequence
<220> FEATURE:
<223> OTHER INFORMATION: Synthetic construct

<400> SEQUENCE: 237

Tyr Leu Gln Lys Pro Gly Gln Ser Pro Lys Leu Leu Ile Tyr Lys Val
1               5                   10                  15

Ser Asn Arg Phe Ser Gly Val Pro Asp Arg Phe Ser Gly Ser Gly Ser
            20                  25                  30

Gly Thr Asp
        35

<210> SEQ ID NO 238
<211> LENGTH: 35
<212> TYPE: PRT
<213> ORGANISM: Artificial Sequence
<220> FEATURE:
<223> OTHER INFORMATION: Synthetic construct

```
<400> SEQUENCE: 238

Phe Leu Gln Arg Pro Gly Gln Ser Pro Gln Leu Leu Ile Tyr Arg Met
1               5                   10                  15

Ser Asn Leu Ala Ser Gly Val Pro Asp Arg Phe Gly Gly Ser Gly Ser
            20                  25                  30

Gly Thr Ala
        35

<210> SEQ ID NO 239
<211> LENGTH: 35
<212> TYPE: PRT
<213> ORGANISM: Artificial Sequence
<220> FEATURE:
<223> OTHER INFORMATION: Synthetic construct

<400> SEQUENCE: 239

Tyr Gln Gln Lys Pro Gly Asn Ala Pro Arg Leu Leu Ile Ser Gly Ala
1               5                   10                  15

Thr Ser Leu Glu Thr Gly Val Pro Ser Arg Phe Ser Gly Ser Gly Ser
            20                  25                  30

Gly Lys Asp
        35

<210> SEQ ID NO 240
<211> LENGTH: 35
<212> TYPE: PRT
<213> ORGANISM: Artificial Sequence
<220> FEATURE:
<223> OTHER INFORMATION: Synthetic construct

<400> SEQUENCE: 240

Tyr Gln Gln Lys Pro Gly Thr Ser Pro Lys Arg Trp Ile Phe Asp Thr
1               5                   10                  15

Ser Lys Leu Ala Ser Gly Val Pro Gly Arg Phe Ile Gly Ser Gly Ser
            20                  25                  30

Gly Thr Ser
        35

<210> SEQ ID NO 241
<211> LENGTH: 35
<212> TYPE: PRT
<213> ORGANISM: Artificial Sequence
<220> FEATURE:
<223> OTHER INFORMATION: Synthetic construct

<400> SEQUENCE: 241

Phe Gln Gln Lys Pro Gly Lys Ser Pro Lys Thr Leu Ile Tyr Arg Ala
1               5                   10                  15

Asn Arg Leu Val Asp Gly Val Pro Ser Arg Phe Ser Gly Ser Gly Ser
            20                  25                  30

Gly Gln Asp
        35

<210> SEQ ID NO 242
<211> LENGTH: 35
<212> TYPE: PRT
<213> ORGANISM: Artificial Sequence
<220> FEATURE:
<223> OTHER INFORMATION: Synthetic construct
```

<400> SEQUENCE: 242

Val Gln Glu Lys Pro Asp His Leu Phe Thr Gly Leu Ile Gly Thr
1               5                   10                  15

Asn Asn Arg Ala Pro Gly Val Pro Ala Arg Phe Ser Gly Ser Leu Ile
            20                  25                  30

Gly Asp Lys
        35

<210> SEQ ID NO 243
<211> LENGTH: 35
<212> TYPE: PRT
<213> ORGANISM: Artificial Sequence
<220> FEATURE:
<223> OTHER INFORMATION: Synthetic construct

<400> SEQUENCE: 243

Leu Leu Gln Arg Pro Gly Gln Ser Pro Lys Arg Leu Ile Tyr Leu Val
1               5                   10                  15

Ser Lys Leu Asp Ser Gly Val Pro Asp Arg Phe Thr Gly Ser Gly Ser
            20                  25                  30

Gly Thr Asp
        35

<210> SEQ ID NO 244
<211> LENGTH: 35
<212> TYPE: PRT
<213> ORGANISM: Artificial Sequence
<220> FEATURE:
<223> OTHER INFORMATION: Synthetic construct

<400> SEQUENCE: 244

Leu Leu Gln Arg Pro Gly Gln Ser Pro Lys Arg Leu Ile Tyr Leu Val
1               5                   10                  15

Ser Glu Leu Asp Ser Gly Val Pro Asp Arg Phe Thr Gly Ser Gly Ser
            20                  25                  30

Gly Thr Asp
        35

<210> SEQ ID NO 245
<211> LENGTH: 35
<212> TYPE: PRT
<213> ORGANISM: Artificial Sequence
<220> FEATURE:
<223> OTHER INFORMATION: Synthetic construct

<400> SEQUENCE: 245

Tyr Leu Lys Lys Pro Gly Gln Ser Pro Lys Leu Leu Ile Tyr Lys Val
1               5                   10                  15

Ser Asn Arg Phe Ser Gly Val Pro Asp Arg Phe Ser Gly Ser Gly Ser
            20                  25                  30

Gly Thr Asp
        35

<210> SEQ ID NO 246
<211> LENGTH: 35
<212> TYPE: PRT
<213> ORGANISM: Artificial Sequence
<220> FEATURE:
<223> OTHER INFORMATION: Synthetic construct

<400> SEQUENCE: 246

Tyr Gln Gln Lys Pro Gly Gln Pro Pro Lys Leu Leu Ile Tyr Trp Ala
1               5                   10                  15

Ser Thr Arg Glu Ser Gly Val Pro Asp Arg Phe Thr Gly Ser Gly Ser
            20                  25                  30

Gly Thr Asp
        35

<210> SEQ ID NO 247
<211> LENGTH: 35
<212> TYPE: PRT
<213> ORGANISM: Artificial Sequence
<220> FEATURE:
<223> OTHER INFORMATION: Synthetic construct

<400> SEQUENCE: 247

Tyr Gln Gln Lys Pro Gly Lys Pro Pro Ser Phe Leu Ile Tyr Tyr Ala
1               5                   10                  15

Thr Glu Leu Ala Glu Gly Val Pro Ser Arg Phe Ser Gly Ser Gly Ser
            20                  25                  30

Gly Ser Asp
        35

<210> SEQ ID NO 248
<211> LENGTH: 35
<212> TYPE: PRT
<213> ORGANISM: Artificial Sequence
<220> FEATURE:
<223> OTHER INFORMATION: Synthetic construct

<400> SEQUENCE: 248

Tyr Gln Gln Lys Ser Gly Thr Ser Pro Lys Leu Leu Ile Tyr Arg Thr
1               5                   10                  15

Ser Asn Leu Ala Ser Gly Val Pro Ser Arg Phe Ser Gly Ser Gly Ser
            20                  25                  30

Gly Thr Phe
        35

<210> SEQ ID NO 249
<211> LENGTH: 37
<212> TYPE: PRT
<213> ORGANISM: Artificial Sequence
<220> FEATURE:
<223> OTHER INFORMATION: Synthetic construct

<400> SEQUENCE: 249

Phe Thr Leu Lys Ile Ser Arg Val Glu Ala Glu Asp Leu Gly Val Tyr
1               5                   10                  15

Tyr Cys Phe Gln Gly Ser His Val Pro Trp Thr Phe Gly Gly Gly Thr
            20                  25                  30

Lys Leu Glu Ile Lys
        35

<210> SEQ ID NO 250
<211> LENGTH: 37
<212> TYPE: PRT
<213> ORGANISM: Artificial Sequence
<220> FEATURE:
<223> OTHER INFORMATION: Synthetic construct

<400> SEQUENCE: 250

Phe Thr Leu Arg Ile Ser Arg Val Glu Ala Glu Asp Val Gly Phe Tyr
1               5                   10                  15

Tyr Cys Met Gln His Leu Glu Tyr Pro Tyr Thr Phe Gly Gly Gly Thr
            20                  25                  30

Arg Leu Glu Ile Lys
        35

<210> SEQ ID NO 251
<211> LENGTH: 37
<212> TYPE: PRT
<213> ORGANISM: Artificial Sequence
<220> FEATURE:
<223> OTHER INFORMATION: Synthetic construct

<400> SEQUENCE: 251

Tyr Thr Leu Ser Ile Thr Ser Leu Gln Thr Glu Asp Val Ala Thr Tyr
1               5                   10                  15

Tyr Cys Gln Gln Tyr Trp Ser Ser Pro Leu Thr Phe Gly Ala Gly Thr
            20                  25                  30

Lys Leu Glu Leu Lys
        35

<210> SEQ ID NO 252
<211> LENGTH: 37
<212> TYPE: PRT
<213> ORGANISM: Artificial Sequence
<220> FEATURE:
<223> OTHER INFORMATION: Synthetic construct

<400> SEQUENCE: 252

Tyr Ser Leu Thr Ile Ser Thr Met Glu Ala Glu Asp Ala Ala Thr Tyr
1               5                   10                  15

Tyr Cys His Gln Arg Ser Ala Tyr Pro Trp Thr Phe Gly Gly Gly Thr
            20                  25                  30

Lys Leu Glu Ile Lys
        35

<210> SEQ ID NO 253
<211> LENGTH: 37
<212> TYPE: PRT
<213> ORGANISM: Artificial Sequence
<220> FEATURE:
<223> OTHER INFORMATION: Synthetic construct

<400> SEQUENCE: 253

Tyr Ser Leu Thr Ile Ser Ser Leu Glu Tyr Glu Asp Met Gly Ile Tyr
1               5                   10                  15

Tyr Cys Leu Gln Tyr Asp Glu Phe Pro Tyr Thr Phe Gly Gly Gly Thr
            20                  25                  30

Lys Leu Glu Ile Lys
        35

<210> SEQ ID NO 254
<211> LENGTH: 37
<212> TYPE: PRT
<213> ORGANISM: Artificial Sequence
<220> FEATURE:
<223> OTHER INFORMATION: Synthetic construct

<400> SEQUENCE: 254

Phe Thr Leu Arg Ile Ser Arg Val Glu Ala Glu Asp Val Gly Val Tyr
1               5                   10                  15

Tyr Cys Met Gln His Leu Glu Tyr Pro Tyr Thr Phe Gly Gly Gly Thr
            20                  25                  30

Lys Leu Glu Ile Lys
        35

<210> SEQ ID NO 255
<211> LENGTH: 37
<212> TYPE: PRT
<213> ORGANISM: Artificial Sequence
<220> FEATURE:
<223> OTHER INFORMATION: Synthetic construct

<400> SEQUENCE: 255

Ala Ala Leu Thr Ile Thr Gly Ala Gln Thr Glu Asp Glu Ala Ile Tyr
1               5                   10                  15

Phe Cys Ala Leu Trp Tyr Ser Asn His Trp Val Phe Gly Gly Gly Thr
            20                  25                  30

Lys Leu Thr Val Leu
        35

<210> SEQ ID NO 256
<211> LENGTH: 37
<212> TYPE: PRT
<213> ORGANISM: Artificial Sequence
<220> FEATURE:
<223> OTHER INFORMATION: Synthetic construct

<400> SEQUENCE: 256

Phe Thr Leu Lys Ile Ser Arg Val Glu Ala Glu Asp Leu Gly Val Tyr
1               5                   10                  15

Tyr Cys Trp Gln Gly Thr His Phe Pro Phe Thr Phe Gly Ser Gly Thr
            20                  25                  30

Lys Leu Glu Ile Lys
        35

<210> SEQ ID NO 257
<211> LENGTH: 37
<212> TYPE: PRT
<213> ORGANISM: Artificial Sequence
<220> FEATURE:
<223> OTHER INFORMATION: Synthetic construct

<400> SEQUENCE: 257

Phe Thr Leu Arg Ile Ser Arg Val Glu Ala Glu Asp Leu Gly Val Tyr
1               5                   10                  15

Tyr Cys Phe Gln Gly Ser His Val Pro Leu Thr Phe Gly Ala Gly Thr
            20                  25                  30

Lys Leu Glu Leu Lys
        35

<210> SEQ ID NO 258
<211> LENGTH: 37
<212> TYPE: PRT
<213> ORGANISM: Artificial Sequence
<220> FEATURE:
<223> OTHER INFORMATION: Synthetic construct -continued

<400> SEQUENCE: 258

Phe Thr Leu Lys Ile Ser Arg Val Glu Ala Glu Asp Leu Gly Met Tyr
1               5                   10                  15

Tyr Cys Phe Gln Gly Ser His Val Pro Leu Thr Phe Gly Ala Gly Thr
            20                  25                  30

Lys Leu Glu Leu Lys
        35

<210> SEQ ID NO 259
<211> LENGTH: 37
<212> TYPE: PRT
<213> ORGANISM: Artificial Sequence
<220> FEATURE:
<223> OTHER INFORMATION: Synthetic construct

<400> SEQUENCE: 259

Phe Thr Leu Thr Ile Ser Ser Val Gln Ala Glu Asp Leu Ala Ile Tyr
1               5                   10                  15

Tyr Cys Gln Asn Asp Tyr Ser Tyr Pro Leu Thr Phe Gly Ala Gly Thr
            20                  25                  30

Lys Leu Glu Leu Lys
        35

<210> SEQ ID NO 260
<211> LENGTH: 37
<212> TYPE: PRT
<213> ORGANISM: Artificial Sequence
<220> FEATURE:
<223> OTHER INFORMATION: Synthetic construct

<400> SEQUENCE: 260

Tyr Ser Leu Thr Ile Ser Asn Leu Glu Ser Glu Asp Phe Ala Asp Tyr
1               5                   10                  15

Tyr Cys Leu Gln Phe Tyr Glu Phe Pro Tyr Thr Phe Gly Gly Gly Thr
            20                  25                  30

Lys Leu Glu Ile Lys
        35

<210> SEQ ID NO 261
<211> LENGTH: 35
<212> TYPE: PRT
<213> ORGANISM: Artificial Sequence
<220> FEATURE:
<223> OTHER INFORMATION: Synthetic construct

<400> SEQUENCE: 261

Tyr Ser Leu Thr Ile Ser Ser Val Glu Ala Glu Asp Ala Ala Asp Tyr
1               5                   10                  15

Tyr Cys His Gln Trp Ser Ser Trp Thr Phe Gly Gly Gly Thr Gln Leu
            20                  25                  30

Glu Ile Lys
        35

<210> SEQ ID NO 262
<211> LENGTH: 37
<212> TYPE: PRT
<213> ORGANISM: Artificial Sequence
<220> FEATURE:
<223> OTHER INFORMATION: Synthetic construct

```
<400> SEQUENCE: 262

Phe Thr Leu Thr Ile Ser Asn Val Gln Pro Glu Asp Leu Ala Val Tyr
1               5                   10                  15

Tyr Cys Gln Asn Asp Tyr Ser Phe Pro Phe Thr Phe Gly Ser Gly Thr
                20                  25                  30

Glu Leu Glu Met Lys
            35

<210> SEQ ID NO 263
<211> LENGTH: 37
<212> TYPE: PRT
<213> ORGANISM: Artificial Sequence
<220> FEATURE:
<223> OTHER INFORMATION: Synthetic construct

<400> SEQUENCE: 263

Phe Thr Leu Lys Ile Ser Arg Val Glu Ala Glu Asp Leu Gly Ile Tyr
1               5                   10                  15

Tyr Cys Trp Gln Gly Thr His Phe Pro Phe Thr Phe Gly Ser Gly Thr
                20                  25                  30

Lys Leu Glu Ile Lys
            35

<210> SEQ ID NO 264
<211> LENGTH: 37
<212> TYPE: PRT
<213> ORGANISM: Artificial Sequence
<220> FEATURE:
<223> OTHER INFORMATION: Synthetic construct

<400> SEQUENCE: 264

Phe Thr Leu Lys Ile Ile Arg Val Glu Ala Glu Asp Leu Gly Ile Tyr
1               5                   10                  15

Tyr Cys Trp Gln Gly Thr His Phe Pro Phe Thr Phe Gly Ser Gly Thr
                20                  25                  30

Lys Leu Glu Val Lys
            35

<210> SEQ ID NO 265
<211> LENGTH: 37
<212> TYPE: PRT
<213> ORGANISM: Artificial Sequence
<220> FEATURE:
<223> OTHER INFORMATION: Synthetic construct

<400> SEQUENCE: 265

Phe Thr Leu Lys Ile Ser Arg Val Glu Ala Glu Asp Leu Gly Val Tyr
1               5                   10                  15

Tyr Cys Phe Gln Gly Ser His Val Pro Leu Thr Phe Gly Ala Gly Thr
                20                  25                  30

Lys Leu Glu Leu Lys
            35

<210> SEQ ID NO 266
<211> LENGTH: 40
<212> TYPE: PRT
<213> ORGANISM: Artificial Sequence
<220> FEATURE:
<223> OTHER INFORMATION: Synthetic construct
```

```
<400> SEQUENCE: 266

Glu Val Gln Leu Val Glu Ser Gly Gly Gly Phe Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala
        35                  40

<210> SEQ ID NO 267
<211> LENGTH: 40
<212> TYPE: PRT
<213> ORGANISM: Artificial Sequence
<220> FEATURE:
<223> OTHER INFORMATION: Synthetic construct

<400> SEQUENCE: 267

Gln Val Gln Leu Lys Gln Ser Gly Ala Glu Leu Val Lys Pro Gly Ala
1               5                   10                  15

Ser Val Lys Ile Ser Cys Lys Ala Ser Gly Tyr Ile Phe Thr Asp Tyr
            20                  25                  30

Tyr Val Asn Trp Val Lys Gln Arg
        35                  40

<210> SEQ ID NO 268
<211> LENGTH: 40
<212> TYPE: PRT
<213> ORGANISM: Artificial Sequence
<220> FEATURE:
<223> OTHER INFORMATION: Synthetic construct

<400> SEQUENCE: 268

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Asn Tyr
            20                  25                  30

Gly Val His Trp Val Arg Gln Pro
        35                  40

<210> SEQ ID NO 269
<211> LENGTH: 40
<212> TYPE: PRT
<213> ORGANISM: Artificial Sequence
<220> FEATURE:
<223> OTHER INFORMATION: Synthetic construct

<400> SEQUENCE: 269

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Asp Tyr
            20                  25                  30

Gly Met His Trp Val Arg Gln Ala
        35                  40

<210> SEQ ID NO 270
<211> LENGTH: 40
<212> TYPE: PRT
<213> ORGANISM: Artificial Sequence
<220> FEATURE:
<223> OTHER INFORMATION: Synthetic construct
```

<400> SEQUENCE: 270

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Glu Arg
        35                  40

<210> SEQ ID NO 271
<211> LENGTH: 40
<212> TYPE: PRT
<213> ORGANISM: Artificial Sequence
<220> FEATURE:
<223> OTHER INFORMATION: Synthetic construct

<400> SEQUENCE: 271

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Ile Gln Arg
        35                  40

<210> SEQ ID NO 272
<211> LENGTH: 40
<212> TYPE: PRT
<213> ORGANISM: Artificial Sequence
<220> FEATURE:
<223> OTHER INFORMATION: Synthetic construct

<400> SEQUENCE: 272

Gln Val Gln Leu Lys Gln Ser Gly Pro Glu Leu Val Arg Pro Gly Ala
1               5                   10                  15

Ser Val Lys Ile Ser Cys Glu Ala Ser Gly Tyr Thr Phe Thr Asp Tyr
            20                  25                  30

Tyr Val Asn Trp Val Lys Gln Arg
        35                  40

<210> SEQ ID NO 273
<211> LENGTH: 40
<212> TYPE: PRT
<213> ORGANISM: Artificial Sequence
<220> FEATURE:
<223> OTHER INFORMATION: Synthetic construct

<400> SEQUENCE: 273

Gln Val Gln Leu Lys Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Val Asn Trp Val Lys Gln Arg
        35                  40

<210> SEQ ID NO 274
<211> LENGTH: 40
<212> TYPE: PRT
<213> ORGANISM: Artificial Sequence
<220> FEATURE:
<223> OTHER INFORMATION: Synthetic construct

<400> SEQUENCE: 274

Glu Val Gln Leu Leu Glu Thr Gly Gly Gly Leu Val Gln Pro Gly Gly
1               5                   10                  15

Ser Arg Gly Leu Ser Cys Glu Gly Ser Gly Phe Thr Phe Ser Gly Phe
            20                  25                  30

Trp Met Ser Trp Val Arg Gln Thr
        35                  40

<210> SEQ ID NO 275
<211> LENGTH: 40
<212> TYPE: PRT
<213> ORGANISM: Artificial Sequence
<220> FEATURE:
<223> OTHER INFORMATION: Synthetic construct

<400> SEQUENCE: 275

His Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Leu Ile Trp Val Lys Gln Arg
        35                  40

<210> SEQ ID NO 276
<211> LENGTH: 40
<212> TYPE: PRT
<213> ORGANISM: Artificial Sequence
<220> FEATURE:
<223> OTHER INFORMATION: Synthetic construct

<400> SEQUENCE: 276

Glu Val Gln Leu Leu Glu Thr Gly Gly Gly Leu Val Gln Pro Gly Gly
1               5                   10                  15

Ser Arg Gly Leu Ser Cys Glu Gly Ser Gly Phe Thr Phe Ser Asp Phe
            20                  25                  30

Trp Met Ser Trp Val Arg Gln Thr
        35                  40

<210> SEQ ID NO 277
<211> LENGTH: 40
<212> TYPE: PRT
<213> ORGANISM: Artificial Sequence
<220> FEATURE:
<223> OTHER INFORMATION: Synthetic construct

<400> SEQUENCE: 277

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met His Trp Val Lys Gln Arg
        35                  40

<210> SEQ ID NO 278
<211> LENGTH: 40
<212> TYPE: PRT
<213> ORGANISM: Artificial Sequence
<220> FEATURE:
<223> OTHER INFORMATION: Synthetic construct

<400> SEQUENCE: 278

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Ile Ser Tyr
            20                  25                  30

Gly Ile Thr Trp Val Lys Gln Arg
        35                  40

<210> SEQ ID NO 279
<211> LENGTH: 40
<212> TYPE: PRT
<213> ORGANISM: Artificial Sequence
<220> FEATURE:
<223> OTHER INFORMATION: Synthetic construct

<400> SEQUENCE: 279

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg
        35                  40

<210> SEQ ID NO 280
<211> LENGTH: 40
<212> TYPE: PRT
<213> ORGANISM: Artificial Sequence
<220> FEATURE:
<223> OTHER INFORMATION: Synthetic construct

<400> SEQUENCE: 280

Gln Val Gln Leu Lys Gln Ser Gly Ala Glu Leu Val Arg Pro Gly Ala
1               5                   10                  15

Ser Val Lys Leu Ser Cys Arg Ala Ser Gly Tyr Thr Phe Thr Asp Phe
            20                  25                  30

Tyr Ile Asn Trp Val Lys Gln Arg
        35                  40

<210> SEQ ID NO 281
<211> LENGTH: 40
<212> TYPE: PRT
<213> ORGANISM: Artificial Sequence
<220> FEATURE:
<223> OTHER INFORMATION: Synthetic construct

<400> SEQUENCE: 281

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Asp
            20                  25                  30

Gly Ile Thr Trp Val Lys Gln Arg
        35                  40

<210> SEQ ID NO 282
<211> LENGTH: 40
<212> TYPE: PRT
<213> ORGANISM: Artificial Sequence
<220> FEATURE:
<223> OTHER INFORMATION: Synthetic construct

<400> SEQUENCE: 282

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser
        35                  40

<210> SEQ ID NO 283
<211> LENGTH: 41
<212> TYPE: PRT
<213> ORGANISM: Artificial Sequence
<220> FEATURE:
<223> OTHER INFORMATION: Synthetic construct

<400> SEQUENCE: 283

Asp Val Gln Leu Gln Glu Ser Gly Pro Gly Leu Val Lys Phe Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe
        35                  40

<210> SEQ ID NO 284
<211> LENGTH: 40
<212> TYPE: PRT
<213> ORGANISM: Artificial Sequence
<220> FEATURE:
<223> OTHER INFORMATION: Synthetic construct

<400> SEQUENCE: 284

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg
        35                  40

<210> SEQ ID NO 285
<211> LENGTH: 40
<212> TYPE: PRT
<213> ORGANISM: Artificial Sequence
<220> FEATURE:
<223> OTHER INFORMATION: Synthetic construct

<400> SEQUENCE: 285

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Asp
            20                  25                  30

Gly Ile Thr Trp Leu Lys Gln Arg
        35                  40

<210> SEQ ID NO 286
<211> LENGTH: 40
<212> TYPE: PRT
<213> ORGANISM: Artificial Sequence
<220> FEATURE:
<223> OTHER INFORMATION: Synthetic construct

<400> SEQUENCE: 286

Gln Val Gln Leu Gln Gln Ser Gly Pro Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg
        35                  40

<210> SEQ ID NO 287
<211> LENGTH: 41
<212> TYPE: PRT
<213> ORGANISM: Artificial Sequence
<220> FEATURE:
<223> OTHER INFORMATION: Synthetic construct

<400> SEQUENCE: 287

Pro Glu Lys Gly Leu Glu Trp Val Ala Tyr Ile Ser Ser Gly Ser Ser
1               5                   10                  15

Ile Ile Tyr Tyr Ala Asp Thr Val Lys Gly Arg Phe Thr Ile Ser Arg
            20                  25                  30

Asp Asn Ala Lys Asn Thr Leu Phe Leu
        35                  40

<210> SEQ ID NO 288
<211> LENGTH: 41
<212> TYPE: PRT
<213> ORGANISM: Artificial Sequence
<220> FEATURE:
<223> OTHER INFORMATION: Synthetic construct

<400> SEQUENCE: 288

Pro Gly Gln Gly Leu Glu Trp Ile Gly Lys Ile Gly Pro Gly Ser Val
1               5                   10                  15

Ser Ile Tyr Tyr Asn Glu Lys Phe Lys Gly Lys Ala Thr Leu Thr Ala
            20                  25                  30

Asp Lys Ser Ser Ser Thr Ala Tyr Met
        35                  40

<210> SEQ ID NO 289
<211> LENGTH: 40
<212> TYPE: PRT
<213> ORGANISM: Artificial Sequence
<220> FEATURE:
<223> OTHER INFORMATION: Synthetic construct

<400> SEQUENCE: 289

Pro Gly Lys Gly Leu Glu Trp Leu Val Leu Ile Trp Ser Asp Gly Ser
1               5                   10                  15

Thr Thr Tyr Asn Ser Ala Leu Lys Ser Arg Leu Ser Ile Ser Lys Asp
            20                  25                  30

Asn Ser Lys Ser Gln Val Phe Leu
        35                  40

<210> SEQ ID NO 290
<211> LENGTH: 41
<212> TYPE: PRT
<213> ORGANISM: Artificial Sequence
<220> FEATURE:
<223> OTHER INFORMATION: Synthetic construct

<400> SEQUENCE: 290

Pro Glu Lys Gly Leu Glu Trp Val Ala Tyr Ile Ser Ser Gly Ser Ser
1               5                   10                  15

Ile Leu Tyr Tyr Ala Asp Ile Val Lys Gly Arg Phe Thr Ile Ser Arg
            20                  25                  30

Asp Asn Ala Lys Asn Thr Leu Phe Leu
        35                  40

<210> SEQ ID NO 291
<211> LENGTH: 41
<212> TYPE: PRT
<213> ORGANISM: Artificial Sequence
<220> FEATURE:
<223> OTHER INFORMATION: Synthetic construct

<400> SEQUENCE: 291

Pro Glu Gln Gly Leu Glu Trp Ile Gly Arg Ile Asp Pro Glu Asp Gly
1               5                   10                  15

Asp Ile Glu Tyr Asp Pro Lys Phe Gln Gly Lys Ala Thr Met Thr Ala
            20                  25                  30

Asp Thr Ser Ser Asn Thr Ala Tyr Leu
        35                  40

<210> SEQ ID NO 292
<211> LENGTH: 41
<212> TYPE: PRT
<213> ORGANISM: Artificial Sequence
<220> FEATURE:
<223> OTHER INFORMATION: Synthetic construct

<400> SEQUENCE: 292

Pro Gly Gln Gly Leu Glu Trp Ile Gly Asp Ile Tyr Cys Gly Ser Asp
1               5                   10                  15

Thr Met His Tyr Asn Glu Lys Phe Lys Asn Lys Ala Thr Leu Thr Val
            20                  25                  30

Asp Thr Ser Ser Ser Thr Ala Tyr Met
        35                  40

<210> SEQ ID NO 293
<211> LENGTH: 41
<212> TYPE: PRT
<213> ORGANISM: Artificial Sequence
<220> FEATURE:
<223> OTHER INFORMATION: Synthetic construct

<400> SEQUENCE: 293

Pro Gly Arg Gly Leu Glu Trp Ile Gly Lys Ile Gly Pro Gly Ser Val
1               5                   10                  15

Ser Ile Tyr Tyr Asn Glu Lys Phe Lys Asp Lys Ala Thr Leu Thr Ala
            20                  25                  30

Asp Lys Ser Ser Ser Thr Ala Tyr Met
        35                  40

<210> SEQ ID NO 294
<211> LENGTH: 41
<212> TYPE: PRT
<213> ORGANISM: Artificial Sequence
<220> FEATURE:
<223> OTHER INFORMATION: Synthetic construct

```
<400> SEQUENCE: 294

Pro Gly Gln Gly Leu Glu Trp Ile Gly Lys Ile Gly Pro Glu Ser Val
1               5                   10                  15

Ser Ile Tyr Tyr Ser Glu Lys Phe Lys Ala Lys Ala Thr Leu Thr Ala
            20                  25                  30

Asp Lys Ser Ser Ser Thr Ala Tyr Met
        35                  40

<210> SEQ ID NO 295
<211> LENGTH: 41
<212> TYPE: PRT
<213> ORGANISM: Artificial Sequence
<220> FEATURE:
<223> OTHER INFORMATION: Synthetic construct

<400> SEQUENCE: 295

Pro Gly Lys Thr Leu Glu Trp Ile Gly Asp Ile Asn Ser Asp Gly Ser
1               5                   10                  15

Ala Ile Asn Tyr Ala Pro Ser Ile Lys Asp Arg Phe Thr Ile Phe Arg
            20                  25                  30

Asp Asn Asp Lys Asn Thr Leu Tyr Leu
        35                  40

<210> SEQ ID NO 296
<211> LENGTH: 41
<212> TYPE: PRT
<213> ORGANISM: Artificial Sequence
<220> FEATURE:
<223> OTHER INFORMATION: Synthetic construct

<400> SEQUENCE: 296

Thr Gly Gln Gly Leu Glu Trp Ile Gly Glu Ile Tyr Pro Arg Ser Gly
1               5                   10                  15

Asn Thr Tyr Tyr Asn Glu Lys Phe Lys Gly Lys Ala Thr Leu Thr Ala
            20                  25                  30

Asp Ile Ser Ser Ser Thr Ala Tyr Met
        35                  40

<210> SEQ ID NO 297
<211> LENGTH: 41
<212> TYPE: PRT
<213> ORGANISM: Artificial Sequence
<220> FEATURE:
<223> OTHER INFORMATION: Synthetic construct

<400> SEQUENCE: 297

Pro Gly Lys Thr Leu Glu Trp Ile Gly Asp Ile Asn Ser Asp Gly Ser
1               5                   10                  15

Ala Val Asn Tyr Ala Pro Ser Ile Lys Asp Gln Phe Thr Ile Phe Arg
            20                  25                  30

Asp Asn Asp Lys Arg Thr Leu His Leu
        35                  40

<210> SEQ ID NO 298
<211> LENGTH: 41
<212> TYPE: PRT
<213> ORGANISM: Artificial Sequence
<220> FEATURE:
<223> OTHER INFORMATION: Synthetic construct
```

```
<400> SEQUENCE: 298

Pro Glu Gln Gly Leu Glu Trp Ile Gly Cys Ile Asp Pro Glu Asn Gly
1               5                   10                  15

Asp Thr Glu Tyr Ala Ser Lys Phe Gln Asp Lys Ala Thr Ile Thr Thr
                20                  25                  30

Asp Thr Ser Ser Asn Thr Ala Tyr Leu
            35                  40

<210> SEQ ID NO 299
<211> LENGTH: 41
<212> TYPE: PRT
<213> ORGANISM: Artificial Sequence
<220> FEATURE:
<223> OTHER INFORMATION: Synthetic construct

<400> SEQUENCE: 299

Thr Gly Gln Gly Leu Glu Trp Ile Gly Glu Ile His Pro Arg Ser Gly
1               5                   10                  15

Asn Thr Tyr Tyr Asn Glu Asn Phe Lys Asp Arg Ala Ser Leu Thr Ala
                20                  25                  30

Asp Lys Ser Ser Ser Thr Ala Tyr Met
            35                  40

<210> SEQ ID NO 300
<211> LENGTH: 41
<212> TYPE: PRT
<213> ORGANISM: Artificial Sequence
<220> FEATURE:
<223> OTHER INFORMATION: Synthetic construct

<400> SEQUENCE: 300

Thr Gly Gln Gly Leu Glu Trp Ile Gly Gln Ile Tyr Pro Arg Ser Asp
1               5                   10                  15

Asn Thr Tyr Tyr Asn Glu Arg Phe Lys Gly Lys Ala Thr Leu Thr Ala
                20                  25                  30

Asp Lys Ser Ser Ser Thr Ala Tyr Met
            35                  40

<210> SEQ ID NO 301
<211> LENGTH: 41
<212> TYPE: PRT
<213> ORGANISM: Artificial Sequence
<220> FEATURE:
<223> OTHER INFORMATION: Synthetic construct

<400> SEQUENCE: 301

Pro Glu Gln Gly Leu Glu Trp Ile Gly Cys Ile Asp Pro Glu Asn Gly
1               5                   10                  15

Asp Thr Glu Tyr Ala Ser Lys Phe Gln Gly Lys Ala Thr Ile Thr Ala
                20                  25                  30

Asp Thr Ser Ser Asn Thr Val Tyr Leu
            35                  40

<210> SEQ ID NO 302
<211> LENGTH: 41
<212> TYPE: PRT
<213> ORGANISM: Artificial Sequence
<220> FEATURE:
<223> OTHER INFORMATION: Synthetic construct
```

<400> SEQUENCE: 302

Pro Gly Gln Gly Leu Glu Trp Ile Ala Arg Ile Tyr Pro Gly Ser Asp
1               5                   10                  15

Glu Thr Tyr Tyr Asn Glu Lys Phe Lys Asp Lys Val Thr Leu Thr Ala
            20                  25                  30

Glu Lys Ser Ser Ser Thr Ala Tyr Met
        35                  40

<210> SEQ ID NO 303
<211> LENGTH: 41
<212> TYPE: PRT
<213> ORGANISM: Artificial Sequence
<220> FEATURE:
<223> OTHER INFORMATION: Synthetic construct

<400> SEQUENCE: 303

Thr Gly Gln Gly Leu Glu Trp Ile Gly Gln Ile His Pro Arg Ser Gly
1               5                   10                  15

Asn Thr Tyr Tyr Asn Gly Lys Phe Lys Gly Lys Ala Thr Leu Thr Ala
            20                  25                  30

Asp Arg Ser Ser Ser Thr Thr Tyr Met
        35                  40

<210> SEQ ID NO 304
<211> LENGTH: 41
<212> TYPE: PRT
<213> ORGANISM: Artificial Sequence
<220> FEATURE:
<223> OTHER INFORMATION: Synthetic construct

<400> SEQUENCE: 304

His Gly Lys Ser Leu Glu Trp Ile Gly Tyr Ile Asn Pro Asn Asn Gly
1               5                   10                  15

Gly Thr Ser Tyr Asn Gln Lys Phe Lys Asp Lys Ala Thr Leu Thr Val
            20                  25                  30

Asn Lys Ser Ser Ser Thr Ala Phe Met
        35                  40

<210> SEQ ID NO 305
<211> LENGTH: 40
<212> TYPE: PRT
<213> ORGANISM: Artificial Sequence
<220> FEATURE:
<223> OTHER INFORMATION: Synthetic construct

<400> SEQUENCE: 305

Pro Gly Asn Lys Leu Glu Trp Met Gly Tyr Ile Arg His Asp Gly Ser
1               5                   10                  15

Asn Asn Tyr Asn Pro Ser Leu Lys Asn Arg Ile Ser Ile Thr Arg Asp
            20                  25                  30

Thr Ser Lys Asn Gln Phe Phe Leu
        35                  40

<210> SEQ ID NO 306
<211> LENGTH: 41
<212> TYPE: PRT
<213> ORGANISM: Artificial Sequence
<220> FEATURE:
<223> OTHER INFORMATION: Synthetic construct

<400> SEQUENCE: 306

Pro Gly Gln Gly Leu Glu Trp Ile Ala Arg Ile Tyr Pro Gly Asn Gly
1               5                   10                  15

Asn Thr Asp Tyr Asn Glu Lys Phe Lys Asp Lys Ala Thr Leu Thr Ala
            20                  25                  30

Glu Lys Ser Ser Thr Thr Ala Tyr Ile
        35                  40

<210> SEQ ID NO 307
<211> LENGTH: 41
<212> TYPE: PRT
<213> ORGANISM: Artificial Sequence
<220> FEATURE:
<223> OTHER INFORMATION: Synthetic construct

<400> SEQUENCE: 307

Thr Gly Gln Gly Leu Glu Trp Ile Gly Gln Ile His Pro Arg Ser Gly
1               5                   10                  15

Asn Thr Tyr Tyr Asn Glu Lys Phe Lys Gly Lys Ala Thr Leu Thr Ala
            20                  25                  30

Asp Lys Ser Ser Ser Thr Ala Tyr Met
        35                  40

<210> SEQ ID NO 308
<211> LENGTH: 41
<212> TYPE: PRT
<213> ORGANISM: Artificial Sequence
<220> FEATURE:
<223> OTHER INFORMATION: Synthetic construct

<400> SEQUENCE: 308

Thr Gly Gln Gly Leu Glu Trp Ile Gly Gln Ile His Pro Arg Ser Gly
1               5                   10                  15

Asn Thr Tyr Tyr Asn Glu Asn Phe Lys Gly Lys Ala Thr Leu Thr Ala
            20                  25                  30

Ala Lys Ser Ser Ser Thr Ala Tyr Leu
        35                  40

<210> SEQ ID NO 309
<211> LENGTH: 41
<212> TYPE: PRT
<213> ORGANISM: Artificial Sequence
<220> FEATURE:
<223> OTHER INFORMATION: Synthetic construct

<400> SEQUENCE: 309

Pro Glu Gln Gly Leu Glu Trp Ile Gly Cys Ile Asp Pro Glu Asn Gly
1               5                   10                  15

Asp Ile Glu Tyr Ala Ser Arg Phe Gln Gly Lys Ala Thr Met Thr Ala
            20                  25                  30

Asp Thr Ser Ser Asn Thr Ala Tyr Leu
        35                  40

<210> SEQ ID NO 310
<211> LENGTH: 38
<212> TYPE: PRT
<213> ORGANISM: Artificial Sequence
<220> FEATURE:
<223> OTHER INFORMATION: Synthetic construct

<400> SEQUENCE: 310

Gln Met Thr Ser Leu Arg Ser Glu Asp Thr Ala Met Tyr Tyr Cys Ala
1               5                   10                  15

Arg Asp His Tyr His Gly Asn Gly Ser Asp Tyr Trp Gly Gln Gly Thr
            20                  25                  30

Thr Leu Thr Val Ser Ser
        35

<210> SEQ ID NO 311
<211> LENGTH: 35
<212> TYPE: PRT
<213> ORGANISM: Artificial Sequence
<220> FEATURE:
<223> OTHER INFORMATION: Synthetic construct

<400> SEQUENCE: 311

Gln Leu Ser Ser Leu Thr Ser Glu Asp Ser Ala Val Tyr Phe Cys Ala
1               5                   10                  15

Ser Tyr Tyr Tyr Gly Phe Ala Tyr Trp Gly Gln Gly Thr Leu Val Thr
            20                  25                  30

Val Ser Ala
        35

<210> SEQ ID NO 312
<211> LENGTH: 43
<212> TYPE: PRT
<213> ORGANISM: Artificial Sequence
<220> FEATURE:
<223> OTHER INFORMATION: Synthetic construct

<400> SEQUENCE: 312

Lys Met Asn Ser Leu Gln Thr Gly Asp Thr Ala Met Tyr Tyr Cys Ala
1               5                   10                  15

Arg His Pro Tyr Asp Asp Tyr Ser Gly Tyr Tyr Tyr Thr Met Asp Tyr
            20                  25                  30

Trp Gly Gln Gly Thr Ser Val Thr Val Ser Ser
        35                  40

<210> SEQ ID NO 313
<211> LENGTH: 39
<212> TYPE: PRT
<213> ORGANISM: Artificial Sequence
<220> FEATURE:
<223> OTHER INFORMATION: Synthetic construct

<400> SEQUENCE: 313

Gln Phe Ser Ser Leu Thr Ser Glu Asp Thr Ala Val Tyr Tyr Cys Val
1               5                   10                  15

Thr Asp Tyr Asp Tyr Asp Gly Gly Trp Phe Ala Tyr Trp Gly Gln Gly
            20                  25                  30

Thr Leu Val Thr Val Ser Ala
        35

<210> SEQ ID NO 314
<211> LENGTH: 41
<212> TYPE: PRT
<213> ORGANISM: Artificial Sequence
<220> FEATURE:
<223> OTHER INFORMATION: Synthetic construct

<400> SEQUENCE: 314

Gln Leu Ser Ser Leu Thr Ser Glu Asp Ser Ala Val Tyr Tyr Cys Ala
1               5                   10                  15

Arg Trp Trp Asp Tyr Gly Ser Ser Tyr Asp Tyr Phe Asp Tyr Trp Gly
            20                  25                  30

Gln Gly Thr Thr Leu Thr Val Ser Ser
        35                  40

<210> SEQ ID NO 315
<211> LENGTH: 35
<212> TYPE: PRT
<213> ORGANISM: Artificial Sequence
<220> FEATURE:
<223> OTHER INFORMATION: Synthetic construct

<400> SEQUENCE: 315

Gln Leu Ser Gly Leu Thr Ser Glu Asp Ser Ala Val Tyr Phe Cys Ala
1               5                   10                  15

Ser Tyr Tyr Tyr Gly Phe Ala Tyr Trp Gly Gln Gly Thr Leu Val Thr
            20                  25                  30

Val Ser Ala
        35

<210> SEQ ID NO 316
<211> LENGTH: 37
<212> TYPE: PRT
<213> ORGANISM: Artificial Sequence
<220> FEATURE:
<223> OTHER INFORMATION: Synthetic construct

<400> SEQUENCE: 316

Gln Met Asn Asn Val Arg Ser Glu Asp Thr Ala Thr Tyr Phe Cys Val
1               5                   10                  15

Arg Tyr Asp Asp Tyr Gly Tyr Phe Asp Val Trp Gly Thr Gly Thr Thr
            20                  25                  30

Val Thr Val Ser Ser
        35

<210> SEQ ID NO 317
<211> LENGTH: 35
<212> TYPE: PRT
<213> ORGANISM: Artificial Sequence
<220> FEATURE:
<223> OTHER INFORMATION: Synthetic construct

<400> SEQUENCE: 317

Glu Leu Arg Ser Leu Thr Ser Glu Asp Ser Ala Val Tyr Phe Cys Ala
1               5                   10                  15

Ser Ser Ser Pro His Gly Asp Tyr Trp Gly Gln Gly Thr Thr Leu Thr
            20                  25                  30

Val Ser Ser
        35

<210> SEQ ID NO 318
<211> LENGTH: 37
<212> TYPE: PRT
<213> ORGANISM: Artificial Sequence
<220> FEATURE:
<223> OTHER INFORMATION: Synthetic construct -continued

<400> SEQUENCE: 318

Gln Met Ile Asn Val Arg Ser Glu Asp Thr Ala Thr Tyr Phe Cys Val
1               5                   10                  15

Arg Tyr Asp Asp Tyr Gly Tyr Phe Asp Val Trp Gly Thr Gly Thr Thr
            20                  25                  30

Val Thr Val Ser Ser
        35

<210> SEQ ID NO 319
<211> LENGTH: 34
<212> TYPE: PRT
<213> ORGANISM: Artificial Sequence
<220> FEATURE:
<223> OTHER INFORMATION: Synthetic construct

<400> SEQUENCE: 319

Gln Leu Ser Ser Leu Thr Ser Glu Asp Thr Ala Val Tyr Tyr Cys Thr
1               5                   10                  15

Thr Tyr Val Gly Phe Ala Tyr Trp Gly Gln Gly Thr Leu Val Thr Val
            20                  25                  30

Ser Thr

<210> SEQ ID NO 320
<211> LENGTH: 34
<212> TYPE: PRT
<213> ORGANISM: Artificial Sequence
<220> FEATURE:
<223> OTHER INFORMATION: Synthetic construct

<400> SEQUENCE: 320

Glu Val Arg Ser Leu Thr Ser Glu Asp Ser Ala Val Tyr Phe Cys Ala
1               5                   10                  15

Arg Gly Gly Pro Gly Asp Tyr Trp Gly Gln Gly Thr Thr Leu Thr Val
            20                  25                  30

Ser Ser

<210> SEQ ID NO 321
<211> LENGTH: 34
<212> TYPE: PRT
<213> ORGANISM: Artificial Sequence
<220> FEATURE:
<223> OTHER INFORMATION: Synthetic construct

<400> SEQUENCE: 321

Ala Leu Arg Ser Leu Thr Ser Glu Asp Ser Ala Val Tyr Phe Cys Ala
1               5                   10                  15

Arg Glu Gly Gly Pro Asp Tyr Trp Gly Gln Gly Thr Thr Leu Thr Val
            20                  25                  30

Ser Ser

<210> SEQ ID NO 322
<211> LENGTH: 34
<212> TYPE: PRT
<213> ORGANISM: Artificial Sequence
<220> FEATURE:
<223> OTHER INFORMATION: Synthetic construct

<400> SEQUENCE: 322

Gln Leu Ser Ser Leu Thr Ser Glu Asp Thr Ala Val Tyr Tyr Cys Thr
1               5                   10                  15

```
Thr Tyr Val Gly Phe Gly Tyr Trp Gly Gln Gly Thr Leu Val Thr Val
            20                  25                  30

Ser Ala

<210> SEQ ID NO 323
<211> LENGTH: 33
<212> TYPE: PRT
<213> ORGANISM: Artificial Sequence
<220> FEATURE:
<223> OTHER INFORMATION: Synthetic construct

<400> SEQUENCE: 323

Gln Leu Ser Ser Leu Thr Ser Glu Asp Ser Ala Val Tyr Phe Cys Ala
1               5                   10                  15

Leu Trp Phe Phe Asp Val Trp Gly Thr Gly Thr Thr Val Thr Val Ser
            20                  25                  30

Ser

<210> SEQ ID NO 324
<211> LENGTH: 34
<212> TYPE: PRT
<213> ORGANISM: Artificial Sequence
<220> FEATURE:
<223> OTHER INFORMATION: Synthetic construct

<400> SEQUENCE: 324

Glu Leu Arg Ser Leu Thr Ser Glu Asp Ser Ala Val Tyr Phe Cys Ala
1               5                   10                  15

Lys Thr Gly Thr Gly Asp Tyr Trp Gly Gln Gly Thr Leu Thr Val
            20                  25                  30

Ser Ser

<210> SEQ ID NO 325
<211> LENGTH: 34
<212> TYPE: PRT
<213> ORGANISM: Artificial Sequence
<220> FEATURE:
<223> OTHER INFORMATION: Synthetic construct

<400> SEQUENCE: 325

Glu Leu Arg Ser Leu Ala Ser Glu Asp Ser Ala Val Tyr Tyr Cys Ala
1               5                   10                  15

Arg Ser Asp Trp Glu Asp Cys Trp Gly Gln Gly Thr Thr Leu Thr Val
            20                  25                  30

Ser Ser

<210> SEQ ID NO 326
<211> LENGTH: 43
<212> TYPE: PRT
<213> ORGANISM: Artificial Sequence
<220> FEATURE:
<223> OTHER INFORMATION: Synthetic construct

<400> SEQUENCE: 326

Lys Leu Asn Ser Val Ile Thr Glu Asp Thr Ala Thr Tyr Tyr Cys Val
1               5                   10                  15

Arg Glu Ile Tyr Asp Gly Ser Ser Gly Tyr Phe Asp Val Trp Gly Thr
            20                  25                  30

Gly Thr Thr Val Thr Val Val Thr Val Ser Ser
            35                  40
```

```
<210> SEQ ID NO 327
<211> LENGTH: 33
<212> TYPE: PRT
<213> ORGANISM: Artificial Sequence
<220> FEATURE:
<223> OTHER INFORMATION: Synthetic construct

<400> SEQUENCE: 327

Gln Leu Ser Ser Leu Thr Ser Glu Asp Ser Ala Val Tyr Phe Cys Cys
1               5                   10                  15

Leu Trp Tyr Phe Asp Val Trp Gly Thr Gly Thr Thr Leu Thr Val Ser
            20                  25                  30

Ser

<210> SEQ ID NO 328
<211> LENGTH: 34
<212> TYPE: PRT
<213> ORGANISM: Artificial Sequence
<220> FEATURE:
<223> OTHER INFORMATION: Synthetic construct

<400> SEQUENCE: 328

Glu Leu Arg Ser Leu Thr Ser Glu Asp Ser Ala Val Tyr Phe Cys Ala
1               5                   10                  15

Arg Glu Gly Gly Pro Asp Tyr Trp Gly Gln Gly Thr Leu Val Thr Val
            20                  25                  30

Ser Ala

<210> SEQ ID NO 329
<211> LENGTH: 34
<212> TYPE: PRT
<213> ORGANISM: Artificial Sequence
<220> FEATURE:
<223> OTHER INFORMATION: Synthetic construct

<400> SEQUENCE: 329

Gln Leu Thr Ser Leu Thr Ser Ala Asp Thr Ala Val Tyr Tyr Cys Thr
1               5                   10                  15

Thr Tyr Val Gly Phe Gly Tyr Trp Gly Gln Gly Thr Leu Val Thr Val
            20                  25                  30

Ser Ala

<210> SEQ ID NO 330
<211> LENGTH: 72
<212> TYPE: PRT
<213> ORGANISM: Artificial Sequence
<220> FEATURE:
<223> OTHER INFORMATION: Synthetic construct

<400> SEQUENCE: 330

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser
65                  70
```

<210> SEQ ID NO 331
<211> LENGTH: 72
<212> TYPE: PRT
<213> ORGANISM: Artificial Sequence
<220> FEATURE:
<223> OTHER INFORMATION: Synthetic construct

<400> SEQUENCE: 331

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr
65                  70

<210> SEQ ID NO 332
<211> LENGTH: 72
<212> TYPE: PRT
<213> ORGANISM: Artificial Sequence
<220> FEATURE:
<223> OTHER INFORMATION: Synthetic construct

<400> SEQUENCE: 332

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Thr Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr
65                  70

<210> SEQ ID NO 333
<211> LENGTH: 72
<212> TYPE: PRT
<213> ORGANISM: Artificial Sequence
<220> FEATURE:
<223> OTHER INFORMATION: Synthetic construct

<400> SEQUENCE: 333

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Val Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr
65                  70

<210> SEQ ID NO 334
<211> LENGTH: 72
<212> TYPE: PRT
<213> ORGANISM: Artificial Sequence
<220> FEATURE:
<223> OTHER INFORMATION: Synthetic construct

<400> SEQUENCE: 334

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Gln Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr
65                  70

<210> SEQ ID NO 335
<211> LENGTH: 72
<212> TYPE: PRT
<213> ORGANISM: Artificial Sequence
<220> FEATURE:
<223> OTHER INFORMATION: Synthetic construct

<400> SEQUENCE: 335

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Val Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Thr Ser Gly Val Pro Ser Arg Phe Ser Gly
    50                  55                  60

Ser Gly Ser Gly Thr Asp Tyr Thr
65                  70

<210> SEQ ID NO 336
<211> LENGTH: 35
<212> TYPE: PRT
<213> ORGANISM: Artificial Sequence
<220> FEATURE:
<223> OTHER INFORMATION: Synthetic construct

<400> SEQUENCE: 336

Leu Thr Ile Ser Ser Leu Glu Tyr Glu Asp Met Gly Ile Tyr Tyr Cys
1               5                   10                  15

Leu Gln Tyr Asp Glu Phe Pro Tyr Thr Phe Gly Gly Thr Lys Leu
            20                  25                  30

Glu Ile Lys
        35

<210> SEQ ID NO 337
<211> LENGTH: 35
<212> TYPE: PRT
<213> ORGANISM: Artificial Sequence
<220> FEATURE:
<223> OTHER INFORMATION: Synthetic construct

<400> SEQUENCE: 337

Leu Thr Ile Ser Ser Leu Gln Pro Glu Asp Phe Ala Thr Tyr Tyr Cys
1               5                   10                  15

Leu Gln Tyr Asp Glu Phe Pro Tyr Thr Phe Gly Gly Thr Lys Val
            20                  25                  30

Glu Ile Lys
        35

<210> SEQ ID NO 338
<211> LENGTH: 74
<212> TYPE: PRT
<213> ORGANISM: Artificial Sequence
<220> FEATURE:
<223> OTHER INFORMATION: Synthetic contruct

<400> SEQUENCE: 338

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Trp Ile Thr Trp Val Ile Gln Arg Pro Gly Gln Gly Leu Glu Trp Ile
            35                  40                  45

Gly Asp Ile Tyr Cys Gly Ser Asp Thr Met His Tyr Asn Glu Lys Phe
        50                  55                  60

Lys Asn Lys Ala Thr Leu Thr Val Asp Thr
65                  70

<210> SEQ ID NO 339
<211> LENGTH: 74
<212> TYPE: PRT
<213> ORGANISM: Artificial Sequence
<220> FEATURE:
<223> OTHER INFORMATION: Synthetic construct

<400> SEQUENCE: 339

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Thr Trp Val Arg Gln Ala Pro Gly Gln Gly Leu Glu Trp Met
            35                  40                  45

Gly Asp Ile Tyr Ser Gly Ser Asp Thr Met His Tyr Ala Glu Lys Phe
        50                  55                  60

Gln Gly Arg Val Thr Leu Thr Val Asp Thr
65                  70

<210> SEQ ID NO 340
<211> LENGTH: 74
<212> TYPE: PRT
<213> ORGANISM: Artificial Sequence
<220> FEATURE:
<223> OTHER INFORMATION: Synthetic construct

<400> SEQUENCE: 340

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Thr Trp Val Arg Gln Ala Pro Gly Gln Gly Leu Glu Trp Met
            35                  40                  45

Gly Asp Ile Tyr Ser Gly Ser Asp Thr Thr His Tyr Ala Glu Lys Phe
        50                  55                  60

Gln Gly Arg Val Thr Leu Thr Val Asp Thr
65                  70

<210> SEQ ID NO 341
<211> LENGTH: 74
<212> TYPE: PRT
<213> ORGANISM: Artificial Sequence
<220> FEATURE:
<223> OTHER INFORMATION: Synthetic construct

<400> SEQUENCE: 341

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Ser Trp Val Arg Gln Ala Pro Gly Gln Gly Leu Glu Trp Met
        35                  40                  45

Gly Asp Ile Tyr Ser Gly Ser Asp Thr Thr His Tyr Ala Glu Lys Phe
    50                  55                  60

Gln Gly Arg Val Thr Leu Thr Val Asp Thr
65                  70

<210> SEQ ID NO 342
<211> LENGTH: 48
<212> TYPE: PRT
<213> ORGANISM: Artificial Sequence
<220> FEATURE:
<223> OTHER INFORMATION: Synthetic construct

<400> SEQUENCE: 342

Ser Ser Ser Thr Ala Tyr Met Gln Leu Ser Ser Leu Thr Ser Glu Asp
1               5                   10                  15

Ser Ala Val Tyr Tyr Cys Ala Arg Trp Trp Asp Tyr Gly Ser Ser Tyr
            20                  25                  30

Asp Tyr Phe Asp Tyr Trp Gly Gln Gly Thr Thr Leu Thr Val Ser Ser
        35                  40                  45

<210> SEQ ID NO 343
<211> LENGTH: 48
<212> TYPE: PRT
<213> ORGANISM: Artificial Sequence
<220> FEATURE:
<223> OTHER INFORMATION: Synthetic construct

<400> SEQUENCE: 343

Ser Thr Ser Thr Ala Tyr Met Glu Leu Ser Ser Leu Arg Ser Glu Asp
1               5                   10                  15

Thr Ala Val Tyr Tyr Cys Ala Arg Trp Trp Asp Tyr Gly Ser Ser Tyr
            20                  25                  30

Asp Tyr Phe Asp Tyr Trp Gly Gln Gly Thr Leu Val Thr Val Ser Ser
        35                  40                  45

<210> SEQ ID NO 344
<211> LENGTH: 60
<212> TYPE: PRT
<213> ORGANISM: Artificial Sequence
<220> FEATURE:
<223> OTHER INFORMATION: Synthetic construct

<400> SEQUENCE: 344

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

```
Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser
    50                  55                  60

<210> SEQ ID NO 345
<211> LENGTH: 60
<212> TYPE: PRT
<213> ORGANISM: Artificial Sequence
<220> FEATURE:
<223> OTHER INFORMATION: Synthetic construct

<400> SEQUENCE: 345

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser
    50                  55                  60

<210> SEQ ID NO 346
<211> LENGTH: 60
<212> TYPE: PRT
<213> ORGANISM: Artificial Sequence
<220> FEATURE:
<223> OTHER INFORMATION: Synthetic construct

<400> SEQUENCE: 346

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Thr Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser
    50                  55                  60

<210> SEQ ID NO 347
<211> LENGTH: 60
<212> TYPE: PRT
<213> ORGANISM: Artificial Sequence
<220> FEATURE:
<223> OTHER INFORMATION: Synthetic construct

<400> SEQUENCE: 347

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Val Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser
    50                  55                  60

<210> SEQ ID NO 348
<211> LENGTH: 60
<212> TYPE: PRT
<213> ORGANISM: Artificial Sequence
<220> FEATURE:
<223> OTHER INFORMATION: Synthetic construct
```

<400> SEQUENCE: 348

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Gln Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser
    50                  55                  60

<210> SEQ ID NO 349
<211> LENGTH: 60
<212> TYPE: PRT
<213> ORGANISM: Artificial Sequence
<220> FEATURE:
<223> OTHER INFORMATION: Synthetic construct

<400> SEQUENCE: 349

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Val Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Thr Ser Gly Val Pro Ser
    50                  55                  60

<210> SEQ ID NO 350
<211> LENGTH: 47
<212> TYPE: PRT
<213> ORGANISM: Artificial Sequence
<220> FEATURE:
<223> OTHER INFORMATION: Synthetic construct

<400> SEQUENCE: 350

Arg Phe Ser Gly Ser Gly Ser Gly Gln Asp Tyr Ser Leu Thr Ile Ser
1               5                   10                  15

Ser Leu Glu Tyr Glu Asp Met Gly Ile Tyr Tyr Cys Leu Gln Tyr Asp
            20                  25                  30

Glu Phe Pro Tyr Thr Phe Gly Gly Gly Thr Lys Leu Glu Ile Lys
        35                  40                  45

<210> SEQ ID NO 351
<211> LENGTH: 47
<212> TYPE: PRT
<213> ORGANISM: Artificial Sequence
<220> FEATURE:
<223> OTHER INFORMATION: Synthetic construct

<400> SEQUENCE: 351

Arg Phe Ser Gly Ser Gly Ser Gly Thr Asp Tyr Thr Leu Thr Ile Ser
1               5                   10                  15

Ser Leu Gln Pro Glu Asp Phe Ala Thr Tyr Tyr Cys Leu Gln Tyr Asp
            20                  25                  30

Glu Phe Pro Tyr Thr Phe Gly Gly Gly Thr Lys Val Glu Ile Lys
        35                  40                  45

<210> SEQ ID NO 352
<211> LENGTH: 60
<212> TYPE: PRT

<213> ORGANISM: Artificial Sequence
<220> FEATURE:
<223> OTHER INFORMATION: Synthetic construct

<400> SEQUENCE: 352

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Ile Gln Arg Pro Gly Gln Gly Leu Glu Trp Ile
        35                  40                  45

Gly Asp Ile Tyr Cys Gly Ser Asp Thr Met His Tyr
    50                  55                  60

<210> SEQ ID NO 353
<211> LENGTH: 60
<212> TYPE: PRT
<213> ORGANISM: Artificial Sequence
<220> FEATURE:
<223> OTHER INFORMATION: Synthetic construct

<400> SEQUENCE: 353

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Gly Leu Glu Trp Met
        35                  40                  45

Gly Asp Ile Tyr Ser Gly Ser Asp Thr Met His Tyr
    50                  55                  60

<210> SEQ ID NO 354
<211> LENGTH: 60
<212> TYPE: PRT
<213> ORGANISM: Artificial Sequence
<220> FEATURE:
<223> OTHER INFORMATION: Synthetic construct

<400> SEQUENCE: 354

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Gly Leu Glu Trp Met
        35                  40                  45

Gly Asp Ile Tyr Ser Gly Ser Asp Thr Thr His Tyr
    50                  55                  60

<210> SEQ ID NO 355
<211> LENGTH: 60
<212> TYPE: PRT
<213> ORGANISM: Artificial Sequence
<220> FEATURE:
<223> OTHER INFORMATION: Synthetic construct

<400> SEQUENCE: 355

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

```
Trp Ile Ser Trp Val Arg Gln Ala Pro Gly Gln Gly Leu Glu Trp Met
        35                  40                  45

Gly Asp Ile Tyr Ser Gly Ser Asp Thr Thr His Tyr
    50                  55                  60

<210> SEQ ID NO 356
<211> LENGTH: 60
<212> TYPE: PRT
<213> ORGANISM: Artificial Sequence
<220> FEATURE:
<223> OTHER INFORMATION: Synthetic construct

<400> SEQUENCE: 356

Asn Glu Lys Phe Lys Asn Lys Ala Thr Leu Thr Val Asp Thr Ser Ser
1               5                   10                  15

Ser Thr Ala Tyr Met Gln Leu Ser Ser Leu Thr Ser Glu Asp Ser Ala
            20                  25                  30

Val Tyr Tyr Cys Ala Arg Trp Trp Asp Tyr Gly Ser Ser Tyr Asp Tyr
        35                  40                  45

Phe Asp Tyr Trp Gly Gln Gly Thr Thr Leu Thr Val
    50                  55                  60

<210> SEQ ID NO 357
<211> LENGTH: 60
<212> TYPE: PRT
<213> ORGANISM: Artificial Sequence
<220> FEATURE:
<223> OTHER INFORMATION: Synthetic construct

<400> SEQUENCE: 357

Ala Glu Lys Phe Gln Gly Arg Val Thr Leu Thr Val Asp Thr Ser Thr
1               5                   10                  15

Ser Thr Ala Tyr Met Glu Leu Ser Ser Leu Arg Ser Glu Asp Thr Ala
            20                  25                  30

Val Tyr Tyr Cys Ala Arg Trp Trp Asp Tyr Gly Ser Ser Tyr Asp Tyr
        35                  40                  45

Phe Asp Tyr Trp Gly Gln Gly Thr Thr Val Thr Val
    50                  55                  60

<210> SEQ ID NO 358
<211> LENGTH: 56
<212> TYPE: PRT
<213> ORGANISM: Artificial Sequence
<220> FEATURE:
<223> OTHER INFORMATION: Synthetic construct

<400> SEQUENCE: 358

Asp Ile Gln Met Thr Gln Ala Ser Ser Ser Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr
    50                  55

<210> SEQ ID NO 359
<211> LENGTH: 56
<212> TYPE: PRT
<213> ORGANISM: Artificial Sequence
<220> FEATURE:
```

<223> OTHER INFORMATION: Synthetic construct

<400> SEQUENCE: 359

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr
    50                  55

<210> SEQ ID NO 360
<211> LENGTH: 56
<212> TYPE: PRT
<213> ORGANISM: Artificial Sequence
<220> FEATURE:
<223> OTHER INFORMATION: Synthetic construct

<400> SEQUENCE: 360

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Val Pro Lys Leu Leu Ile
        35                  40                  45

Ser Gly Ala Thr Ser Leu Glu Thr
    50                  55

<210> SEQ ID NO 361
<211> LENGTH: 51
<212> TYPE: PRT
<213> ORGANISM: Artificial Sequence
<220> FEATURE:
<223> OTHER INFORMATION: Synthetic construct

<400> SEQUENCE: 361

Gly Val Pro Ser Arg Phe Ser Gly Ser Gly Ser Gly Lys Asp Tyr Thr
1               5                   10                  15

Leu Ser Ile Thr Ser Leu Gln Thr Glu Asp Val Ala Thr Tyr Tyr Cys
            20                  25                  30

Gln Gln Tyr Trp Ser Ser Pro Leu Thr Phe Gly Ala Gly Thr Lys Leu
        35                  40                  45

Glu Leu Lys
    50

<210> SEQ ID NO 362
<211> LENGTH: 51
<212> TYPE: PRT
<213> ORGANISM: Artificial Sequence
<220> FEATURE:
<223> OTHER INFORMATION: Synthetic construct

<400> SEQUENCE: 362

Gly Val Pro Ser Arg Phe Ser Gly Ser Gly Ser Gly Thr Asp Tyr Thr
1               5                   10                  15

Phe Thr Ile Ser Ser Leu Gln Pro Glu Asp Ile Ala Thr Tyr Tyr Cys
            20                  25                  30

Gln Gln Tyr Trp Ser Ser Pro Leu Thr Phe Gly Gly Gly Thr Lys Val
        35                  40                  45

```
Glu Ile Lys
    50

<210> SEQ ID NO 363
<211> LENGTH: 51
<212> TYPE: PRT
<213> ORGANISM: Artificial Sequence
<220> FEATURE:
<223> OTHER INFORMATION: Synthetic construct

<400> SEQUENCE: 363

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Val Ala Thr Tyr Tyr Cys
            20                  25                  30

Gln Gln Tyr Trp Ser Ser Pro Leu Thr Phe Gly Gly Gly Thr Lys Val
        35                  40                  45

Glu Ile Lys
    50

<210> SEQ ID NO 364
<211> LENGTH: 49
<212> TYPE: PRT
<213> ORGANISM: Artificial Sequence
<220> FEATURE:
<223> OTHER INFORMATION: Synthetic construct

<400> SEQUENCE: 364

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Asn Tyr
            20                  25                  30

Gly Val His Trp Val Arg Gln Pro Pro Gly Lys Gly Leu Glu Trp Leu
        35                  40                  45

Val

<210> SEQ ID NO 365
<211> LENGTH: 49
<212> TYPE: PRT
<213> ORGANISM: Artificial Sequence
<220> FEATURE:
<223> OTHER INFORMATION: Synthetic construct

<400> SEQUENCE: 365

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asn Tyr
            20                  25                  30

Gly Val His Trp Val Arg Gln Pro Pro Gly Lys Gly Leu Glu Trp Ile
        35                  40                  45

Val

<210> SEQ ID NO 366
<211> LENGTH: 49
<212> TYPE: PRT
<213> ORGANISM: Artificial Sequence
<220> FEATURE:
<223> OTHER INFORMATION: Synthetic construct

<400> SEQUENCE: 366

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Phe Ser Leu Ser Asn Tyr
            20                  25                  30

Gly Val His Trp Val Arg Gln Pro Pro Gly Lys Gly Leu Glu Trp Ile
            35                  40                  45

Gly

<210> SEQ ID NO 367
<211> LENGTH: 48
<212> TYPE: PRT
<213> ORGANISM: Artificial Sequence
<220> FEATURE:
<223> OTHER INFORMATION: Synthetic construct

<400> SEQUENCE: 367

Leu Ile Trp Ser Asp Gly Ser Thr Thr Tyr Asn Ser Ala Leu Lys Ser
1               5                   10                  15

Arg Leu Ser Ile Ser Lys Asp Asn Ser Lys Ser Gln Val Phe Leu Lys
            20                  25                  30

Met Asn Ser Leu Gln Thr Gly Asp Thr Ala Met Tyr Tyr Cys Ala Arg
            35                  40                  45

<210> SEQ ID NO 368
<211> LENGTH: 48
<212> TYPE: PRT
<213> ORGANISM: Artificial Sequence
<220> FEATURE:
<223> OTHER INFORMATION: Synthetic construct

<400> SEQUENCE: 368

Leu Ile Trp Ser Asp Gly Ser Thr Thr Tyr Asn Ser Ala Leu Lys Ser
1               5                   10                  15

Arg Val Thr Ile Ser Lys Asp Thr Ser Lys Asn Gln Val Ser Leu Lys
            20                  25                  30

Leu Ser Ser Val Thr Ala Ala Asp Thr Ala Val Tyr Tyr Cys Ala Arg
            35                  40                  45

<210> SEQ ID NO 369
<211> LENGTH: 48
<212> TYPE: PRT
<213> ORGANISM: Artificial Sequence
<220> FEATURE:
<223> OTHER INFORMATION: Synthetic construct

<400> SEQUENCE: 369

Leu Ile Trp Ser Asp Gly Ser Thr Thr Tyr Ala Ser Ala Leu Lys Ser
1               5                   10                  15

Arg Val Thr Ile Ser Lys Asp Thr Ser Lys Asn Gln Val Ser Leu Lys
            20                  25                  30

Leu Ser Ser Val Thr Ala Ala Asp Thr Ala Val Tyr Tyr Cys Ala Arg
            35                  40                  45

<210> SEQ ID NO 370
<211> LENGTH: 48
<212> TYPE: PRT
<213> ORGANISM: Artificial Sequence
<220> FEATURE:
<223> OTHER INFORMATION: Synthetic construct

<400> SEQUENCE: 370

Leu Ile Trp Ser Asp Gly Ser Thr Thr Tyr Asn Pro Ser Leu Lys Ser
1               5                   10                  15
```

```
Arg Val Thr Ile Ser Lys Asp Thr Ser Lys Asn Gln Val Ser Leu Lys
            20                  25                  30

Leu Ser Ser Val Thr Ala Ala Asp Thr Ala Val Tyr Tyr Cys Ala Arg
            35                  40                  45

<210> SEQ ID NO 371
<211> LENGTH: 48
<212> TYPE: PRT
<213> ORGANISM: Artificial Sequence
<220> FEATURE:
<223> OTHER INFORMATION: Synthetic construct

<400> SEQUENCE: 371

Leu Ile Trp Ser Glu Gly Ser Thr Thr Tyr Ala Ser Ala Leu Lys Ser
1               5                   10                  15

Arg Val Thr Ile Ser Lys Asp Thr Ser Lys Asn Gln Val Ser Leu Lys
            20                  25                  30

Leu Ser Ser Val Thr Ala Ala Asp Thr Ala Val Tyr Tyr Cys Ala Arg
            35                  40                  45

<210> SEQ ID NO 372
<211> LENGTH: 25
<212> TYPE: PRT
<213> ORGANISM: Artificial Sequence
<220> FEATURE:
<223> OTHER INFORMATION: Synthetic construct

<400> SEQUENCE: 372

His Pro Tyr Asp Asp Tyr Ser Gly Tyr Tyr Tyr Thr Met Asp Tyr Trp
1               5                   10                  15

Gly Gln Gly Thr Ser Val Thr Val Ser
            20                  25

<210> SEQ ID NO 373
<211> LENGTH: 25
<212> TYPE: PRT
<213> ORGANISM: Artificial Sequence
<220> FEATURE:
<223> OTHER INFORMATION: Synthetic construct

<400> SEQUENCE: 373

His Pro Tyr Asp Asp Tyr Ser Gly Tyr Tyr Tyr Thr Met Asp Tyr Trp
1               5                   10                  15

Gly Gln Gly Thr Leu Val Thr Val Ser
            20                  25

<210> SEQ ID NO 374
<211> LENGTH: 17
<212> TYPE: PRT
<213> ORGANISM: Artificial Sequence
<220> FEATURE:
<223> OTHER INFORMATION: Synthetic construct

<400> SEQUENCE: 374

Asp Ile Tyr Ser Gly Ser Asp Thr Thr His Tyr Ala Glu Lys Phe Gln
1               5                   10                  15

Gly
```

ANTIBODIES FOR SIGLEC-15 AND METHODS OF USE THEREOF

CROSS-REFERENCE TO RELATED APPLICATIONS

This application is a 371 application of International Application No. PCT/US2017/052714, which claims benefit of and priority to U.S. Provisional Patent Applications 62/500,578 filed on May 3, 2017, 62/451,271 filed on Jan. 27, 2017, and 62/397,794 filed on Sep. 21, 2016, all of which are incorporate by reference in their entireties where permissible.

REFERENCE TO SEQUENCE LISTING

The Sequence Listing submitted on Feb. 7, 2020, as a text file named "064467_003_replacement_seqlisting" and having a size of 206 KB is hereby incorporated by reference pursuant to 37 C.F.R. § 1.52(e)(5).

FIELD OF THE INVENTION

The invention is generally related to the field of immunomodulation, and more particularly to compositions and methods for modulating Siglec-15 and signaling initiated therefrom.

BACKGROUND OF THE INVENTION

Sialic acid-binding Ig-like lectins ("Siglecs") are members of the Ig superfamily. These type 1 transmembrane proteins include a sialic acid-binding N-terminal V-set domain, variable numbers of C2-set Ig domains, a transmembrane region and a cytosolic tail, and bind specifically to sialic acids attached to the terminal regions of cell-surface glycoconjugates. Two primary subsets of Siglecs have been identified: one subset includes CD-33 and CD33-related Siglecs such as siglecs-5, -6, -7, -8, -9, 10, -11, -14 and -16 in humans, and CD33 and siglecs-E, -F, -G and -H in mice (Crocker and Redelinghuys, *Biochemical Society Transactions*, 36 (6):1467-1471 (2008)). The second subset is made of Sn (sialoadhesin) (siglec-1), CD22 (siglec-2), MAG (myelin-associated glycoprotein) (siglec-4) and siglec-15, all of which are well-conserved in mammals. With the exception of MAG, which is expressed in the nervous system, Siglecs are differentially expressed on various subsets of leucocytes where they play a role in the positive and negative regulation of immune and inflammatory responses (McMillan and Crocker, *Carbohydr. Res.*, 343:2050-2056 (2008) and Crocker, et al., *Nat. Rev. Immunol.*, 7:255 266 (2007)).

Research indicates that many Siglecs are expressed on immune cells and have immunosuppressive properties. However, a subset of Siglecs, including Siglec-15, are associated with the signal adaptor molecule DNAX activation protein of 12 kDa (DAP12), which has an immunoreceptor tyrosine-based activation motif (ITAM) and is involved in immune cell activation (Takamiya, et al., *Glycobiology*, 23(2):178-87 (2013)). Siglec-15 is specifically expressed on macrophages and dendritic cells of spleen and lymph nodes and preferentially recognizes the sTn antigen (Angata, et al., *Glycobiology*, 17(8):838-46 (2007) Epub 2007 May 4.). H157 cells overexpressing sTn (H157/ST6GalNAc-1) stimulated secretion of TGF-β from Siglec-15-expressing M-CSF-induced macrophages (Takamiya, et al., *Glycobiology*, 23(2):178-87 (2013)). Additionally, secretion of TGF-β from THP-1 cells is enhanced by the overexpression of Siglec-15 in THP-1 cells and ST6GalNAc-I (the enzyme responsible for the biosynthesis of the sTn structure) in H157 cells, respectively, in a manner that may be at least partially dependent on Siglec-15-DAP12 induced signaling as well as one or more DAP12-independent, Sky-dependent, or possibly Sky-independent pathways. TGF-β is produced by both tumor cells and tumor-infiltrating leukocytes including macrophages and contributes to tumor progression and metastasis, by, for example, enhancing tumor cell invasion and by inhibiting the function of immune cells (Flavell, et al., *Nat Rev Immunol*, 10:554-567 (2010)). These data may indicate that the recognition of tumor-associated sTn by Siglec-15 activates the DAP12-Syk pathway of signal transduction pathway that enhances TGF-β production from the myeloid cells, and eventually modifies the tumor microenvironment that is advantageous to the tumor cells (Takamiya, et al., *Glycobiology*, 23(2): 178-87 (2013)). Siglec 15 has a typical ITIM domain (SN YENL (SEQ ID NO: 191)) in its cytoplasmic domain. Its function remains to be characterized.

However, there remains a need for tools and techniques for modulating Siglec-15 and signaling initiated therefrom.

Thus, it is an object of the invention to provide compositions for detecting and modulating Siglec-15.

It is also an object of the invention to provide methods of modulating Siglec-15 and signaling initiated therefrom to increase an immune response or reduce or reverse immune suppression.

It is also an object of the invention to provide method of modulating osteoclast differentiation to reduce bone resorption or increase bone formation.

It is also an object of the invention to provide methods of treating diseases and disorders by modulating Siglec-15 and signaling initiated therefrom.

SUMMARY OF THE INVENTION

Siglec-15 binding molecules are provided. The molecules are typically an antibody or antigen binding fragment thereof that immunospecifically binds to Siglec-15. For example, in some embodiments the Siglec-15 binding molecule includes six complementarity determining regions (CDRs), wherein the CDRs includes the three light chain CDRs of a polypeptide selected from the group consisting of SEQ ID NO:3, 4, 5, 6, 7, 8, 9, 10, 11, 12, 96, 97, 98, 99, 100, 101, 102, 103, 104, 105, 106, or 107, or a variant thereof having at least 50%, 60%, 70%, 80%, 85%, 90%, 95%, 99%, or more sequence identity to SEQ ID NO: 3, 4, 5, 6, 7, 8, 9, 10, 11, 12, 96, 97, 98, 99, 100, 101, 102, 103, 104, 105, 106, or 107, and the three heavy chain CDRs of a polypeptide selected from the group consisting of SEQ ID NO:13, 14, 15, 16, 17, 18, 19, 20, 21, 22, 23, 108, 109, 110, 111, 112, 113, 114, 115, 116, 117, 118, or 119, or a variant thereof including at least 50%, 60%, 70%, 80%, 85%, 90%, 95%, 99%, or more sequence identity to SEQ ID NO:13, 14, 15, 16, 17, 18, 19, 20, 21, 22, 23, 108, 109, 110, 111, 112, 113, 114, 115, 116, 117, 118, or 119, and wherein the Siglec-15 binding molecule binds to Siglec-15. In some embodiments, the Siglec-15 binding molecule includes the light and/or heavy chain CDRs of one of the mouse anti-human monoclonal antibody referred to herein as 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A.

In some embodiments, the Siglec-15 binding molecule includes a light chain variable region including the amino acid sequence a polypeptide selected from the group consisting of SEQ ID NO:3, 4, 5, 6, 7, 8, 9, 10, 11, 12, 96, 97, 98, 99, 100, 101, 102, 103, 104, 105, 106, or 107, or a variant thereof having at least 50%, 60%, 70%, 80%, 85%, 90%, 95%, 99%, or more sequence identity to SEQ ID NO:3, 4, 5, 6, 7, 8, 9, 10, 11, 12, 96, 97, 98, 99, 100, 101, 102, 103, 104, 105, 106, or 107, and/or a heavy chain variable region comprising the amino acid sequence a polypeptide selected from the group consisting of SEQ ID NO:13, 14, 15, 16, 17, 18, 19, 20, 21, 22, 23, 108, 109, 110, 111, 112, 113, 114, 115, 116, 117, 118, or 119, or a variant thereof having at least 50%, 60%, 70%, 80%, 85%, 90%, 95%, 99%, or more sequence identity to SEQ ID NO: 13, 14, 15, 16, 17, 18, 19, 20, 21, 22, 23, 108, 109, 110, 111, 112, 113, 114, 115, 116, 117, 118, or 119. In some embodiments, the Siglec-15 binding molecule includes the light and/or heavy chain variable region(s) of one of the mouse anti-human monoclonal antibodies referred to herein as 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A.

In some embodiments, Siglec-15 binding molecule binds to Siglec-15
  (I) arrayed on the surface of a cell (preferably a live cell);
  (II) arrayed on the surface of a cell (preferably a live cell) at an endogenous concentration;
  (III) arrayed on the surface of a live cell, and modulates binding between Siglec-15 (e.g., SEQ ID NO: 1, SEQ ID NO:2, etc.) and Neu5Acα2-6GalNAcα, LRRC4C, an Siglec-15-counter-receptor (S15-CR), or a combination thereof;
  (IV) arrayed on the surface of a live cell, and reduces, prevents, or inhibits TGF-β secretion;
  (V) arrayed on the surface of a live cell; or
  (IV) a combination thereof.

Cells that endogenously express Siglec-15 include macrophages, dendritic cells, and cancer cells.

The Siglec-15 binding molecule can include one or more constant domains from an immunoglobulin constant region (Fc). The constant domains can be human constant domains, for example, IgA, IgD, IgE, IgG or IgM domains. In particular embodiments, the human IgG constant domains are IgG1, IgG2, IgG3, or IgG4 domains. The Siglec-15 binding molecule can be detectably labeled or comprises a conjugated toxin, drug, receptor, enzyme, receptor ligand. The Siglec-15 binding molecule can be a monoclonal antibody, a human antibody, a chimeric antibody, a humanized antibody, or a single chain antibody, or an antigen binding fragment thereof. The antibody can be a monospecific, bispecific, trispecific, or multispecific antibody.

One embodiment provides a humanized anti-SIGLEC-15 antibody having one or more variable light chains having an amino acid sequence of SEQ ID NO: 195, 197, 199, 201, or 209.

Another embodiment provides a humanized anti-SIGLEC-15 antibody having one or more variable heavy chains having an amino acid sequence of SEQ ID NO:203, 206, or 207.

Another embodiment provides a humanized anti-SIGLEC-15 antibody having one or more variable light chains having an amino acid sequence of SEQ ID NO: 195, 197, 199, 201, or 209 and one or more variable heavy chains having an amino acid sequence of SEQ ID NO:203, 206, and 207.

One embodiment provides and antibody having light chain CDRs of SEQ ID NO:209, 195, 207, 199, or 201 and heavy chain CDRs of SEQ ID NO:203, 206, or 207 and combinations thereof.

Another embodiment provides an antibody having a light chain amino acid sequence according to SEQ ID NO:209, 210 or 211.

Another embodiment provides and antibody having a heavy chain amino sequence according to SEQ ID NO: 212, 213, 215, or 216.

Another embodiment provides an antibody having a light chain amino acid sequence according to SEQ ID NO:209, 210 or 211 and a heavy chain amino sequence according to SEQ ID NO: 212, 213, 215, or 216.

In some embodiments, the Siglec-15 binding molecule is modified so that the molecule will exhibit diminished or no Fc receptor (FcR) binding activity. In some embodiments, the Siglec-15 binding molecule is modified to exhibit enhanced antibody-dependent cell-mediated cytotoxicity (ADCC) or complement dependent cytotoxicity (CDC) activities.

One embodiment provides a fusion protein that is at least 50, 60, 70, 80, 85, 90, 95, 96, 97, 98, 99, or 100% identical to SEQ ID NO:193 or 194.

Pharmaceutical compositions including a Siglec-15 binding molecule and a physiologically acceptable carrier or excipient are also provided. In some embodiments, the Siglec-15 binding molecule reduces or prevents binding of Siglec-15 to a ligand and/or counter-receptor thereof, reduces or prevents Siglec-15-mediated signal transduction, or a combination thereof. The ligand can be a sialylated glycoprotein. The ligand can be expressed on the surface of a tumor cell. The Examples below show that Leucine-rich repeat-containing protein 4C (LRRC4C) is a ligand for Siglec-15, and may be expressed by cancer cells. A Siglec-15-counter-receptor may also be expressed on the surface of immune cells such as T cells, which when engaged by Siglec-15, leads to T cell inhibition.

Methods of treating subjects in need thereof are also provided. Typically, the methods include administering to the subject an effective amount of a Siglec-15 binding molecule, for example, in a pharmaceutical composition.

In some embodiments, antagonistic Siglec-15 binding molecule increases an immune response, retards or prevents tumor growth, inhibits tumor-mediated immune suppression, eliminates tumors, depletes or blocks the activity of tumor-associated macrophages (TAMs) so as to alter their activity, decreases TAM-mediated immune suppression, reduces or reverses T cell suppression, increases T cell proliferation, or a combination thereof. In some embodiments, the cancer or tumor includes macrophages expressing Siglec-15. The Siglec-15 binding molecule can be administered to the subject in an effective amount to reduce expression and/or secretion of TGF-β by the macrophages. In some embodiments, the subject has cancer or an infectious disease. The cancer can include cells expressing or over-expressing a ligand of Siglec-15.

Methods of reducing osteoclast differentiation, reducing bone resorption, increasing bone formation, and combinations thereof by administering subject an effective amount of antagonistic Siglec-15 binding molecules are also provided.

In some embodiments, agonistic Siglec-15 binding molecule decrease an immune response, increases or enhances T cell suppression, increases T cell proliferation, or a combination thereof. The Siglec-15 binding molecule can be administered to the subject in an effective amount to increase expression and/or secretion of TGF-β by the macrophages. In some embodiments, the subject has inflammation, an autoimmune disease, or is a transplant recipient.

Some embodiments include administering to the subject a second therapeutic agent.

Methods of detection and diagnosis are also provided. Any of the methods of detection and diagnosis can be couple to a method of treatment. For example, a method of detection or diagnosis of a disease, disorder or infection can include (a) assaying the expression of Siglec-15 in cells or in a tissue sample of a subject using the disclosed Siglec-15 binding molecules and (b) comparing the level of the Siglec-15 with a control level, wherein an increase in the assayed level of Siglec-15 compared to the control level is indicative of the disease, disorder or infection.

A method for monitoring the progression of a disease, disorder or infection can include (a) assaying the expression of Siglec-15 in cells or in a tissue sample of a subject obtained at a first time point and later time point using the disclosed Siglec-15 binding molecules; and (b) comparing the level of expression of Siglec-15 in the cells or in the tissue sample of the subject at the first and later times points, wherein an increase in the assayed level of Siglec-15 at the later time point compared to the first time point is indicative of the progression of disease, disorder or infection.

A method for monitoring a response to a treatment is provided that includes (a) assaying the expression of Siglec-15 in cells or in a tissue sample of a subject prior to and after the treatment using the disclosed Siglec-15 binding molecules; and (b) comparing the level of Siglec-15 over time, whereby a decrease in the assayed level of Siglec-15 after treatment compared to the level of Siglec-15 prior to treatment is indicative of a favorable response to the treatment.

BRIEF DESCRIPTION OF THE DRAWINGS

Figure 2A:
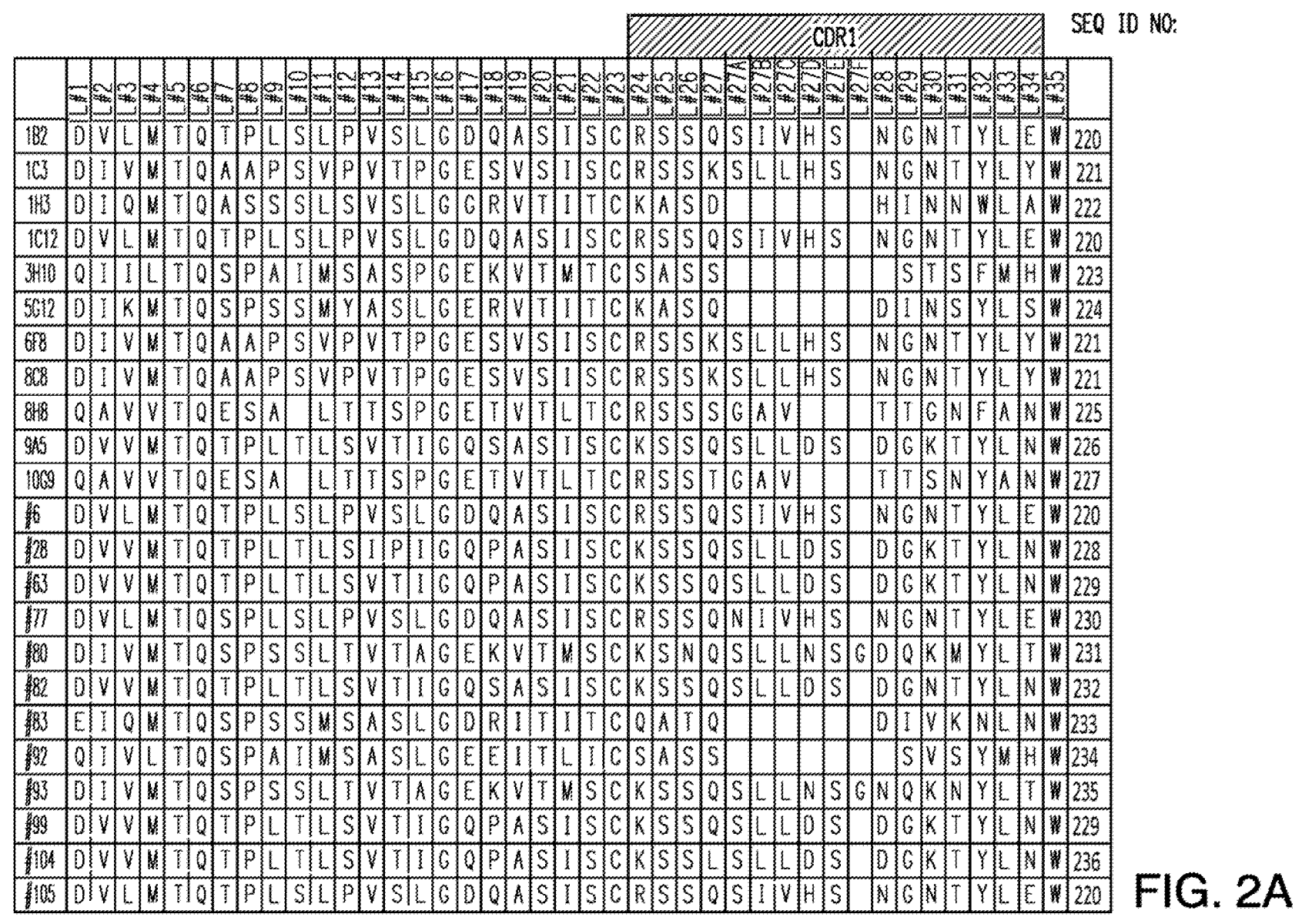
Figure 2C:
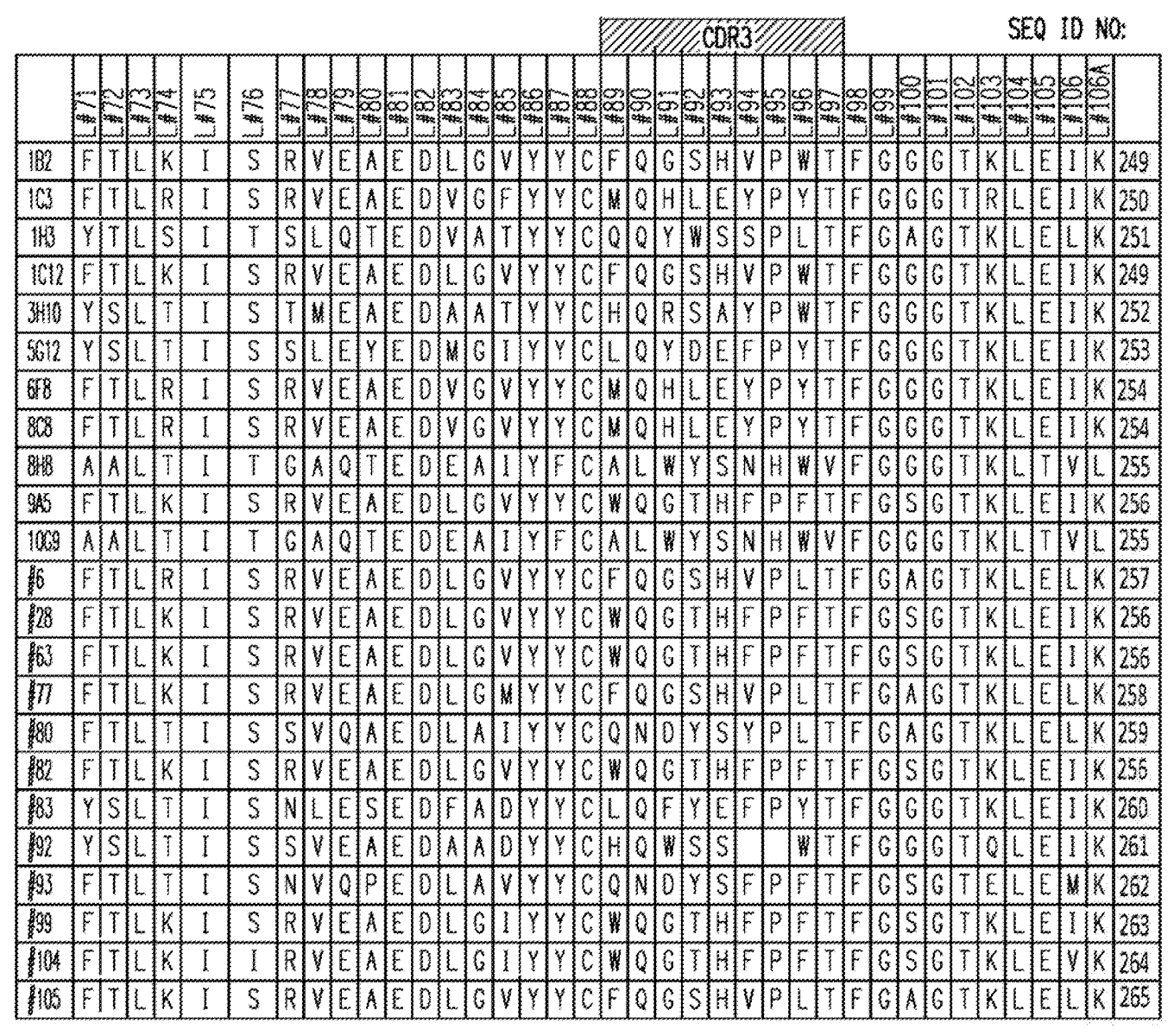

FIGS. 2A-2C are alignments showing the sequences light chain variable region of 1B2, 1C3, 1H3, 1C12, 3H10, 5G12, 6F8, 8C8, 8H8, 9A5, 10G9, 6A, 28A, 63A, 77A, 80A, 82B, 83B, 92A, 93B, 99B, 104B, and 105A and highlighting the first (2A), second (2B), and third (2C) complementarity determining regions (CDRs).

Figure 3A:
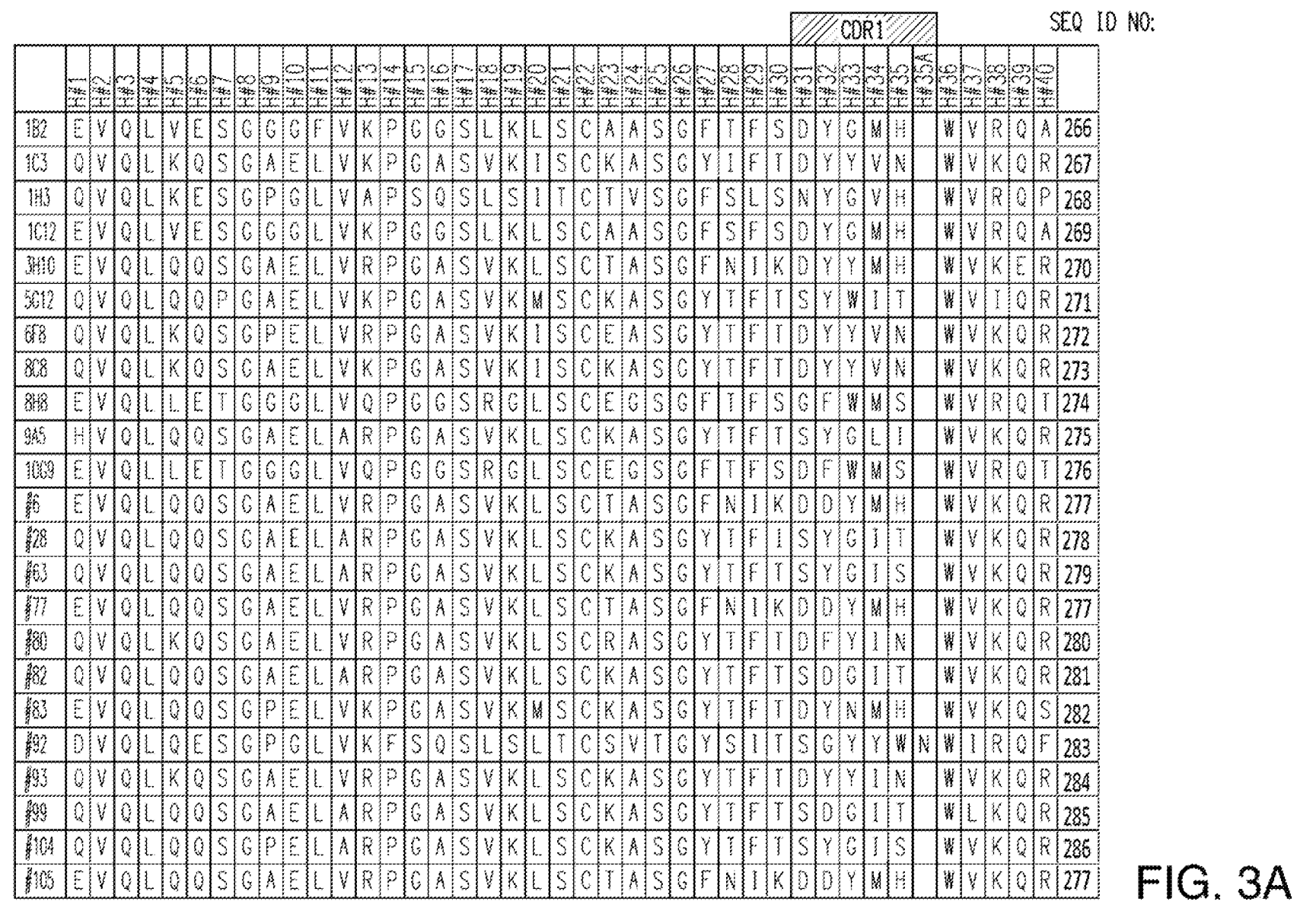
Figure 3B:
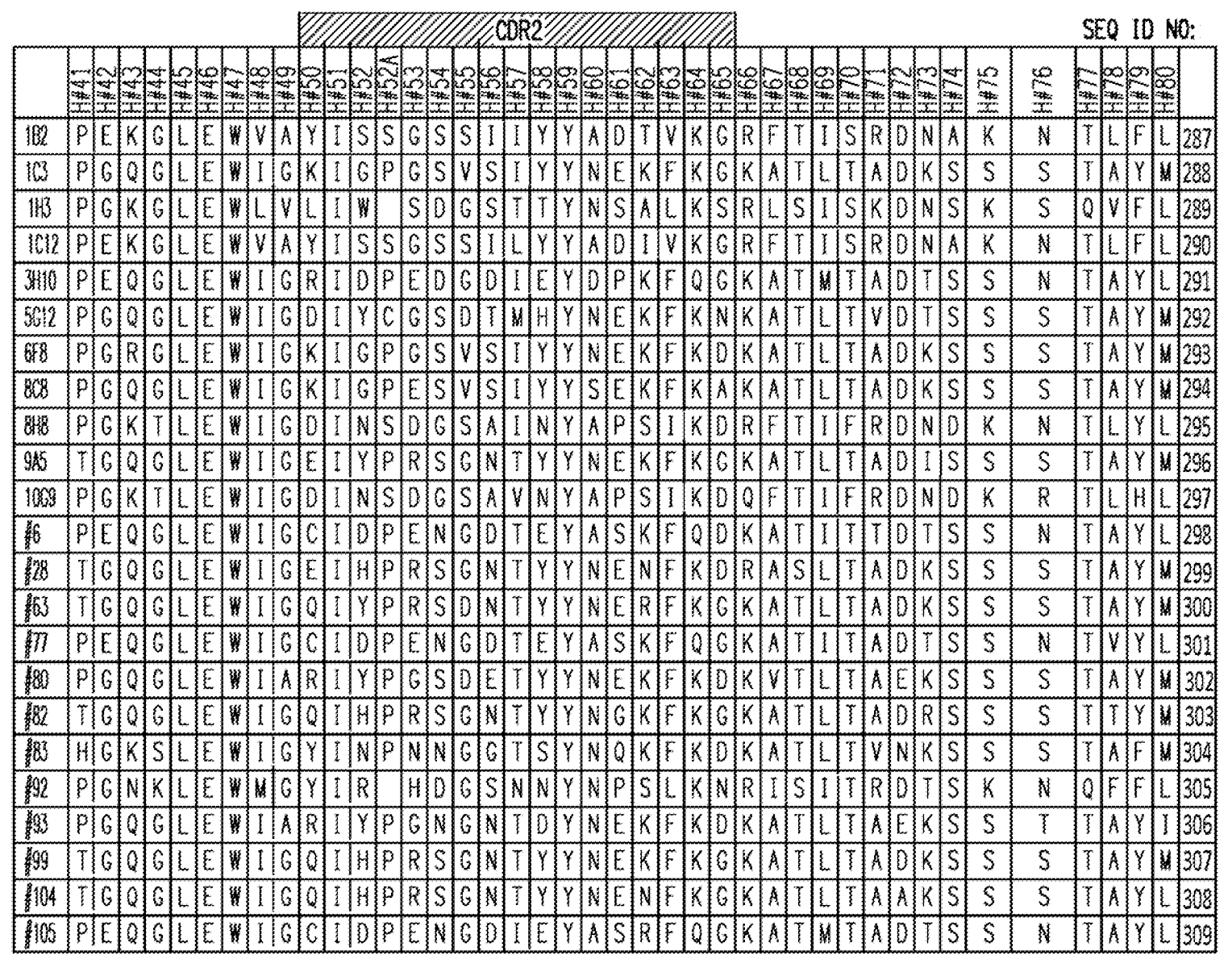
Figure 3C:
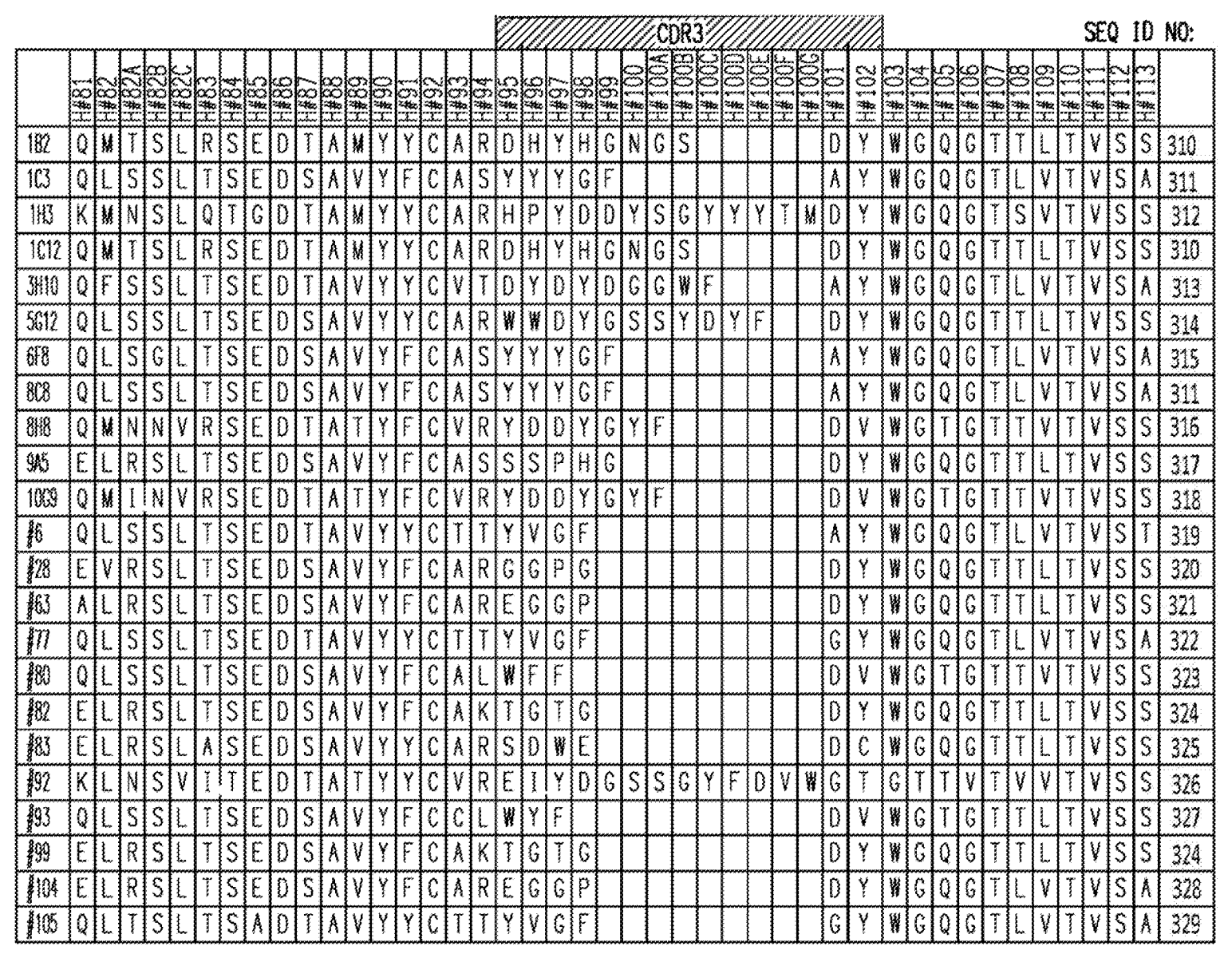

FIGS. 3A-3C are alignments showing the sequences heavy chain variable region of 1B2, 1C3, 1H3, 1C12, 3H10, 5G12, 6F8, 8C8, 8H8, 9A5, 10G9, 6A, 28A, 63A, 77A, 80A, 82B, 83B, 92A, 93B, 99B, 104B, and 105A and highlighting the first (3A), second (3B), and third (3C) complementarity determining regions (CDRs).

FIGS. 8D-8G are bar graphs showing S15 mAb reversal of hS15.hG1-mediated suppression of Human T Cells as the % divided of CD8+ T cells (FIGS. 8D and 8F) and CD4+ T cells (FIGS. 8E and 8G) for assays carried out with hS15.hG1, for antibodies 1B2, 1C3, 1C12 1H3, 3H10, 5G12, 6F8, 8C8, 8H8, 9A5, and 10G9 (FIGS. 8D and 12E) and 6A (NC6), 28A (NC28), 63A (NC63), 77A (NC77), 80A (NC80), 82B (NC82), 83B (NC83), 92A (NC92), 93B (NC93), 99B (NC99), 104B (NC104), and 105A (NC105) (FIGS. 8F and 8G).

MACS column sorting (left panel) or attachment to plastic in serum free media (right panel).

Figure 11:
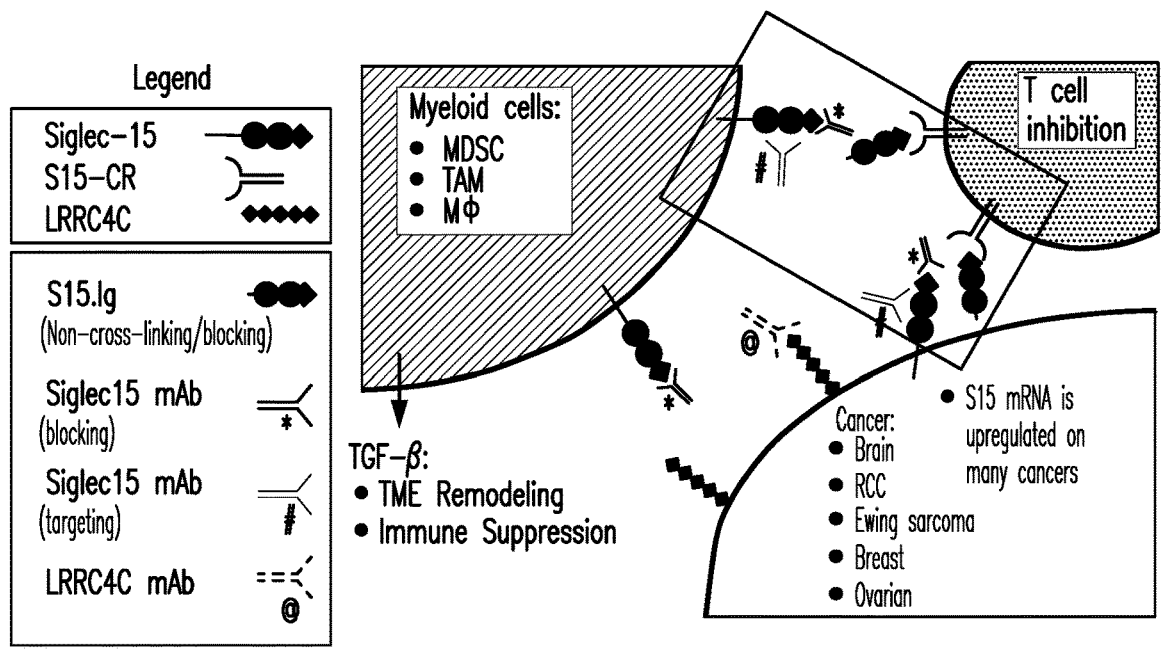

FIG. 11 is a diagram illustrating a model for Siglec-15 negative regulation of immunity in the tumor microenvironment (TME) including Siglec-15 (S15):Siglec-15-Counter-receptor (S15-CR) >>>T cell directed inhibition of proliferation and cytokines, and/or Siglec-15:LRRC4C >>> Macrophage production of TGF-β and immune suppression in the TME. The diagram shows myeloid cell, T cell, and cancer cell expression of Siglec-15 and ligands thereof, and signaling therefrom, as well as interactions between the molecules anti-Siglec-15 (blocking and targeting) and LRRC4C antibodies and Siglec-15 fusion proteins (non-crosslinking/blocking).

Figures 12A, 12B:
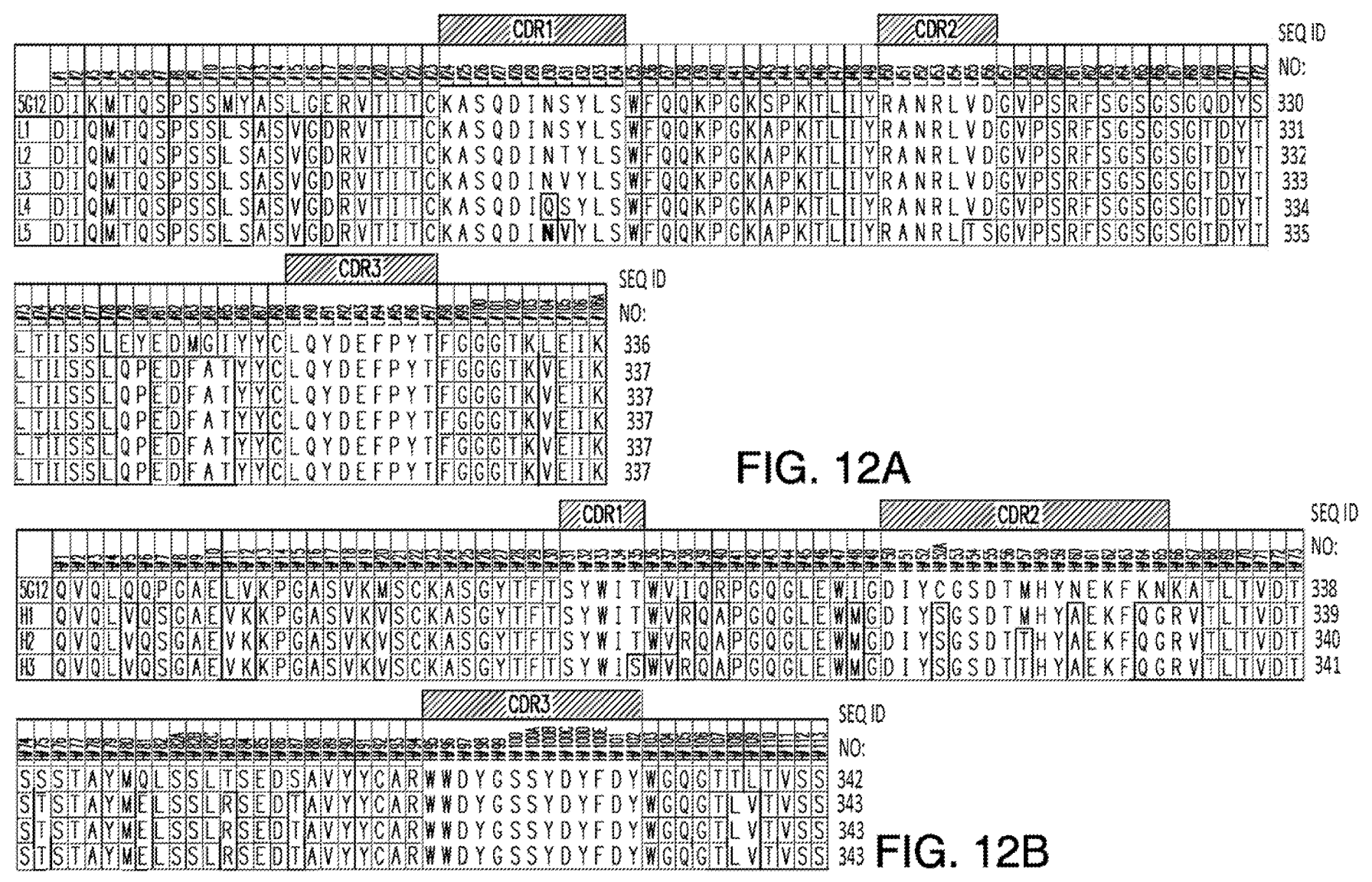

FIG. 12A is a table showing the amino acid sequence of humanized 5G12 variable light chains L1-L5. FIG. 12B is a table showing the amino acid sequence of humanized 5G12 variable heavy chains H1-H3.

FIG. 13A shows the sequence alignment of humanized 5G12 variable light chains VL1-V15 against murine VL. FIG. 13B shows the sequence alignment of humanized 5G12 variable heavy chains VH1-VH3.

Figure 14A:
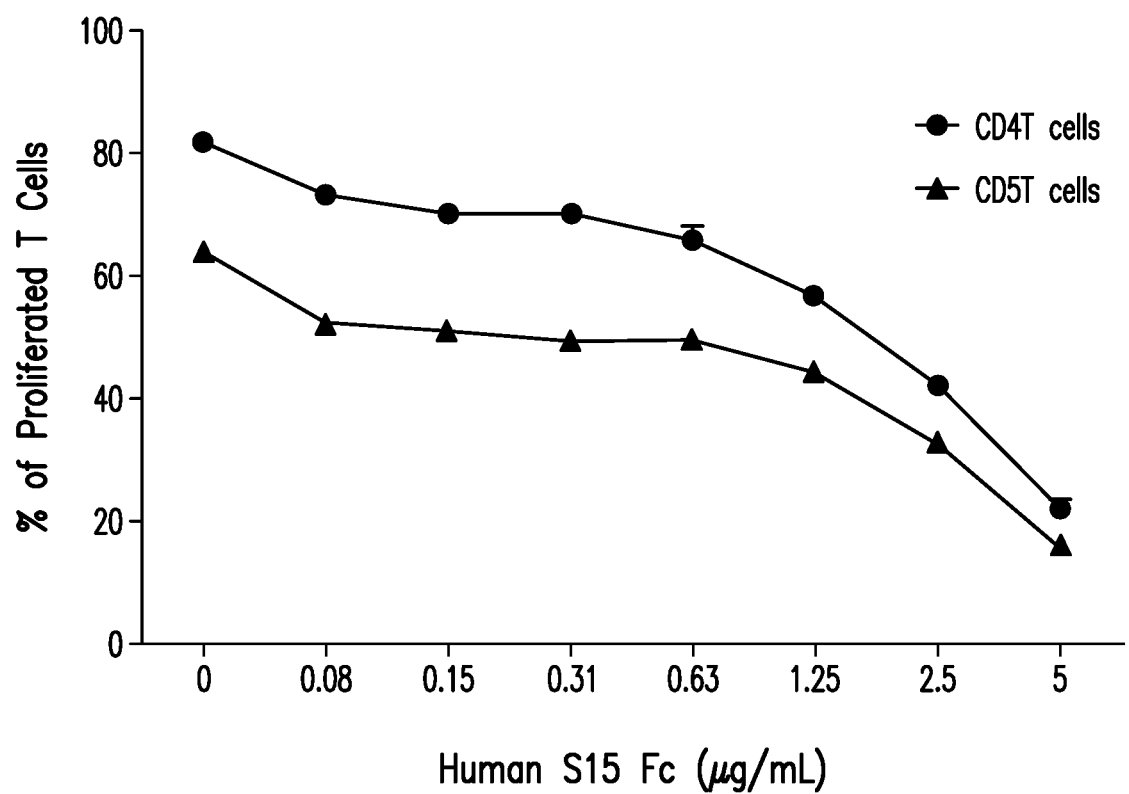
Figure 14B:
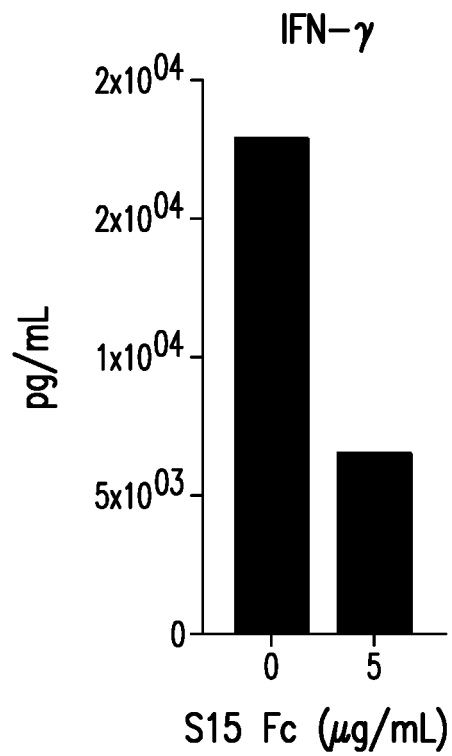
Figure 14C:
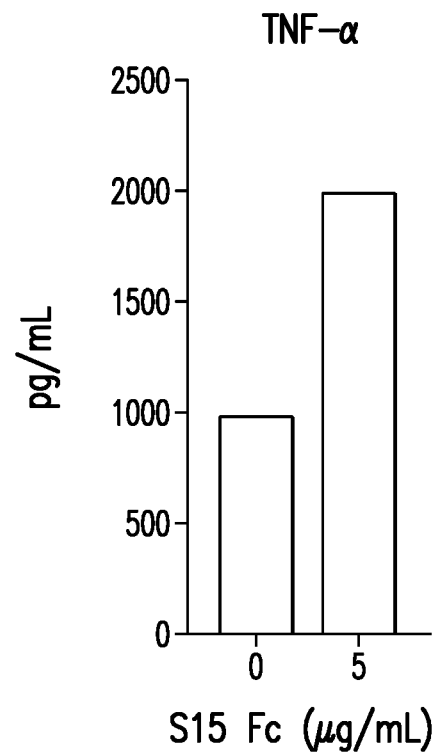
Figure 14D:
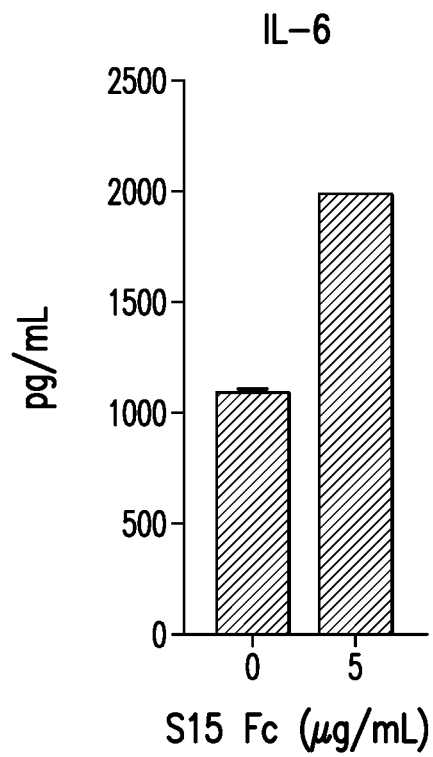

FIG. 14A is a line graph of % Proliferation of T cells versuse human S15 Fc (μg/mL) showing % proliferation of T cells is reduced as concentration of S15 Fc increases. FIG. 14B is a bar graph of pg/ml of IFN-γ in conditioned supernatants from cells treated with 0 or 5 μg/mL of S15 Fc. FIG. 14C is a bar graph of pg/ml of TNF-α in conditioned supernatants from cells treated with 0 or 5 μg/mL of S15 Fc. FIG. 14D is a bar graph of pg/ml of IL-6 in conditioned supernatants from cells treated with 0 or 5 μg/mL of S15 Fc.

Figure 15A:
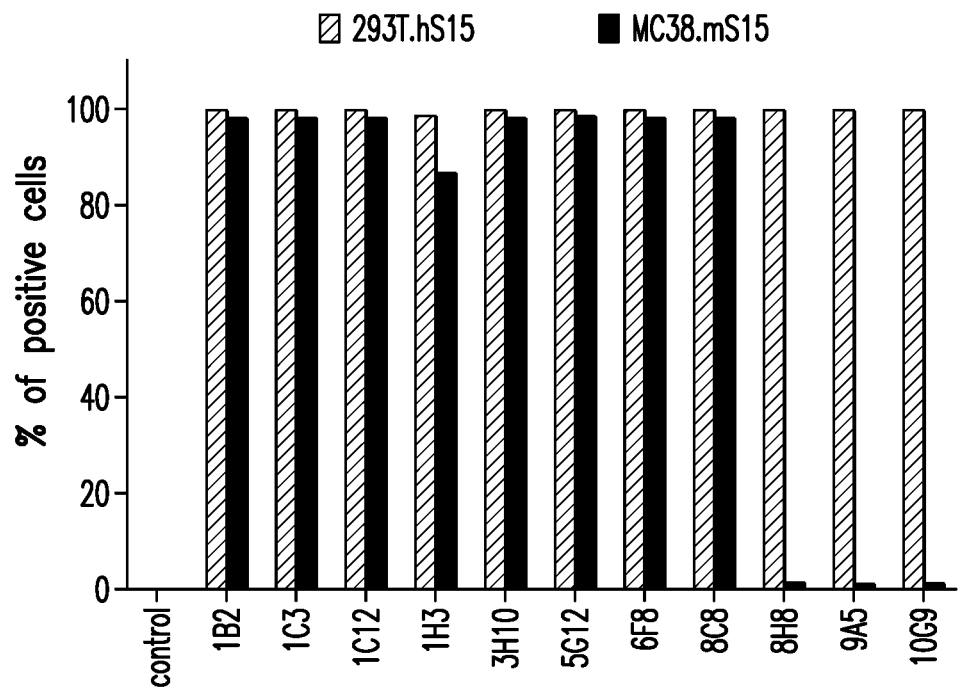
Figure 15B:
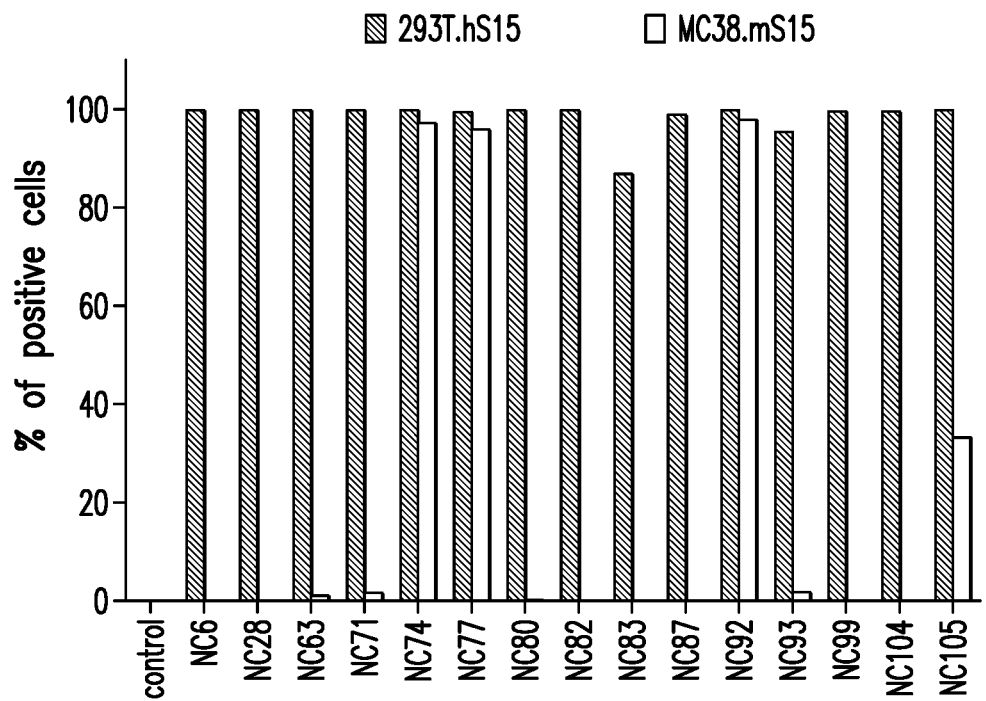

FIGS. 15A and 15B are bar graphs showing the percentage of positive cells for binding of S15 mAb purified from hybridoma to cells expressing human S15 or mouse S15.

Figure 16A:
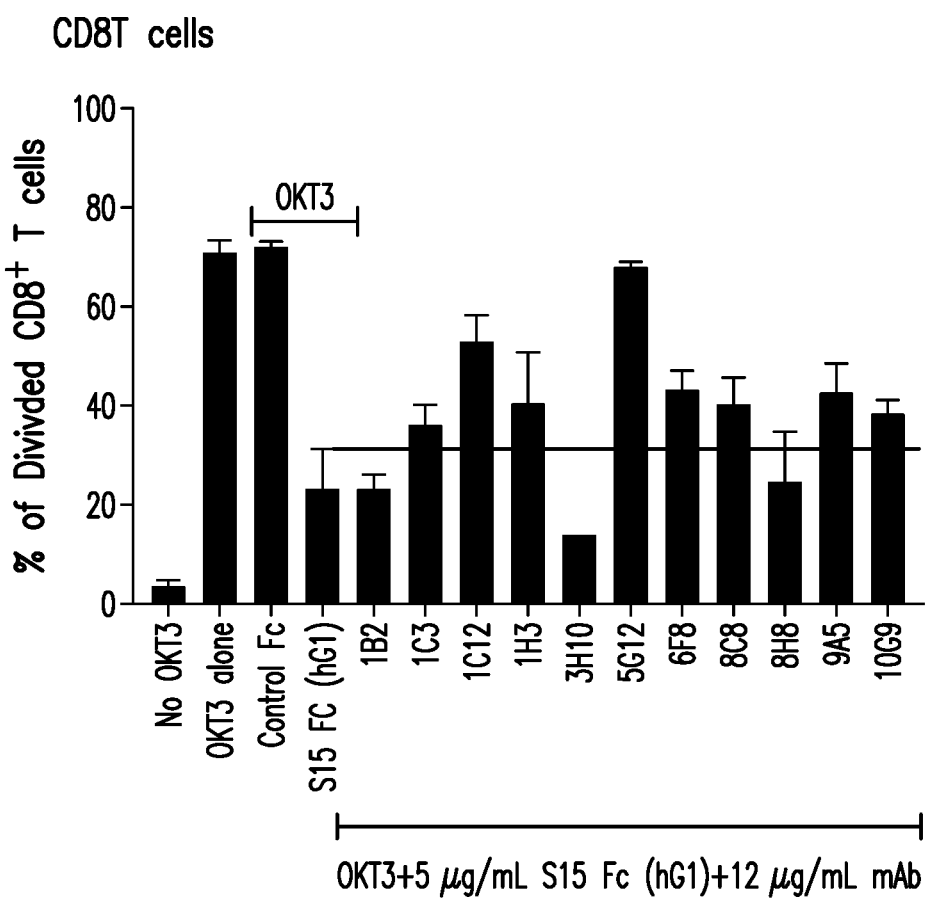
Figure 16B:
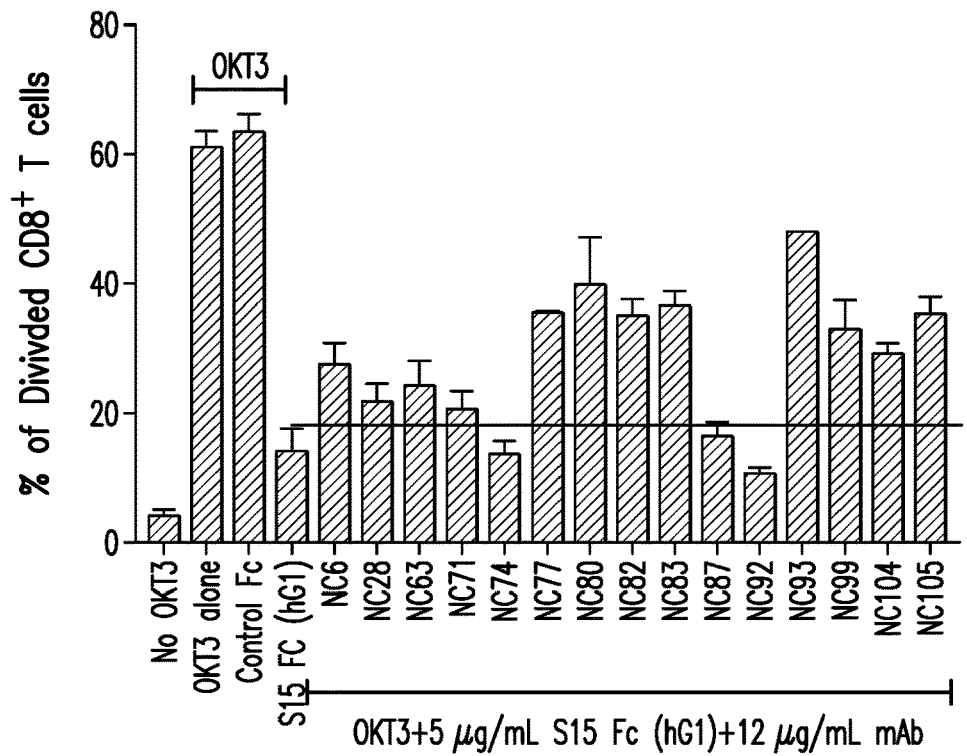
Figure 16C:
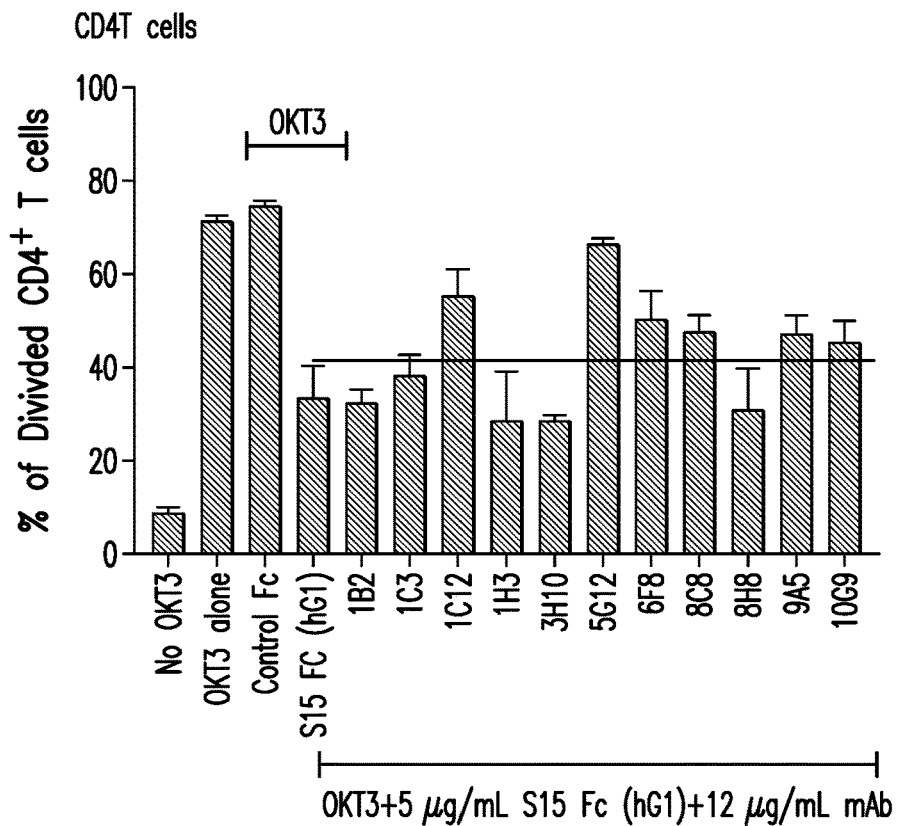
Figure 16D:
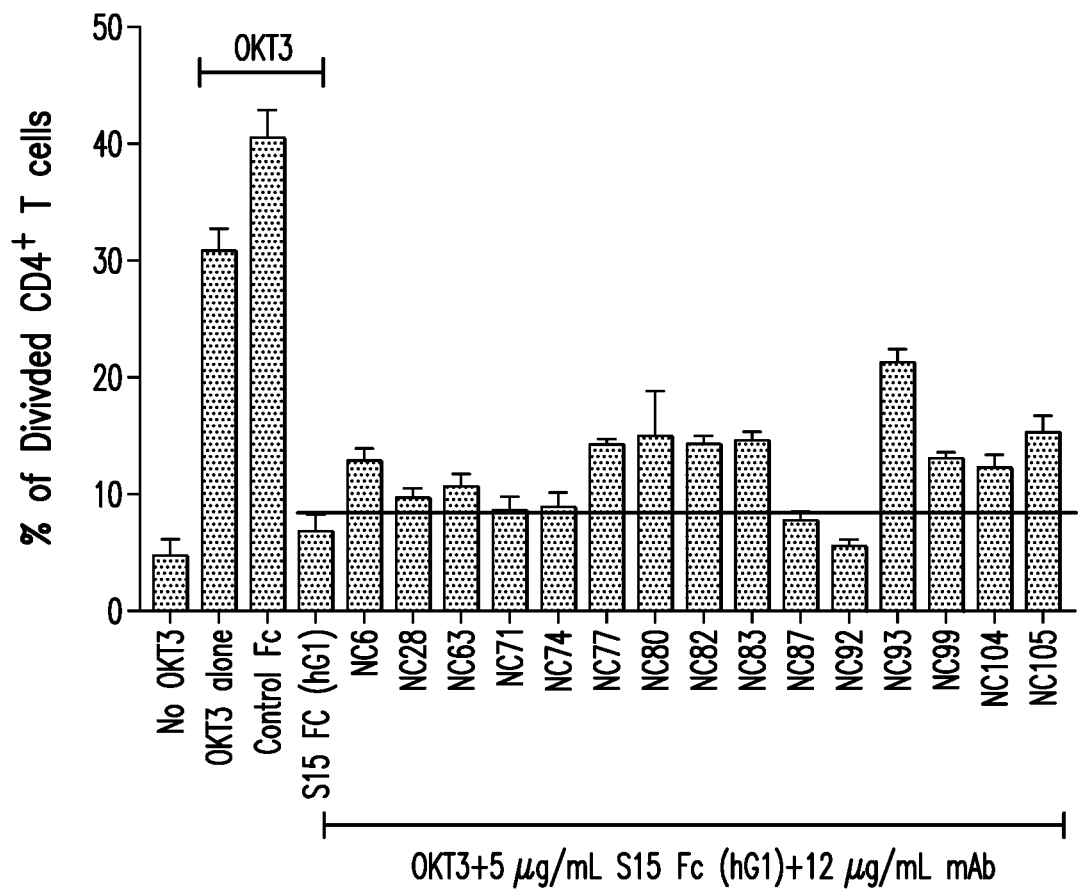

FIGS. 16A and 16B are bar graphs of percent of Divided CD8+ T cells treated with the indicated antibodies. FIGS. 16C and 16D are bar graphs of the percentage of Divided CD4+ T cells treated with the indicated antibodies.

Figure 17A:
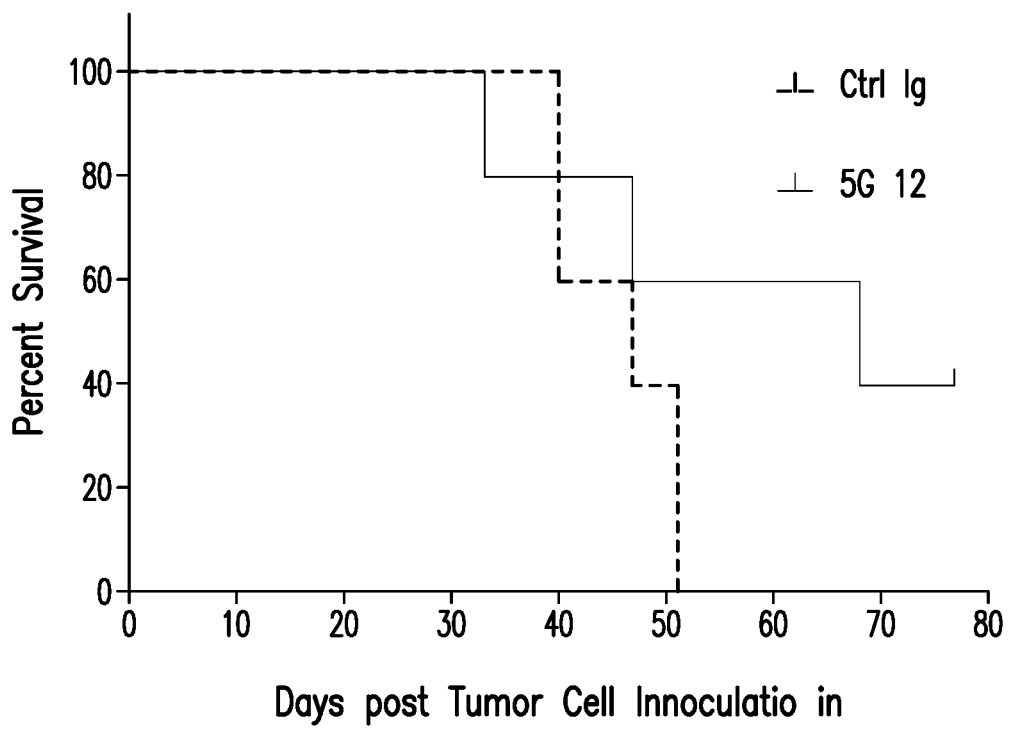
Figure 17B:
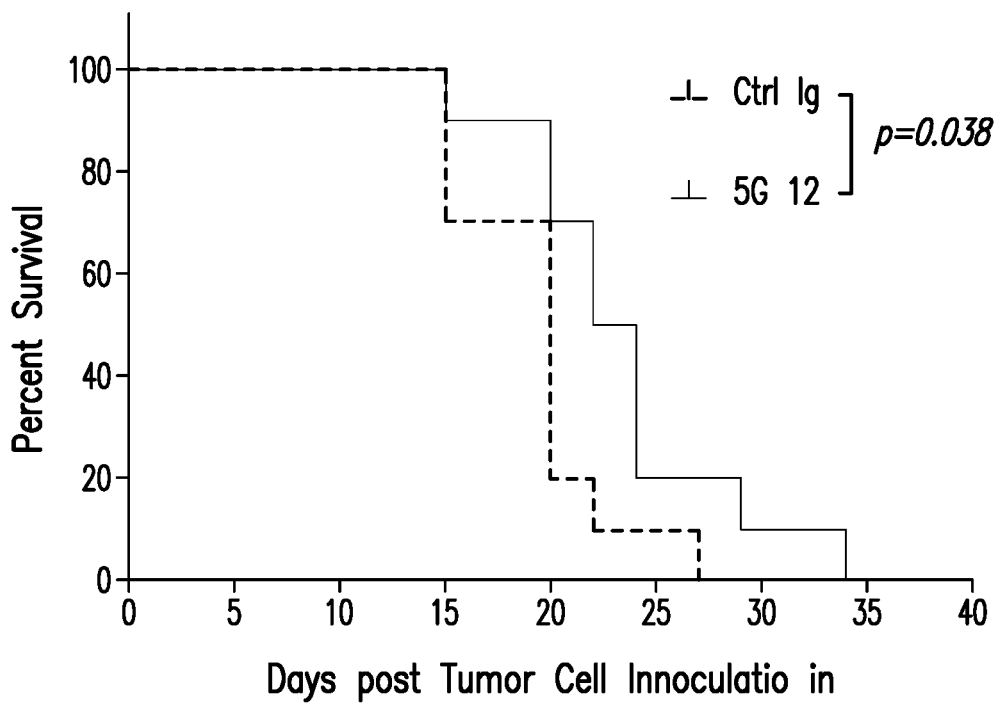
Figure 17C:
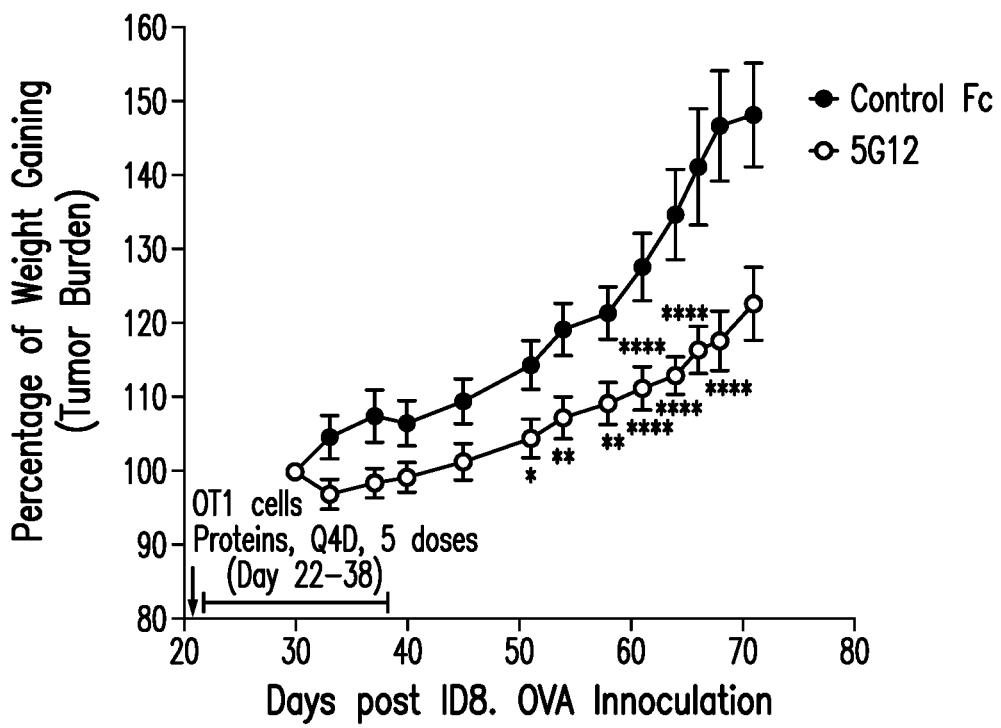

FIGS. 17A and 17B are line graphs showing percent survival versus days post tumor cell inoculation in animals treated with 5G12. FIG. 17C is a line graph of percentage of weight gain versus days post ID8.OVA inoculation.

Figure 18:
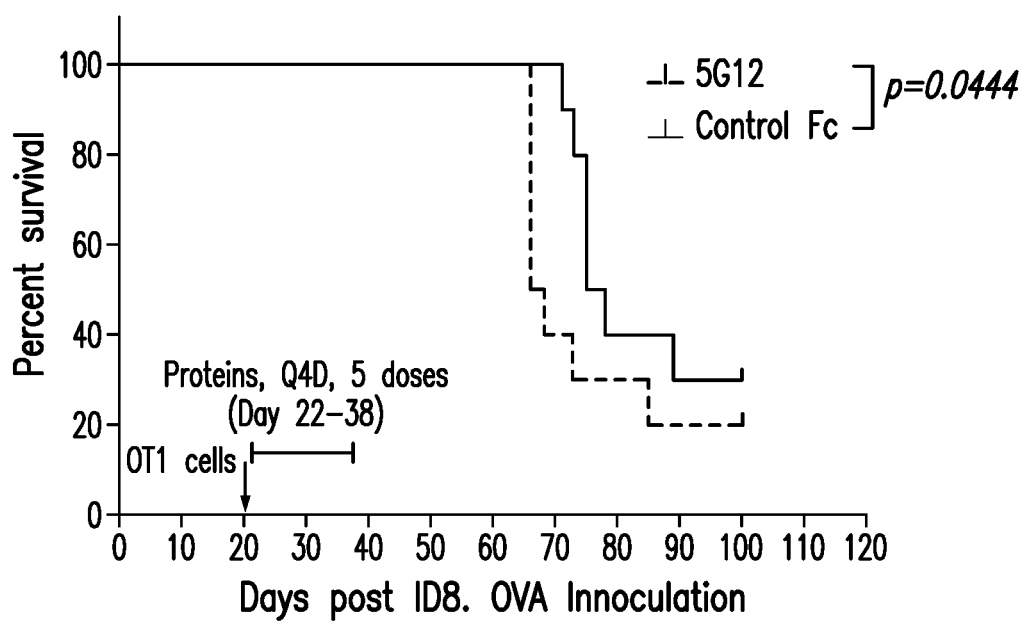

FIG. 18 is a line graph of percentage of weight gain versus days post ID8.OVA inoculation.

Figure 19A:
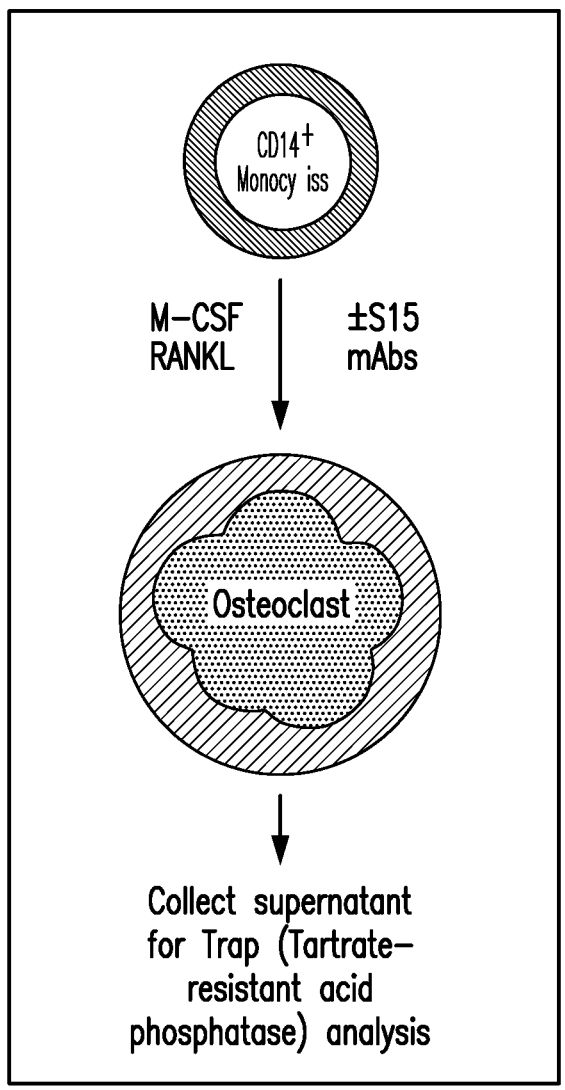
Figure 19B:
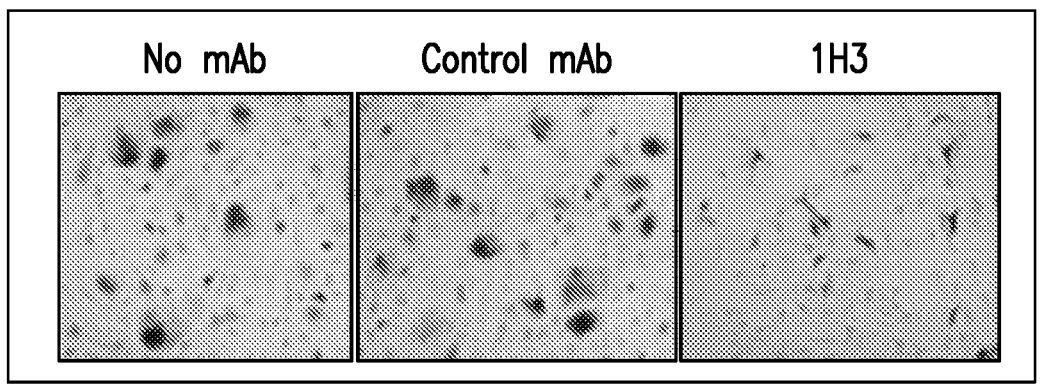
Figure 19C:
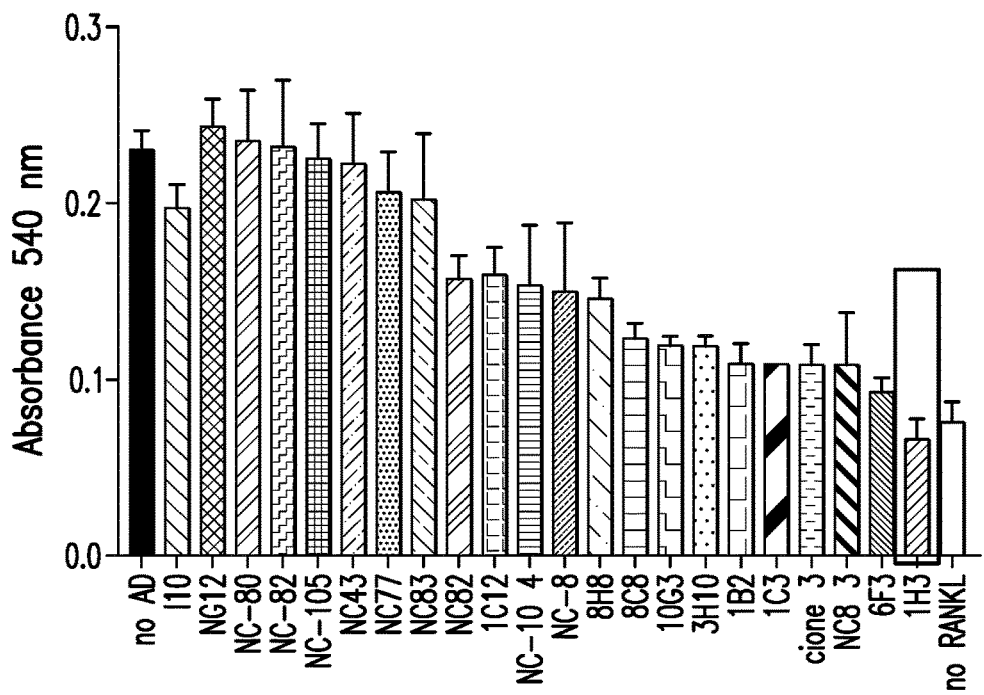

FIG. 19A is a schematic diagram showing human CD14+ monocytes harvested from human PBMC using Mitenyi monocyte magnetic beads followed by seeding in 96-well plates in the presence of human M-CSF and human RANKL together with indicated antibodies. FIG. 19B is a micrograph showing osteoclasts treated as indicated with 1H3. FIG. 19C is a bar graph of absorbance 540 nm of supernatant collected after 7 days for Tartrate-resistance acid phosphatase analysis.

Figure 20:
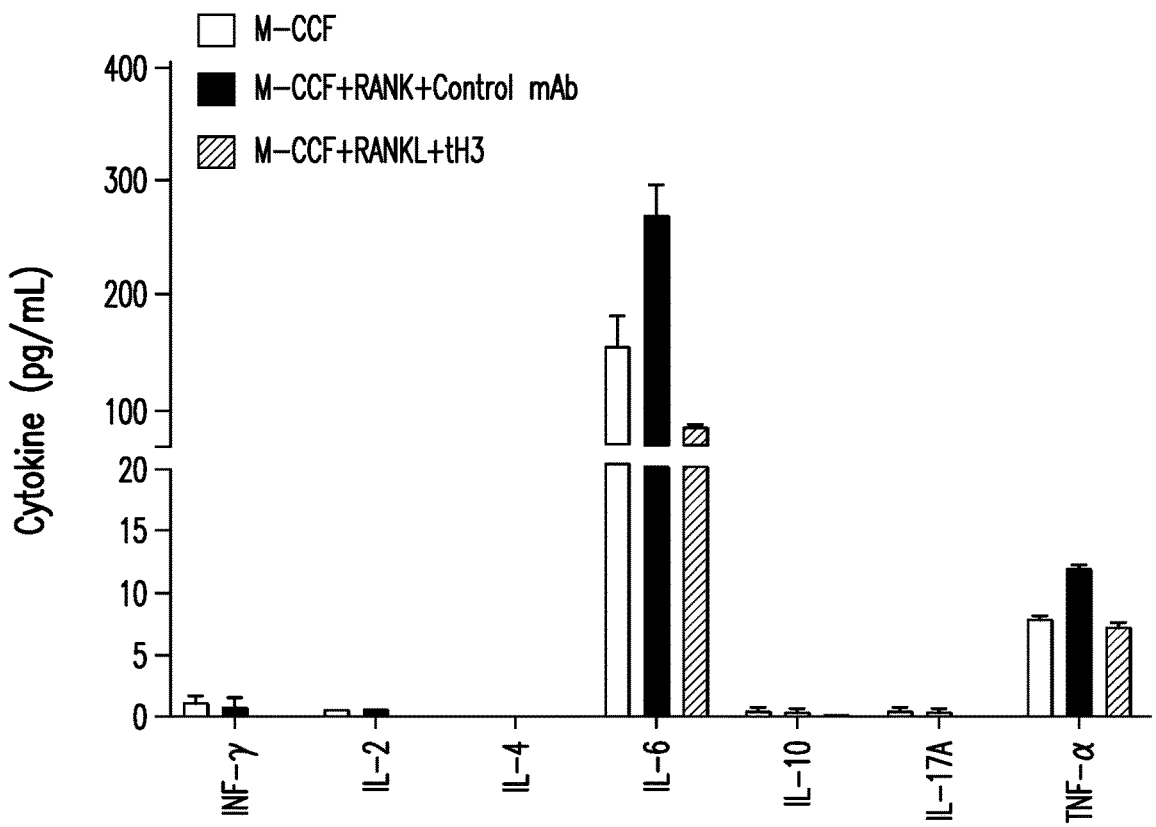

FIG. 20 is a bar graph showing cytokine (pg/mL) for INF-γ, IL-2, IL-4, IL-6, IL-10, IL-17A, and TNF-α.

Figure 21:
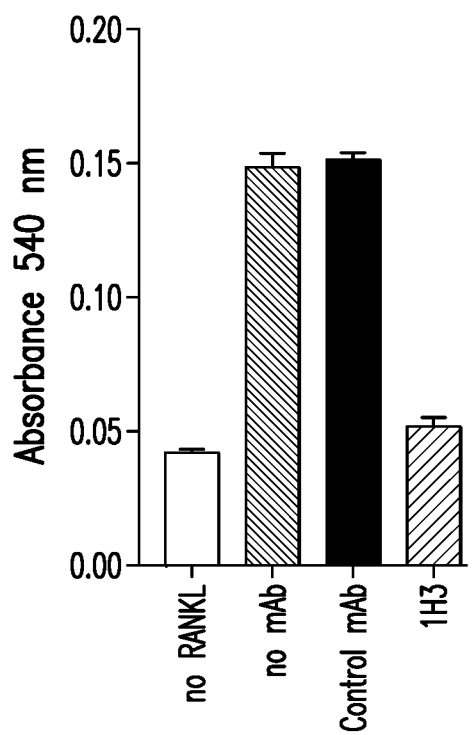

FIG. 21 is a bar graph of absorbance 540 nm mouse RAW 264.7 macrophage cells cultured in the presence of RANKL together with the indicated antibodies.

Figure 22:
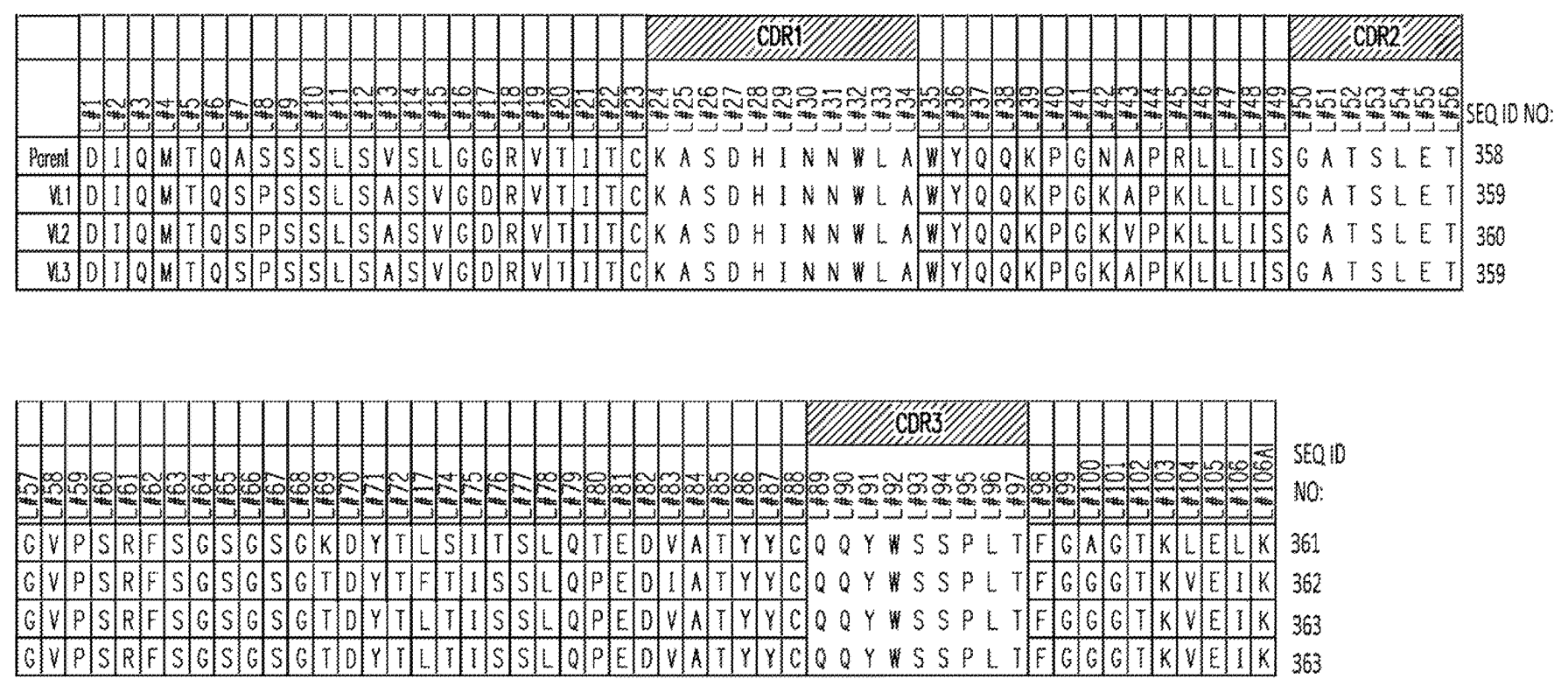

FIG. 22 shows a comparison of exemplary humanized amino acid sequences of 1H3 variable light chains.

FIG. 23 shows a comparison of exemplary humanized amino acid sequences of 1H3 variable heavy chains.

Figure 24:
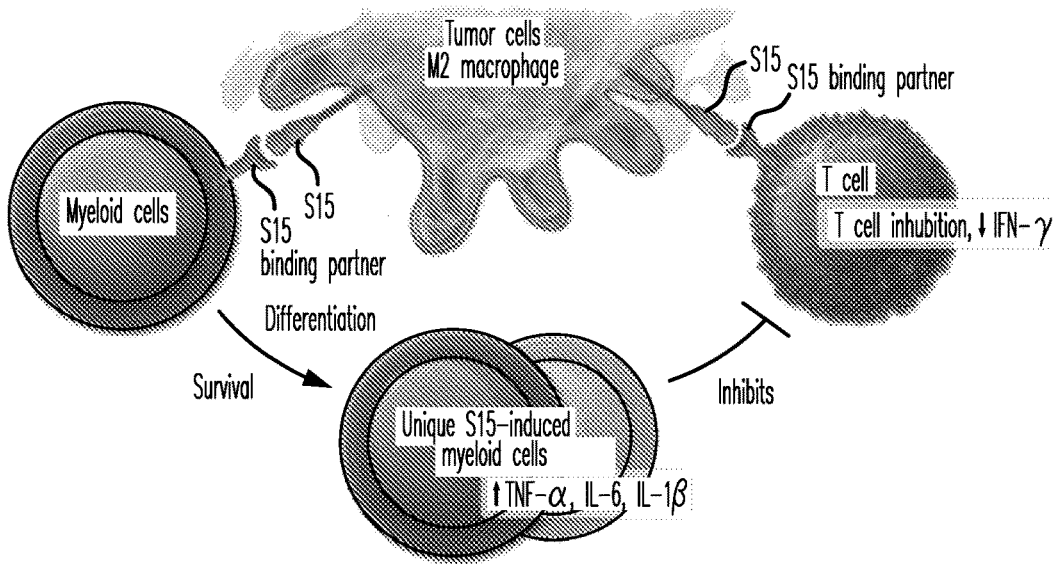

FIG. 24 is an illustration of a proposed mode of action for Siglec-15.

Figure 25A:
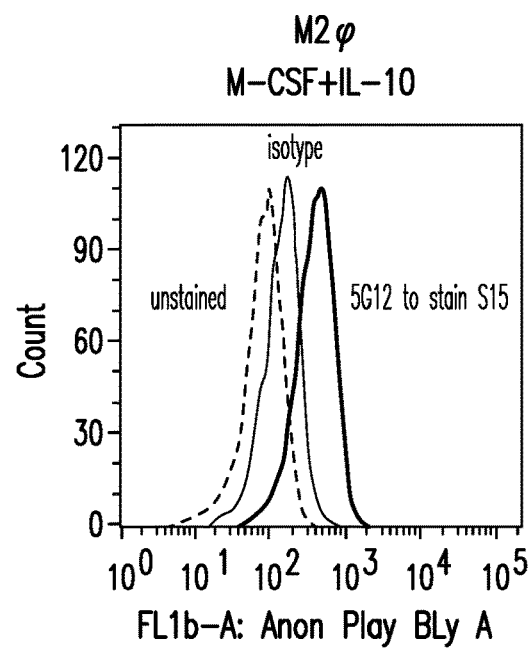
Figure 25B:
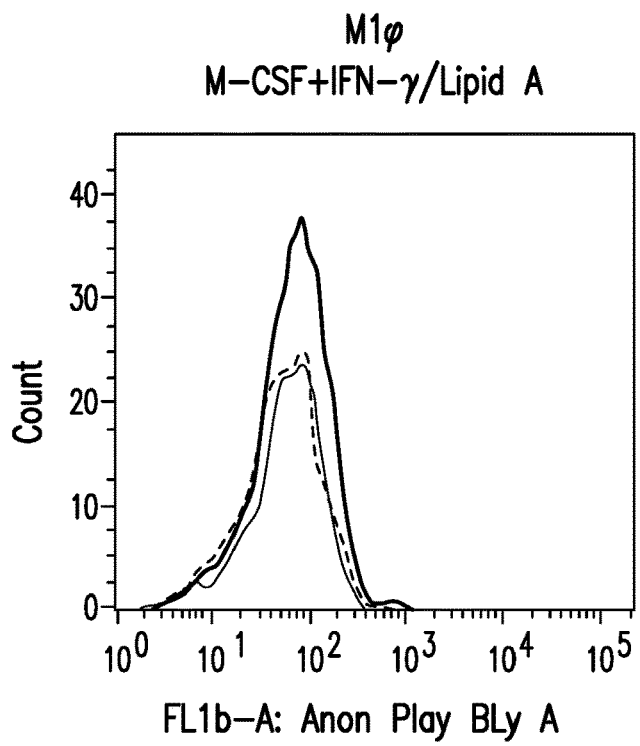
Figure 25C:
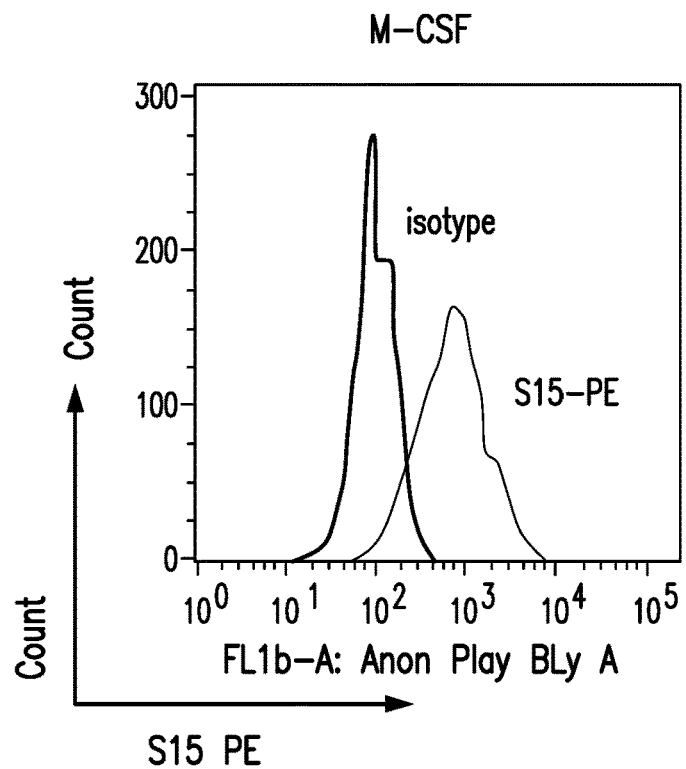
Figure 25D:
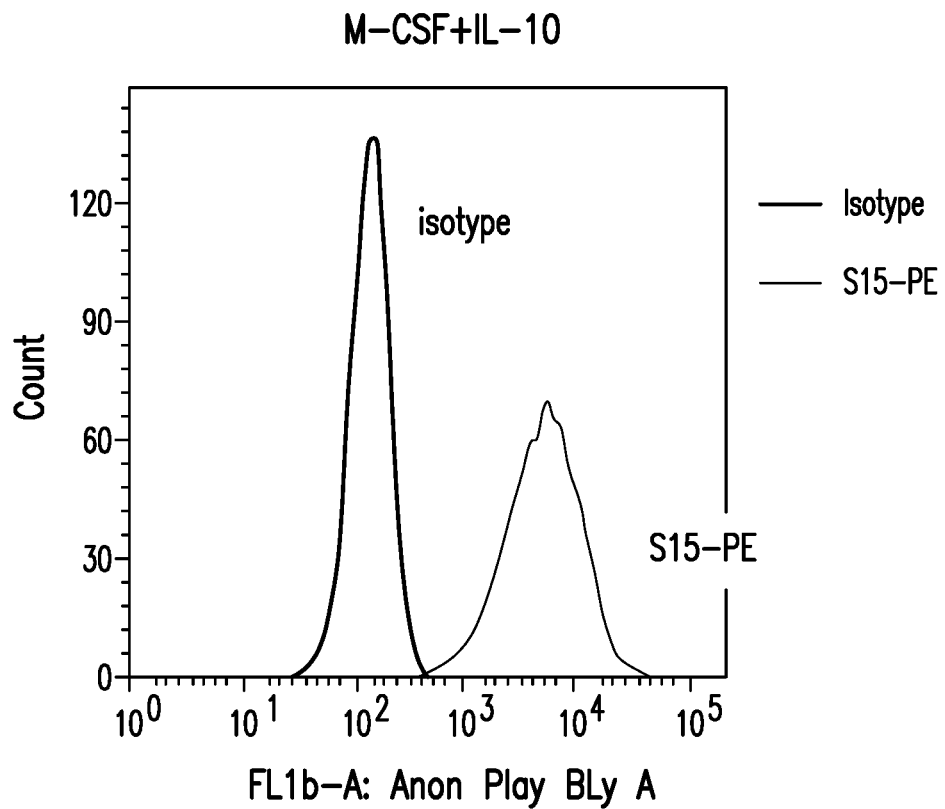
Figure 25E:
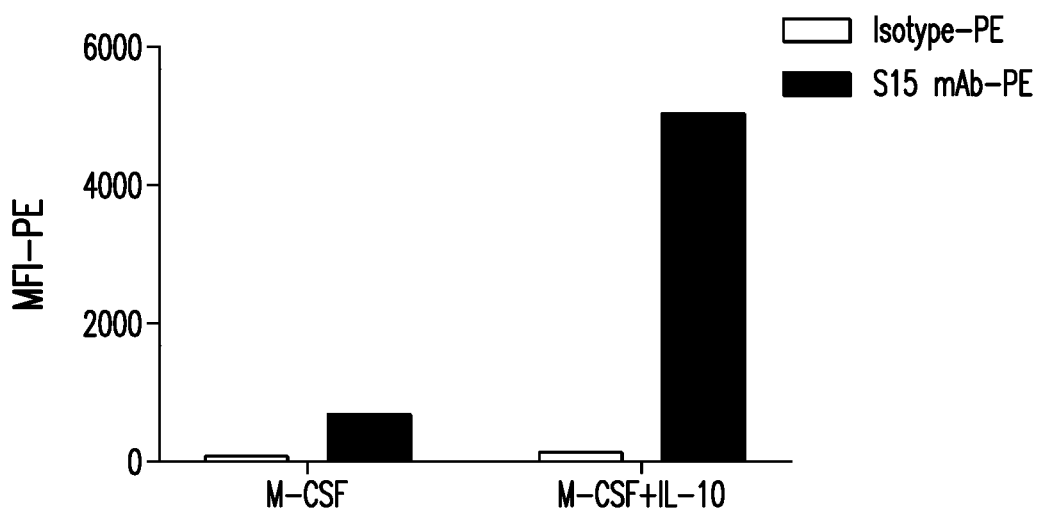

FIG. 25A is FACS histogram of count versus Siglec-15 PE showing M2 macrophages express Siglec-15. FIG. 25B is FACS histogram of count versus Siglec-15 PE for M1 macrophage. FIG. 25C is FACS histogram of count versus Siglec-15 PE for mouse bone marrow-derived myeloid cells treated with Macrophage Colony Stimulating Factor (M-CSF). FIG. 25D is FACS histogram of count versus Siglec-15 PE for mouse bone marrow-derived myeloid cells treated with M-CSF and interleukin-10 (IL-10). FIG. 25E is a bar graph of MFI-PE for mouse bone marrow-derived myeloid cells treated with M-CSF or M-CSF+IL10 and stained with isotype-PE (grey box) or anti-Siglec-15 PE.

Figure 26A:
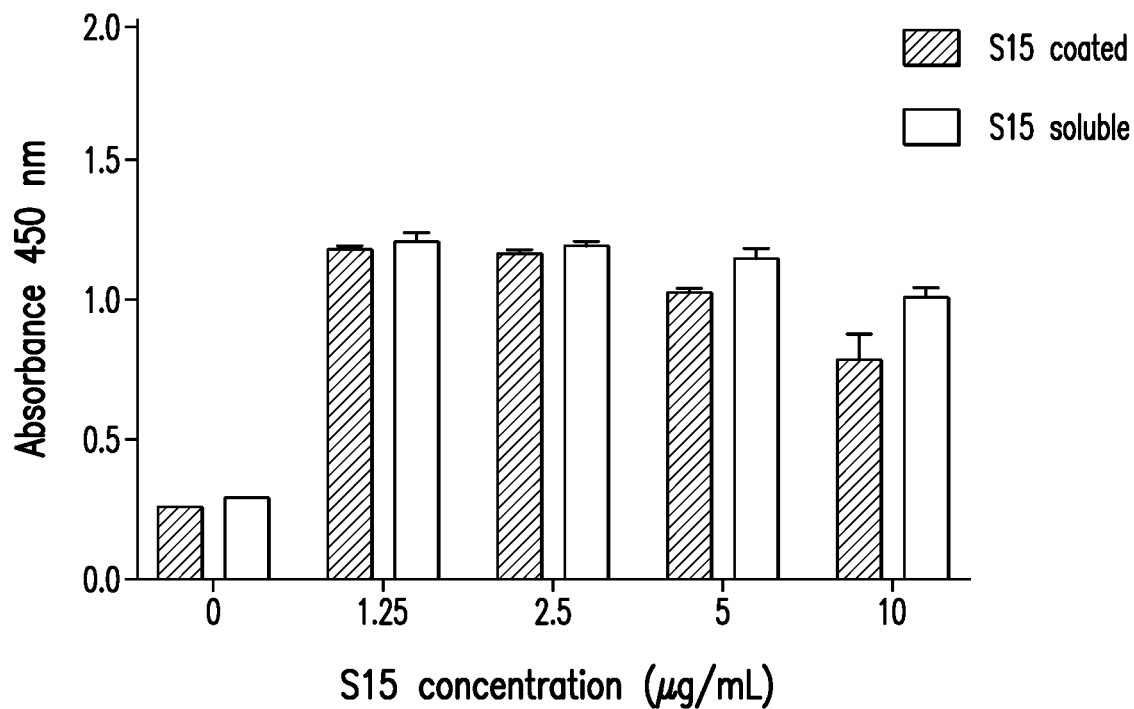
Figure 26B:
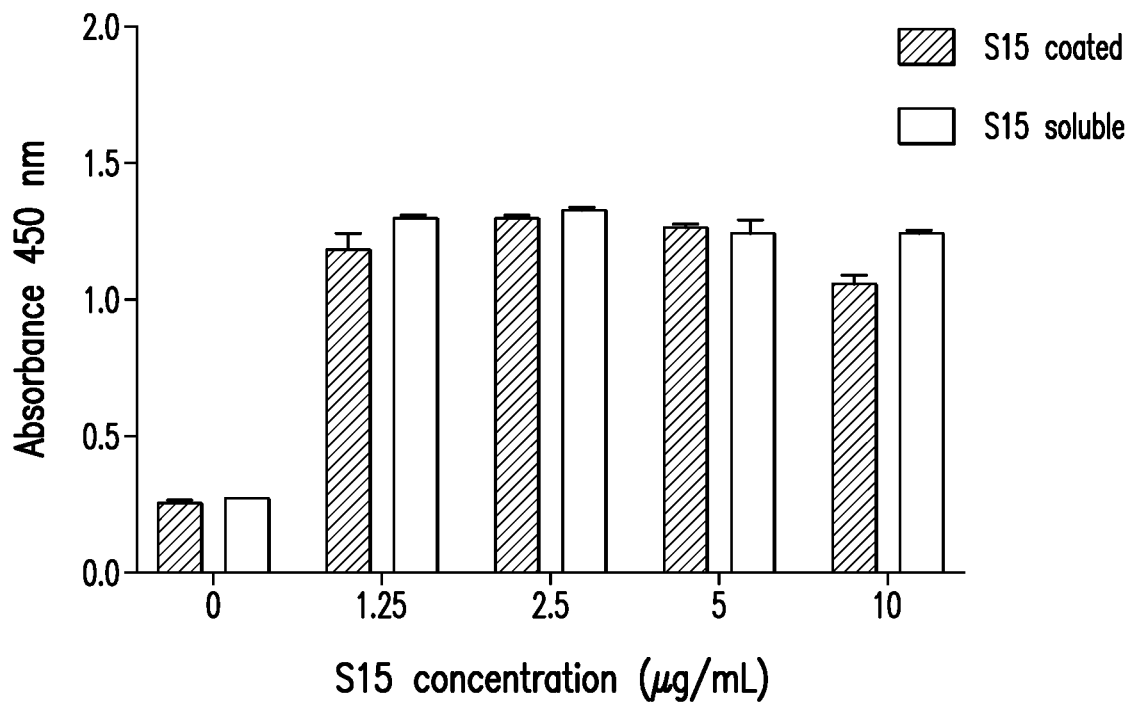
Figure 26C:
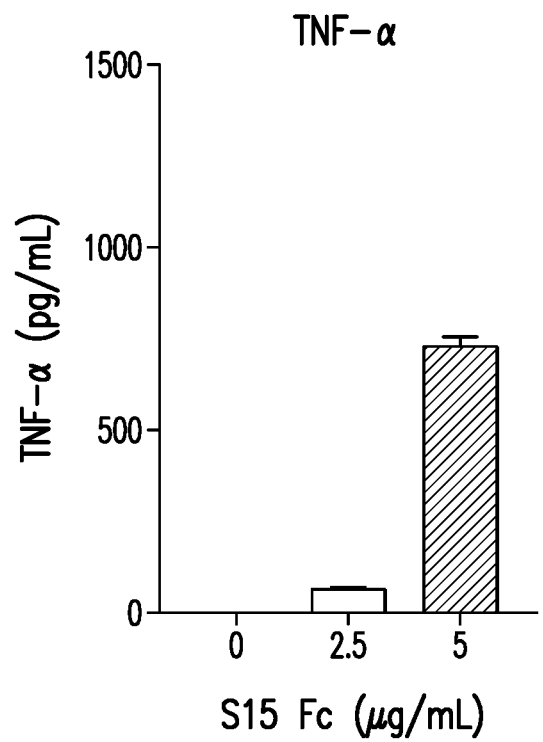
Figure 26D:
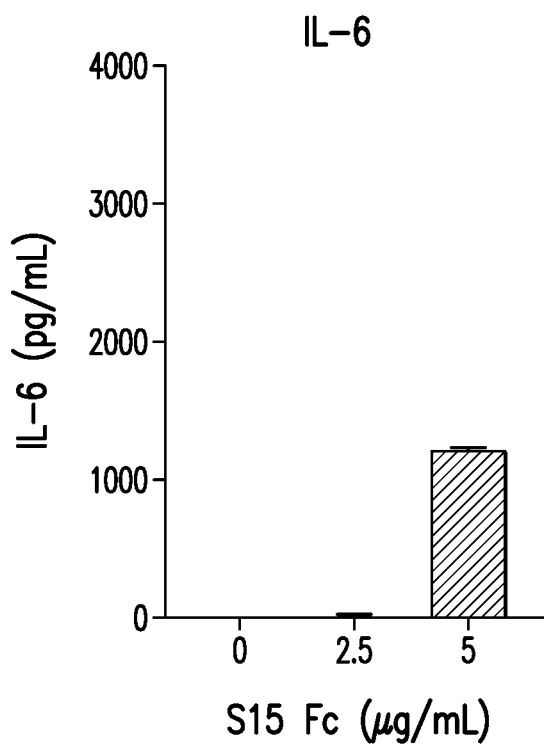
Figure 26E:
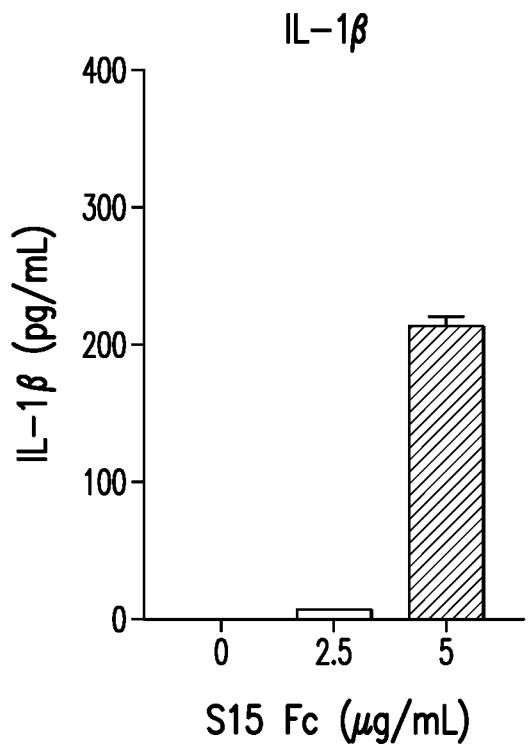
Figure 26F:
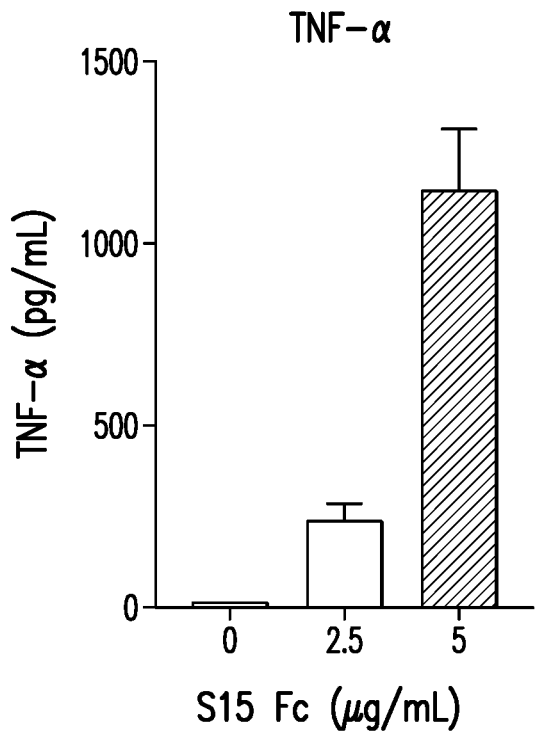
Figure 26G:
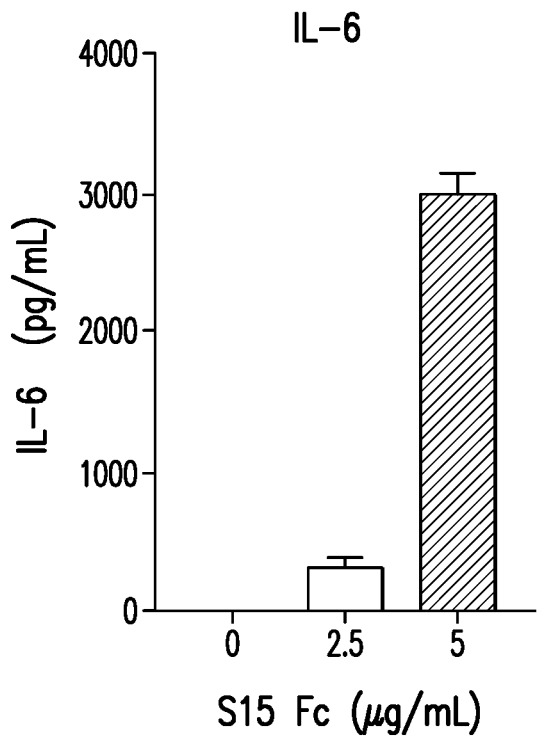
Figure 26H:
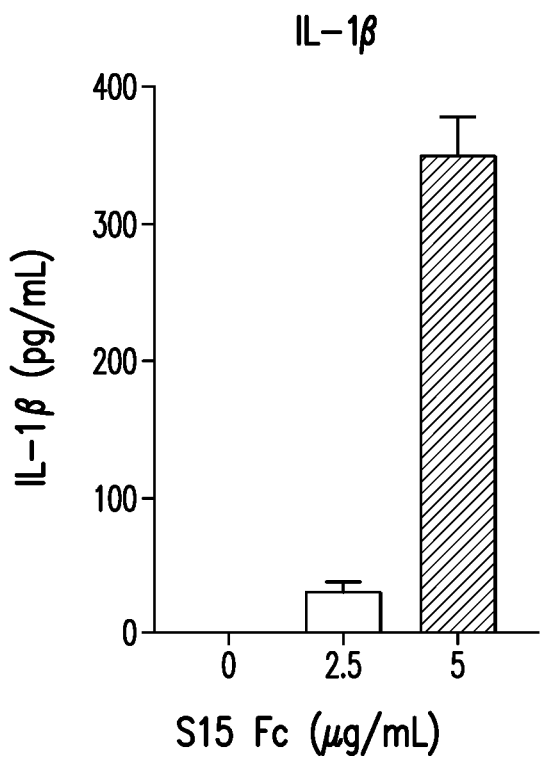

FIG. 26A is a bar graph of absorbance 450 nm for supernatants from human CD14+ monocytes from donor #1603 seeded in plates coated with Siglec-15 Fc (left column of concentration point) or soluble Siglec-15 (right column of each concentration point). FIG. 26B is a bar graph of absorbance 450 nm for supernatants from human CD14+ monocytes from donor #1704 seeded in plates coated with Siglec-15 Fc (left column of concentration point) or soluble Siglec-15 (right column of each concentration point). FIG. 26C is a bar graph of TNF-α (pg/mL) versus Siglec-15 Fc (μg/mL) for cells from donor #1603. FIG. 26D is a bar graph of IL-6 (pg/mL) versus Siglec-15 Fc (μg/mL) for cells from donor #1603. FIG. 26E is a bar graph of IL-1β (pg/mL) versus Siglec-15 Fc (μg/mL) for cells from donor #1603. FIG. 26F is a bar graph of TNF-α (pg/mL) versus Siglec-15 Fc (μg/mL) for cells from donor #1704. FIG. 26G is a bar graph of IL-6 (pg/mL) versus Siglec-15 Fc (μg/mL) for cells from donor #1704. FIG. 26H is a bar graph of IL-1β (pg/mL) versus Siglec-15 Fc (μg/mL) for cells from donor #1704.

Figure 27A:
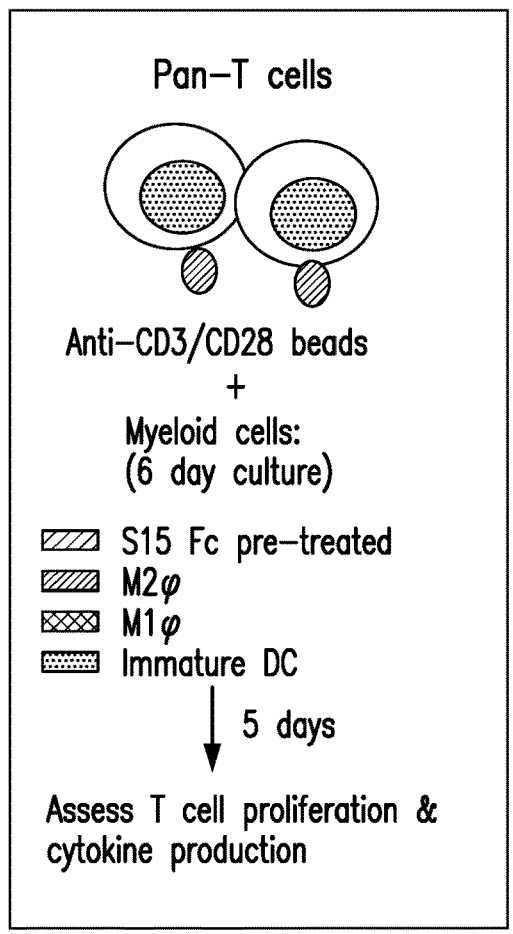
Figure 27B:
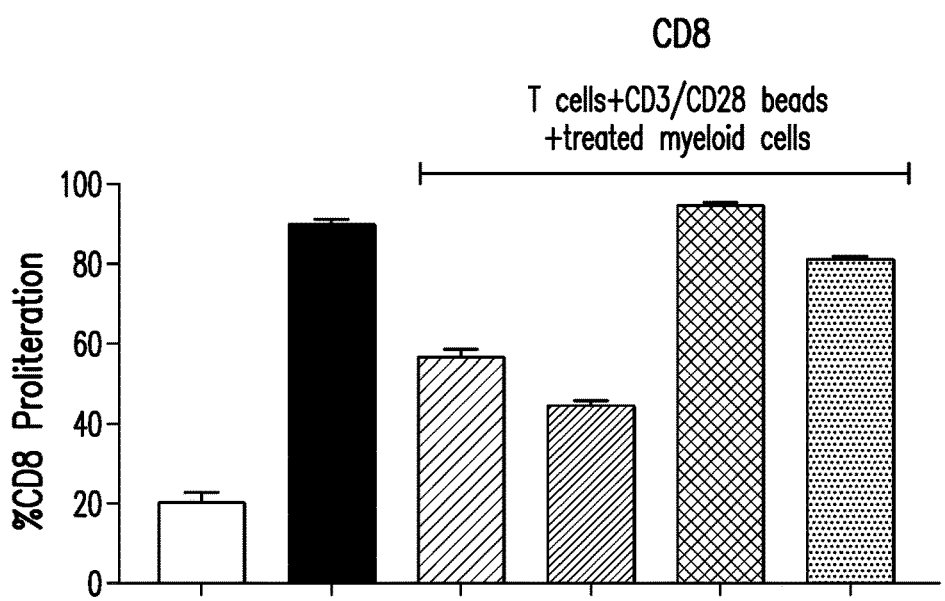
Figure 27C:
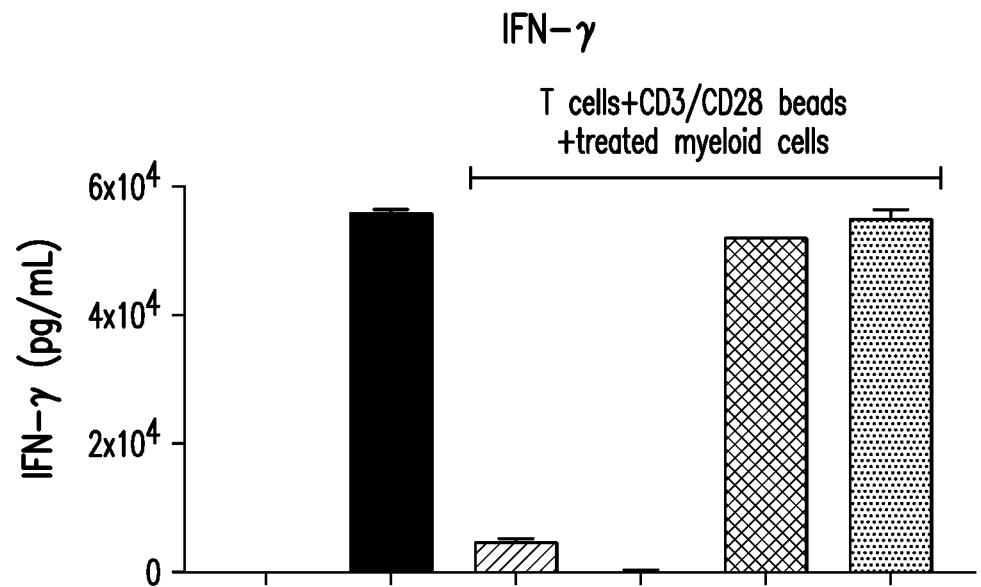
Figure 27D:
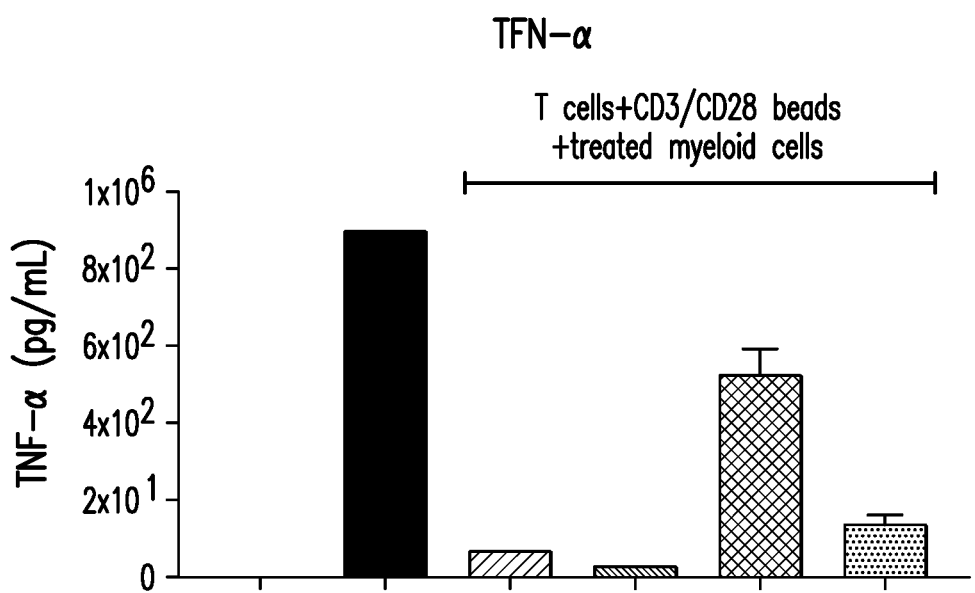
Figure 27E:
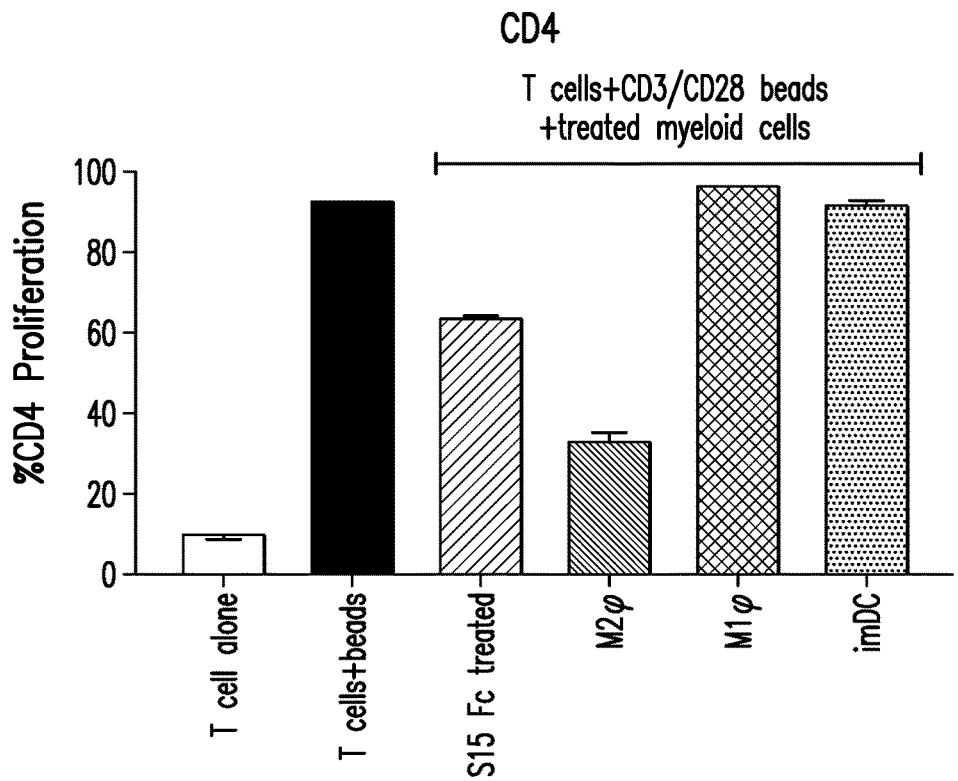
Figure 27F:
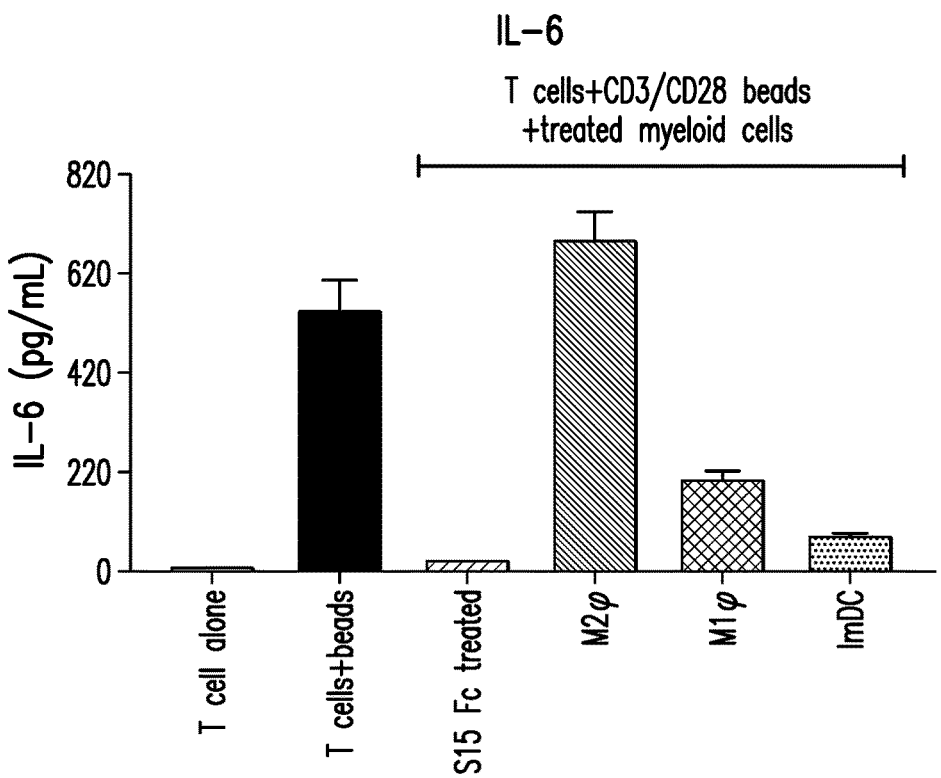
Figure 27G:
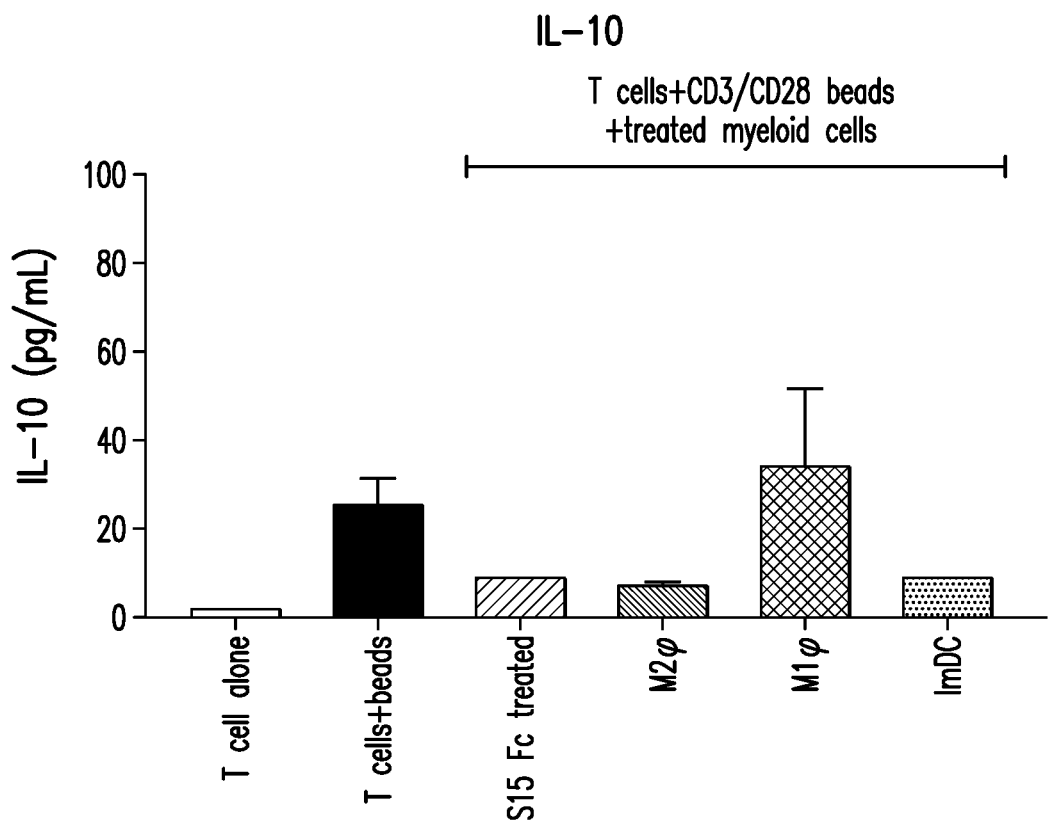

FIG. 27A is a diagram of an experimental protocol for Example 19. FIG. 27B is a bar graph of % CD8 proliferation of human myeloid cells pre-treated with S15 Fc; M2φ, M1φ and immature DCs cocultured with CFSE labeled negatively selected autologous pan-T cells at a cell ratio of 1 myeloid cell:2 T cell together with anti-CD3/CD28 beads (1 pan-T cell:2 beads). Columns from left to right are: T cell alone, T cells+beads, S15 Fc treated, M2φ, M1φ, and imDC for FIGS. 27C to 27G. FIG. 27C is a bar graph of IFN-γ (pg/mL) for the cells as treated above. FIG. 27D is a bar graph of TNF-α (pg/mL) for the cells as treated above. FIG. 27E is percent CD4 proliferation for the cells as treated above. FIG. 27F is a bar graph of IL-6 (pg/mL) for the cells as treated above. FIG. 27G is a bar graph of IL-10 (pg/mL) for the cell as treated above.

FIG. 28A is a line graph of absorbance 450 nm versus mAb (μg/mL) for cells from donor 1709. Top line is control mAb and the bottom line is S15 mAb. FIG. 28B is the same as FIG. 28A but for cells from donor 1713.

FIG. 29 is a diagram illustrating the role Siglec-15 plays in osteoclast formation.

Figures 30A, 30B:
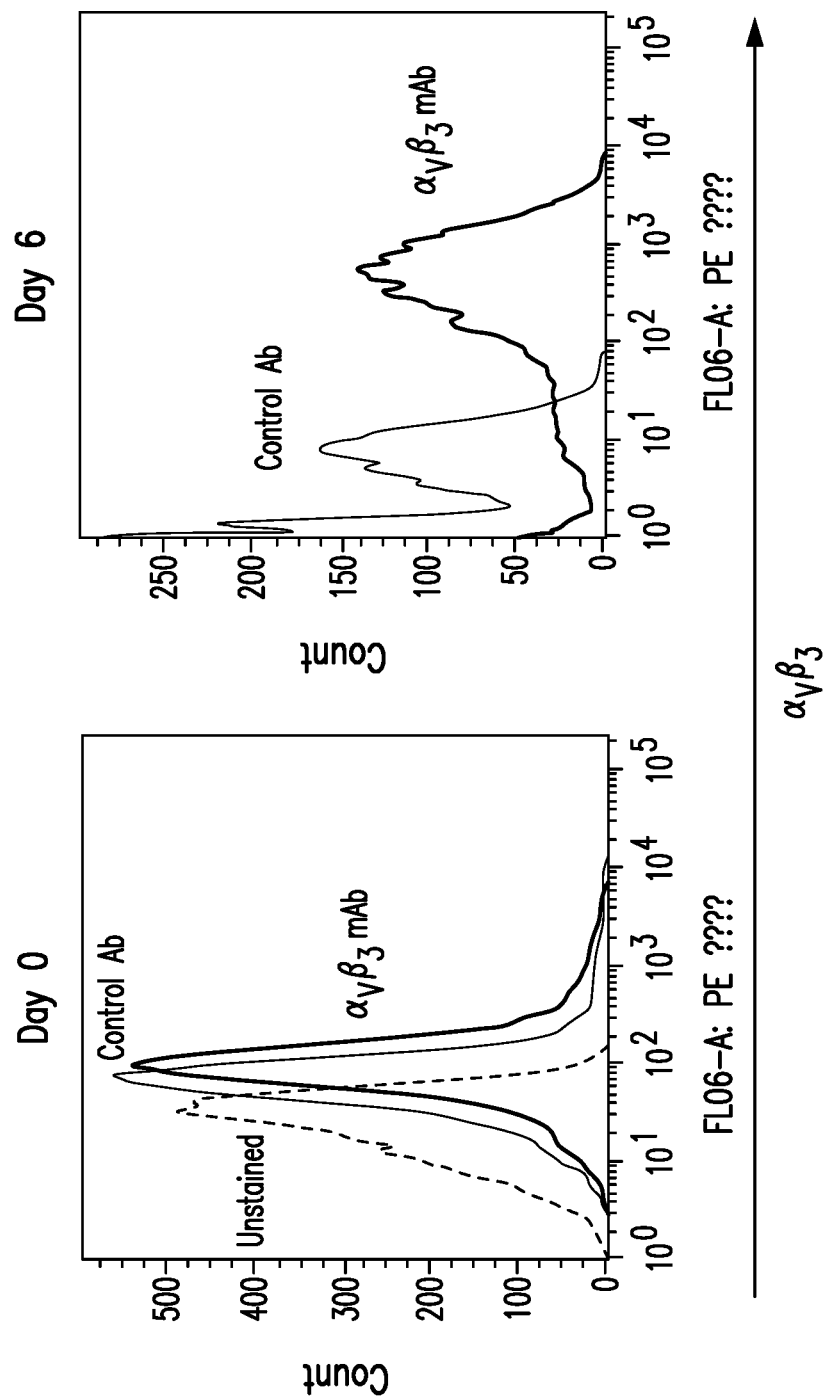

FIG. 30A is a FACS histogram of human CD14+ monocytes treated with S15 Fc and stained with anti-$\alpha_v\beta_3$ integrin mAb at day 0. FIG. 30B is a FACS histogram of human CD14+ monocytes treated with S15 Fc and stained with anti-$\alpha_v\beta_3$ integrin mAb at day 6.

DETAILED DESCRIPTION OF THE INVENTION

I. Definitions

As used herein, a molecule is said to be able to "immunospecifically bind" a second molecule if such binding exhibits the specificity and affinity of an antibody to its cognate antigen. Antibodies are said to be capable of immunospecifically binding to a target region or conformation ("epitope") of an antigen if such binding involves the antigen recognition site of the immunoglobulin molecule.

An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. Preferably, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein, a molecule is said to "physiospecifically bind" a second molecule if such binding exhibits the specificity and affinity of a receptor to its cognate binding ligand. A molecule can be capable of physiospecifically binding to more than one other molecule.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', F(ab')$_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

As used herein the term "modulate" relates to a capacity to alter an effect, result, or activity (e.g, signal transduction). Such modulation can agonistic or antagonistic. Antagonistic modulation can be partial (i.e., attenuating, but not abolishing) or it can completely abolish such activity (e.g., neutralizing). Modulation can include internalization of a receptor following binding of an antibody or a reduction in expression of a receptor on the target cell. Agonistic modulation can enhance or otherwise increase or enhance an activity (e.g., signal transduction). In a still further embodiment, such modulation can alter the nature of the interaction between a ligand and its cognate receptor so as to alter the nature of the elicited signal transduction. For example, the molecules can, by binding to the ligand or receptor, alter the ability of such molecules to bind to other ligands or receptors and thereby alter their overall activity. Preferably, such modulation will provide at least a 10% change in a measurable immune system activity, more preferably, at least a 50% change in such activity, or at least a 2-fold, 5-fold, 10-fold, or still more preferably, at least a 100-fold change in such activity.

The term "substantially," as used in the context of binding or exhibited effect, is intended to denote that the observed effect is physiologically or therapeutically relevant. Thus, for example, a molecule is able to substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the "co-stimulatory" signals encompass positive co-stimulatory signals (e.g., signals that result in enhancing an activity) and negative co-stimulatory signals (e.g., signals that result in inhibiting an activity).

As used herein, the term "derivative" refers to an antibody or antigen-binding fragment thereof that immunospecifically binds to the same target of a parent or reference antibody but which differs in amino acid sequence from the parent or reference antibody or antigen binding fragment thereof by including one, two, three, four, five or more amino acid substitutions, additions, deletions or modifications relative to the parent or reference antibody or antigen binding fragment thereof. Preferably such derivatives will have substantially the same immunospecificity and/or characteristics, or the same immunospecificity and characteristics as the parent or reference antibody or antigen binding fragment thereof. The amino acid substitutions or additions of such derivatives can include naturally occurring (i.e., DNA-encoded) or non-naturally occurring amino acid residues. The term "derivative" encompasses, for example, chimeric or humanized variants, as well as variants having altered CH1, hinge, CH2, CH3 or CH4 regions, so as to form, for example antibodies, etc., having variant Fc regions that exhibit enhanced or impaired effector or binding characteristics.

As used herein, a "chimeric antibody" is a molecule in which different portions of the antibody are derived from different immunoglobulin molecules such as antibodies having a variable region derived from a non-human antibody and a human immunoglobulin constant region.

As used herein, the term "humanized antibody" refers to an immunoglobulin including a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they should be substantially identical to human immunoglobulin constant regions, i.e., at least about 85-99%, preferably about 95% or more identical. Hence, all parts of a humanized immunoglobulin, except possibly the CDR's, are substantially identical to corresponding parts of natural human immunoglobulin sequences. A humanized antibody is an antibody including a humanized light chain and a humanized heavy chain immunoglobulin. For example, a humanized antibody would not encompass a typical chimeric antibody, because, e.g., the entire variable region of a chimeric antibody is non-human.

As used herein, the term "endogenous concentration" refers to the level at which a molecule is natively expressed (i.e., in the absence of expression vectors or recombinant promoters) by a cell (which cell can be a normal cell, a cancer cell or an infected cell).

As used herein, the terms "treat," "treating," "treatment" and "therapeutic use" refer to the elimination, reduction or amelioration of one or more symptoms of a disease or disorder exacerbated by Siglec-15 or a ligand thereof.

As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "cancer" refers to a neoplasm or tumor resulting from abnormal uncontrolled growth of cells.

As used herein, cancer explicitly includes, leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

As used herein, an "immune cell" refers to any cell from the hemopoietic origin including, but not limited to, T cells, B cells, monocytes, dendritic cells, and macrophages.

As used herein, "valency" refers to the number of binding sites available per molecule.

As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

As used herein, an "immunogenic agent" or "immunogen" is capable of inducing an immunological response against itself on administration to a mammal, optionally in conjunction with an adjuvant.

As used herein, the terms "individual," "host," "subject, and "patient" are used interchangeably herein, and refer to a mammal, including, but not limited to, humans, rodents, such as mice and rats, and other laboratory animals.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the terms "antigenic determinant" and "epitope" are used interchangeably and refer to the structure recognized by an antibody.

As used herein, a "conformational epitope" is an epitope that includes discontinuous sections of the antigen's amino acid sequence. Antibodies bind a conformational epitope based on 3-D surface features, shape, or tertiary structure of the antigen.

As used herein, a "linear epitope" is an epitope that formed by a continuous sequence of amino acids from the antigen. Linear epitopes typically include about 5 to about 10 continuous amino acid residues. Antibodies bind a linear epitope based on the primary sequence of the antigen.

As used herein, a "paratope," also called an "antigen-binding site," is a part of an antibody which recognizes and binds to an antigen.

II. Compositions

A. Siglec-15 Sequences

Sialic acid-binding Ig-like lectin 15 ("Siglec-15", also referred to as CD33 antigen-like 3, and CD33L3) is a type 1 transmembrane protein expressed on macrophages and/or dendritic cells of human spleen and lymph nodes (Angata, et al., *Glycobiology*, 17(8):838-46 (2007), which is specifically incorporated by reference herein in its entirety). The extracellular domain of Siglec-15 binds to sialylated glycoproteins and preferentially recognizes the Neu5Acα2-6GalNAcα-structure.

Siglec-15 associates with the activating adaptor proteins DNAX activation protein (DAP)12 and DAP10 via its lysine residue (residue K274) in the transmembrane domain, indicating that it functions as an activating signaling molecule. Orthologs of Siglec-15 are present not only in mammals but also in other branches of vertebrates, and believed to play a conserved, regulatory role in the immune system of vertebrates.

Siglec-15 directly regulates T cell function by inhibiting T cell proliferation and proinflammatory cytokine production. Siglec-15 indirectly affects T cell function via myeloid cells. Siglec-15 expressed on tumor cells or M2 macrophages interacts with its binding partner on myeloid cells providing survival and differentiation signal resulting in a unique myeloid cell population that produces TNF-α, IL-6 and IL-1β. The secreted cytokines further promote tumor growth. This subset of myeloid cells may affect T cell function by reducing IFN-γ production in T cells.

Amino acid sequences for human Siglec-15 are known in the art and include, for example, (SEQ ID NO: 1)
MEKSIWLLACLAWVLPTGS*FVRTKIDTTENLLNTEVHSS*

*PAQRWSMQVPPEVSAEAGDAAVLPCTFTHPHRHYDGPLTA*

*IWRAGEPYAGRQVFRCAARGSELCQTALSLHGRFRLLG*

*DVHDRYESRHGNPRRNDLSLRVERLALADDRRYFCRVEFAG*

*VRLHVTAE*PRIVNISVLPSP*HAFRALCTAEGEPPPALAWS*

*GPALGNSLAAVRSPREGHGHLVTAELPALTHDGR*

*YTCTAANSLGRSEASVYLFRFHGASGAST*VALLLGALGFKALL

LLGVLAARAARRRPEHLDTPDTPPRSQAQESNYENLSQ

MNPRSPPATMCSP,

UniProtKB-Q6ZMC9 (SIGi5_HUMAN), and which is specifically incorporated by reference in its entirety.

Human Siglec-15 includes a signal peptide sequence from amino acids 1-19 of SEQ ID NO: 1, an extracellular domain from amino acids 20-263 of SEQ ID NO: 1 (illustrated with bold and italic lettering), a transmembrane domain from amino acids 264-284 of SEQ ID NO:1, and a cytoplasmic domain from amino acids 285-328 of SEQ ID NO: 1. The Ig-like V-type domain is predicted to be from amino acids 40-158 of SEQ ID NO:1 (illustrated with single underlining) and the Ig-like C2-type domain is predicted to be from amino acids 168-251 of SEQ ID NO: 1 (illustrated with double underlining). Disulfide bonds are believed to form between residues 64 and 142; 95 and 104; and 187 and 237, and glycosylation is predicted at residue 172. Amino acids 276-279 has been referred to as a poly-leucine domain. A known variant is a F273L substitution variant.

Amino acid sequences for mouse Siglec-15 are known in the art and include for example, (SEQ ID NO: 2)
MEGSLQLLACLACVLQMGSLVKT*RRDASGDILNTEAHSA*

*PAQRWSMQVPAEVNAEAGDAAVLPCTFTHPHRHY*

*DGPLTAIWRSGEPYAGPQVFRCTAAPGSELCQT*

*ALSLHGRFRLLGNPRRNDLSLRVERLALADSGRYFCRVE*

*FTGDAHDRYESRHGVRLRTAAE*PRIVNISVLPG

PRIVNISVLPGGEPPPALAWSGPAPGNSSAAL

QGQGHGYQVTAELPALTRDGRYTCTAANSLGRAEASVY

*LFRFHGAPGTST*LALLLGALGLKALLLLGILGARATRRRLDHLVPQ

DTPPRSQAQESNYENLSQMSPPGHQLPRVCCEELLSHHHLVIHHEK,

UniProtKB-A7E1W8 (A7E1W8_MOUSE), and which is specifically incorporated by reference in its entirety.

Mouse Siglec-15 includes a signal peptide sequence from amino acids 1-23 of SEQ ID NO:2, an extracellular domain from amino acids 24-262 of SEQ ID NO:2 (illustrated with bold and italic lettering), a transmembrane domain from amino acids 263-283 of SEQ ID NO:2, and a cytoplasmic domain from amino acids 284-342 of SEQ ID NO:2. The Ig-like V-type domain is predicted to be from amino acids 40-145 of SEQ ID NO:2 (illustrated with single underlining) and the Ig-like C2-type domain is predicted to be from amino acids 169-250 of SEQ ID NO:2 (illustrated with double underlining).

B. Siglec-15-Binding Molecules

Siglec-15-binding molecules, such as antibodies and antigen binding fragments thereof and other polypeptides that bind to Siglec-15 are provided. The sequences of the heavy and light chain variable regions, and CDRs thereof, from mouse anti-Siglec-15 antibodies are provided below. Antibodies, antigen binding fragments and other polypeptides including one or more of the sequences below, and variants thereof are provided. For example, antibodies, antigen binding fragments, and polypeptides including one, two, or three CDRs of an anti-Siglec-15 antibody light chain variable region and/or one, two, or three CDRs of an anti-Siglec-15 antibody heavy chain variable region that bind to Siglec-15 are provided. In some embodiments, the antibodies, antigen binding fragments, and polypeptides include the light chain variable region of an anti-Siglec-15 antibody, the heavy chain variable region of an anti-Siglec-15, or a combination thereof, and can bind to Siglec-15.

For example, the disclosed molecules can immunospecifically bind to Siglec-15 (e.g., SEQ ID NO:1, SEQ ID NO:2, etc.). For example, molecules are provided that can immunospecifically bind to human Siglec-15:

(I) arrayed on the surface of a cell (preferably a live cell);
(II) arrayed on the surface of a cell (preferably a live cell) at an endogenous concentration;
(III) arrayed on the surface of a live cell, and modulates binding between Siglec-15 (e.g., SEQ ID NO: 1, SEQ ID NO:2, etc.) and Neu5Acα2-6GalNAcα, LRRC4C, an Siglec-15-counter-receptor (S15-CR), or a combination thereof;

(IV) arrayed on the surface of a live cell, and reduces, prevents, or inhibits TGF-β secretion;

(V) arrayed on the surface of a live cell, wherein the cell is a myeloid cell such as a macrophage or dendritic cell, or a cancer cell (e.g., brain cancer cell, renal cell carcinoma cell (RCC), Ewing sarcoma cell, breast cancer cell, or ovarian cancer cell);

(VI) combinations thereof.

1. Mouse Anti-Human Siglec-15 Antibody Sequences

As described in the Examples below, Siglec-15 knock out mice (n=2) were immunized with hS15.mIg (human Siglec 15 extracellular domain [ECD] fused with mouse IgG2a) emulsified with CFA (complete Freund adjuvant) to generate a panel of mouse anti-human Siglec-15 mAbs.

The sequences of light and heavy chain variable regions for monoclonal antibodies produced by twenty-four hybridomas, referred to herein as 1B2, 1C3, 1H3, 1C12, 3H10, 5G12, 6F8, 8C8, 8H8, 9A5, 10G9, 6A (also NC6 and #6), 28A (also NC28 and #28), 63A (also referred to as NC63 and #63), 71A (also referred to as NC71 and #71), 77A (also referred to as NC77 and #77), 80A (also referred to as NC80 and #80), 82B (also referred to as NC82 and #82), 83B (also referred to as NC83 and #83), 92A (also referred to as NC92 and #92), 93B (also referred to as NC93 and #93), 99B (also referred to as NC99 and #99), 104B (also referred to as NC104 and #104), and 105A (also referred to as NC105 and #105) are provided below. CDRs are underlined and bolded in the context of the light and heavy chain sequences. Sequences and CDRs are also illustrated in the alignments of FIGS. 2A-3C.

a. 1B2 Sequences:
i. Light Chain
1B2 Light Chain Variable Region Amino Acid Sequence is:

```
                                            (SEQ ID NO: 3)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYYC**FQGSHVP

WT**FGGGTKLEIK,
with
```

1B2 Light Chain CDR1:
(SEQ ID NO: 24)
RSSQSIVHSNGNTYLE

1B2 Light Chain CDR2:
(SEQ ID NO: 32)
KVSNRFS

1B2 Light Chain CDR3:
(SEQ ID NO: 39)
FQGSHVPWT.

A nucleic acid sequence encoding the 1B2 light chain variable region is:

```
                                            (SEQ ID NO: 74)
GATGTTTTGATGACCCAAACTCCACTCTCCCTGCCTGTCAGTCTTGGAGA

TCAAGCCTCCATCTCTTGCAGATCTAGTCAGAGCATTGTACATAGTAATG

GAAACACCTATTTAGAATGGTACCTGCAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

TGGACGTTCGGTGGAGGCACCAAGCTGGAAATCAAG.
``` ii. Heavy Chain
1B2 Heavy Chain Variable Region Amino Acid Sequence is:

```
                                            (SEQ ID NO: 13)
EVQLVESGGGFVKPGGSLKLSCAASGFTFSDYGMHWVRQAPEKGLEWVA**Y

ISSGSSIIYYADTVKGRFTISRDNAKNTLFLQMTSLRSEDTAMYYCARDH

YHGNGSDY**WGQGTTLTVSS,
with
```

1B2 Heavy Chain CDR1:
(SEQ ID NO: 46)
GFTFSDYGMH

1B2 Heavy Chain CDR2:
(SEQ ID NO: 56)
YISSGSSIIYYADTVKG

1B2 Heavy Chain CDR3:
(SEQ ID NO: 67)
DHYHGNGSDY.

A nucleic acid sequence encoding the 1B2 heavy chain variable region is:

```
                                            (SEQ ID NO: 85)
GAGGTGCAGCTGGTGGAGTCTGGGGGAGGCTTCGTGAAGCCTGGAGGGTC

CCTGAAACTCTCCTGTGCAGCCTCTGGATTCACTTTCAGTGACTATGGAA

TGCACTGGGTTCGTCAGGCTCCAGAGAAGGGGCTGGAGTGGGTTGCATAC

ATTAGTAGTGGCAGTAGTATCATCTACTATGCAGACACAGTGAAGGGCCG

ATTCACCATCTCCAGAGACAATGCCAAGAACACCCTGTTCCTGCAAATGA

CCAGTCTGAGGTCTGAGGACACGGCCATGTATTACTGTGCAAGGGACCAC

TACCATGGTAACGGGTCCGACTACTGGGGCCAAGGCACCACTCTCACAGT

CTCCTCA.
``` b. 1C3 Sequences:
i. Light Chain
1C3 Light Chain Variable Region Amino Acid Sequence is:

```
                                            (SEQ ID NO: 4)
DIVMTQAAPSVPVTPGESVSISCRSSKSLLHSNGNTYLYWFLQRPGQSPQ

LLIYRMSNLASGVPDRFGGSGSGTAFTLRISRVEAEDVGFYYC**MQHLEYP

YT**FGGGTRLEIK,
with
```

1C3 Light Chain CDR1:
(SEQ ID NO: 25)
RSSKSLLHSNGNTYLY

1C3 Light Chain CDR2:
(SEQ ID NO: 33)
RMSNLAS

1C3 Light Chain CDR3:
(SEQ ID NO: 40)
MQHLEYPYT.

A nucleic acid sequence encoding the 1C3 light chain variable region is:

(SEQ ID NO: 75)
GATATTGTGATGACTCAGGCTGCACCCTCTGTACCTGTCACTCCTGGAGA

GTCAGTATCCATCTCCTGCAGGTCTAGTAAGAGTCTCCTGCATAGTAATG

GCAACACTTACTTATATTGGTTCCTGCAGAGGCCAGGCCAGTCTCCTCAG

CTCCTGATATATCGGATGTCCAACCTTGCCTCAGGAGTCCCAGACAGGTT

CGGTGGCAGTGGGTCAGGAACTGCTTTCACACTGAGAATCAGTAGAGTGG

AGGCTGAGGATGTGGGTTTTTATTACTGTATGCAACATCTAGAATATCCG

TACACGTTCGGAGGGGGGACCAGGCTGGAAATAAAA.

ii. Heavy Chain

1C3 Heavy Chain Variable Region Amino Acid Sequence is:

(SEQ ID NO: 14)
QVQLKQSGAELVKPGASVKISCKASGYIFTDYYVNWVKQRPGQGLEWIGK

IGPGSVSIYYNEKFKGKATLTADKSSSTAYMQLSSLTSEDSAVYFCASYY

YGFAYWGQGTLVTVSA,
with

1C3 Heavy Chain CDR1:
(SEQ ID NO: 47)
GYIFTDYYVN

1C3 Heavy Chain CDR2:
(SEQ ID NO: 57)
KIGPGSVSIYYNEKFKG

1C3 Heavy Chain CDR3:
(SEQ ID NO: 68)
YYYGFAY.

A nucleic acid sequence encoding the 1C3 heavy chain variable region is:

(SEQ ID NO: 86)
CAGGTCCAGCTGAAGCAGTCTGGAGCTGAGCTGGTGAAGCCTGGGGCTTC

AGTGAAGATATCCTGCAAGGCTTCTGGCTACATCTTCACTGACTATTATG

TAAACTGGGTGAAGCAGAGGCCTGGACAGGGCCTTGAGTGGATTGGAAAG

ATTGGTCCTGGAAGTGTTAGTATTTACTACAATGAGAAGTTCAAGGGCAA

GGCCACACTGACTGCAGACAAATCCTCCAGCACAGCCTACATGCAGCTCA

GCAGCCTGACATCTGAGGACTCTGCAGTCTATTTCTGTGCAAGTTATTAC

TACGGGTTTGCTTACTGGGGCCAAGGGACTCTGGTCACTGTCTCTGCA.

c. 1H3 Sequences:

i. Light Chain

1H3 Light Chain Variable Region Amino Acid Sequence is:

(SEQ ID NO: 5)
DIQMTQASSSLSVSLGGRVTITCKASDHINNWLAWYQQKPGNAPRLLISG

ATSLETGVPSRFSGSGSGKDYTLSITSLQTEDVATYYCQQYWSSPLTFGA

GTKLELK, with

1H3 Light Chain CDR1:
(SEQ ID NO: 26)
KASDHINNWLA

1H3 Light Chain CDR2:
(SEQ ID NO: 34)
GATSLET

1H3 Light Chain CDR3:
(SEQ ID NO: 41)
QQYWSSPLT.

A nucleic acid sequence encoding the 1H3 light chain variable region is:

(SEQ ID NO: 76)
GACATCCAGATGACACAGGCTTCATCCTCCTTGTCTGTATCTCTAGGAGG

CAGAGTCACCATTACTTGCAAGGCAAGTGACCACATTAATAATTGGTTGG

CCTGGTATCAGCAGAAACCAGGAAATGCTCCTAGGCTCTTAATATCTGGT

GCAACCAGTTTGGAAACTGGGGTTCCTTCAAGATTCAGTGGCAGTGGATC

TGGAAAGGATTACACTCTCAGCATTACCAGTCTTCAGACTGAAGATGTTG

CTACTTATTACTGTCAACAGTATTGGAGTTCTCCTCTCACGTTCGGTGCT

GGGACCAAGCTGGAGCTGAAA.

ii. Humanized Light Chain

One embodiment provides a humanized anti-SIGLEC-15 antibody having a variable light chain amino acid sequence of (SEQ ID NO: 209)
DIQMTQ$\underline{SP}$SSLS$\underline{A}$S$\underline{V}$G$\underline{D}$RVTITCKASDHINNWLAWYQQKPG$\underline{KAP}$KLLISG

ATSLETGVPSRFSGSGSG$\underline{T}$DYT$\underline{F}$T$\underline{I}$SSLQ$\underline{P}$ED$\underline{I}$ATYYCQQYWSSPLTFG$\underline{G}$ GTK$\underline{V}$E$\underline{I}$K
with 1H3 Light Chain CDR1:
(SEQ ID NO: 26)
KASDHINNWLA

1H3 Light Chain CDR2:
(SEQ ID NO: 34)
GATSLET

1H3 Light Chain CDR3:
(SEQ ID NO: 41)
QQYWSSPLT.

The underlined amino acids are changed with regard to the parent sequence.

Another embodiment provides a humanized anti-SIGLEC-15 antibody having a variable light chain amino acid sequence of (SEQ ID NO: 210)
DIQMTQ$\underline{SP}$SSLS$\underline{A}$S$\underline{V}$G$\underline{D}$RVTITCKASDHINNWLAWYQQKPG$\underline{KV}$PKLLISG

ATSLETGVPSRFSGSGSG$\underline{T}$DYTLT$\underline{I}$SSLQ$\underline{P}$EDVATYYCQQYWSSPLTFG$\underline{G}$ GTK$\underline{V}$E$\underline{I}$K
with 1H3 Light Chain CDR1:
(SEQ ID NO: 26)
KASDHINNWLA

1H3 Light Chain CDR2:
(SEQ ID NO: 34)
GATSLET

1H3 Light Chain CDR3:
(SEQ ID NO: 41)
QQYWSSPLT.

The underlined amino acids are changed with regard to the parent sequence.

Still another embodiment provides a humanized anti-SIGLEC-15 antibody having a variable light chain amino acid sequence of (SEQ ID NO: 211)
DIQMTQSPSSLSASVGDRVTITCKASDHINNWLAWYQQKPGKAPKLLISG
ATSLETGVPSRFSGSGSGTDYTLTISSLQPEDVATYYCQQYWSSPLTFGG
GTKVEIK
with 1H3 Light Chain CDR1:
(SEQ ID NO: 26)
KASDHINNWLA 1H3 Light Chain CDR2:
(SEQ ID NO: 34)
GATSLET 1H3 Light Chain CDR3:
(SEQ ID NO: 41)
QQYWSSPLT.

The underlined amino acids are changed with regard to the parent sequence.

iii. Heavy Chain

1H3 Heavy Chain Variable Region Amino Acid Sequence is:

(SEQ ID NO: 15)
QVQLKESGPGLVAPSQSLSITCTVSGFSLSNYGVHWVRQPPGKGLEWLVL
IWSDGSTTYNSALKSRLSISKDNSKSQVFLKMNSLQTGDTAMYYCARHPY
DDYSGYYYTMDYWGQGTSVTVSS,
with 1H3 Heavy Chain CDR1:
(SEQ ID NO: 48)
NYGVH 1H3 Heavy Chain CDR2:
(SEQ ID NO: 58)
LIWSDGSTTYNSALKS 1H3 Heavy Chain CDR3:
(SEQ ID NO: 69)
HPYDDYSGYYYTMDY.

A nucleic acid sequence encoding the 1H3 heavy chain variable region is:

(SEQ ID NO: 87)
CAGGTGCAGCTGAAGGAGTCAGGACCTGGCCTGGTGGCGCCCTCACAGAG

CCTGTCCATCACATGCACCGTCTCAGGGTTCTCATTAAGCAATTATGGTG

TACACTGGGTTCGCCAGCCTCCAGGAAAGGGTCTGGAGTGGCTGGTACTG

ATATGGAGTGATGGAAGCACAACCTATAATTCAGCTCTCAAATCCAGACT

GAGCATCAGCAAGGACAACTCCAAGAGCCAAGTTTTCTTAAAAATGAACA

GTCTCCAAACTGGTGACACAGCCATGTACTACTGTGCCAGACATCCCTAT

GATGATTATTCCGGCTATTACTATACTATGGACTACTGGGGTCAAGGAAC

CTCAGTCACCGTCTCCTCA.

iv. Humanized Heavy Chains

One embodiment provides a humanized anti-SIGLEC 15 antibody having a variable heavy chain amino acid sequence of (SEQ ID NO: 212)
QVQLQESGPGLVKPSETLSLTCTVSGFSLSNYGVHWVRQPPGKGLEWIVL
IWSDGSTTYNSALKSRVTISKDTSKNQVSLKLSSVTAADTAVYYCARHPY
DDYSGYYYTMDYWGQGTLVTVSS
with 1H3 Heavy Chain CDR1:
(SEQ ID NO: 48)
NYGVH 1H3 Heavy Chain CDR2:
(SEQ ID NO: 58)
LIWSDGSTTYNSALKS 1H3 Heavy Chain CDR3:
(SEQ ID NO: 69)
HPYDDYSGYYYTMDY.

The underlined amino acids are changed with regard to the parent sequence.

Another embodiment provides a humanized anti-SIGLEC 15 antibody having a variable heavy chain amino acid sequence of (SEQ ID NO: 213)
QVQLQESGPGLVKPSETLSLTCTVSGFSLSNYGVHWVRQPPGKGLEWIGL
IWSDGSTTYASALKSRVTISKDTSKNQVSLKLSSVTAADTAVYYCARHPY
DDYSGYYYTMDYWGQGTLVTVS
with 1H3 Heavy Chain CDR1:
(SEQ ID NO: 48)
NYGVH 1H3 Heavy Chain CDR2:
(SEQ ID NO: 214)
LIWSDGSTTYASALKS 1H3 Heavy Chain CDR3:
(SEQ ID NO: 69)
HPYDDYSGYYYTMDY.

The underlined amino acids are changed with regard to the parent sequence.

Still another embodiment provides a humanized anti-SIGLEC 15 antibody having a variable heavy chain amino acid sequence of (SEQ ID NO: 215)
QVQLQESGPGLVKPSETLSLTCTVSGFSLSNYGVHWVRQPPGKGLEWIGL
IWSDGSTTYNPSLKSRVTISKDTSKNQVSLKLSSVTAADTAVYYCARHPY
DDYSGYYYTMDYWGQGTLVTVS with 1H3 Heavy Chain CDR1:
(SEQ ID NO: 48)
NYGVH 1H3 Heavy Chain CDR2:
(SEQ ID NO: 224)
LIWSDGSTTYNPSLKS 1H3 Heavy Chain CDR3:
(SEQ ID NO: 69)
HPYDDYSGYYYTMDY.

The underlined amino acids are changed with regard to the parent sequence.

Another embodiment provides a humanized anti-SIGLEC 15 antibody having a variable heavy chain amino acid sequence of (SEQ ID NO: 216)
QVQLQESGPGLVKPSETLSLTCTVSGFSLSNYGVHWVRQPPGKGLEWIGL

IWSEGSTTYASALKSRVTISKDTSKNQVSLKLSSVTAADTAVYYCARHPY**

DDYSGYYYTMDYWGQGTLVTVS
with

1H3 Heavy Chain CDR1:
(SEQ ID NO: 48)
NYGVH

1H3 Heavy Chain CDR2:
(SEQ ID NO: 217)
LIWSEGSTTYASALKS

1H3 Heavy Chain CDR3:
(SEQ ID NO: 69)
HPYDDYSGYYYTMDY.

d. 1C12 Sequences:
i. Light Chain
1C12 Light Chain Variable Region Amino Acid Sequence is:

(SEQ ID NO: 3)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

WTFGGGTKLEIK,
with

1C12 Light Chain CDR1:
(SEQ ID NO: 24)
RSSQSIVHSNGNTYLE

1C12 Light Chain CDR2:
(SEQ ID NO: 32)
KVSNRFS

1C12 Light Chain CDR3:
(SEQ ID NO: 39)
FQGSHVPWT.

A nucleic acid sequence encoding the 1C12 light chain variable region is:

(SEQ ID NO: 77)
GATGTTTTGATGACCCAAACTCCACTCTCCCTGCCTGTCAGTCTTGGAGA

TCAAGCCTCCATCTCTTGCAGATCTAGTCAGAGCATTGTACATAGTAATG

GAAACACCTATTTAGAATGGTACCTGCAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

TGGACGTTCGGTGGAGGCACCAAGCTGGAAATCAA.

ii. Heavy Chain
1C12 Heavy Chain Variable Region Amino Acid Sequence is:

(SEQ ID NO: 16)
EVQLVESGGGLVKPGGSLKLSCAASGFSFSDYGMHWVRQAPEKGLEWVAY

ISSGSSILYYADIVKGRFTISRDNAKNTLFLQMTSLRSEDTAMYYCARDH

YHGNGSDYWGQGTTLTVSS,
with

1C12 Heavy Chain CDR1:
(SEQ ID NO: 49)
GFSFSDYGMH

1C12 Heavy Chain CDR2:
(SEQ ID NO: 59)
YISSGSSILYYADIVK

1C12 Heavy Chain CDR3:
(SEQ ID NO: 67)
DHYHGNGSDY.

A nucleic acid sequence encoding the 1C12 heavy chain variable region is:

(SEQ ID NO: 88)
GAGGTGCAGCTGGTGGAGTCTGGGGGAGGCTTAGTGAAGCCTGGAGGGTC

CCTGAAACTCTCCTGTGCAGCCTCTGGTTTCTCTTTCAGTGACTATGGAA

TGCACTGGGTTCGTCAGGCTCCAGAGAAGGGGCTGGAGTGGGTTGCATAC

ATTAGTAGTGGCAGTAGTATCCTCTACTATGCAGACATAGTGAAGGGCCG

ATTCACCATCTCCAGAGACAATGCCAAGAACACCCTGTTCCTGCAAATGA

CCAGTCTGAGGTCTGAGGACACGGCCATGTATTACTGTGCAAGGGACCAC

TACCATGGTAACGGGTCCGACTACTGGGGCCAAGGCACCACTCTCACAGT

CTCCTCA.

e. 3H10 Sequences:
i. Light Chain
3H10 Light Chain Variable Region Amino Acid Sequence is:

(SEQ ID NO: 6)
QIILTQSPAIMSASPGEKVTMTCSASSSTSFMHWYQQKPGTSPKRWIFDT

SKLASGVPGRFIGSGSGTSYSLTISTMEAEDAATYYCHQRSAYPWTFGGG

TKLEIK,
with

3H10 Light Chain CDR1:
(SEQ ID NO: 27)
SASSSTSFMH

3H10 Light Chain CDR2:
(SEQ ID NO: 35)
DTSKLA

3H10 Light Chain CDR3:
(SEQ ID NO: 42)
HQRSAYPWT.

A nucleic acid sequence encoding the 3H10 light chain variable region is:

(SEQ ID NO: 78)
CAAATTATTCTCACCCAGTCTCCAGCAATCATGTCTGCATCTCCAGGGGA
GAAGGTCACCATGACCTGCAGTGCCAGCTCAAGTACAAGTTTCATGCACT
GGTACCAGCAGAAGCCAGGCACCTCCCCCAAAAGATGGATTTTTGACACA
TCCAAACTGGCTTCTGGAGTCCCTGGTCGCTTCATTGGTAGTGGGTCTGG
GACCTCTTATTCTCTCACAATCAGCACCATGGAGGCTGAAGATGCTGCCA
CTTATTACTGCCATCAGCGGAGTGCTTACCCATGGACGTTCGGTGGAGGC
ACCAAGCTGGAAATCAAA.

ii. Heavy Chain

3H10 Heavy Chain Variable Region Amino Acid Sequence is:

(SEQ ID NO: 17)
EVQLQQSGAELVRPGASVKLSCTASGFNIKDYYMHWVKERPEQGLEWIGR
IDPEDGDIEYDPKFQGKATMTADTSSNTAYLQFSSLTSEDTAVYYCVTDY
DYDGGWFAYWGQGTLVTVSA,
with 3H10 Heavy Chain CDR1:
(SEQ ID NO: 50)
GFNIKDYYMH 3H10 Heavy Chain CDR2:
(SEQ ID NO: 60)
RIDPEDGDIEYDPKFQG 3H10 Heavy Chain CDR3:
(SEQ ID NO: 70)
DYDYDGGWFAY.

A nucleic acid sequence encoding the 3H10 heavy chain variable region is:

(SEQ ID NO: 89)
GAGGTTCAGCTGCAGCAGTCTGGGGCAGAGCTTGTGAGGCCAGGGGCCTC
AGTCAAGTTGTCCTGCACAGCTTCTGGCTTCAACATTAAAGACTACTATA
TGCACTGGGTGAAAGAGAGGCCTGAACAGGGCCTGGAGTGGATTGGAAGG
ATTGATCCTGAGGATGGTGATATTGAATATGACCCGAAGTTCCAGGGCAA
GGCCACTATGACTGCAGATACATCCTCCAACACAGCCTACCTGCAGTTCA
GCAGCCTGACATCTGAGGACACTGCCGTCTATTATTGTGTCACGGACTAT
GATTACGACGGAGGCTGGTTTGCTTACTGGGGCCAAGGGACTCTGGTCAC
TGTCTCTGCA.

f. 5G12 Sequences:
i. Light Chain
5G12 Light Chain Variable Region Amino Acid Sequence is:

(SEQ ID NO: 7)
DIKMTQSPSSMYASLGERVTITCKASQDINSYLSWFQQKPGKSPKTLIYR
ANRLVDGVPSRFSGSGSGQDYSLTISSLEYEDMGIYYCLQYDEFPYTFGG
GTKLEIKR,
with 5G12 Light Chain CDR1:
(SEQ ID NO: 28)
KASQDINSYLS 5G12 Light Chain CDR2:
(SEQ ID NO: 36)
RANRLVD 5G12 Light Chain CDR3:
(SEQ ID NO: 43)
LQYDEFPYT.

A nucleic acid sequence encoding the 5G12 light chain variable region is:

(SEQ ID NO: 79)
GACATCAAGATGACCCAGTCTCCATCTTCCATGTATGCATCTCTAGGAGA
GAGAGTCACTATCACTTGCAAGGCGAGTCAGGACATTAATAGCTATTTAA
GCTGGTTCCAGCAGAAACCAGGGAAATCTCCTAAGACCCTGATCTATCGT
GCAAACAGATTGGTAGATGGGGTCCCATCAAGGTTCAGTGGCAGTGGATC
TGGGCAAGATTATTCTCTCACCATCAGCAGCCTGGAGTATGAAGATATGG
GAATTTATTATTGTCTACAGTATGATGAGTTTCCGTACACGTTCGGAGGG
GGGACCAAGCTGGAAATAAAA.

ii. Heavy Chain
5G12 Heavy Chain Variable Region Amino Acid Sequence is:

(SEQ ID NO: 18)
QVQLQQPGAELVKPGASVKMSCKASGYTFTSYWITWVIQRPGQGLEWIGD
IYCGSDTMHYNEKFKNKATLIVDTSSSTAYMQLSSLISEDSAVYYCARWW
DYGSSYDYFDYWGQGTTLTVSS,
with 5G12 Heavy Chain CDR1:
(SEQ ID NO: 51)
GYTFTSYWIT 5G12 Heavy Chain CDR2:
(SEQ ID NO: 61)
DIYCGSDTMHYNEKFKN 5G12 Heavy Chain CDR3:
(SEQ ID NO: 71)
WWDYGSSYDYFDY.

A nucleic acid sequence encoding the 5G12 heavy chain variable region is:

(SEQ ID NO: 90)
CAGGTCCAACTGCAGCAGCCTGGGGCTGAGCTTGTGAAGCCTGGGGCTTC
AGTGAAGATGTCCTGCAAGGCTTCTGGCTACACCTTCACCAGCTACTGGA

TAACCTGGGTGATACAGAGGCCGGGACAAGGCCTTGAGTGGATTGGAGAT

ATTTATTGTGGTAGTGATACTATGCACTACAATGAGAAGTTCAAGAACAA

GGCCACACTGACTGTAGACACATCCTCCAGCACAGCCTACATGCAGCTCA

GCAGCCTGACATCTGAGGACTCTGCGGTCTATTACTGTGCAAGATGGTGG

GACTACGGTAGTAGCTACGACTACTTTGACTACTGGGGCCAAGGCACCAC

TCTCACAGTCTCCTCA.

g. 6F8 Sequences:
i. Light Chain
6F8 Light Chain Variable Region Amino Acid Sequence is:

(SEQ ID NO: 8)
DIVMTQAAPSVPVTPGESVSISCRSSKSLLHSNGNTYLYWFLQRPGQSPQ

LLIYRMSNLASGVPDRFGGSGSGTAFTLRISRVEAEDVGVYYCMQHLEYP

YTFGGGTKLEIKR,
with

6F8 Light Chain CDR1:
(SEQ ID NO: 25)
RSSKSLLHSNGNTYLY

6F8 Light Chain CDR2:
(SEQ ID NO: 33)
RMSNLAS

6F8 Light Chain CDR3:
(SEQ ID NO: 40)
MQHLEYPYT.

A nucleic acid sequence encoding the 6F8 light chain variable region is:

(SEQ ID NO: 80)
GATATTGTGATGACTCAGGCTGCACCCTCTGTACCTGTCACTCCTGGAGA

GTCAGTATCCATCTCCTGCAGGTCTAGTAAGAGTCTCCTGCATAGTAATG

GCAACACTTACTTGTATTGGTTCCTGCAGAGGCCAGGCCAGTCTCCTCAG

CTCCTGATATATCGGATGTCCAACCTTGCCTCAGGAGTCCCAGACAGGTT

CGGTGGCAGTGGGTCAGGAACTGCTTTCACACTGAGAATCAGTAGAGTGG

AGGCTGAGGATGTGGGTGTTTATTATTGTATGCAACATCTAGAATATCCG

TACACGTTCGGAGGGGGGACCAAGCTGGAAATAAAA.

ii. Heavy Chain
6F8 Heavy Chain Variable Region Amino Acid Sequence is:

(SEQ ID NO: 19)
QVQLKQSGPELVRPGASVKISCEASGYTFTDYYVNWVKQRPGRGLEWIGK

IGPGSVSIYYNEKFKDKATLTADKSSTAYMQLSGLTSEDSAVYFCASYY

YGFAYWGQGTLVTVSA,
with

6F8 Heavy Chain CDR1:
(SEQ ID NO: 52)
GYTFTDYYVN

6F8 Heavy Chain CDR2:
(SEQ ID NO: 62)
KIGPGSVSIYYNEKFKD

6F8 Heavy Chain CDR3:
(SEQ ID NO: 68)
YYYGFAY.

A nucleic acid sequence encoding the 6F8 heavy chain variable region is:

(SEQ ID NO: 91)
CAGGTCCAGCTGAAGCAGTCTGGACCTGAACTGGTGAGGCCTGGGGCTTC

AGTGAAGATATCCTGCGAGGCTTCTGGCTACACCTTCACTGACTATTATG

TAAACTGGGTGAAGCAGAGGCCTGGACGGGGCCTTGAGTGGATTGGAAAG

ATTGGTCCTGGAAGTGTTAGTATTTACTACAATGAGAAGTTCAAGGACAA

GGCCACACTGACTGCAGACAAATCCTCCAGCACAGCCTACATGCAGCTCA

GCGGCCTGACATCTGAGGACTCTGCAGTCTATTTCTGTGCAAGTTATTAC

TACGGTTTTGCTTACTGGGGCCAAGGGACTCTGGTCACTGTCTCTGCA.

h. 8C8 sequences:
i. Light Chain
8C8 Light Chain Variable Region Amino Acid Sequence is:

(SEQ ID NO: 9)
DIVMTQAAPSVPVTPGESVSISCRSSKSLLHSNGNTYLYWFLQRPGQSPQ

LLIYRMSNLASGVPDRFGGSGSGTAFTLRISRVEAEDVGVYYCMQHLEYP

YTFGGGTKLEIK,
with

8C8 Light Chain CDR1:
(SEQ ID NO: 25)
RSSKSLLHSNGNTYLY

8C8 Light Chain CDR2:
(SEQ ID NO: 33)
RMSNLAS

8C8 Light Chain CDR3:
(SEQ ID NO: 40)
MQHLEYPYT.

A nucleic acid sequence encoding the 8C8 light chain variable region is:

(SEQ ID NO: 81)
GATATTGTGATGACTCAGGCTGCACCCTCTGTACCTGTCACTCCTGGAGA

GTCAGTATCCATCTCCTGCAGGTCTAGTAAGAGTCTCCTGCATAGTAATG

GCAACACTTACTTGTATTGGTTCCTGCAGAGGCCAGGCCAGTCTCCTCAG

CTCCTGATATATCGGATGTCCAACCTTGCCTCAGGAGTCCCAGACAGGTT

CGGTGGCAGTGGGTCAGGAACTGCTTTCACACTGAGAATCAGTAGAGTGG

AGGCTGAGGATGTGGGTGTTTATTACTGTATGCAACATCTAGAATATCCG

TACACGTTCGGAGGGGGGACCAAGCTGGAAATAAAA.

ii. Heavy Chain
8C8 Heavy Chain Variable Region Amino Acid Sequence is:

(SEQ ID NO: 20)
QVQLKQSGAELVKPGASVKISCKASGYTFTDYYVNWVKQRPGQGLEWIGK

IGPESVSIYYSEKFKAKATLTADKSSSTAYMQLSSLTSEDSAVYFCASYY

YGFAYWGQGTLVTVSA,
with

8C8 Heavy Chain CDR1:
(SEQ ID NO: 52)
GYTFTDYYVN

8C8 Heavy Chain CDR2:
(SEQ ID NO: 63)
KIGPESVSIYYSEKFKA

8C8 Heavy Chain CDR3:
(SEQ ID NO: 68)
YYYGFAY.

A nucleic acid sequence encoding the 8C8 heavy chain variable region is:

(SEQ ID NO: 92)
CAGGTCCAGCTGAAGCAGTCTGGAGCTGAGCTGGTGAAGCCTGGGGCTTC

AGTGAAGATATCCTGCAAGGCTTCTGGCTACACCTTCACTGACTATTATG

TAAACTGGGTGAAGCAGAGGCCTGGACAGGGCCTTGAGTGGATTGGAAAG

ATTGGTCCTGAAAGTGTTAGTATTTATTACAGTGAGAAGTTCAAGGCCAA

GGCCACACTGACTGCAGACAAATCCTCCAGCACAGCCTACATGCAACTCA

GCAGCCTGACATCTGAGGACTCTGCAGTCTATTTCTGTGCAAGTTATTAC

TACGGGTTTGCTTACTGGGGCCAAGGGACTCTGGTCACTGTCTCTGCA.

i. 8H8 Sequences:
i. Light Chain
8H8 Light Chain Variable Region Amino Acid Sequence is:

(SEQ ID NO: 10)
QAVVTQESALTTSPGETVTLTCRSSSGAVTTGNFANWVQEKPDHLFTGLI

GGTNNRAPGVPARFSGSLIGDKAALTITGAQTEDEAIYFCALWYSNHWVF

GGGTKLTVL,
with

8H8 Light Chain CDR1:
(SEQ ID NO: 29)
RSSSGAVTTGNFAN

8H8 Light Chain CDR2:
(SEQ ID NO: 37)
GTNNRAP

8H8 Light Chain CDR3:
(SEQ ID NO: 44)
ALWYSNHWV.

A nucleic acid sequence encoding the 8H8 light chain variable region is:

(SEQ ID NO: 82)
CAGGCTGTTGTGACTCAGGAATCTGCACTCACCACATCACCTGGTGAAAC

AGTCACACTCACTTGTCGCTCAAGTTCTGGGGCTGTTACAACTGGTAACT

TTGCCAACTGGGTCCAAGAAAAACCAGATCATTTATTCACTGGTCTAATA

GGTGGTACCAACAACCGAGCTCCAGGTGTTCCTGCCAGATTCTCAGGCTC

CCTGATTGGAGACAAGGCTGCCCTCACCATCACAGGGGCACAGACTGAGG

ATGAGGCAATATATTTCTGTGCTCTATGGTACAGCAACCACTGGGTGTTC

GGTGGAGGAACCAAACTGACTGTCCTA.

ii. Heavy Chain
8H8 Heavy Chain Variable Region Amino Acid Sequence is:

(SEQ ID NO: 21)
EVQLLETGGGLVQPGGSRGLSCEGSGFTFSGFWMSWVRQTPGKTLEWIGD

INSDGSAINYAPSIKDRFTIFRDNDKNTLYLQMNNVRSEDTATYFCVRYD

DYGYFDVWGTGTTVTVSS,
with

8H8 Heavy Chain CDR1:
(SEQ ID NO: 53)
GFTFSGFWMS

8H8 Heavy Chain CDR2:
(SEQ ID NO: 64)
DINSDGSAINYAPSIKD

8H8 Heavy Chain CDR3:
(SEQ ID NO: 72)
YDDYGYFDV.

A nucleic acid sequence encoding the 8H8 heavy chain variable region is:

(SEQ ID NO: 93)
GAAGTGCAGCTGTTGGAGACTGGAGGAGGCTTGGTGCAACCGGGGGGGTC

ACGGGGACTCTCTTGTGAAGGCTCAGGGTTCACTTTTAGTGGCTTCTGGA

TGAGCTGGGTTCGACAGACACCTGGGAAGACCCTGGAGTGGATTGGAGAC

ATTAATTCTGATGGCAGTGCAATAAACTACGCACCATCCATAAAGGATCG

ATTCACTATCTTCAGAGACAATGACAAGAACACCCTGTACCTGCAGATGA

ACAATGTGCGATCGGAGGACACAGCCACGTATTTCTGTGTGAGATATGAT

GATTACGGGTACTTCGATGTCTGGGGCACAGGGACCACGGTCACCGTCTC

CTCA.

j. 9A5 Sequences:
i. Light Chain
9A5 Light Chain Variable Region Amino Acid Sequence is:

(SEQ ID NO: 11)
DVVMTQTPLTLSVTIGQSASISCKSSQSLLDSDGKTYLNWLLQRPGQSPK

RLIYLVSKLDSGVPDRFTGSGSGTDFTLKISRVEAEDLGVYYCWQGTHFP

FTFGSGTKLEIK,
with

9A5 Light Chain CDR1:
(SEQ ID NO: 30)
KSSQSLLDSDGKTYLN

9A5 Light Chain CDR2:
(SEQ ID NO: 38)
LVSKLDS

9A5 Light Chain CDR3:

(SEQ ID NO: 45)
WQGTHFPFT.

A nucleic acid sequence encoding the 9A5 light chain variable region is:

(SEQ ID NO: 83)
GATGTTGTGATGACCCAGACTCCACTCACTTTGTCGGTTACCATTGGACA

GTCAGCCTCCATCTCTTGCAAGTCAAGTCAGAGCCTCTTAGATAGTGATG

GAAAGACATATTTGAATTGGTTGTTACAGAGGCCAGGCCAGTCTCCAAAG

CGCCTAATCTATCTGGTGTCTAAACTGGACTCTGGAGTCCCTGACAGGTT

CACTGGCAGTGGATCAGGGACAGATTTCACACTGAAAATCAGCAGAGTGG

AGGCTGAGGATTTGGGAGTTTATTATTGCTGGCAAGGTACACATTTTCCA

TTCACGTTCGGCTCGGGGACAAAGTTGGAAATAAAA.

ii. Heavy Chain

9A5 Heavy Chain Variable Region Amino Acid Sequence is:

(SEQ ID NO: 22)
HVQLQQSGAELARPGASVKLSCKASGYTFTSYGLIWVKQRTGQGLEWIGE

IYPRSGNTYYNEKFKGKATLTADISSSTAYMELRSLTSEDSAVYFCASSS

PHGDYWGQGTTLTVSS,
with

9A5 Heavy Chain CDR1:
(SEQ ID NO: 54)
GYTFTSYGLI

9A5 Heavy Chain CDR2:
(SEQ ID NO: 65)
EIYPRSGNTYYNEKFKG

9A5 Heavy Chain CDR3:
(SEQ ID NO: 73)
SSPHGDY.

A nucleic acid sequence encoding the 9A5 heavy chain variable region is:

(SEQ ID NO: 94)
CACGTTCAGCTGCAGCAGTCTGGAGCTGAGTTGGCGAGGCCTGGGCTTC

AGTGAAGCTGTCCTGCAAGGCTTCTGGCTACACCTTCACAAGCTATGGTT

TAATCTGGGTGAAGCAGAGAACTGGACAGGGCCTTGAGTGGATTGGAGAG

ATTTATCCTAGAAGTGGTAATACTTACTACAATGAGAAGTTCAAGGGCAA

GGCCACACTGACTGCAGACATATCCTCCAGCACAGCGTACATGGAGCTCC

GCAGCCTGACATCTGAGGACTCTGCGGTCTATTTCTGTGCAAGTTCCTCT

CCTCACGGGGACTACTGGGGCCAAGGCACCACTCTCACAGTCTCCTCA.

k. 10G9 Sequences:
i. Light Chain
10G9 Light Chain Variable Region Amino Acid Sequence is:

(SEQ ID NO: 12)
QAVVTQESALTTSPGETVTLTCRSSTGAVTTSNYANWVQEKPDHLFTGLI

GGTNNRAPGVPARFSGSLIGDKAALTITGAQTEDEAIYFCALWYSNHWVF

GGGTKLTVL,
with

10G9 Light Chain CDR1:
(SEQ ID NO: 31)
RSSTGAVTTSNYAN

10G9 Light Chain CDR2:
(SEQ ID NO: 37)
GTNNRAP

10G9 Light Chain CDR3:
(SEQ ID NO: 44)
ALWYSNHWV.

A nucleic acid sequence encoding the 10G9 light chain variable region is:

(SEQ ID NO: 84)
CAGGCTGTTGTGACTCAGGAATCTGCACTCACCACATCACCTGGTGAAAC

AGTCACACTCACTTGTCGCTCAAGTACTGGGGCTGTTACAACTAGTAACT

ATGCCAACTGGGTCCAAGAAAAACCAGATCATTTATTCACTGGTCTAATA

GGTGGTACCAACAACCGAGCTCCAGGTGTTCCTGCCAGATTCTCAGGCTC

CCTGATTGGAGACAAGGCTGCCCTCACCATCACAGGGGCACAGACTGAGG

ATGAGGCAATATATTTCTGTGCTCTATGGTACAGCAACCACTGGGTGTTC

GGTGGAGGAACCAAACTGACTGTCCTA.

ii. Heavy Chain

10G9 Heavy Chain Variable Region Amino Acid Sequence is:

(SEQ ID NO: 23)
EVQLLETGGGLVQPGGSRGLSCEGSGFTFSDFWMSWVRQTPGKTLEWIGD

INSDGSAVNYAPSIKDQFTIFRDNDKRTLHLQMINVRSEDTATYFCVRYD

DYGYFDVWGTGTTVTVSS,
with

10G9 Heavy Chain CDR1:
(SEQ ID NO: 55)
GFTFSDFWMS

10G9 Heavy Chain CDR2:
(SEQ ID NO: 66)
DINSDGSAVNYAPSIKD

10G9 Heavy Chain CDR3:
(SEQ ID NO: 72)
YDDYGYFDV.

A nucleic acid sequence encoding the 10G9 heavy chain variable region is:

(SEQ ID NO: 95)
GAAGTGCAGCTGTTGGAGACTGGAGGAGGCTTAGTGCAACCTGGGGGGTC

ACGGGGACTCTCTTGTGAAGGCTCAGGGTTCACTTTTAGTGACTTCTGGA

-continued

TGAGCTGGGTTCGACAGACACCTGGGAAGACCCTGGAGTGGATTGGAGAC

ATTAATTCTGATGGCAGTGCAGTTAACTACGCACCATCCATAAAGGATCA

ATTCACTATCTTCAGAGACAATGACAAGAGGACCCTGCACCTGCAGATGA

TCAATGTTCGATGGAGGACACAGCCACGTATTTCTGTGTGAGATATGAT

GATTACGGGTACTTCGATGTCTGGGGCACAGGGACCACGGTCACCGTCTC

CTCA.

l. 6A Sequences
i. Light Chain
6A Light Chain Variable Region Amino Acid Sequence is:

(SEQ ID NO: 96)
DVLMTQTPLSLPVSLGDQASISCRSSQSIVHSNGNTYLEWYLQKPGQSPK

LLIYKVSNRFSGVPDRFSGSGSGTDFTLRISRVEAEDLGVYYCFQGSHVP

LTFGAGTKLELK,
with

6A Light Chain CDR1:
(SEQ ID NO: 24)
RSSQSIVHSNGNTYLE

6A Light Chain CDR2:
(SEQ ID NO: 32)
KVSNRFS

6A Light Chain CDR3:
(SEQ ID NO: 157)
FQGSHVPLT.

A nucleic acid sequence encoding the 6A light chain variable region is:

(SEQ ID NO: 120)
GATGTTTTGATGACCCAAACTCCACTCTCCCTGCCTGTCAGTCTTGGAGA

TCAAGCCTCCATCTCTTGCAGATCTAGTCAGAGTATTGTACATAGTAATG

GAAACACCTATTTAGAATGGTACCTGCAGAAGCCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAGGATCAGCAGAGTGG

AGGCTGAGGATCTGGGAGTTTATTACTGCTTTCAAGGTTCACATGTTCCG

CTCACGTTCGGTGCTGGGACCAAGCTGGAGCTGAAA.

ii. Heavy Chain
6A Heavy Chain Variable Region Amino Acid Sequence is:

(SEQ ID NO: 108)
EVQLQQSGAELVRPGASVKLSCTASGFNIKDDYMHWVKQRPEQGLEWIGC

IDPENGDTEYASKFQDKATITTDTSSNTAYLQLSSLTSEDTAVYYCTTYV

GFAYWGQGTLVTVST,
with

6A Heavy Chain CDR1:
(SEQ ID NO: 162)
DDYMH

6A Heavy Chain CDR2:
(SEQ ID NO: 170)
CIDPENGDTEYASKFQD

6A Heavy Chain CDR3:
(SEQ ID NO: 182)
YVGFAY.

A nucleic acid sequence encoding the 6A heavy chain variable region is:

(SEQ ID NO: 133)
GAGGTTCAGCTGCAGCAGTCTGGGGCTGAACTTGTGAGGCCAGGGGCCTC

AGTCAAGTTGTCCTGCACAGCTTCTGGCTTTAACATTAAAGACGACTATA

TGCACTGGGTGAAACAGAGGCCTGAACAGGGCCTGGAGTGGATTGGATGC

ATTGATCCTGAGAATGGTGATACTGAATATGCCTCGAAATTCCAGGACAA

GGCCACTATAACAACAGACACATCCTCCAACACAGCCTACCTGCAGCTCA

GCAGCCTGACATCTGAGGACACTGCCGTCTATTACTGTACTACATACGTT

GGATTTGCTTACTGGGGCCAAGGGACTCTGGTCACTGTCTCTACA.

m. 28A Sequences
i. Light Chain
28A Light Chain Variable Region Amino Acid Sequence is:

(SEQ ID NO: 97)
DVVMTQTPLTLSIPIGQPASISCKSSQSLLDSDGKTYLNWLLQRPGQSPK

RLIYLVSELDSGVPDRFTGSGSGTDFTLKISRVEAEDLGVYYCWQGTHFP

FTFGSGTKLEIK,
with

28A Light Chain CDR1:
(SEQ ID NO: 30)
KSSQSLLDSDGKTYLN

28A Light Chain CDR2:
(SEQ ID NO: 153)
LVSELDS

28A Light Chain CDR3:
(SEQ ID NO: 45)
WQGTHFPFT.

A nucleic acid sequence encoding the 28A light chain variable region is:

(SEQ ID NO: 121)
GATGTTGTGATGACCCAGACTCCACTCACTTTGTCGATTCCCATTGGACA

ACCAGCCTCCATCTCTTGTAAGTCAAGTCAGAGCCTCTTAGATAGTGATG

GAAAGACATATTTGAATTGGTTGTTACAGAGGCCAGGCCAGTCTCCAAAG

CGCCTCATCTATCTGGTGTCTGAACTGGACTCTGGAGTCCCTGACAGGTT

CACTGGCAGTGGATCAGGGACAGATTTCACACTGAAAATCAGCAGAGTGG

AGGCTGAAGATTTGGGAGTTTATTATTGTTGGCAAGGTACACATTTTCCA

TTCACGTTCGGCTCGGGGACAAAGTTGGAAATAAAA.

ii. Heavy Chain
28A Heavy Chain Variable Region Amino Acid Sequence is:

(SEQ ID NO: 109)
QVQLQQSGAELARPGASVKLSCKASGYTFISYGITWVKQRTGQGLEWIGE

IHPRSGNTYYNENFKDRASLTADKSSSTAYMEVRSLTSEDSAVYFCARGG

PGDYWGQGTTLTVSS, with

28A Heavy Chain CDR1:
(SEQ ID NO: 163)
SYGIT

28A Heavy Chain CDR2:
(SEQ ID NO: 171)
EIHPRSGNTYYNENFKD

28A Heavy Chain CDR3:
(SEQ ID NO: 183)
GGPGDY.

A nucleic acid sequence encoding the 28A heavy chain variable region is:

(SEQ ID NO: 134)
CAGGTTCAGCTGCAGCAGTCTGGAGCTGAGCTGGCGAGGCCTGGGGCTTC

AGTGAAGCTGTCCTGCAAGGCTTCTGGCTACACCTTCATAAGCTATGGTA

TAACCTGGGTGAAGCAGAGAACTGGACAGGGCCTTGAGTGGATTGGAGAG

ATTCATCCTAGAAGTGGTAATACTTACTACAATGAGAATTTCAAGGACAG

GGCCTCACTGACTGCAGACAAATCCTCCAGCACAGCGTACATGGAGGTCC

GCAGCCTGACATCTGAGGACTCTGCGGTCTATTTCTGTGCAAGGGGTGGG

CCGGGGGACTACTGGGGCCAAGGCACCACTCTCACAGTCTCCTCA.

n. 63A Sequences
i. Light Chain
63A Light Chain Variable Region Amino Acid Sequence is:

(SEQ ID NO: 98)
DVVMTQTPLTLSVTIGQPASISCKSSQSLLDSDGKTYLNWLLQRPGQSPK

RLIYLVSKLDSGVPDRFTGSGSGTDFTLKISRVEAEDLGVYYCWQGTHFP

FTFGSGTKLEIK,
with

63A Light Chain CDR1:
(SEQ ID NO: 30)
KSSQSLLDSDGKTYLN

63A Light Chain CDR2:
(SEQ ID NO: 38)
LVSKLDS

63A Light Chain CDR3:
(SEQ ID NO: 45)
WQGTHFPFT.

A nucleic acid sequence encoding the 63A light chain variable region is:

(SEQ ID NO: 122)
GATGTTGTGATGACCCAGACTCCACTCACTTTGTCGGTTACCATTGGACA

ACCAGCCTCCATCTCTTGCAAGTCAAGTCAGAGCCTCTTAGATAGTGATG

GAAAGACATATTTGAATTGGTTGTTACAGAGGCCAGGCCAGTCTCCAAAG

CGCCTAATCTATCTGGTGTCTAAACTGGACTCTGGAGTCCCTGACAGGTT

CACTGGCAGTGGATCAGGGACAGATTTCACACTGAAAATCAGCAGAGTGG

AGGCTGAGGATTTGGGAGTTTATTATTGTTGGCAAGGTACACATTTTCCA

TTCACGTTCGGCTCGGGGACAAAGTTGGAAATAAAA.

ii. Heavy Chain
63A Heavy Chain Variable Region Amino Acid Sequence is:

(SEQ ID NO: 110)
QVQLQQSGAELARPGASVKLSCKASGYTFTSYGISWVKQRTGQGLEWIGQ

IYPRSDNTYYNERFKGKATLTADKSSSTAYMALRSLTSEDSAVYFCAREG

GPDYWGQGTTLTVSS,
with

63A Heavy Chain CDR1:
(SEQ ID NO: 164)
SYGIS

63A Heavy Chain CDR2:
(SEQ ID NO: 172)
QIYPRSDNTYYNERFKGK

63A Heavy Chain CDR3:
(SEQ ID NO: 184)
EGGPDY.

A nucleic acid sequence encoding the 63A heavy chain variable region is:

(SEQ ID NO: 135)
CAGGTTCAGCTGCAGCAGTCTGGAGCTGAGCTGGCGAGGCCTGGGGCTTC

AGTGAAGCTGTCCTGCAAGGCTTCTGGCTACACCTTCACAAGCTATGGTA

TAAGCTGGGTGAAGCAGAGAACTGGACAGGGCCTTGAGTGGATTGGACAG

ATTTATCCTAGAAGTGACAATACTTACTACAATGAGAGGTTCAAGGGCAA

GGCCACACTGACTGCAGACAAATCCTCCAGCACAGCGTACATGGCGCTCC

GCAGCCTGACATCTGAGGACTCTGCGGTCTATTTCTGTGCAAGAGAGGGG

GGTCCCGACTACTGGGGCCAAGGCACCACTCTCACAGTCTCCTCA.

o. 71A Sequences
i. Light Chain
71A Light Chain Variable Region Amino Acid Sequence is:

(SEQ ID NO: 99)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

LTFGAGTKLELK,
with

71A Light Chain CDR1:
(SEQ ID NO: 24)
RSSQSIVHSNGNTYLE

71A Light Chain CDR2:
(SEQ ID NO: 32)
KVSNRFS

71A Light Chain CDR3:
(SEQ ID NO: 157)
FQGSHVPLT.

A nucleic acid sequence encoding the 71A light chain variable region is:

(SEQ ID NO: 123)
GACGTTTTGATGACCCAAACTCCACTCTCCCTGCCTGTCAGTCTTGGAGA

TCAAGCCTCCATCTCTTGCAGATCTAGTCAGAGTATTGTACATAGTAATG

-continued

GAAACACCTATTTAGAATGGTACCTACAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

CTCACGTTCGGTGCTGGGACCAAGCTGGAGCTGAAA.

ii. Heavy Chain

71A Heavy Chain Variable Region Amino Acid Sequence is:

(SEQ ID NO: 111)
EVQLQQSGAELVRPGASVKLSCTASGFNIKDDYMHWVKQRPEQGLEWIGC
IDPENGDIEYASRFQGKATMTADTSSNTAYLQLTSLTSADTAVYYCTTYV
GFGYWGQGTLVTVSA,
with 71A Heavy Chain CDR1:
(SEQ ID NO: 162)
DDYMH 71A Heavy Chain CDR2:
(SEQ ID NO: 173)
CIDPENGDIEYASRFQG 71A Heavy Chain CDR3:
(SEQ ID NO: 185)
YVGFGY.

A nucleic acid sequence encoding the 71A heavy chain variable region is:

(SEQ ID NO: 136)
GAGGTTCAGCTGCAGCAGTCTGGGGCTGAGCTTGTGAGGCCAGGGGCCTC

AGTCAAGTTGTCCTGCACAGCTTCTGGCTTTAACATTAAAGACGACTATA

TGCACTGGGTGAAACAGAGGCCTGAACAGGGCCTGGAGTGGATTGGATGC

ATTGATCCTGAGAATGGTGATATTGAATATGCCTCGAGGTTCCAGGGCAA

GGCCACTATGACAGCAGACACATCCTCCAACACAGCCTACCTGCAGCTCA

CCAGCCTGACATCTGCGGACACTGCCGTCTATTACTGTACTACATACGTT

GGATTTGGTTACTGGGGCCAAGGGACTCTGGTCACTGTCTCTGCA.

p. 77A Sequences i. Light Chain

77A Light Chain Variable Region Amino Acid Sequence is:

(SEQ ID NO: 100)
DVLMTQSPLSLPVSLGDQASISCRSSQNIVHSNGNTYLEWYLKKPGQSPK
LLIYKVSNRFSGVPDRFSGSGSGTDFTLKISRVEAEDLGMYYCFQGSHVP
LTFGAGTKLELK,
with 77A Light Chain CDR1:
(SEQ ID NO: 146)
RSSQNIVHSNGNTYLE 77A Light Chain CDR2:
(SEQ ID NO: 32)
KVSNRFS 77A Light Chain CDR3:
(SEQ ID NO: 157)
FQGSHVPLT.

A nucleic acid sequence encoding the 77A light chain variable region is:

(SEQ ID NO: 124)
GATGTTTTGATGACCCAAAGTCCACTCTCCCTGCCTGTCAGTCTTGGAGA

TCAAGCCTCCATCTCTTGCAGATCTAGTCAGAACATAGTACATAGTAATG

GTAACACCTATTTAGAATGGTACCTGAAGAAACCAGGCCAGTCTCCAAAG

CTCCTGATCTACAAAGTCTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAATGTATTACTGCTTTCAAGGTTCACATGTTCCG

CTCACGTTCGGAGCTGGGACCAAGCTGGAGCTGAAA.

ii. Heavy Chain

77A Heavy Chain Variable Region Amino Acid Sequence is:

(SEQ ID NO: 112)
EVQLQQSGAELVRPGASVKLSCTASGFNIKDDYMHWVKQRPEQGLEWIGC
IDPENGDTEYASKFQGKATITADTSSNTVYLQLSSLTSEDTAVYYCTTYV
GFGYWGQGTLVTVSA,
with 77A Heavy Chain CDR1:
(SEQ ID NO: 162)
DDYMH 77A Heavy Chain CDR2:
(SEQ ID NO: 174)
CIDPENGDTEYASKFQG 77A Heavy Chain CDR3:
(SEQ ID NO: 185)
YVGFGY.

A nucleic acid sequence encoding the 77A heavy chain variable region is:

(SEQ ID NO: 137)
GAGGTTCAGCTGCAGCAGTCTGGGGCTGAGCTTGTGAGGCCAGGGGCCTC

AGTCAAGTTGTCCTGCACAGCTTCTGGCTTTAACATTAAAGACGACTATA

TGCACTGGGTGAAACAGAGGCCTGAACAGGGCCTGGAGTGGATTGGATGT

ATTGATCCTGAGAATGGTGATACTGAATATGCCTCGAAGTTCCAGGGCAA

GGCCACTATAACAGCAGACACATCCTCCAACACAGTCTACCTGCAGCTCA

GCAGCCTGACATCTGAGGACACTGCCGTCTATTACTGTACTACATACGTT

GGATTTGGTTACTGGGGCCAGGGGACTCTGGTCACTGTCTCTGCA.

q. 80A Sequences i. Light Chain

80A Light Chain Variable Region Amino Acid Sequence is:

(SEQ ID NO: 101)
DIVMTQSPSSLTVTAGEKVTMSCKSNQSLLNSGDQKNYLTWYQQKPGQP
PKLLIYWASTRESGVPDRFTGSGSGTDFTLTISSVQAEDLAIYYCQNDY
SYPLTFGAGTKLELK, with
80A Light Chain CDR1:
(SEQ ID NO: 147)
KSNQSLLNSGDQKNYLT
80A Light Chain CDR2:
(SEQ ID NO: 154)
WASTRES
80A Light Chain CDR3:
(SEQ ID NO: 158)
QNDYSYPLT.

A nucleic acid sequence encoding the 80A light chain variable region is:

(SEQ ID NO: 125)
GACATTGTGATGACACAGTCTCCATCCTCCCTGACTGTGACAGCAGGAG

AGAAGGTCACTATGAGCTGCAAGTCCAATCAGAGTCTGTTAAACAGTGG

AGATCAAAAGAACTACTTGACCTGGTACCAGCAGAAACCAGGGCAGCCT

CCTAAACTATTGATCTACTGGGCATCCACTAGGGAATCTGGGGTCCCTG

ATCGCTTCACAGGCAGTGGATCTGGAACAGATTTCACTCTCACCATCAG

CAGTGTGCAGGCTGAAGACCTGGCAATTTATTACTGTCAGAATGATTAT

AGTTATCCACTCACGTTCGGTGCTGGGACCAAGCTGGAGCTGAAA.

ii. Heavy Chain

80A Heavy Chain Variable Region Amino Acid Sequence is:

(SEQ ID NO: 113)
QVQLKQSGAELVRPGASVKLSCRASGYTFTDFYINWVKQRPGQGLEWIA

RIYPGSDETYYNEKFKDKVTLTAEKSSSTAYMQLSSLTSEDSAVYFCAL

WFFDVWGTGTTVTVSS,
with

80A Heavy Chain CDR1:
(SEQ ID NO: 165)
DFYIN
80A Heavy Chain CDR2:
(SEQ ID NO: 175)
RIYPGSDETYYNEKFKD
80A Heavy Chain CDR3:
(SEQ ID NO: 186)
WFFDV.

A nucleic acid sequence encoding the 80A heavy chain variable region is:

(SEQ ID NO: 138)
CAGGTCCAACTGAAGCAGTCTGGGGCTGAACTGGTGAGGCCTGGGGCTT

CAGTGAAGCTGTCCTGCAGGGCTTCTGGCTACACTTTCACTGACTTCTA

CATAAACTGGGTGAAGCAGAGGCCTGGACAGGGACTTGAGTGGATTGCA

AGGATTTATCCTGGAAGTGATGAGACTTACTACAATGAGAAGTTTAAGG

ACAAGGTCACACTGACTGCAGAAAAATCCTCCAGCACTGCCTACATGCA

GCTCAGCAGCCTGACATCTGAGGACTCTGCTGTCTATTTCTGTGCCCTC

TGGTTCTTCGATGTCTGGGGCACAGGGACCACGGTCACCGTCTCCTCA.

r. 82B Sequences
i. Light Chain
82B Light Chain Variable Region Amino Acid Sequence is:

(SEQ ID NO: 102)
DVVMTQTPLTLSVTIGQSASISCKSSQSLLDSDGNTYLNWLLQRPGQSP

KRLIYLVSELDSGVPDRFTGSGSGTDFTLKISRVEAEDLGVYYCWQGTH

FPFTFGSGTKLEIK,
with

82B Light Chain CDR1:
(SEQ ID NO: 148)
KSSQSLLDSDGNTYLN

82B Light Chain CDR2:
(SEQ ID NO: 153)
LVSELDS

82B Light Chain CDR3:
(SEQ ID NO: 45)
WQGTHFPFT.

A nucleic acid sequence encoding the 82B light chain variable region is:

(SEQ ID NO: 126)
GATGTTGTGATGACCCAGACTCCACTCACTTTGTCGGTTACTATTGGAC

AATCAGCCTCCATCTCTTGCAAGTCAAGTCAGAGCCTCCTAGATAGTGA

TGGAAACACATATTTGAATTGGTTGTTACAGAGGCCAGGCCAGTCTCCA

AAGCGCCTAATCTATTTGGTGTCTGAACTGGACTCTGGAGTCCCTGACA

GGTTCACTGGCAGTGGATCAGGGACAGATTTCACACTGAAAATCAGCAG

AGTGGAGGCTGAGGATTTGGGAGTTTATTATTGCTGGCAAGGTACACAT

TTTCCATTCACGTTCGGCTCGGGGACAAAGTTGGAAATAAAA.

ii. Heavy Chain

82B Heavy Chain Variable Region Amino Acid Sequence is:

(SEQ ID NO: 114)
QVQLQQSGAELARPGASVKLSCKASGYTFTSDGITWVKQRTGQGLEWIG

QIHPRSGNTYYNGKFKGKATLTADRSSSTTYMELRSLTSEDSAVYFCAK

TGTGDYWGQGTTLTVSS,
with

82B Heavy Chain CDR1:
(SEQ ID NO: 166)
SDGIT

82B Heavy Chain CDR2:
(SEQ ID NO: 176)
QIHPRSGNTYYNGKFKG

82B Heavy Chain CDR3:
(SEQ ID NO: 187)
TGTGDY.

A nucleic acid sequence encoding the 82B heavy chain variable region is:

(SEQ ID NO: 139)
CAGGTTCAGCTGCAGCAGTCTGGAGCTGAGTTGGCGAGGCCTGGGGCTT

CAGTGAAGCTGTCCTGCAAGGCTTCGGGCTACACCTTCACAAGCGATGG s. 83B Sequences
i. Light Chain

83B Light Chain Variable Region Amino Acid Sequence is:

(SEQ ID NO: 103)
EIQMTQSPSSMSASLGDRITITCQATQDIVKNLNWYQQKPGKPPSFLIYYATELAEGVPSRFSGSGSGSDYSLTISNLESEDFADYYCLQFYEFPYTFGGGTKLEIK,
with 83B Light Chain CDR1:
(SEQ ID NO: 149)
QATQDIVKNLN 83B Light Chain CDR2:
(SEQ ID NO: 155)
YATELAE 83B Light Chain CDR3:
(SEQ ID NO: 159)
LQFYEFPYT.

A nucleic acid sequence encoding the 83B light chain variable region is:

(SEQ ID NO: 127)
GAAATCCAGATGACCCAGTCTCCATCCTCTATGTCTGCATCTCTGGGAG
ACAGAATAACCATCACTTGCCAGGCAACTCAAGACATTGTTAAGAATTT
AAACTGGTATCAGCAGAAACCAGGGAAACCCCCTTCATTCCTGATCTAT
TATGCAACTGAACTGGCAGAAGGGGTCCCATCAAGGTTCAGTGGCAGTG
GGTCTGGGTCAGACTATTCTCTGACAATCAGCAACCTGGAGTCTGAAGA
TTTTGCAGACTATTACTGTCTACAGTTTTATGAATTTCCGTACACGTTC
GGAGGGGGGACCAAGCTGGAAATAAAA.

ii. Heavy Chain

83B Heavy Chain Variable Region Amino Acid Sequence is:

(SEQ ID NO: 115)
EVQLQQSGPELVKPGASVKMSCKASGYTFTDYNMHWVKQSHGKSLEWIGYINPNNGGTSYNQKFKDKATLTVNKSSSTAFMELRSLASEDSAVYYCARSDWEDCWGQGTTLTVSS,
with 83B Heavy Chain CDR1:
(SEQ ID NO: 167)
DYNMH 83B Heavy Chain CDR2:
(SEQ ID NO: 177)
YINPNNGGTSYNQKFKD 83B Heavy Chain CDR3:
(SEQ ID NO: 188)
SDWEDC.

A nucleic acid sequence encoding the 83B heavy chain variable region is:

(SEQ ID NO: 140)
GAGGTCCAGCTGCAACAGTCTGGACCTGAGCTGGTGAAGCCTGGGGCTT
CAGTGAAGATGTCCTGCAAGGCTTCTGGATACACATTCACTGACTACAA
CATGCACTGGGTGAAGCAGAGCCATGGAAAGAGCCTTGAGTGGATTGGA
TATATTAACCCTAACAATGGTGGTACTAGCTACAACCAGAAGTTCAAGG
ACAAGGCCACATTGACTGTAAACAAGTCCTCCAGCACAGCCTTCATGGA
GCTCCGCAGCCTGGCATCGGAGGATTCTGCAGTCTATTACTGTGCAAGG
TCTGACTGGGAAGACTGCTGGGGCCAAGGCACCACTCTCACAGTCTCC
TCA.

t. 92A Sequences
i. Light Chain

92A Light Chain Variable Region Amino Acid Sequence is:

(SEQ ID NO: 104)
QIVLTQSPAIMSASLGEEITLICSASSSVSYMHWYQQKSGTSPKLLIYRTSNLASGVPSRFSGSGSGTFYSLTISSVEAEDAADYYCHQWSSWTFGGGTQLEIK,
with 92A Light Chain CDR1:
(SEQ ID NO: 150)
SASSSVSYMH 92A Light Chain CDR2:
(SEQ ID NO: 156)
RTSNLAS 92A Light Chain CDR3:
(SEQ ID NO: 160)
HQWSSWT.

A nucleic acid sequence encoding the 92A light chain variable region is:

(SEQ ID NO: 128)
CAAATTGTTCTCACCCAGTCTCCAGCAATCATGTCTGCATCTCTAGGGG
AGGAGATCACCCTAATTTGCAGTGCCAGCTCGAGTGTAAGTTACATGCA
CTGGTACCAGCAGAAGTCAGGCACTTCTCCCAAACTCTTGATTTATCGC
ACATCCAACCTGGCTTCTGGAGTCCCTTCTCGCTTCAGTGGCAGTGGGT
CTGGGACCTTTTATTCTCTTACAATCAGCAGTGTGGAGGCTGAAGATGC
TGCCGATTATTACTGCCATCAGTGGAGTAGTTGGACGTTCGGTGGAGGC
ACCCAGCTGGAAATCAAA.

ii. Heavy Chain
92A Heavy Chain Variable Region Amino Acid Sequence is:

(SEQ ID NO: 116)
DVQLQESGPGLVKFSQSLSLTCSVTGYSITSGYYWNWIRQFPGNKLEWM

GYIRHDGSNNYNPSLKNRISITRDTSKNQFFLKLNSVITEDTATYYCVR

EIYDGSSGYFDVWGTGTTVTVSS,
with

92A Heavy Chain CDR1:
(SEQ ID NO: 168)
SGYYWN

92A Heavy Chain CDR2:
(SEQ ID NO: 178)
YIRHDGSNNYNPSLKN

92A Heavy Chain CDR3:
(SEQ ID NO: 189)
EIYDGSSGYFDVWGT.

A nucleic acid sequence encoding the 92A heavy chain variable region is:

(SEQ ID NO: 141)
GATGTACAGCTTCAGGAGTCAGGACCTGGCCTCGTGAAATTTTCTCAGT

CTCTGTCTCTCACCTGCTCTGTCACTGGCTACTCCATCACCAGTGGTTA

TTACTGGAACTGGATCCGGCAGTTTCCAGGAAACAAACTGGAATGGATG

GGCTACATAAGACACGATGGTAGCAATAACTACAACCCGTCTCTCAAAA

ATCGAATCTCCATCACTCGTGACACATCTAAGAACCAGTTTTTCCTGAA

GTTGAATTCTGTGATTACTGAGGACACAGCCACATATTACTGTGTAAGA

GAGATCTATGATGGTTCCTCCGGGTACTTCGATGTCTGGGGCACAGGGA

CCACGGTCACCGTCTCCTCA.

u. 93B Sequences
i. Light Chain
93B Light Chain Variable Region Amino Acid Sequence is:

(SEQ ID NO: 105)
DIVMTQSPSSLTVTAGEKVTMSCKSSQSLLNSGNQKNYLTWYQQKPGQP

PKLLIYWASTRESGVPDRFTGSGSGTDFTLTISNVQPEDLAVYYCQNDY

SFPFTFGSGTELEMK,
with

93B Light Chain CDR1:
(SEQ ID NO: 151)
KSSQSLLNSGNQKNYLT

93B Light Chain CDR2:
(SEQ ID NO: 154)
WASTRES

93B Light Chain CDR3:
(SEQ ID NO: 161)
QNDYSFPFT.

A nucleic acid sequence encoding the 93B light chain variable region is:

(SEQ ID NO: 129)
GACATTGTGATGACACAGTCTCCATCCTCCCTGACTGTGACAGCAGGAG
AGAAGGTCACTATGAGCTGCAAGTCCAGTCAGAGTCTGTTAAACAGTGG

AAATCAAAAGAATTACTTGACCTGGTACCAGCAGAAACCAGGACAGCCT

CCTAAACTGTTGATCTACTGGGCATCCACTAGGGAATCTGGGGTCCCTG

ATCGCTTCACAGGCAGTGGATCTGGAACAGATTTCACTCTCACCATTAG

CAATGTGCAGCCTGAAGACCTGGCAGTTTATTACTGTCAGAATGATTAT

AGTTTTCCATTCACGTTCGGCTCGGGGACAGAGTTGGAAATGAAA.

ii. Heavy Chain
93B Heavy Chain Variable Region Amino Acid Sequence is:

(SEQ ID NO: 117)
QVQLKQSGAELVRPGASVKLSCKASGYTFTDYYINWVKQRPGQGLEWIA

RIYPGNGNTDYNEKFKDKATLTAEKSSTTAYIQLSSLTSEDSAVYFCCL

WYFDVWGTGTTVTVSS,
with

93B Heavy Chain CDR1:
(SEQ ID NO: 169)
DYYIN

93B Heavy Chain CDR2:
(SEQ ID NO: 179)
RIYPGNGNTDYNEKFKD

93B Heavy Chain CDR3:
(SEQ ID NO: 190)
WYFDV.

A nucleic acid sequence encoding the 93B heavy chain variable region is:

(SEQ ID NO: 142)
CAGGTCCAGCTGAAGCAGTCTGGGGCTGAACTGGTGAGGCCTGGGGCTT

CAGTGAAGCTGTCCTGCAAGGCTTCTGGCTACACTTTCACTGACTACTA

TATAAACTGGGTGAAGCAGAGGCCTGGACAGGGACTTGAGTGGATTGCA

AGGATTTATCCTGGAAATGGTAATACTGACTACAATGAGAAGTTCAAGG

ACAAGGCCACACTGACTGCAGAAAAATCCTCCACCACTGCCTACATACA

ACTCAGCAGTCTGACATCTGAGGACTCTGCTGTCTATTTCTGTTGCCTC

TGGTACTTCGATGTCTGGGGCACAGGAACCACGGTCACCGTCTCCTCA.

v. 99B Sequences
i. Light Chain
99B Light Chain Variable Region Amino Acid Sequence is:

(SEQ ID NO: 106)
DVVMTQTPLTLSVTIGQPASISCKSSQSLLDSDGKTYLNWLLQRPGQSP

KRLIYLVSKLDSGVPDRFTGSGSGTDFTLKISRVEAEDLGIYYCWQGTH

FPFTFGSGTKLEIK,
with

99B Light Chain CDR1:
(SEQ ID NO: 30)
KSSQSLLDSDGKTYLN

99B Light Chain CDR2:
(SEQ ID NO: 38)
LVSKLDS

99B Light Chain CDR3:
(SEQ ID NO: 45)
WQGTHFPFT.

A nucleic acid sequence encoding the 99B light chain variable region is:

(SEQ ID NO: 130)
GATGTTGTGATGACCCAGACTCCACTCACTTTGTCGGTTACCATTGGAC

AACCAGCCTCCATCTCTTGCAAGTCAAGTCAGAGCCTCTTAGATAGTGA

TGGAAAGACATATTTGAATTGGTTGTTACAGAGGCCAGGCCAGTCTCCA

AAGCGCCTAATCTATCTGGTGTCTAAACTGGACTCTGGAGTCCCTGACA

GGTTCACTGGCAGTGGATCAGGGACAGATTTCACACTGAAAATCAGCAG

AGTGGAGGCTGAGGATTTGGGAATTTATTATTGCTGGCAAGGTACACAT

TTTCCATTCACGTTCGGCTCGGGGACAAAGTTGGAAATAAAA.

ii. Heavy Chain

99B Heavy Chain Variable Region Amino Acid Sequence is:

(SEQ ID NO: 118)
QVQLQQSGAELARPGASVKLSCKASGYTFTSDGITWLKQRTGQGLEWIG

QIHPRSGNTYYNEKFKGKATLTADKSSSTAYMELRSLTSEDSAVYFCAK

TGTGDYWGQGTTLTVSS,
with

99B Heavy Chain CDR1:
(SEQ ID NO: 166)
SDGIT

99B Heavy Chain CDR2:
(SEQ ID NO: 180)
QIHPRSGNTYYNEKFKG

99B Heavy Chain CDR3:
(SEQ ID NO: 187)
TGTGDY.

A nucleic acid sequence encoding the 99B heavy chain variable region is:

(SEQ ID NO: 143)
CAGGTTCAGCTGCAGCAGTCTGGAGCTGAGCTGGCGAGGCCTGGGCTT

CAGTGAAGCTGTCCTGCAAGGCTTCGGGCTACACCTTCACAAGCGACGG

TATAACCTGGCTGAAACAGAGAACTGGACAGGGCCTTGAGTGGATTGGA

CAGATTCATCCTAGAAGTGGTAATACCTACTACAATGAGAAGTTCAAGG

GCAAGGCCACACTGACTGCAGACAAATCCTCCAGCACAGCGTACATGGA

ACTCCGCAGCCTGACATCTGAGGACTCTGCGGTCTATTTCTGTGCAAAA

ACTGGGACGGGGACTACTGGGGCCAAGGCACCACTCTCACAGTCTCC

TCA.

w. 104B Sequences i. Light Chain

104B Light Chain Variable Region Amino Acid Sequence is:

(SEQ ID NO: 107)
DVVMTQTPLTLSVTIGQPASISCKSSLSLLDSDGKTYLNWLLQRPGQSP

KRLIYLVSKLDSGVPDRFTGSGSGTDFTLKIIRVEAEDLGIYYCWQGTH

FPFTFGSGTKLEVK,
with

104B Light Chain CDR1:
(SEQ ID NO: 152)
KSSLSLLDSDGKTYLN

104B Light Chain CDR2:
(SEQ ID NO: 38)
LVSKLDS

104B Light Chain CDR3:
(SEQ ID NO: 45)
WQGTHFPFT.

A nucleic acid sequence encoding the 104B light chain variable region is:

(SEQ ID NO: 131)
GATGTTGTGATGACCCAGACTCCACTCACTTTGTCGGTTACCATTGGAC

AACCAGCCTCCATCTCTTGCAAGTCAAGTCTGAGCCTCTTAGATAGTGA

TGGAAAGACATATTTGAATTGGTTGTTACAGAGGCCAGGCCAGTCTCCA

AAGCGCCTAATCTATCTGGTGTCTAAACTGGACTCTGGAGTCCCTGACA

GGTTCACTGGCAGTGGATCAGGGACAGATTTCACACTGAAAATCATCAG

AGTGGAGGCTGAGGATTTGGGAATTTATTATTGCTGGCAAGGTACACAT

TTTCCATTCACGTTCGGCTCGGGGACAAAGTTGGAAGTAAAA.

ii. Heavy Chain

104B Heavy Chain Variable Region Amino Acid Sequence is:

(SEQ ID NO: 119)
QVQLQQSGPELARPGASVKLSCKASGYTFTSYGISWVKQRTGQGLEWIG

QIHPRSGNTYYNENFKGKATLTAAKSSSTAYLELRSLTSEDSAVYFCAR

EGGPDYWGQGTTLTVSS,
with

104B Heavy Chain CDR1:
(SEQ ID NO: 164)
SYGIS

104B Heavy Chain CDR2:
(SEQ ID NO: 181)
QIHPRSGNTYYNENFKG

104B Heavy Chain CDR3:
(SEQ ID NO: 184)
EGGPDY.

A nucleic acid sequence encoding the 104B heavy chain variable region is:

(SEQ ID NO: 144)
CAGGTTCAGCTGCAGCAGTCTGGGCCTGAGCTGGCGAGGCCTGGGGCCT

CAGTGAAGCTGTCCTGCAAGGCTTCTGGCTACACCTTCACAAGCTATGG

```
TATAAGCTGGGTGAAGCAAAGAACTGGACAGGGCCTTGAGTGGATTGGA

CAGATTCATCCTAGAAGTGGTAATACTTACTACAATGAGAACTTCAAGG

GCAAGGCCACACTGACTGCAGCCAAATCCTCCAGCACAGCGTACCTGGA

GCTCCGCAGCCTGACATCTGAGGACTCTGCGGTCTATTTCTGTGCAAGA

GAGGGGGGTCCCGACTACTGGGGCCAAGGCACCACTCTCACAGTCTC

CTCA.
``` x. 105A Sequences
i. Light Chain
105A Light Chain Variable Region Amino Acid Sequence is:

(SEQ ID NO: 99)
DVLMTQTPLSLPVSLGDQASISCRSSQSIVHSNGNTYLEWYLQKPGQSP

KLLIYKVSNRFSGVPDRFSGSGSGTDFTLKISRVEAEDLGVYYCFQGSH

VPLTFGAGTKLELK,
with

105A Light Chain CDR1:
(SEQ ID NO: 24)
RSSQSIVHSNGNTYLE

105A Light Chain CDR2:
(SEQ ID NO: 32)
KVSNRFS

105A Light Chain CDR3:
(SEQ ID NO: 157)
FQGSHVPLT.

A nucleic acid sequence encoding the 105A light chain variable region is:

```
                                      (SEQ ID NO: 132)
GATGTTTTGATGACCCAAACTCCACTCTCCCTGCCTGTCAGTCTTGGAG

ATCAAGCCTCCATCTCTTGCAGATCTAGTCAGAGTATTGTACATAGTAA

TGGAAACACCTATTTAGAATGGTACCTACAGAAACCAGGCCAGTCTCCA

AAGCTCCTGATCTACAAAGTTTCCAACCGATTTTCTGGGGTCCCAGACA

GGTTCAGTGGCAGTGGATCAGGGACAGATTTCACACTCAAGATCAGCAG

AGTGGAGGCTGAGGATCTGGGAGTTTATTACTGCTTTCAAGGTTCACAT

GTTCCGCTCACGTTCGGTGCTGGGACCAAGCTGGAGCTGAAA.
``` ii. Heavy Chain
105A Heavy Chain Variable Region Amino Acid Sequence is:

(SEQ ID NO: 111)
EVQLQQSGAELVRPGASVKLSCTASGFNIKDDYMHWVKQRPEQGLEWIG

CIDPENGDIEYASRFQGKATMTADTSSNTAYLQLTSLTSADTAVYYCTT

YVGFGYWGQGTLVTVSA,
with

105A Heavy Chain CDR1:
(SEQ ID NO: 162)
DDYMH

105A Heavy Chain CDR2:
(SEQ ID NO: 173)
CIDPENGDIEYASRFQG

105A Heavy Chain CDR3:
(SEQ ID NO: 185)
YVGFGY.

A nucleic acid sequence encoding the 105A heavy chain variable region is:

```
                                      (SEQ ID NO: 145)
GAGGTTCAGCTGCAGCAGTCTGGGGCTGAGCTTGTGAGGCCAGGGGCCTC

AGTCAAGTTGTCCTGCACAGCTTCTGGCTTTAACATTAAAGACGACTATA

TGCACTGGGTGAAACAGAGGCCTGAACAGGGCCTGGAGTGGATTGGATGC

ATTGATCCTGAGAATGGTGATATTGAATATGCCTCGAGGTTCCAGGGCAA

GGCCACTATGACAGCAGACACATCCTCCAACACAGCCTACCTGCAGCTCA

CCAGCCTGACATCTGCGGACACTGCCGTCTATTACTGTACTACATACGTT

GGATTTGGTTACTGGGGCCAAGGGACTCTGGTCACTGTCTCTGCA.
```

2. Anti-Siglec-15 Antibodies and Antigen Binding Fragments Thereof

Siglec-15 binding molecules, including antibodies and antigen binding fragments thereof, that bind to one or more Siglec-15 polypeptides or fusion proteins, or fragments or variants thereof are disclosed. The antibodies disclosed herein are typically monoclonal antibodies, or antigen binding fragments thereof, that bind to an epitope present on a Siglec-15 polypeptide, or fragment or fusion thereof. In some embodiments the antibody binds to a conformational epitope. In some embodiments the antibody binds to a linear epitope. A linear epitope can be 4, 5, 6, 7, 8, 9, 10, 11, or more continuous amino acids in length. The epitope can include one or more non-amino acid elements, post-translation modifications, or a combination thereof. Examples of post-translational modifications include, but are not limited to glycosylation, phosphorylation, acetylation, citrullination and ubiquitination. For example, antibodies can bind an epitope that is formed at least in-part by one or more sugar groups.

The antibody or antigen binding fragment thereof can bind to an epitope that is present on an endogenous Siglec-15 polypeptide, or a recombinant Siglec-15 polypeptide, or a combination thereof. In some embodiments, the antibody or antigen binding fragment thereof binds to the extracellular domain, or a fragment thereof, or an epitope formed therefrom of Siglec-15. In some embodiments, the antibody or antigen binding fragment thereof is a function blocking antibody that reduces or prevents Siglec-15 from binding to one or more of its ligands, reduces intracellular signaling modulated by Siglec-15, or a combination thereof.

As discussed above, Siglec-15 sialylated glycoproteins and preferentially recognizes the Neu5Acα2-6GalNAcα-structure. The experimental Examples below illustrate that Siglec-15 binds to Leucine-rich repeat-containing protein 4C (LRRC4C) (also referred to as Netrin-G1 ligand, and NGL-1), which may be depend or independent of a Neu5Acα2-6GalNAcα-structure. Nucleic acid and polypeptide sequences for LRRC4C are known in the art and include, for example, (SEQ ID NO: 192
MLNKMTLHPQQIMIGPRFNRALFDPLLVVLLALQLLVVAGLVRAQTCPSV

CSCSNQFSKVICVRKNLREVPDGISTNTRLLNLHENQIQIIKVNSFKHLR

-continued

HLEILQLSRNHIRTIEIGAFNGLANLNTLELFDNRLTTIPNGAFVYLSKL

KELWLRNNPIESIPSYAFNRIPSLRRLDLGELKRLSYISEGAFEGLSNLR

YLNLAMCNLREIPNLTPLIKLDELDLSGNHLSAIRPGSFQGLMHLQKLWM

IQSQIQVIERNAFDNLQSLVEINLAHNNLTLLPHDLFTPLHHLERIHLHH

NPWNCNCDILWLSWWIKDMAPSNTACCARCNTPPNLKGRYIGELDQNYFT

CYAPVIVEPPADLNVTEGMAAELKCRASTSLTSVSWITPNGTVMTHGAYK

VRIAVLSDGTLNFTNVTVQDTGMYTCMVSNSVGNTTASATLNVTAATTTP

FSYFSTVTVETMEPSQDEARTTDNNVGPTPVVDWETTNVTTSLTPQSTRS

TEKTFTIPVTDINSGIPGIDEVMKTTKIIIGCFVAITLMAAVMLVIFYKM

RKQHHRQNHHAPTRTVEIINVDDEITGDTPMESHLPMPAIEHEHLNHYNS

YKSPFNHTTTVNTINSIHSSVHEPLLIRMNSKDNVQETQI,

UniProtKB-Q9HCJ2 LRC4C_HUMAN and which is specifically incorporated by reference herein in its entirety).

Siglec-15 may also bind to a counter-receptor (S15-CR) on immune cells such as T cells.

Thus, in some embodiments, a function blocking (antagonistic) Siglec-15 binding molecule reduces, inhibits, or prevent interaction between Siglec-15 and ligand thereof such as a glycoprotein having the Neu5Acα2-6GalNAcα-structure, LRRC4C, or an Siglec-15-counter-receptor.

In some embodiments, binding of the antibody or antigen binding fragment thereof to Siglec-15 can increase immune activation, reduce immune suppression, or a combination thereof. For example, in particular embodiments, the antibody or antigen binding fragment thereof binds to the Ig-like V-type domain or the Ig-like C2-type domain of Siglec-15. In some embodiments, the epitope includes the sialic acid binding site of Siglec-15, (e.g., the epitope include residue 143 of SEQ ID NO: 1).

In some embodiments, the antibody binds to part or the all of the same epitope as monoclonal antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A. The epitope can be a linear epitope or a conformational epitope. In some embodiments, the antibody has the same epitope specificity as monoclonal antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A. This can be achieved by producing a recombinant antibody that contains the paratope of monoclonal antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A. In some embodiments, the Siglec-15 binding molecule includes some or all of the light chain CDRs, the entire light chain variable region, some or all of the heavy chain CDRs, the entire heavy chain variable region, or a combination thereof of any of mouse anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A.

The Siglec-15-binding molecules can include a CDR that is at least 45%, at least 50%, at least 55%, at least 60%, at least 65%, at least 70%, at least 75%, at least 80%, at least 85%, at least 90%, at least 95%, or at least 99% identical to the amino acid sequence of a CDR of the above-listed clones and which exhibit immunospecific binding to Siglec-15.

For example, the disclosed molecules can include one or more of the light chain CDR having the amino acid sequences of any of SEQ ID NO:24-45 and 146-161. The molecule can include at least one light chain CDR1, one light chain CDR2, and one light chain CDR3. For example, the molecule can include a light chain CDR1 including an amino acid sequence selected from the group consisting of SEQ ID NO:24-31 and 146-152. The molecule can include a light chain CDR2 including an amino acid sequence selected from the group consisting of SEQ ID NO:32-38 and 153-156. The molecule can include a light chain CDR3 including an amino acid sequence selected from the group consisting of SEQ ID NO:39-45 and 157-161.

In particular embodiments, the molecule includes a light chain CDR1, a light chain CDR2, and a light chain CDR3 wherein the light chain CDR1, the light chain CDR2, and the light chain CDR3 include the amino acid sequences:

|  | LCDR1 SEQ ID NO: | LCDR2 SEQ ID NO: | LCDR3 SEQ ID NO: |
|---|---|---|---|
| 1B2 | 24 | 32 and | 39; |
| 1C3 | 25 | 33 and | 40; |
| 1H3 | 26 | 34 and | 41; |
| 1C12 | 24 | 32 and | 39; |
| 3H10 | 27 | 35 and | 42; |
| 5G12 | 28 | 36 and | 43; |
| 6F8 | 25 | 33 and | 40; |
| 8C8 | 25 | 33 and | 40; |
| 8H8 | 29 | 37 and | 44; |
| 9A5 | 30 | 38 and | 45; |
| 10G9 | 31 | 37 and | 44; |
| #6 | 24 | 32 and | 157; |
| #28 | 30 | 153 and | 45; |
| #63 | 30 | 38 and | 45; |
| #71 | 24 | 32 and | 157; |
| #77 | 146 | 32 and | 157; |
| #80 | 147 | 154 and | 158; |
| #82 | 148 | 153 and | 45; |
| #83 | 149 | 155 and | 159; |
| #92 | 150 | 156 and | 160; |
| #93 | 151 | 154 and | 161; |
| #99 | 30 | 38 and | 45; |
| #104 | 152 | 38 and | 45; or |
| #105 | 24 | 32 and | 157. |

The disclosed molecules can include one or more of the heavy chain CDR having the amino acid sequences of any of SEQ ID NO:46-73 and 162-190. The molecule can include at least one heavy chain CDR1, one heavy chain CDR2, and one heavy chain CDR3. The molecule can include a heavy chain CDR1 including an amino acid sequence selected from the group consisting of SEQ ID NO:46-55 and 162-169. The molecule can include a heavy chain CDR2 including an amino acid sequence selected from the group consisting of SEQ ID NO:56-66 and 170-181. The molecule can include a heavy chain CDR3 including an amino acid sequence selected from the group consisting of SEQ ID NO:67-73 and 182-190.

In particular embodiments, the molecule includes a heavy chain CDR1, a heavy chain CDR2, and a heavy chain CDR3 wherein the heavy chain CDR1, the heavy chain CDR2, and the heavy chain CDR3 include the amino acid sequences:

|  | HCDR1 SEQ ID NO: | HCDR2 SEQ ID NO: | HCDR3 SEQ ID NO: |
|---|---|---|---|
| 1B2 | 46 | 56 and | 67; |
| 1C3 | 47 | 57 and | 68; |
| 1H3 | 48 | 58 and | 69; |
| 1C12 | 49 | 59 and | 67; |
| 3H10 | 50 | 60 and | 70; |

-continued

| | HCDR1 SEQ ID NO: | HCDR2 SEQ ID NO: | HCDR3 SEQ ID NO: |
|---|---|---|---|
| 5G12 | 51 | 61 and | 71; |
| 6F8 | 52 | 62 and | 68; |
| 8C8 | 52 | 63 and | 68; |
| 8H8 | 53 | 64 and | 72; |
| 9A5 | 54 | 65 and | 73; |
| 10G9 | 55 | 66 and | 72; |
| #6 | 162 | 170 and | 182; |
| #28 | 163 | 171 and | 183; |
| #63 | 164 | 172 and | 184; |
| #71 | 162 | 173 and | 185; |
| #77 | 162 | 174 and | 185; |
| #80 | 165 | 175 and | 186; |
| #82 | 166 | 176 and | 187; |
| #83 | 167 | 177 and | 188; |
| #92 | 168 | 178 and | 189; |
| #93 | 169 | 179 and | 190; |
| #99 | 166 | 180 and | 187; |
| #104 | 164 | 181 and | 184; or |
| #105 | 162 | 173 and | 185. |

The Siglec-15-binding molecules can include an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, at least 99%, or 100% identical to the amino acid sequence of the variable heavy chain and/or light chain of the antibody produced by any of the above clones, and which exhibits immunospecific binding to human Siglec-15.

For example, the disclosed Siglec-15-binding molecules can include a light chain variable region having the amino acids sequence of SEQ ID NO:3, 4, 5, 6, 7, 8, 9, 10, 11, 12, 96, 97, 98, 99, 100, 101, 102, 103, 104, 105, 106, or 107, or a variant thereof comprising at least 50%, 60%, 70%, 80%, 85%, 90%, 95%, 99%, or more sequence identity to SEQ ID NO:3, 4, 5, 6, 7, 8, 9, 10, 11, 12, 96, 97, 98, 99, 100, 101, 102, 103, 104, 105, 106, or 107, and which exhibits immunospecifically binding to Siglec-15.

Additionally or alternatively the disclosed Siglec-15-binding molecules can include a heavy chain variable region having the amino acids sequence of SEQ ID NO:13, 14, 15, 16, 17, 18, 19, 20, 21, 22, 23, 108, 109, 110, 111, 112, 113, 114, 115, 116, 117, 118, or 119, or a variant thereof comprising at least 50%, 60%, 70%, 80%, 85%, 90%, 95%, 99%, or more sequence identity to SEQ ID NO:13, 14, 15, 16, 17, 18, 19, 20, 21, 22, 23, 108, 109, 110, 111, 112, 113, 114, 115, 116, 117, 118, or 119, and which exhibits immunospecifically binding to Siglec-15.

The Siglec-15-binding molecule can be an immunoglobulin molecule (e.g., an antibody, diabody, fusion protein, etc.) that includes one, two or three light chain CDRs and one, two or three heavy chain CDRs (e.g., in some embodiments, three light chain CDRs and three heavy chain CDRs), wherein the light chain CDRs include:

(1) the light chain CDR1 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(2) the light chain CDR2 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(3) the light chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(4) the light chain CDR1 and the light chain CDR2 of mouse anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(5) the light chain CDR1 and the light chain CDR3 of mouse anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(6) the light chain CDR2 and the light chain CDR3 of mouse anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

or (7) the light chain CDR1, the light chain CDR2, and the light chain CDR3 mouse of anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or humanized variant thereof.

The molecule can be an immunoglobulin molecule includes one, two or three light chain CDRs and one, two or three heavy chain CDRs (e.g., in some embodiments, three light chain CDRs and three heavy chain CDRs), wherein the heavy chain CDRs include:

(1) the heavy chain CDR1 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(2) the heavy chain CDR2 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(3) the heavy chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(4) the heavy chain CDR1 and the heavy chain CDR2 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(5) the heavy chain CDR1 and the heavy chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(6) the heavy chain CDR2 and the heavy chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

or (7) the heavy chain CDR1, the heavy chain CDR2, and the heavy chain CDR3 murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof.

The molecule can be an immunoglobulin molecule that includes one, two or three light chain CDRs and one, two or three heavy chain CDRs (e.g., in some embodiments, three light chain CDRs and three heavy chain CDRs), wherein the light chain CDRs include:

(1) the light chain CDR1 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(2) the light chain CDR2 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(3) the light chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(4) the light chain CDR1 and the light chain CDR2 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(5) the light chain CDR1 and the light chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(6) the light chain CDR2 and the light chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

or (7) the light chain CDR1, the light chain CDR2, and the light chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof, and wherein the heavy chain CDRs include:

(1) the heavy chain CDR1 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(2) the heavy chain CDR2 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(3) the heavy chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(4) the heavy chain CDR1 and the heavy chain CDR2 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(5) the heavy chain CDR1 and the heavy chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

(6) the heavy chain CDR2 and the heavy chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof;

or (7) the heavy chain CDR1, the heavy chain CDR2, and the heavy chain CDR3 of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a humanized variant thereof.

For example, the antibody can have one or more CDR of murine 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A, or a chimeric antibody thereof, or a humanized variant having the CDR(s) corresponding to the CDR(s) of murine anti-human Siglec-15 antibody 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, or 105A.

One embodiment provides a humanized monoclonal antibody having a variable light chain amino acid sequence that is at least 45%, at least 50%, at least 55%, at least 60%, at least 65%, at least 70%, at least 75%, at least 80%, at least 85%, at least 90%, at least 95%, at least 99%, or 100% identical to the amino acid sequence selected from the group consisting of SEQ ID NO: 227, 228, and 229 and/or a variable heavy chain amino acid sequence that is at least 45%, at least 50%, at least 55%, at least 60%, at least 65%, at least 70%, at least 75%, at least 80%, at least 85%, at least 90%, at least 95%, at least 99%, or 100% identical to the amino acid sequence selected from the group consisting of SEQ ID NO: 230, 231, 233, and 235.

3. Antibody Compositions

The disclosed Siglec-15-binding molecules can antibodies or antigen binding fragments thereof. The disclosed antibodies and antigen binding fragments thereof include whole immunoglobulin (i.e., an intact antibody) of any class, fragments thereof, and synthetic proteins containing at least the antigen binding variable domain of an antibody. In some embodiments, the disclosed molecule contains both an antibody light chain as well as at least the variable domain of an antibody heavy chain. In other embodiments, such molecules can further include one or more of the CH1, hinge, CH2, CH3, and CH4 regions of the heavy chain (especially, the CH1 and hinge regions, or the CH1, hinge and CH2 regions, or the CH1, hinge, CH2 and CH3 regions). The antibody can be selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the antibody exhibit cytotoxic activity, and the class is typically $IgG_1$. In other embodiments, where such cytotoxic activity is not desirable, the constant domain can be of the $IgG_2$ or $IgG_4$ class. The antibody can include sequences from more than one class or isotype, and selecting particular constant domains to optimize desired effector functions is within the ordinary skill in the art.

The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A monoclonal antibody is obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

a. Chimeric and Humanized Antibodies

Chimeric antibodies and antigen binding fragments thereof including one or more of the disclosed sequences and functional variants thereof are also provided.

Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415, 5,807, 715, 4,816,567, and 4,816,397. Chimeric antibodies including one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, *Molecular Immunology* 28(4/5):489-498; Studnicka et al., 1994, *Protein Engineering* 7:805; and Roguska et al., 1994, *Proc. Natl. Acad. Sci. USA* 91:969), and chain shuffling (U.S. Pat. No. 5,565,332).

The disclosed molecules can be human or humanized antibodies, or antigen binding fragments thereof. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art, see, for example, European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; Molecular Immunology 28(4/5):489-498; Studnicka et al., 1994, Protein Engineering 7(6):805-814; Roguska et al., 1994, PNAS 91:969-973; Tan et al., 2002, J. Immunol. 169:1119-1125; Caldas et al., 2000, Protein Eng. 13:353-360; Morea et al., 2000, Methods 20:267-79; Baca et al., 1997, J. Biol. Chem. 272:10678-10684; Roguska et al., 1996, Protein Eng. 9:895-904; Couto et al., 1995, Cancer Res. 55 (23 Supp):5973s-5977s; Couto et al., 1995, Cancer Res. 55:1717-22; Sandhu, 1994, Gene 150:409-10; Pedersen et al., 1994, J. Mol. Biol. 235:959-973; Jones et al., 1986, Nature 321:522-525; Reichmann et al., 1988, Nature 332:323-329; and Presta, 1992, Curr. Op. Struct. Biol. 2:593-596).

Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a non-human antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies can be very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

A human, humanized or chimeric antibody derivative can include substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Such antibodies can also includes at least a portion of an immunoglobulin constant region (Fc), typically that of a human immunoglobulin. The constant domains of such antibodies can be selected with respect to the proposed function of the antibody, in particular the effector function which may be required. In some embodiments, the constant domains of such antibodies are or can include human IgA, IgD, IgE, IgG or IgM domains. In a specific embodiment, human IgG constant domains, especially of the IgG1 and IgG3 isotypes are used, when the humanized antibody derivative is intended for a therapeutic use and antibody effector functions such as antibody-dependent cell-mediated cytotoxicity (ADCC) and complement-dependent cytotoxicity (CDC) activity are needed. In alternative embodiments, IgG2 and IgG4 isotypes are used when the antibody is intended for therapeutic purposes and antibody effector function is not required. Fc constant domains including one or more amino acid modifications which alter antibody effector functions such as those disclosed in U.S. Patent Application Publication Nos. 2005/0037000 and 2005/0064514.

The framework and CDR regions of a humanized antibody need not correspond precisely to the parental sequences, e.g., the donor CDR or the consensus framework can be mutagenized by substitution, insertion or deletion of at least one residue so that the CDR or framework residue at that site does not correspond to either the consensus or the donor antibody. In some embodiments, such mutations not extensive. Usually, at least 75% of the humanized antibody residues will correspond to those of the parental framework region (FR) and CDR sequences, more often 90%, or greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, Proc. Natl. Acad. Sci. 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, J. Immunol. 169:1119-25, Caldas et al., 2000, Protein Eng. 13:353-60, Morea et al., 2000, Methods 20:267-79, Baca et al., 1997, J. Biol. Chem. 272:10678-84, Roguska et al., 1996, Protein Eng. 9:895-904, Couto et al., 1995, Cancer Res. 55 (23 Supp):5973s-5977s, Couto et al., 1995, Cancer Res. 55:1717-22, Sandhu, 1994, Gene 150:409-10, Pedersen et al., 1994, J. Mol. Biol. 235:959-73, Jones et al., 1986, Nature 321:522-525, Riechmann et al., 1988, Nature 332:323, and Presta, 1992, Curr. Op. Struct. Biol. 2:593-596.

Often, framework residues in the framework regions will be substituted with the corresponding residue from the CDR donor antibody to alter, for example improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693, 762; 5,693,761; 5,585,089; and 5,530,101 and Riechmann et al., 1988, *Nature* 332:323).

Human, chimeric or humanized derivatives of the disclosed murine anti-human Siglec-15 antibodies can be used for in vivo methods in humans. Murine antibodies or antibodies of other species can be advantageously employed for many uses (for example, in vitro or in situ detection assays, acute in vivo use, etc.). Such a human or humanized antibody can include amino acid residue substitutions, deletions or additions in one or more non-human CDRs. The humanized antibody derivative can have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Such human antibodies can be made by a variety of methods known in the art including phage display methods using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Such human antibodies can be produced using transgenic mice which are incapable of expressing functional endogenous immunoglobulins, but which can express human immunoglobulin genes.

For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

DNA sequences coding for human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions can be naturally occurring or consensus framework regions, and human framework regions (see, e.g., Chothia et al., 1998, "Structural Determinants In The Sequences Of Immunoglobulin Variable Domain," *J. Mol. Biol.* 278: 457-479 for a listing of human framework regions).

i. Humanized 5G12

One embodiment provides a humanized 5G12 antibody or antigen binding fragment thereof.

b. Single-Chain Antibodies

The Siglec-15-binding molecules can be single-chain antibodies. Methods for the production of single-chain antibodies are well known to those of skill in the art. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

c. Monovalent Antibodies

In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the $F(ab')_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The $F(ab')_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

d. Conjugates or Fusions of Antibody Fragments

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Such coupling of the antibody or fragment with the therapeutic agent can be achieved by making an immunoconjugate or by making a fusion protein, or by linking the antibody or fragment to a nucleic acid such as an siRNA, comprising the antibody or antibody fragment and the therapeutic agent.

In some embodiments, the antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. Antibodies can be engineered with Fc variants that extend half-life, e.g., using Xtend™ antibody half-life prolongation technology (Xencor, Monrovia, Calif.). In other embodiments, the half-life of the anti-DNA antibody is decreased to reduce potential side effects. The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

e. Mono and Multi-Specific Antibodies

In some embodiments the disclosed antibodies are mono-specific, binding only to Siglec-15. Bispecific derivatives of such antibodies, trispecific derivatives of such antibodies or derivative antibodies of greater multi-specificity, that exhibit specificity to different immune system targets in addition to their specificity for human Siglec-15 are also provided. For example, such antibodies can bind to both human Siglec-15 and to an antigen that is important for targeting the antibody to a particular cell type or tissue (for example, to an antigen associated with a cancer antigen of a tumor being treated). In another embodiment, such multispecific antibody binds to molecules (receptors or ligands) involved in alternative immunomodulatory pathways, such as B7-H1, PD-1, CTLA4, TIM3, TIM4, OX40, CD40, GITR, 4-1-BB, LIGHT or LAG3, in order to enhance the immunomodulatory effects and combine multiple mechanisms of action, such as ligand blocking, immune cell activation and direct tumor targeting, in one molecule.

f. Derivatives

Production and use of "derivatives" of any of the disclosed Siglec-15-binding molecules are also disclosed. A derivative molecule, for example an antibody or antibody fragment, can be modified by chemical modifications using techniques known to those of skill in the art, including, but not limited to, specific chemical cleavage, acetylation, formulation, metabolic synthesis of tunicamycin, etc. The term derivative encompasses non amino acid modifications, for example, amino acids that can be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/ blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function.

In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma RIII*," Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha (1-6) Dextran Increases Its Affinity For Antigen*," J. Exp. Med. 168(3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region*," J. Immunol. 143(8): 2595-2601; Routledge, E. G. et al. (1995) "*The Effect Of Aglycosylation On The Immunogenicity Of A Humanized Therapeutic CD3 Monoclonal Antibody*," Transplantation 60(8):847-53; Elliott, S. et al. (2003) "*Enhancement Of Therapeutic Protein In Vivo Activities Through Glycoengineering*," Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277 (30): 26733-26740).

The disclosed antibodies can be modified by recombinant means to increase greater efficacy of the antibody in mediating the desired function. Thus, antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., *Mol. Immunol.* 30:105-08 (1993). The modification in amino acids includes deletions, additions, substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to Siglec-15 polypeptides, or fragments, or fusions thereof. See e.g., *Antibody Engineering: A Practical Approach* (Oxford University Press, 1996).

In some embodiments, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody. Substitutions, additions or deletions in the derivatized antibodies can be in the Fc region of the antibody and can thereby serve to modify the binding affinity of the antibody to one or more FcγR. Methods for modifying antibodies with modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821.

In some embodiments, antibodies whose Fc region have been deleted (for example, an Fab or F(ab)2, etc.) or modified so that the molecule exhibits diminished or no Fc receptor (FcR) binding activity, or exhibits enhanced antibody-dependent cell-mediated cytotoxicity (ADCC) or complement dependent cytotoxicity (CDC) activities. In some embodiments, the antibodies have altered affinity for an activating FcγR, e.g., FcγRIIIA. Such modifications can also have an altered Fc-mediated effector function. Modifications that affect Fc-mediated effector function are well known in the art (see U.S. Pat. No. 6,194,551, and WO 00/42072). In one particular embodiment, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1q binding activity, an altered complement-dependent cytotoxicity activity (CDC), a phagocytic activity, or any combination thereof.

Derivatized antibodies can be used to alter the half-lives (e.g., serum half-lives) of parental antibodies in a mammal, such as a human. For example, such alteration can result in a half-life of greater than 15 days, greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies or fragments thereof in a mammal, such as a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The humanized antibodies can be engineered to increase biological half-lives (see, e.g. U.S. Pat. No. 6,277,375). For example, humanized antibodies can be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The antibodies can also be modified by the methods and coupling agents described by Davis et al. (See U.S. Pat. No. 4,179,337) in order to provide compositions that can be injected into the mammalian circulatory system with substantially no immunogenic response.

The framework residues of the humanized antibodies can be modified. Residues in the framework regions can be substituted with the corresponding residue from the CDR donor antibody to alter, for example improve, antigen binding. These framework substitutions can be identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann, L. et al. (1988) "*Reshaping Human Antibodies For Therapy*," Nature 332:323-327). The disclosed Siglec-15-binding molecules can be recombinantly fused or chemically conjugated (including both covalently and non-covalently conjugations) to a heterologous molecule (i.e., an unrelated molecule). The fusion does not necessarily need to be direct, but may occur through linker sequences.

In some embodiments such heterologous molecules are polypeptides having at least 10, at least 20, at least 30, at least 40, at least 50, at least 60, at least 70, at least 80, at least 90 or at least 100 amino acids. Such heterologous molecules can alternatively be enzymes, hormones, cell surface receptors, drug moieties, such as: macrophage-specific targeting reagents (such as the intracellular carboxylesterase, hCE1 (Needham, L. A. et al. (2011) "*Drug Targeting To Monocytes And Macrophages Using Esterase-Sensitive Chemical Motif*" J. Pharmacol. Exp. Ther. DOI:10.1124/jpet.111.183640), chitin and chitosan (Muzzarelli, R. A. (2010) "*Chitins And Chitosans As Immunoadjuvants And Non-Allergenic Drug Carriers*," Mar Drugs 8(2):292-312), galactosylated low-density lipoprotein (Wu, F. et al. (009) "*Galactosylated LDL Nanoparticles: A Novel Targeting Delivery System To Deliver Antigen To Macrophages And Enhance Antigen Specific T Cell Responses*," Molec. Pharm. 6(5): 1506-1517), N-formyl-Met-Leu-Phe (fMLF), a macrophage-specific chemo-attractant (Wan, L. et al. (2008) "*Optimizing Size And Copy Number For PEG-Fmlf (N-Formyl-Methionyl-Leucyl-Phenylalanine) Nanocarrier Uptake By Macrophages*," Bioconjug. Chem. 19(1):28-38), maleylated or mannosylated protein, such as maleylated albumin (Anatelli, F. et al. (2006) "*Macrophage-Targeted Photosensitizer Conjugate Delivered By Intratumoral Injection*," Mol Pharm. 3(6):654-664; Bansal, P. et al. (1999) "*MHC Class I-Restricted Presentation Of Maleylated Protein Binding To Scavenger Receptors*," J. Immunol. 162(8): 4430-4437); see also Mukhopadhyay, A. et al. (2003) "*Intracellular Delivery Of Drugs To Macrophages*," Adv. Biochem. Eng. Biotechnol. 84:183-209), toxins (such as abrin, ricin A, *pseudomonas* exotoxin (i.e., PE-40), diphtheria toxin, ricin, gelonin, or pokeweed antiviral protein), proteins (such as tumor necrosis factor, interferon (e.g., α-interferon, β-interferon), nerve growth factor, platelet derived growth factor, tissue plasminogen activator, or an apoptotic agent (e.g., tumor necrosis factor-α, tumor necrosis factor-β)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF"), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

In another embodiment, the molecules are conjugated to a second antibody to form an antibody heteroconjugate as described by Segal in U.S. Pat. No. 4,676,980. Such heteroconjugate antibodies can additionally bind to haptens (such as fluorescein, etc.), or to cellular markers (e.g., 4-1-BB, B7-H1, PD-1, CD4, CD8, CD14, CD25, CD27, CD40, CD68, CD163, CTLA4, GITR, LAG-3, OX40, TIM3, TIM4, TLR2, LIGHT, etc.) or to cytokines (e.g., IL-4, IL-7, IL-10, IL-12, IL-15, IL-17, TGF-beta, IFNg, Flt3, BLys) or chemokines (e.g., CCL21), etc.

The Fc portion of the fusion protein can be varied by isotype or subclass, can be a chimeric or hybrid, and/or can be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al. (1997) "*Humanized Porcine VCAM-Specific Monoclonal Antibodies With Chimeric IgG2/G4 Constant Regions Block Human Leukocyte Binding To Porcine Endothelial Cells*," Mol. Immun. 34(6):441-452, Swann, P. G. (2008) "*Considerations For The Development Of Therapeutic Monoclonal Antibodies*," Curr. Opin. Immun. 20:493-499 (2008), and Presta, L. G. (2008) "*Molecular Engineering And Design Of Therapeutic Antibodies*," Curr. Opin. Immun. 20:460-470. In some embodiments the Fc region is the native IgG1, IgG2, or IgG4 Fc region. In some embodiments the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region can include the entire hinge region, or less than the entire hinge region.

The therapeutic outcome in patients treated with rituximab (a chimeric mouse/human IgG1 monoclonal antibody against CD20) for non-Hodgkin's lymphoma or Waldenstrom's macroglobulinemia correlated with the individual's expression of allelic variants of Fcγ receptors with distinct intrinsic affinities for the Fc domain of human IgG1. In particular, patients with high affinity alleles of the low affinity activating Fc receptor CD16A (FcγRIIIA) showed higher response rates and, in the cases of non-Hodgkin's lymphoma, improved progression-free survival. Therefore, the Fc domain can the disclosed antibodies and fragments contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA).

Another embodiment includes IgG2-4 hybrids and IgG4 mutants that have reduced binding to FcγR, which increases their half-life. Representative IgG2-4 hybrids and IgG4 mutants are described in Angal, S. et al. (1993) "*A Single Amino Acid Substitution Abolishes The Heterogeneity Of Chimeric Mouse/Human (Igg4) Antibody*," Molec. Immunol. 30(1):105-108; Mueller, J. P. et al. (1997) "*Humanized Porcine VCAM-Specific Monoclonal Antibodies With Chimeric IgG2/G4 Constant Regions Block Human Leukocyte Binding To Porcine Endothelial Cells*," Mol. Immun. 34(6):441-452; and U.S. Pat. No. 6,982,323. In some embodiments the IgG1 and/or IgG2 domain is modified; for example, Angal, S. et al. (1993) describe IgG1 and IgG2 variants in which serine 241 is replaced with proline.

In some embodiments, the Fc domain of such molecules contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890. Exemplary variants of human IgG1 Fc domains with reduced binding to CD32B and/or increased binding to CD16A contain F243L, R929P, Y300L, V305I or P296L substitutions. These amino acid substitutions can be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297Q substitution, as this mutation abolishes FcR binding.

Techniques for conjugating therapeutic moieties to antibodies are well known; see, e.g., Arnon et al., "*Monoclonal Antibodies For Immunotargeting Of Drugs In Cancer Therapy*", in Monoclonal Antibodies And Cancer Therapy, Reisfeld et al. (eds.), 1985, pp. 243-56, Alan R. Liss, Inc.); Hellstrom et al., "*Antibodies For Drug Delivery*", in Controlled Drug Delivery (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in Monoclonal Antibodies '84: Biological And Clinical Applications, Pinchera et al. (eds.), 1985, pp. 475-506); "*Analysis, Results, And Future Prospective Of The Therapeutic Use Of Radiolabeled Antibody In Cancer Therapy*", in Monoclonal Antibodies For Cancer Detection And Therapy, Baldwin et al. (eds.), 1985, pp. 303-16, Academic Press; and Thorpe et al. (1982) "*The Preparation And Cytotoxic Properties Of Antibody-Toxin Conjugates*," Immunol. Rev. 62:119-158.

Any of the disclosed molecules can be fused to marker sequences, such as a peptide, to facilitate purification. In some embodiments, the marker amino acid sequence is a hexa-histidine peptide, the hemagglutinin "HA" tag, which corresponds to an epitope derived from the influenza hemagglutinin protein (Wilson, I. A. et al. (1984) "*The Structure Of An Antigenic Determinant In A Protein*," Cell, 37:767-778) and the "flag" tag (Knappik, A. et al. (1994) "*An Improved Affinity Tag Based On The FLAG Peptide For The Detection And Purification Of Recombinant Antibody Fragments*," Biotechniques 17(4):754-761).

The disclosed Siglec-15-binding molecules can be conjugated to a diagnostic or therapeutic agent, or another molecule for which serum half-life is desired to be increased. The antibodies can be used diagnostically (in vivo, in situ or in vitro) to, for example, monitor the development or progression of a disease, disorder or infection as part of a clinical testing procedure to, e.g., determine the efficacy of a given treatment regimen or to select patients more likely to respond to a particular therapy (such as those expressing high levels of Siglec-15).

Detection can be facilitated by coupling the molecule, such as antibody or an antigen binding fragment thereof, to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance can be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb) yttrium ($^{90}$Y), zinc ($^{65}$Zn); positron emitting metals using various positron emission tomographies, and nonradioactive paramagnetic metal ions.

The disclosed molecules can be attached to solid supports, which are particularly useful for immunoassays or purification of the target antigen or of other molecules that are capable of binding to target antigen that has been immobilized to the support via binding to an antibody or antigen-binding fragment. Such solid supports include, but are not limited to, glass, cellulose, polyacrylamide, nylon, polystyrene, polyvinyl chloride or polypropylene. Nucleic acid molecules (DNA or RNA) that encode any such antibodies, fusion proteins or fragments, as well as vector molecules (such as plasmids) that are capable of transmitting or of replicating such nucleic acid molecules are also disclosed. The nucleic acids can be single-stranded, double-stranded, can contain both single-stranded and double-stranded portions.

3. Method of Making

The Siglec-15-binding molecules can be produced by any method known in the art useful for the production of polypeptides, e.g., in vitro synthesis, recombinant DNA production, and the like. The humanized antibodies are typically produced by recombinant DNA technology. The antibodies can be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., *Gene Expression Technology Methods in Enzymology* Vol. 185 Academic Press (1991), and Borreback, *Antibody Engineering*, W. H. Freeman (1992). *Additional information concerning the generation, design and expression of recombinant antibodies can be found in Mayforth, Designing Antibodies*, Academic Press, San Diego (1993).

An exemplary process for the production of the recombinant chimeric antibodies can include the following: a) constructing, by conventional molecular biology methods, an expression vector that encodes and expresses an antibody heavy chain in which the CDRs and variable region of an anti-Siglec-15 antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-human Siglec-15 monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized antibodies can include the following: a) constructing, by conventional molecular biology methods, an expression vector that encodes and expresses an anti-human Siglec-15 heavy chain in which the CDRs and a minimal portion of the variable region framework that are required to retain donor antibody binding specificity are derived from the humanized variants of anti-human Siglec-15 antibody(ies), and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as the disclosed murine anti-human Siglec-15 antibodies, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells can be co-transfected with such expression vectors, which can contain different selectable markers but, with the exception of the heavy and light chain coding sequences, can be identical. This procedure provides for equal expression of heavy and light chain polypeptides. Alternatively, a single vector can be used which encodes both heavy and light chain polypeptides. The coding sequences for the heavy and light chains can include cDNA or genomic DNA or both. The host cell used to express the recombinant antibody can be either a bacterial cell such as *Escherichia coli*, or a eukaryotic cell (e.g., a Chinese hamster ovary (CHO) cell or a HEK-293 cell). The choice of expression vector is dependent upon the choice of host cell, and can be selected so as to have the desired expression and regulatory characteristics in the selected host cell. Other cell lines that can be used include, but are not limited to, CHO-K1, NSO, and PER.C6 (Crucell, Leiden, Netherlands).

Any of the disclosed antibodies can be used to generate anti-idiotype antibodies using techniques well known to those skilled in the art (see, e.g., Greenspan, N. S. et al. (1989) "*Idiotypes: Structure And Immunogenicity*," FASEB J. 7:437-444; and Nisinoff, A. (1991) "*Idiotypes: Concepts And Applications,*" J. Immunol. 147(8):2429-2438).

C. Siglec-15 Ligand-Binding Molecules

Molecules that bind to Siglec-15 ligands, such as Siglec-15 proteins, Siglec-15 fusion proteins, and fragments and variants thereof are also provided. The Siglec-15 ligand-binding molecule can bind to Siglec-15 ligand such as a sialylated glycoprotein, LRRC4C, a Siglec-15-counter receptor, etc. In some embodiments, the Siglec-15 ligand-binding molecule can induce signal transduction through the Siglec-15 ligand. In some embodiments, the Siglec-15 ligand-binding molecule blocks or otherwise reduces interaction between Siglec-15 and its ligand, without inducing signal transduction through Siglec-15 or its ligand. Siglec-15 ligand-binding molecules can be used to modulate Siglec-15 activity as discussed in more detail below and illustrated in the Examples, and can be used to therapeutically to treat a subject in need thereof.

1. Siglec-15 Polypeptides

In some embodiments, the Siglec-15 ligand-binding molecule is Siglec-15, or fragment or variant thereof. For example, in some embodiments, the Siglec-15 ligand-binding molecules includes a polypeptide at least 50, 60, 70, 80, 85, 90, 95, 96, 97, 98, 99, or 100% identical to SEQ ID NO:1 or 2, or a fragment thereof such as the extracellular domain, or a subdomain thereof such as the IgV domain, the IgC domain or the combination thereof. In some embodiments, the Siglec-15 polypeptide is soluble or otherwise cell-free. For example, in some embodiments, the Siglec-15 lacks one or more of the transmembrane domain, the cytoplasmic domain, or the leader sequence.

2. Siglec-15 Fusion Proteins

In some embodiments, the Siglec-15 ligand-binding molecule is a Siglec-15 fusion protein. Fusion proteins containing Siglec-15 polypeptides coupled to other polypeptides to form fusion proteins are provided. Siglec-15 fusion polypeptides can have a first fusion partner comprising all or a part of a Siglec-15 protein fused (i) directly to a second polypeptide or, (ii) optionally, fused to a linker peptide sequence that is fused to the second polypeptide. The fusion proteins optionally contain a domain that functions to dimerize or multimerize two or more fusion proteins. In some embodiments the fusion protein is not or does not dimerize or multimerize. The peptide/polypeptide linker domain can either be a separate domain, or alternatively can be contained within one of one of the other domains (Siglec-15 polypeptide or second polypeptide) of the fusion protein. Similarly, the domain that functions to dimerize or multimerize the fusion proteins can either be a separate domain, or alternatively can be contained within one of one of the other domains (Siglec-15 polypeptide, second polypeptide or peptide/polypeptide linker domain) of the fusion protein. In some embodiments, the dimerization/multimerization domain and the peptide/polypeptide linker domain are the same.

Fusion proteins disclosed herein are of formula I:

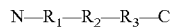

$$N—R_1—R_2—R_3—C$$

wherein "N" represents the N-terminus of the fusion protein, "C" represents the C-terminus of the fusion protein, "$R_1$" is a Siglec-15 polypeptide, "$R_2$" is an optional peptide/polypeptide linker domain, and "$R_3$" is a second polypeptide. Alternatively, $R_3$ may be the Siglec-15 polypeptide and $R_1$ may be the second polypeptide.

The fusion proteins can be dimerized or multimerized. Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric. As discussed above, in some embodiments the fusion protein is not or does not dimerize or multimerize.

In some embodiments, the second polypeptide contains one or more domains of an immunoglobulin heavy chain constant region, for example an amino acid sequence corresponding to the hinge, $C_H2$ and/or $C_H3$ regions of a human immunoglobulin Cγ1 chain, the hinge, $C_H2$ and/or $C_H3$ regions of a murine immunoglobulin Cγ2a chain, $C_H2$ and/or $C_H3$ regions of a human immunoglobulin Cγ1, ect.

The Fc portion of the fusion protein may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, et al., *Mol. Immun.*, 34(6):441-452 (1997), Swann, et al., *Cur. Opin. Immun.*, 20:493-499 (2008), and Presta, *Cur. Opin. Immun.* 20:460-470 (2008). In some embodiments the Fc region is the native IgG1, IgG2, or IgG4 Fc region. In some embodiments the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region may include the entire hinge region, or less than the entire hinge region.

The therapeutic outcome in patients treated with rituximab (a chimeric mouse/human IgG1 monoclonal antibody against CD20) for non-Hodgkin's lymphoma or Waldenstrom's macroglobulinemia correlated with the individual's expression of allelic variants of Fcγ receptors with distinct intrinsic affinities for the Fc domain of human IgG1. In particular, patients with high affinity alleles of the low affinity activating Fc receptor CD16A (FcγRIIIA) showed higher response rates and, in the cases of non-Hodgkin's lymphoma, improved progression-free survival. In another embodiment, the Fc domain may contain one or more amino acid insertions, deletions or substitutions that reduce binding to the low affinity inhibitory Fc receptor CD32B (FcγRIIB)

and retain wild-type levels of binding to or enhance binding to the low affinity activating Fc receptor CD16A (FcγRIIIA).

Another embodiment includes IgG2-4 hybrids and IgG4 mutants that have reduce binding to FcR which increase their half life. Representative IG2-4 hybrids and IgG4 mutants are described in Angal, S. et al., *Molecular Immunology*, 30(1): 105-108 (1993); Mueller, J. et al., *Molecular Immonology*, 34(6): 441-452 (1997); and U.S. Pat. No. 6,982,323 to Wang et al. In some embodiments the IgG1 and/or IgG2 domain is deleted for example, Angal et al. describe IgG1 and IgG2 having serine 241 replaced with a proline.

In some embodiments, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, et al., *Cancer Res.*, 57(18):8882-90 (2007). Exemplary variants of human IgG1 Fc domains with reduced binding to CD32B and/or increased binding to CD16A contain F243L, R929P, Y300L, V305I or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297Q substitution, as this mutation abolishes FcR binding.

The disclosed fusion proteins optionally contain a peptide or polypeptide linker domain that separates the Siglec-15 polypeptide from the second polypeptide. In some embodiments, the linker domain contains the hinge region of an immunoglobulin. In a preferred embodiment, the hinge region is derived from a human immunoglobulin. Suitable human immunoglobulins that the hinge can be derived from include IgG, IgD and IgA. In a preferred embodiment, the hinge region is derived from human IgG. Amino acid sequences of immunoglobulin hinge regions and other domains are well known in the art.

An exemplary fusion protein is Siglec 15 ECD-IgG1 Fc Fusion Protein (L234F/L235E/P331S).

(SEQ ID NO:193)
MEWSWVFLFFLSVTTGVHS*FVRTKIDTTENLLNTEVHSSPAQRWSMQVPPEVS*

*AEAGDAAVLPCTFTHPHRHYDGPLTAIWRAGEPYAGPQVFRCAAARGSELCQT*

*ALSLHGRFRLLGNPRRNDLSLRVERLALADDRRYFCRVEFAGDVHDRYESRHG*

*VRLHVTAAPRIVNISVLPSPAHAFRALCTAEGEPPPALAWSGPALGNSLAAVR*

*SPREGHGHLVTAELPALTHDGRYTCTAANSLGRSEASVYLFRFHGASG*DKTHT

CPPCPAPEFE̤G̤G̤PSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAS

IEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYT

QKSLSLSPG.

A Murine Leader Sequence is illustrated in underlined. A Siglec-15 extracellular domain (ECD) is in italics. A Hinge Region is double underlined. The remaining sequence is derived from IgG1 Fc. L234F/L235E/P331S mutations in the IgG1 Fc domain bolded and dotted-underlined.

In some embodiments, the leader sequence is cleaved or otherwise missing from fusion protein. For example, the fusion protein can have the sequence:

(SEQ ID NO: 194)
*FVRTKIDTTENLLNTEVHSSPAQRWSMQVPPEVSAEAGDAAVLPCTFTHPHRH*

*YDGPLTAIWRAGEPYAGPQVFRCAAARGSELCQTALSLHGRFRLLGNPRRNDL*

*SLRVERLALADDRRYFCRVEFAGDVHDRYESRHGVRLHVTAAPRIVNISVLPS*

*PAHAFRALCTAEGEPPPALAWSGPALGNSLAAVRSPREGHGHLVTAELPALTH*

-continued

*DGRYTCTAANSLGRSEASVYLFRFHGASG*DKTHTCPPCPAPEFEGGPSVFLFP

PKPKDTLMISRTPEVTCVVVDVSHEDPEVKFNWYVDGVEVHNAKTKPREEQYN

STYRVVSVLTVLHQDWLNGKEYKCKVSNKALPASIEKTISKAKGQPREPQVYT

LPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPG.

In some embodiments, the fusion protein is at least 50, 60, 70, 80, 85, 90, 95, 96, 97, 98, 99, or 100% identical to SEQ ID NO:193 or 194.

In some embodiments, the leader sequence, the linker (e.g., the hinge region), the second fusion partner (e.g., IgG1 Fc domain), or a combination thereof are substitute for another sequence(s) (e.g., an alternative leader sequence, hinge, Fc domain, etc.). Suitable substitutes are well known in the art. See, for example, U.S. Pat. No. 9,005,616, which is specifically incorporated by reference in its entirety.

3. Siglec-15 Nucleic Acids and Cells

Vectors encoding Siglec-15 polypeptides, fragments and fusions thereof are also provided. Nucleic acids, such as those described above, can be inserted into vectors for expression in cells. Thus cells containing and expressing Siglec-15 polypeptides, fragments and fusions thereof are also provided As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A. In some embodiments, a nucleic acid molecule encoding a Siglec-15 fusion polypeptide is present in a vector containing nucleic acids that encode one or more domains of an Ig heavy chain constant region, for example, an amino acid sequence corresponding to the hinge, $C_H2$ and $C_H3$ regions of a human immunoglobulin Cγ1 chain.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the Siglec-15 fusion polypeptides described herein.

The vectors described can be used to express Siglec-15 in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. For example, nucleic acids encoding polypeptides disclosed herein can be administered directly to lymphoid tissues or tumors. Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs are known in the art.

Nucleic acids may also be administered in vivo by viral means. Nucleic acid molecules encoding fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

D. Pharmaceutical Compositions

Pharmaceutical compositions including the disclosed Siglec-15-binding molecules are provided. Pharmaceutical compositions containing a Siglec-15-binding molecule can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed Siglec-15-binding molecules, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally, for intravenous injection or infusion, dosage may be lower.

The dosage administered to a patient is typically 0.01 mg/kg to 100 mg/kg of the patient's body weight. The dosage administered to a patient can be, for example, between 0.01 mg/kg and 20 mg/kg, 0.01 mg/kg and 10 mg/kg, 0.01 mg/kg and 5 mg/kg, 0.01 and 2 mg/kg, 0.01 and 1 mg/kg, 0.01 mg/kg and 0.75 mg/kg, 0.01 mg/kg and 0.5 mg/kg, 0.01 mg/kg to 0.25 mg/kg, 0.01 to 0.15 mg/kg, 0.01 to 0.10 mg/kg, 0.01 to 0.05 mg/kg, or 0.01 to 0.025 mg/kg of the patient's body weight. Exemplary specific dosages include, but are not limited to 0.2 mg/kg, 0.3 mg/kg, 1 mg/kg, 3 mg/kg, 6 mg/kg or 10 mg/kg. A dose as low as 0.01 mg/kg is believed to be suitable to have appreciable pharmacodynamic effects. Dose levels of 0.10-1 mg/kg are predicted to be most appropriate. Higher doses (e.g., 1-30 mg/kg) would also be expected to be active.

Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In certain embodiments, the Siglec-15-binding molecule is administered locally, for example by injection directly into a site to be treated. Typically, the injection causes an increased localized concentration of the Siglec-15-binding molecule composition which is greater than that which can be achieved by systemic administration. The Siglec-15-binding molecule compositions can be combined with a matrix as described below to assist in creating an increased localized concentration of the polypeptide compositions by reducing the passive diffusion of the polypeptides out of the site to be treated.

1. Formulations for Parenteral Administration

In some embodiments, compositions disclosed herein, are administered in an aqueous solution, by parenteral injection or infusion. The formulation may also be in the form of a suspension or emulsion. In general, pharmaceutical compositions are provided including effective amounts of a Siglec-15-binding molecule, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Controlled Delivery Polymeric Matrices

The Siglec-15-binding molecules disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides. These may be natural or synthetic polymers. Synthetic polymers typically have a better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release,* 5:13-22 (1987); Mathiowitz, et al., *Reactive Polymers,* 6:275-283 (1987); and Mathiowitz, et al., *J. Appl. Polymer Sci.,* 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Method of Use

Methods of using the disclosed Siglec-15-binding and Siglec-15 ligand-binding molecules are also provided. Uses of such molecules to increase immune responses, retard or prevent tumor growth, inhibit tumor-mediated immune suppression, eliminate tumors and/or deplete or block the activity of tumor-associated macrophages (TAMs) so as to alter their activity, decrease TAM-mediated immune suppression, reduce or reverse T cell suppression, and/or are disclosed. Also provided are uses of such molecules in the diagnosis and the treatment of cancer and other diseases.

TAMs provide a link between inflammation and cancer. Macrophages are immune system cells derived from activated blood monocytes. They are primarily recognized as participating in inflammatory responses induced by pathogens or tissue damage by acting to remove (i.e., phagocytose) pathogens, dead cells, cellular debris, and various components of the extra-cellular matrix (ECM). Macrophages have been found to constitute an important constituent in the tumor microenvironment and to represent up to 50% of the tumor mass.

In addition to mediating phagocytosis, macrophages secrete pro-angiogenic growth factors and matrix-remodeling proteases, and thus play a role in the development of the vascular infrastructure (i.e., angiogenesis) needed for tumor development and growth (Pollard, J. W. (2009), *Nat. Rev. Immunol.* 9:259-270). The presence of macrophages within a tumor appears to assist the growth of the tumor. A number of studies provide evidence that the presence of tumor-associated macrophages within the tumor is a negative prognostic factor of survival (Farinha, P. et al. (2005), *Blood* 106:2169-2174; Dave, S. S. et al. (2004), *N. Engl. J Med.* 351:2159-2169; Solinas, G. et al. (2009), *J. Leukoc. Biol.* 86(5):1065-1073). TAMs, as well as neutrophils, fibroblasts and other cells cooperate with tumor cells to facilitate angiogenesis in tumors (Nucera, S. et al. (2011), *Int. J. Dev. Biol.* doi: 10.1387/ijdb.103227sn; Zamarron, B. F. et al. (2011), *Int. J. Biol. Sci.* 7(5):651-658; Liu, J. et al. (2011), *PLoS One.* 6(4):e19495; Rigo, A. et al. (2010), *Molec. Cancer* 9(273):1-13; Lin, J. Y. et al. (2011), *Chin. J. Cancer* 30(4):280-286; Vergati, M. (2011), *J. Biomed. Biotechnol.* 2011:182413).

Studies show that Siglec-15 is inducibly expressed on TAMs and enhances TGF-β secretion by coupling tumor cell recognition with the DAP12-Syk signal transduction pathway (Takamiya, et al., *Glycobiology,* 23(2):178-87 (2013). In a specific model proposed by Takamiya, M-CSF secreted by tumor cells induces monocyte differentiation to macrophages, accompanied with expression of Siglec-15. Interaction between sialyl-Tn antigen and Siglec-15 enhances TGF-β production from macrophages via the DAP12-Syk pathway, tipping the tumor microenvironment in the direction of immune suppression and thus tumor progression and even metastasis.

Binding of function blocking or reducing anti-Siglec-15 antibodies to Siglec-15 can result in reducing, blocking, antagonizing, attenuating, or in completely abolishing the ability of Siglec-15 to bind to one or more it's ligands and therefore decrease or prevent inhibitory immune signaling, including, but not limited to secretion of TGF-β, mediated by Siglec-15. Increased expression of TGF-β often correlates with the malignancy of many cancers and a defect in the cellular growth inhibition response to TGF-β and leading to immunosuppression-based oncogenesis. Reducing Siglec-15-mediated TGF-β secretion and lead to an overall increase in immune responses and a direct or indirect decrease in tumor progression in the subject.

The Examples below show that function reducing and blocking anti-Siglec-15 antibodies, including those disclosed herein, can reverse Siglec-15-mediated suppression of CD4+ and CD8+ T cell proliferation in a peripheral blood mononuclear cells (PBMC) proliferation assay.

Thus, methods of reducing immune suppression and/or increasing an immune response, most typically by administering to a subject in need thereof an effective amount of anti-Siglec-15 function blocking antibody, are provided.

Suitable antibodies, polypeptides, and fusion proteins are disclosed herein and can be further selected by in vitro assays including but not limited to: proliferation, migration, adhesion, soft agar growth, angiogenesis, cell-cell communication, apoptosis, transport, signal transduction, and in vivo assays such as the inhibition of tumor growth. Exemplary assays for testing the function of the disclosed antibodies are provided in the Examples below.

The antibodies provided herein can also be useful in diagnostic and research applications. For example, non-neutralizing antibodies can bind to the specific antigen without inhibiting the receptor-binding or biological activity of the antigen, and can be used in capture assays and other pull-downs (e.g., ELISA). Neutralizing (e.g., function blocking) antibodies can be useful in competitive binding assays.

Antibodies can also be used to quantify the Siglec-15 polypeptides or its ligand.

A. Immune Response Increasing Molecules

1. Therapeutic and Prophylactic Uses

Therapeutic and/or prophylactic use of molecules (especially antibodies or their antigen-binding fragments) that immunospecifically bind human Siglec-15 and Siglec-15 ligand-binding molecules and that are capable of reducing the binding between Siglec-15 and one or more of its ligands and/or counter-receptors are provided (e.g., antagonist molecules).

In some embodiments, the molecules reduce or prevent binding between Siglec-15 and a sialylated glycoprotein ligand, for example sialylated glycoproteins endogenously expressed by the cells of a subject, and reduce or prevent Siglec-15 mediated signal transduction. Additionally or alternatively, the molecules can reduce or prevent binding between Siglec-15 and a counter-receptor thereof, and reduce or prevent Siglec-15-mediated signal transduction and/or signal transduction through the counter-receptor. For example, the disclosed molecules can bind to antigens at one or more sites on Siglec-15 disruptive of the sialic acid binding site (e.g., an epitope including residue 143 of SEQ ID NO:1) and/or binding site important for binding to a Siglec-15 counter-receptor. Exemplary compositions are illustrated in the Examples below. For example, in some embodiments, 5G12, 6F8, 8C8, 1C3, 1C12, 3H10, and 1B2 are ("strong blockers") and 10G9, 8H8, and 9A5 ("partial blockers"). Therefore, in some embodiments, the molecules used for up-modulating an immune response include one, two, three, four, five, or all six CDR of 5G12, 6F8, 8C8, 1C3, 1C12, 3H10, 1B2, 10G9, 8H8, or 9A5. In some embodiments, the molecules include the light chain variable region and/or the heavy chain variable region of 5G12, 6F8, 8C8, 1C3, 1C12, 3H10, 1B2, 10G9, 8H8, or 9A5. In some embodiments, the is murine anti-human 5G12, 6F8, 8C8, 1C3, 1C12, 3H10, 1B2, 10G9, 8H8, or 9A5, or a chimeric or humanized variant thereof.

As discussed above, interactions between Siglec-15 and sialylated glycoprotein ligands and/or Siglec-15 counter-receptors can inhibit the proliferation of T cells and increase the production of cytokines such as TGF-β. Thus, in some embodiments, the administration of the disclosed Siglec-15-binding molecules to a subject up-modulates the immune system of the subject by blocking or otherwise antagonizing Siglec-15-ligand and/or counterreceptor binding/interaction. In another embodiment, the avidity and/or affinity of the anti-Siglec-15 antibody may be such that it only binds to cells that express very high levels of Siglec-15, which are, for example, tumor associated macrophage (TAMs) or cancer cells, and thus allow specific targeting of this cell population. Thus, in some embodiments, the molecules reduce production of TGF-3, for example, in a tumor microenvironment. In some embodiments, the cells expressing Siglec-15 are monocytes. In more specific embodiments, the cells expressing Siglec-15 are macrophage, for example TAM.

As indicated above, the disclosed antibodies and antigen-binding fragments can bind to and substantially block TAMs so as to modulate their immune suppressive activity. Furthermore, such antibodies can be used to deplete Siglec-15 TAMs within the tumor microenvironment, or deplete their concentration of TAMs in peripheral blood. In one embodiment such modulation or depletion is accomplished using Siglec-15 antibodies that bind to a site so as to impair or disrupt normal Siglec-15 function. As a consequence of such disruption, TAMs activity is decreased (modulated), and/or the actual or effective (functional) concentration of macrophages in the tumor is depleted. Alternatively, such modulation or depletion is accomplished using anti-Siglec-15 antibodies that are conjugated to a toxin, such that their binding to a TAM leads to the death of the macrophage.

Additionally, the disclosed antagonist molecules can be used to induce, increase, or enhance T cell proliferation. In some embodiments, the T cell response is induced by reducing or preventing Siglec-15 from binding to a counter-receptor on the T cell. Up-modulation of the immune system is particularly desirable in the treatment of cancers and chronic infections, and thus the disclosed compositions can be used in the treatment of such disorders.

2. Subjects to be Treated a. Treatment of Cancer

The disclosed function reducing compositions and methods can be used to treat cancer. Generally, the methods include stimulating or enhancing an immune response to cancer, reducing or preventing tumor growth or progression, or a combination thereof in the subject by administering to the subject an amount of a Siglec-15 binding. The method can reduce or more symptoms of the cancer.

Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless explicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

The methods and compositions disclosed herein are useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma.

Cancers caused by aberrations in apoptosis can also be treated by the disclosed methods and compositions. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

The disclosed compositions and methods are particularly useful for the treatment of cancers that are associated with cells that express abnormally high levels of Siglec-15 itself or glycoprotein ligands of Siglec-15, cancers with high numbers of tumor associated macrophage especially if the macrophages express Siglec-15, and/or a cancer in which another cell type(s) express high levels Siglec-15 or Siglec-15 ligands.

Specific cancers and related disorders that can be treated or prevented by methods and compositions disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

b. Treatment of Infections

The disclosed function reducing compositions and methods can be used to treat infections and infectious diseases. Generally, the methods include stimulating or enhancing an immune response to an infection causing agent, reducing or preventing infectious disease progression, or a combination thereof in the subject by administering to the subject an amount of a Siglec-15 binding molecule. The method can reduce one or more symptoms of the infection.

The infection or disease can be caused by a bacterium, virus, protozoan, helminth, or other microbial pathogen that enters intracellularly and is attacked, i.e., by cytotoxic T lymphocytes.

The infection or disease can be acute or chronic. An acute infection is typically an infection of short duration. During an acute microbial infection, immune cells begin expressing immunomodulatory receptors. Accordingly, in some embodiments, the method includes increasing an immune stimulatory response against an acute infection.

The infection can be caused by, for example, but not limited to *Candida albicans, Listeria monocytogenes, Streptococcus pyogenes, Streptococcus pneumoniae, Neisseria meningitidis, Staphylococcus aureus, Escherichia coli, Acinetobacter baumannii, Pseudomonas aeruginosa* or *Mycobacterium*.

In some embodiments, the disclosed compositions are used to treat chronic infections, for example infections in which T cell exhaustion or T cell anergy has occurred causing the infection to remain with the host over a prolonged period of time.

Exemplary infections to be treated are chronic infections cause by a hepatitis virus, a human immunodeficiency virus (HIV), a human T-lymphotrophic virus (HTLV), a herpes virus, an Epstein-Barr virus, or a human papilloma virus.

Because viral infections are cleared primarily by T cells, an increase in T-cell activity would be therapeutically useful in situations where more rapid or thorough clearance of an infective viral agent would be beneficial to an animal or human subject. Thus, the disclosed compositions can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) and other viral infections, caused by, for example, HTLV, hepatitis virus, respiratory syncytial virus, vaccinia virus, and rabies virus. The molecules can be administered topically to treat viral skin diseases such as herpes lesions or shingles, or genital warts. The molecules can also be administered systemically to treat systemic viral diseases, including, but not limited to, AIDS, influenza, the common cold, or encephalitis.

Representative infections that can be treated, include but are not limited to infections cause by microoganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydialpsittaci, Chlamydial trachomatis, Plasmodium falciparum, Trypanosoma brucei, Entamoeba histolytica, Toxoplasma gondii, Trichomonas vaginalis* and *Schistosoma mansoni*.

Other microorganisms that can be treated using the disclosed compositions and methods include, bacteria, such as those of *Klebsiella, Serratia, Pasteurella*; pathogens associated with cholera, tetanus, botulism, anthrax, plague, and Lyme disease; or fungal or parasitic pathogens, such as *Candida (albicans, krusei, glabrata, tropicalis,* etc.), *Cryptococcus, Aspergillus (fumigatus, niger,* etc.), Genus *Mucorales (mucor, absidia, rhizophus), Sporothrix (schenkii), Blastomyces (dermatitidis), Paracoccidioides (brasiliensis), Coccidioides (immitis)* and *Histoplasma (capsulatuma), Entamoeba, histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Toxoplasma gondi,* etc.), *Sporothrix, Blastomyces, Paracoccidioides, Coccidioides, Histoplasma, Entamoeba, Histolytica, Balantidium, Naegleria, Acanthamoeba, Giardia, Cryptosporidium, Pneumocystis, Plasmodium, Babesia,* or *Trypanosoma,* etc.

B. Immune Response Reducing Molecules

1. Therapeutic and Prophylactic Uses

Therapeutic and/or prophylactic use of molecules (especially antibodies or their antigen-binding fragments) that bind human Siglec-15 or to a ligand thereof, and that are capable of increasing or enhancing the binding between Siglec-15 and one or more of its ligands and/or counter-receptors are provided (e.g., agonist molecules) or directly increasing or enhancing Siglec-15 or Siglec-15 counter-receptor mediated signal transduction are also provided.

As discussed above, interactions between Siglec-15 and sialylated glycoprotein ligands and/or Siglec-15 counter-receptors can inhibit the proliferation of T cells and increase the production of cytokines such as TGF-β. Thus, in some embodiments, the administration of function activating Siglec-15-binding molecules or function activating Siglec-15 ligand-binding molecules to a subject down-modulates the immune system of the subject by inducing or otherwise agonizing Siglec-15-ligand and/or counter-receptor binding/ interaction or directly simulating Siglec-15 or Siglec-15 counter-receptor signal transduction. In some embodiments, the molecules increase production of TGF-β and/or secretion thereof from, for example, monocytes such as macrophage.

Additionally, the disclosed agonist Siglec-15-binding and Siglec-15 ligand-binding molecules can be used to reduce or decrease T cell proliferation. In some embodiments, the T cell response is induced by increasing or enhancing Siglec-15 binding to a counter-receptor on the T cell. Down-modulation of the immune system is particularly desirable in the treatment of inflammatory and autoimmune diseases and disorder and to treat or prevent graft rejection and/or graft verse host disease, and thus the disclosed compositions can be used in the treatment of such disorders.

a. Inflammatory Responses

In some embodiments, Siglec-15 agonist molecules are used for treating or alleviating one or more symptoms of inflammation, for example acute, chronic, or persistent inflammation.

An immune response including inflammation can be inhibited or reduced in a subject, preferably a human, by administering an effective amount the Siglec-15-binding molecule to inhibit or reduce the biological activity of an immune cell (e.g., T cells or B cells) or to reduce the amounts of proinflammatory molecules at a site of inflammation. Exemplary proinflammatory molecules include, but are not limited to, IL-113, TNF-α, IFN-γ, IL-18, IL-17, IL-6, IL-23, IL-22, IL-21, and MMPs.

b. Hyper-Inflammatory Response

In some embodiments, the Siglec-15-binding molecules slow down the immune system. For example, a Siglec-15-binding molecule can be used to control an immune stimulatory response to an infection that is causing damage healthy tissues through a hyper-inflammatory response. Accordingly, in some embodiments, the agents are administered to a subject with an infection that is also undergoing a hyper-inflammatory response. In such cases, controlling excessive immune responses can be beneficial to the subject.

c. Inflammatory and Autoimmune Diseases/Disorders

The disclosed compositions can also be used to treat inflammatory or autoimmune diseases and disorders. Representative inflammatory or autoimmune diseases/disorders that can be treated include, but are not limited to, rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis-juvenile, discoid lupus, essential mixed cryoglobulinemia, fibromyalgia-fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis *nodosa*, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiffman syndrome, Takayasu arteritis, temporal arteritis/giant cell arteritis, ulcerative colitis, uveitis, vasculitis, vitiligo, and Wegener's granulomatosis.

In some embodiments the inflammation or autoimmune disease is caused by a pathogen, or is the result of an infection.

d. Transplants

The Siglec-15-binding molecules can be used for reducing or inhibiting transplant rejection in a subject, preferably a human subject. Transplant rejection can be inhibited or reduced in a subject by administering an effective amount of an agonist Siglec-15 binding molecule to inhibit or reduce the biological activity of an immune cell or to reduce the amounts of proinflammatory cytokines or other molecules associated with or that promote inflammation at a site of transplant.

The transplanted material can be cells, tissues, organs, limbs, digits or a portion of the body, preferably the human body. The transplants are typically allogenic or xenogenic. An agonist Siglec-15 molecule is typically administered to a subject in an effective amount to reduce or inhibit transplant rejection. The molecule can be administered systemically or locally by any acceptable route of administration. In some embodiments, the molecules are administered to a site of transplantation prior to, at the time of, or following transplantation.

The molecules can be administered directly to cells, tissue or organ to be transplanted ex vivo. In one embodiment, the transplant material is contacted with a Siglec-15-binding molecule prior to transplantation, after transplantation, or both.

In other embodiments, a Siglec-15-binding molecule is administered to immune tissues or organs, such as lymph nodes or the spleen.

i. Cells

Populations of any types of cells can be transplanted into a subject. The cells can be homogenous or heterogeneous. Heterogeneous means the cell population contains more than one type of cell. Exemplary cells include progenitor cells such as stem cells and pluripotent cells which can be harvested from a donor and transplanted into a subject. The cells are optionally treated ex vivo prior to transplantation. The cells can be autologous or heterologous cells.

ii. Tissues

Any tissue can be used as a transplant. Exemplary tissues include skin, adipose tissue, cardiovascular tissue such as veins, arteries, capillaries, valves; neural tissue, bone marrow, pulmonary tissue, ocular tissue such as corneas and lens, cartilage, bone, and mucosal tissue. The tissue can be modified as discussed above.

iii. Organs

Exemplary organs that can be used for transplant include, but are not limited to kidney, liver, heart, spleen, bladder, lung, stomach, eye, tongue, pancreas, intestine, etc. The organ to be transplanted can also be modified prior to transplantation as discussed above.

One embodiment provides a method of inhibiting or reducing chronic transplant rejection in a subject by administering an effective amount of a Siglec-15-binding molecule to inhibit or reduce chronic transplant rejection relative to a control.

e. Graft-Versus-Host Disease (GVHD)

The molecules can also be used to treat graft-versus-host disease (GVHD) by administering an effective amount a Siglec-15-binding molecule to alleviate one or more symptoms associated with GVHD. GVHD is a major complication associated with allogeneic hematopoietic stem cell transplantation in which functional immune cells in the transplanted marrow recognize the recipient as "foreign" and mount an immunologic attack. It can also take place in a blood transfusion under certain circumstances. Symptoms of GVD include skin rash or change in skin color or texture, diarrhea, nausea, abnormal liver function, yellowing of the skin, increased susceptibility to infection, dry, irritated eyes, and sensitive or dry mouth.

f. Diabetes

The agonist Siglec-15-binding molecules can also be used to treat diabetes. The method includes transplanting insulin producing cells in a subject and administering to the subject an effective amount of a molecule to reduce or inhibit transplant rejection. Preferably the insulin producing cells are beta cells or islet cells. In certain embodiments, the insulin producing cells are recombinant cells engineered to produce insulin.

The insulin producing cells can be encapsulated within a matrix, such as a polymeric matrix, using suitable polymers, including, but not limited to alginate, agarose, hyaluronic acid, collagen, synthetic monomers, albumin, fibrinogen, fibronectin, vitronectin, laminin, dextran, dextran sulfate, chondroitin sulfate, dermatan sulfate, keratan sulfate, chitin, chitosan, heparan, heparan sulfate, or a combination thereof.

C. Therapeutic Inhibition of Osteoclastic Bone Resorption

Studies show that Signlec-15 expression and function are important in osteoclastogenesis (Stuible, et al., *J. Biol Chem.*, 289(10): 6498-6512 (2014), Ishida-Kitagawa, *J. Biol. Chem.*, 287, 17493-17502 (2012), each of which is specifically incorporated by reference in its entirety). Although Siglec-15 protein is highly up-regulated during osteoclast differentiation, the protein is undetectable in non-differentiated cells. Results indicate that Siglec-15 and DAP12 form a complex at endogenous expression levels in osteoclasts. Siglec-15(−/−) knockout mice are mildly osteoporotic.

In vivo studies also show that Siglec-15 antibody can inhibit osteoclast activity in a physiological context and provide a therapeutic strategy for reducing bone loss. Although activation of receptors at the cell surface and their endocytic down-regulation are often coupled as a means of limiting the intensity and duration of signaling, for Siglec-15 signaling and endocytosis appear to occur exclusively of one another, depending on whether antibody ligation induces receptor clustering or simply dimerization.

Siglec-15 is an osteoclast-intrinsic receptor with a highly restricted expression pattern, and thus Siglec-15-targeted therapies are selective. Siglec-15 antibodies inhibit osteoclast differentiation at a relatively late stage thus preserving the coupled communication between osteoclasts and osteoblasts and avoiding complications of existing osteoclast-targeted therapies can induce osteoclast cell death (bisphosphonates) or prevent their differentiation at an early stage (denosumab) leading to unwanted side effects include osteonecrosis of the jaw and atypical fractures of the femur.

Thus, in some embodiments, the disclosed molecules (especially antibodies or their antigen-binding fragments) that immunospecifically bind human Siglec-15, and that are capable of reducing or blocking the binding between Siglec-15 and one or more of its ligands and/or counter-receptors (e.g., agonist molecules) can also be administered to a subject in need thereof in an effective amount to reduce or inhibit osteoclast differentiation, function or a combination thereof. In some embodiments the molecules are administered in an effective amount to reduce bone loss, increase bone formation, increase bone mineral density, or a combination thereof.

D. Targeting and Detection

The disclosed Siglec-15 binding and Siglec-15 ligand-binding molecules, regardless of their effect on Siglec-15 function, can be used for delivering therapeutic cargo and/or detecting the presence of Siglec-15 or a ligand thereof, respectively, on cells or tissue. For example, the Siglec-15 binding and Siglec-15 ligand-binding molecules can be conjugated to a biological molecule of interest to form a conjugate. Cargo including pharmacologically active molecules such as inorganic and organic molecules, pharmaceutical agents, drugs, peptides, proteins, genetic material, etc. can be conjugated the Siglec-15 binding or Siglec-15 ligand-binding molecule, which can then target the cargo to cells or tissue expressing Siglec-15 or a ligand thereof, respectively. Siglec-15 molecules can be chemically linked to a polypeptide by a peptide bond or by a chemical or peptide linker molecule. Methods for attaching a drug or other small molecule pharmaceutical to an antibody fragment are well known and include bifunctional chemical linkers such as N-succinimidyl (4-iodoacetyl)-aminobenzoate; sulfosuccinimidyl(4-iodoacetyl)-aminobenzoate; 4-succinimidyl-oxycarbonyl-.A-inverted.-(2-pyridyldithio) toluene; sulfosuccinimidyl-6-[.alpha.-methyl-.A-inverted.-(pyridyldithiol)-toluami-do]hexanoate; N-succinimidyl-3-(-2-pyridyldithio)-proprionate; succinimidyl-6-[3 (-(-2-pyridyldithio)-proprionamido] hexanoate; sulfosuccinimidyl-6-[3 (-(-2-pyridyldithio)-propionamido] hexanoate; 3-(2-pyridyldithio)-propionyl hydrazide, Ellman's reagent, dichlorotriazinic acid, S-(2-thiopyridyl)-L-cysteine, and the like.

Fusion proteins can be designed to place the protein of interest at the amino or carboxy terminus of either the antibody heavy or light chain, though the entire heavy chain may not be required. Potential configurations include the use of truncated portions of the heavy and light chain with or without spacer sequences as needed to maintain the functional integrity of the attached protein.

Alternatively, a universal carrier system can be devised. For example, various proteins or DNA can be conjugated to a common carrier such as protein A, poly-L-lysine, hex-histidine, and the like. The conjugated carrier will then form a complex with Siglec-15 binding or Siglec-15 ligand-binding molecules. A small portion of the carrier molecule that is responsible for binding immunoglobulin could be used as the carrier. Other similar configurations include design of carriers that interact with proteins engineered into the antibody heavy or light chain.

In some embodiments, Siglec-15 binding or Siglec-15 ligand-binding molecules are conjugated or otherwise incorporated into or onto a nanocarrier to target the nanocarrier to the Siglec-15 or Siglec-15 ligand positive cells. The nanocarrier, for example, micro- or nano-polymeric particles, liposomes, nanotubes, etc., can include an active agent for delivery to the Siglec-15 or Siglect-15 ligand positive cells or their microenvironment.

Likewise, the Siglec-15 binding or Siglec-15 ligand-binding molecules can be conjugated with a detectable marker or can be unconjugated and detected with a secondary reagent to detect Siglec-15 or Siglec-15 ligand expression, respectively, in vitro or in vivo. Thus the molecules can be used for imagine, immunohistochemistry, and other assays.

IV. Combination Therapies

The disclosed Siglec-15-binding and Siglec-15 ligand-binding molecules can be administered to a subject in need thereof alone or in combination with one or more additional therapeutic agents. In some embodiments, the Siglec-15-binding or Siglec-15 ligand-binding molecule and the additional therapeutic agent are administered separately, but simultaneously. The Siglec-15-binding or Siglec-15 ligand-binding molecule and the additional therapeutic agent can also be administered as part of the same composition. In other embodiments, the Siglec-15-binding or Siglec-15 ligand-binding molecule and the second therapeutic agent are administered separately and at different times, but as part of the same treatment regime.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The Siglec-15-binding or Siglec-15 ligand-binding molecule can be the first or the second therapeutic agent. In some embodiments, one or more Siglec-15 binding molecules and one or more Siglec-15 ligand-binding molecules are administered in combination.

The Siglec-15-binding and/or Siglec-15 ligand-binding molecule and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules include, but are not limited to, cytokines, chemotherapeutic agents, radionuclides, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to polyinosinic:polycytidylic acid (polyI:C) and CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the Siglec-15-binding molecule can be co-administered with one or more additional agents that function to enhance or promote an immune response or reduce or inhibit an immune response.

A. Chemotherapeutic Agents

The Siglec-15-binding and Siglec-15 ligand-binding molecules can be combined with one or more chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

B. Other Immunomodulators

1. PD-1 Antagonists

In some embodiments, Siglec-15-binding or Siglec-15 ligand-binding molecules are co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, *Proc. Natl. Acad. Sci. U.S.A.*, 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor.

Other PD-1 antagonists contemplated by the methods of this invention include antibodies that bind to PD-1 or ligands of PD-1, and other antibodies.

Suitable anti-PD-1 antibodies include, but are not limited to, those described in the following U.S. Pat. Nos. 7,332,582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, 9,492,540, all of which are incorporated by reference in their entireties.

See also Berger et al., *Clin. Cancer Res.*, 14:30443051 (2008).

Exemplary anti-B7-H1 (also referred to as anti-PD-L1) antibodies include, but are not limited to, those described in the following U.S. Pat. Nos. 8,383,796, 9,102,725, 9,273,135, 9,393,301, and 9,580,507 all of which are specifically incorporated by reference herein in their entirety.

For anti-B7-DC (also referred to as anti-PD-L2) antibodies see U.S. Pat. Nos. 7,411,051, 7,052,694, 7,390,888, 8,188,238, and 9,255,147 all of which are specifically incorporated by reference herein in their entirety.

Other exemplary PD-1 receptor antagonists include, but are not limited to B7-DC polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., *Immunity*, Vol. 27, pp. 111-122, (2007)). Such fragments also include the soluble ECD portion of the PD-1 protein that includes mutations, such as the A99L mutation, that increases binding to the natural ligands (Molnar et al., *PNAS*, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

2. CTLA4 Antagonists

Other molecules useful in mediating the effects of T cells in an immune response are also contemplated as additional therapeutic agents. In some embodiments, the molecule is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., Clinical Kidney Journal, 3(2):135-137 (2010), published online December 2009.

In other embodiments, the antagonist is a small molecule. A series of small organic compounds have been shown to bind to the B7-1 ligand to prevent binding to CTLA4 (see Erbe et al., J. Biol. Chem., 277:7363-7368 (2002). Such small organics could be administered alone or together with an anti-CTLA4 antibody to reduce inhibitory signal transduction of T cells.

3. Potentiating Agents

In some embodiments, additional therapeutic agents include a potentiating agent. The potentiating agent acts to increase efficacy the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode & Cooke Crit Rev. Immunol. 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB 1-HA tumor model, CTX treatment at Day 9 gives a 75% cure rate. Transfer of purified Treg at Day 12 almost completely inhibited the CTX response (van der Most et al. Cancer Immunol. Immunother. 58:1219-1228 (2009). A similar result was observed in the HHD2 tumor model: adoptive transfer of CD4+CD25+ Treg after CTX pretreatment eliminated therapeutic response to vaccine (Taieb, J. J. Immunol. 176:2722-2729 (2006)).

Numerous human clinical trials have demonstrated that low dose CTX is a safe, well-tolerated, and effective agent for promoting anti-tumor immune responses (Bas, & Mastrangelo Cancer Immunol. Immunother. 47:1-12 (1998)).

The optimal dose for CTX to potentiate an anti-tumor immune response, is one that lowers overall T cell counts by lowering Treg levels below the normal range but is sub-therapeutic (see Machiels et al. Cancer Res. 61:3689-3697 (2001)).

In human clinical trials where CTX has been used as an immunopotentiating agent, a dose of 300 mg/m$^2$ has usually been used. For an average male (6 ft, 170 pound (78 kg) with a body surface area of 1.98 m$^2$), 300 mg/m$^2$ is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. *Cancer Res.* 61:3689-3697 (2001), Hengst et al *Cancer Res.* 41:2163-2167 (1981), Hengst *Cancer Res.* 40:2135-2141 (1980)).

For larger mammals, such as a primate, such as a human, patient, such mg/m$^2$ doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g., Avastin, VEGF-Trap) (see, for example, Li et al., *Clin Cancer Res.* 2006 Nov. 15; 12(22):6808-16.), anthracyclines, oxaliplatin, doxorubicin, TLR4 antagonists, and IL-18 antagonists.

C. Antimicrobials

In one embodiment, Siglec-15-binding or Siglec-15 ligand-binding molecules can be used in a preventive or prophylactic role in the treatment and prevention of disease as discussed above, and also in the context of severe trauma injuries like a major burn, open bone fracture, accidental amputation or other wounds. Therefore, the Siglec-15-binding or Siglec-15 ligand-binding molecules can be administered to the subject in combination with an antimicrobial such as an antibiotic, an antifungal, an antiviral, an antiparasitics, or essential oil.

In some embodiments, the subject is administered the Siglec-15-binding molecules and/or the antimicrobial at time of admission to the hospital to prevent further bacterial, fungal or viral complications. The antibiotic can target pathogens and the Siglec-15-binding or Siglec-15 ligand-binding molecule can stimulate the immune system to provide an enhanced response to treat or prevent further infection or disease.

D. Immunosuppressive Agents

In some embodiments, the immune response, or inflammatory/autoimmune disease/disorder is treated by administering to the subject a Siglec-15-binding or ligand-binding molecule and a second agent that is an immune suppressant. Immunosuppressive agents include, but are not limited to antibodies against other lymphocyte surface markers (e.g., CD40, alpha-4 integrin) or against cytokines), fusion proteins (e.g., CTLA-4-Ig (Orencia®), TNFR-Ig (Enbrel®)), TNF-α blockers such as Enbrel, Remicade, Cimzia and Humira, cyclophosphamide (CTX) (i.e., Endoxan®, Cytoxan®, Neosar®, Procytox®, Revimmune™), methotrexate (MTX) (i.e., Rheumatrex®, Trexall®), belimumab (i.e., Benlysta®), or other immunosuppressive drugs (e.g., cyclosporin A, FK506-like compounds, rapamycin compounds, or steroids), anti-proliferatives, cytotoxic agents, or other compounds that may assist in immunosuppression.

The therapeutic agent can be a CTLA-4 fusion protein, such as CTLA-4-Ig (abatacept). CTLA-4-Ig fusion proteins compete with the co-stimulatory receptor, CD28, on T cells for binding to CD80/CD86 (B7-1/B7-2) on antigen presenting cells, and thus function to inhibit T cell activation. In another embodiment, the therapeutic agent is a CTLA-4-Ig fusion protein known as belatacept. Belatacept contains two amino acid substitutions (L104E and A29Y) that markedly increase its avidity to CD86 in vivo. In another embodiment, the therapeutic agent is Maxy-4.

In another embodiment, the therapeutic agent is cyclophosphamide (CTX). Cyclophosphamide (the generic name for Endoxan®, Cytoxan®, Neosar®, Procytox®, Revimmune™), also known as cytophosphane, is a nitrogen mustard alkylating agent from the oxazophorines group. It is used to treat various types of cancer and some autoimmune disorders. Cyclophosphamide (CTX) is the primary drug used for diffuse proliferative glomerulonephritis in patients with renal lupus.

The therapeutic agent can be administered in an effective amount to reduce the blood or serum levels of anti-double stranded DNA (anti-ds DNA) auto antibodies and/or to reduce proteinuria in a patient in need thereof.

In another embodiment, the therapeutic agent increases the amount of adenosine in the serum, see, for example, WO 08/147482. For example, the second therapeutic agent can be CD73-Ig, recombinant CD73, or another agent (e.g., a cytokine or monoclonal antibody or small molecule) that increases the expression of CD73, see for example WO 04/084933. In another embodiment the therapeutic agent is Interferon-beta.

The therapeutic agent can be Tysabri or another therapeutic for MS. In another embodiment, the second therapeutic agent preferentially treats chronic inflammation, whereby the treatment regimen targets both acute and chronic inflammation. In a preferred embodiment the second therapeutic is a TNF-α blocker.

The therapeutic agent can be a small molecule that inhibits or reduces differentiation, proliferation, activity, and/or cytokine production and/or secretion by Th1, Th17, Th22, and/or other cells that secrete, or cause other cells to secrete, inflammatory molecules, including, but not limited to, IL-13, TNF-α, IFN-γ, IL-18 IL-17, IL-6, IL-23, IL-22, IL-21, and MMPs. In another embodiment, the therapeutic agent is a small molecule that interacts with Tregs, enhances Treg activity, promotes or enhances IL-10 secretion by Tregs, increases the number of Tregs, increases the suppressive capacity of Tregs, or combinations thereof.

In some embodiments, the composition increases Treg activity or production. Exemplary Treg enhancing agents include but are not limited to glucocorticoid fluticasone, salmeteroal, antibodies to IL-12, IFN-γ, and IL-4; vitamin D3, and dexamethasone, and combinations thereof.

In some embodiments, the therapeutic agent is an antibody, for example, a functions blocking antibody against a proinflammatory molecule such as IL-6, IL-23, IL-22 or IL-21.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g.

WO95122972, WO 95116691, WO 95104738, U.S. Pat. Nos. 6,015,809; 5,989,591; 5,567,709; 5,559,112; 5,530,006; 5,484,790; 5,385,908; 5,202,332; 5,162,333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. Preferably, the language "rapamycin compound" as used herein does not include FK506-like compounds.

E. Anti-Inflammatories

Other suitable therapeutic agents include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

V. Diagnostic Methods

The Siglec-15-binding molecules, particularly antibodies and their antigen-binding fragments, can be used for diagnostic purposes, such as to detect, diagnose, or monitor diseases, disorders or infections associated with Siglec-15 expression, or to determine or assist in the determination or identification of suitable patient populations or profiles. Any of the methods can be coupled with a method of treating the subject, for example, by administering the subject an effective amount of one or more therapeutic Siglec-15-binding molecules.

The detection or diagnosis of a disease, disorder or infection, including, but not limited to, cancer can include: (a) assaying the expression of Siglec-15 or derivatives thereof in cells, serum, plasma, blood or in a tissue sample (e.g., a tumor sample) of a subject using one or more antibodies (or fragments thereof) that immunospecifically bind to such antigens; and (b) comparing the level of the antigen with a control level, e.g., levels in normal tissue samples, whereby an increase in the assayed level of antigen compared to the control level of the antigen is indicative of the disease, disorder or infection. Such antibodies and fragments can be employed in immunoassays, such as the enzyme linked immunosorbent assay (ELISA), the radioimmunoassay (RIA) and fluorescence-activated cell sorting (FACS).

In some embodiments, the antibodies or fragments are used for IHC analysis in cells of an in vitro or in situ tissue sample or in vivo. Thus, the antibodies and fragments can be used in the detection and diagnosis of a disease, disorder, or infection in a human. In one embodiment, such diagnosis includes: a) administering to a subject (for example, parenterally, subcutaneously, or intraperitoneally) an effective amount of such labeled antibody or antigen-binding fragment; b) waiting for a time interval following the administration for permitting the labeled molecule to preferentially concentrate at sites in the subject where Siglec-15 is expressed (and for unbound labeled molecule to be cleared to background level); c) determining background level; and d) detecting the labeled antibody in the subject, such that localized detection of labeled antibody above or below the background level indicates that the subject has the disease, disorder, or infection and/or shows the location and relative expression level of Siglec-15+ tissue. In accordance with this embodiment, the antibody can be labeled with an imaging moiety which is detectable in vivo using an imaging system known to one of skill in the art. Background level can be determined by various methods including, comparing the amount of labeled molecule detected to a standard value previously determined for a particular system.

Other methods include, for example, monitoring the progression of a disease, disorder or infection, by (a) assaying the expression of Siglec-15 in cells or in a tissue sample of a subject obtained at a first time point and later time point using a Siglec-15-binding molecule and (b) comparing the level of expression of Siglec-15 in the cells or in the tissue sample of the subject at the first and later times points, wherein an increase in the assayed level of Siglec-15 at the later time point compared to the first time point is indicative of the progression of disease, disorder or infection.

A method for monitoring a response to a treatment, can include, (a) assaying the expression of Siglec-15 in cells or in a tissue sample of a subject prior and after the treatment using a Siglec-15-binding molecule; and (b) comparing the level of Siglec-15 over time, whereby a decrease in the assayed level of Siglec-15 after treatment compared to the level of Siglec-15 prior to treatment is indicative of a favorable response to the treatment.

It will be understood in the art that the size of the subject and the imaging system used will determine the quantity of imaging moiety needed to produce diagnostic images.

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that can be used in the diagnostic methods include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

VI. Kits

The disclosed Siglec-15-binding or Siglec-15 ligand-binding molecules can be packaged in a hermetically sealed container, such as an ampoule or sachette, indicating the quantity. The molecules can be supplied as a dry sterilized lyophilized powder or water free concentrate in a hermetically sealed container and can be reconstituted, e.g., with water or saline to the appropriate concentration for administration to a subject. For example, the molecules can be supplied as a dry sterile lyophilized powder in a hermetically sealed container at a unit dosage of at least 5 mg, or at least 10 mg, at least 15 mg, at least 25 mg, at least 35 mg, at least 45 mg, at least 50 mg, or at least 75 mg. The lyophilized molecules can be stored at between 2 and 8° C. in their original container and are typically administered within 12 hours, or within 6 hours, or within 5 hours, or within 3 hours, or within 1 hour after being reconstituted.

In an alternative embodiment, molecules supplied in liquid form in a hermetically sealed container indicating the quantity and concentration. In some embodiments, the liquid form of the molecules supplied in a hermetically sealed container including at least 1 mg/ml, or at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml of the molecules.

Pharmaceutical packs and kits including one or more containers filled with Siglec-15-binding or Siglec-15 ligand-binding molecules are also provided. Additionally, one or more other prophylactic or therapeutic agents useful for the treatment of a disease can also be included in the pharmaceutical pack or kit. The pharmaceutical pack or kit can also include one or more containers filled with one or more of the ingredients of the disclosed pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

Kits designed for the above-described methods are also provided. Embodiments typically include one or more Siglec-15-binding or Siglec-15 ligand-binding molecules. In particular embodiments, a kit also includes one or more other prophylactic or therapeutic agents useful for the treatment of cancer, in one or more containers.

EXAMPLES

Figure 1:
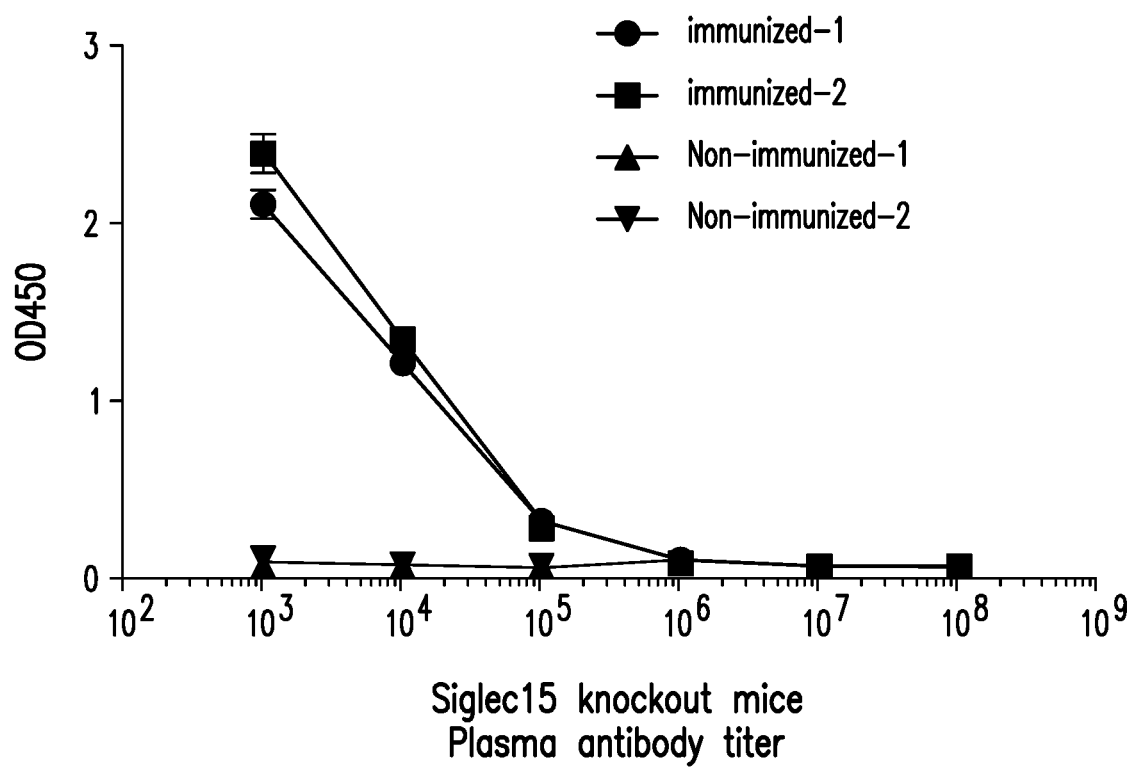
FIG. 1 is a curve showing the plasma antibody titer of two immunized and two non-immunized Siglec-15 knockout mice.

Example 1: SIGLEC-15 Antibodies and Heavy and Light Chains Sequences Thereof Materials and Methods Mouse Anti-Human Siglec-15 Monoclonal Antibodies Siglec-15 knock out mice (n=2) were immunized with hS15.mIg (human Siglec 15 extracellular domain [ECD] fused with mouse IgG2a) emulsified with CFA (complete Freund adjuvant). Mice also received injection of GM-CSF and anti-CD40. Mice were challenged with the same immunogen 2 weeks later. Antisera titer was assessed by testing serum collected from tail bleeding in hS15.hIg (human Siglec 15 ECD fused with human IgG1) coated ELISA plate at various dilution, 1:1000 up to 1:100,000,000. FIG. 1 shows that anti-hS15 antibodies were detected at >1:100,000 dilution. Mice received a $3^{rd}$ dose of antigen two weeks later. Three days after the final boost, mouse splenocytes were harvested and resuspended in RPMI supplemented with 10% FBS and glutamine, and later fused to form hybridomas.

Electrofusion of Siglec-15 Knockout (S15 KO) Splenocytes

Fused cells were plated in methylcellulose gel/media; left over fused cells were cryopreserved and can be thawed for another batch of cloning Single clones were picked and placed in 10×96 well plates (960 clones) Supernatant were collected 2 weeks later.

RACE

RACE (Rapid Amplification of cDNA Ends) identification of the heavy and light chains was performed according to the following protocol: (1) mRNA denaturing, (2) cDNA synthesis, (3) 5'RACE Reaction, (4) analyzed PCR results (on an agarose gel to visualize the amplified DNA fragment—the correct antibody variable region DNA fragments should have a size between 500-700 base pairs, (5) TOPO cloned PCR positive bands; (6) PCR-amplified TOPO clones, followed by gel electrophoresis and recovery from agarose gel, (7) sequenced 218 clones in total, (8) performed CDR analysis using sequencing data (CDR regions were defined using VBASE2 available through vbase2.org).

Results

Antibodies were cloned using RACE methods. After sequencing 218 cloned DNA fragments, antibody sequence analysis identified one heavy chain and one light chain for 24 antibody samples referred to herein as 1B2, 1C3, 1H3, 1C12, 3H10, 5G12, 6F8, 8C8, 8H8, 9A5, 10G9, 6A, 28A, 63A, 71A, 77A, 80A, 82B, 83B, 92A, 93B, 99B, 104B, and 105A. The sequences are provided below and above. Heavy and light chain sequences and CDRs are provided above, below, and illustrated in FIG. 2A-3C.

1B2 SEQUENCES:
1B2 VL Amino Acid Sequence in FASTA format
(SEQ ID NO: 3)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

WTFGGGTKLEIK

1B2 VL Nucleotide Sequence in FASTA format
(SEQ ID NO: 74)
GATGTTTTGATGACCCAAACTCCACTCTCCCTGCCTGTCAGTCTTGGAGA

TCAAGCCTCCATCTCTTGCAGATCTAGTCAGAGCATTGTACATAGTAATG

GAAACACCTATTTAGAATGGTACCTGCAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

TGGACGTTCGGTGGAGGCACCAAGCTGGAAATCAAG

1B2 VH Amino Acid Sequence in FASTA format
(SEQ ID NO: 13)
EVQLVESGGGFVKPGGSLKLSCAASGFTFSDYGMHWVRQAPEKGLEWVAY

ISSGSSIIYYADTVKGRFTISRDNAKNTLFLQMTSLRSEDTAMYYCARDH

YHGNGSDYWGQGTTLTVSS

1B2 VH Nucleotide Sequence in FASTA format
(SEQ ID NO: 85)
GAGGTGCAGCTGGTGGAGTCTGGGGGAGGCTTCGTGAAGCCTGGAGGGTC

CCTGAAACTCTCCTGTGCAGCCTCTGGATTCACTTTCAGTGACTATGGAA

TGCACTGGGTTCGTCAGGCTCCAGAGAAGGGGCTGGAGTGGGTTGCATAC

ATTAGTAGTGGCAGTAGTATCATCTACTATGCAGACACAGTGAAGGGCCG

ATTCACCATCTCCAGAGACAATGCCAAGAACACCCTGTTCCTGCAAATGA

CCAGTCTGAGGTCTGAGGACACGGCCATGTATTACTGTGCAAGGGACCAC

TACCATGGTAACGGGTCCGACTACTGGGGCCAAGGCACCACTCTCACAGT

CTCCTCA

1C3 SEQUENCES:
1C3 VL Amino Acid Sequence in FASTA format
(SEQ ID NO: 4)
DIVMTQAAPSVPVTPGESVSISCRSSKSLLHSNGNTYLYWFLQRPGQSPQ

LLIYRMSNLASGVPDRFGGSGSGTAFTLRISRVEAEDVGFYYCMQHLEYP

YTFGGGTRLEIK

1C3 VL Nucleotide Sequence in FASTA format
(SEQ ID NO: 75)
GATATTGTGATGACTCAGGCTGCACCCTCTGTACCTGTCACTCCTGGAGA

GTCAGTATCCATCTCCTGCAGGTCTAGTAAGAGTCTCCTGCATAGTAATG

GCAACACTTACTTATATTGGTTCCTGCAGAGGCCAGGCCAGTCTCCTCAG

CTCCTGATATATCGGATGTCCAACCTTGCCTCAGGAGTCCCAGACAGGTT

CGGTGGCAGTGGGTCAGGAACTGCTTTCACACTGAGAATCAGTAGAGTGG

AGGCTGAGGATGTGGGTTTTTATTACTGTATGCAACATCTAGAATATCCG

TACACGTTCGGAGGGGGGACCAGGCTGGAAATAAAA

1C3 VH Amino Acid Sequence in FASTA format
(SEQ ID NO: 14)
QVQLKQSGAELVKPGASVKISCKASGYIFTDYYVNWVKQRPGQGLEWIGK

IGPGSVSIYYNEKFKGKATLTADKSSSTAYMQLSSLTSEDSAVYFCASYY

YGFAYWGQGTLVTVSA

1C3 VH Nucleotide Sequence in FASTA format
(SEQ ID NO: 86)
CAGGTCCAGCTGAAGCAGTCTGGAGCTGAGCTGGTGAAGCCTGGGGCTTC

AGTGAAGATATCCTGCAAGGCTTCTGGCTACATCTTCACTGACTATTATG

TAAACTGGGTGAAGCAGAGGCCTGGACAGGGCCTTGAGTGGATTGGAAAG

ATTGGTCCTGGAAGTGTTAGTATTTACTACAATGAGAAGTTCAAGGGCAA

GGCCACACTGACTGCAGACAAATCCTCCAGCACAGCCTACATGCAGCTCA

GCAGCCTGACATCTGAGGACTCTGCAGTCTATTTCTGTGCAAGTTATTAC

TACGGGTTTGCTTACTGGGGCCAAGGGACTCTGGTCACTGTCTCTGCA

1H3 SEQUENCES:
1H3 VL Amino Acid Sequence in FASTA format
(SEQ ID NO: 5)
DIQMTQASSSLSVSLGGRVTITCKASDHINNWLAWYQQKPGNAPRLLISG

ATSLETGVPSRFSGSGSGKDYTLSITSLQTEDVATYYCQQYWSSPLTFGA

GTKLELK

1H3 VL Nucleotide Sequence in FASTA format
(SEQ ID NO: 76)
GACATCCAGATGACACAGGCTTCATCCTCCTTGTCTGTATCTCTAGGAGG

CAGAGTCACCATTACTTGCAAGGCAAGTGACCACATTAATAATTGGTTGG

CCTGGTATCAGCAGAAACCAGGAAATGCTCCTAGGCTCTTAATATCTGGT

GCAACCAGTTTGGAAACTGGGGTTCCTTCAAGATTCAGTGGCAGTGGATC

TGGAAAGGATTACACTCTCAGCATTACCAGTCTTCAGACTGAAGATGTTG

CTACTTATTACTGTCAACAGTATTGGAGTTCTCCTCTCACGTTCGGTGCT

GGGACCAAGCTGGAGCTGAAA

1H3 VH Amino Acid Sequence in FASTA format
(SEQ ID NO: 15)
QVQLKESGPGLVAPSQSLSITCTVSGFSLSNYGVHWVRQPPGKGLEWLVL

IWSDGSTTYNSALKSRLSISKDNSKSQVFLKMNSLQTGDTAMYYCARHPY

DDYSGYYYTMDYWGQGTSVTVSS

1H3 VH Nucleotide Sequence in FASTA format
(SEQ ID NO: 87)
CAGGTGCAGCTGAAGGAGTCAGGACCTGGCCTGGTGGCGCCCTCACAGAG

CCTGTCCATCACATGCACCGTCTCAGGGTTCTCATTAAGCAATTATGGTG

TACACTGGGTTCGCCAGCCTCCAGGAAAGGGTCTGGAGTGGCTGGTACTG

ATATGGAGTGATGGAAGCACAACCTATAATTCAGCTCTCAAATCCAGACT

GAGCATCAGCAAGGACAACTCCAAGAGCCAAGTTTTCTTAAAAATGAACA

GTCTCCAAACTGGTGACACAGCCATGTACTACTGTGCCAGACATCCCTAT

GATGATTATTCCGGCTATTACTATACTATGGACTACTGGGGTCAAGGAAC

CTCAGTCACCGTCTCCTCA

1C12 SEQUENCES:
1C12 VL Amino Acid Sequence in FASTA format
(SEQ ID NO: 3)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

WTFGGGTKLEIK

1C12 VL Nucleotide Sequence in FASTA format
(SEQ ID NO: 77)
GATGTTTTGATGACCCAAACTCCACTCTCCCTGCCTGTCAGTCTTGGAGA

TCAAGCCTCCATCTCTTGCAGATCTAGTCAGAGCATTGTACATAGTAATG

GAAACACCTATTTAGAATGGTACCTGCAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

TGGACGTTCGGTGGAGGCACCAAGCTGGAAATCAA

1C12 VH Amino Acid Sequence in FASTA format
(SEQ ID NO: 16)
EVQLVESGGGLVKPGGSLKLSCAASGFSFSDYGMHWVRQAPEKGLEWVAY

ISSGSSILYYADIVKGRFTISRDNAKNTLFLQMTSLRSEDTAMYYCARDH

YHGNGSDYWGQGTTLTVSS

1C12 VH Nucleotide Sequence in FASTA format
(SEQ ID NO: 88)
GAGGTGCAGCTGGTGGAGTCTGGGGGAGGCTTAGTGAAGCCTGGAGGGTC

CCTGAAACTCTCCTGTGCAGCCTCTGGTTTCTCTTTCAGTGACTATGGAA

TGCACTGGGTTCGTCAGGCTCCAGAGAAGGGGCTGGAGTGGGTTGCATAC

ATTAGTAGTGGCAGTAGTATCCTCTACTATGCAGACATAGTGAAGGGCCG

ATTCACCATCTCCAGAGACAATGCCAAGAACACCCTGTTCCTGCAAATGA

CCAGTCTGAGGTCTGAGGACACGGCCATGTATTACTGTGCAAGGGACCAC

TACCATGGTAACGGGTCCGACTACTGGGGCCAAGGCACCACTCTCACAGT

CTCCTCA

3H10 SEQUENCES:
3H10 VL Amino Acid Sequence in FASTA format
(SEQ ID NO: 6)
QIILTQSPAIMSASPGEKVTMTCSASSSTSFMHWYQQKPGTSPKRWIFDT

SKLASGVPGRFIGSGSGTSYSLTISTMEAEDAATYYCHQRSAYPWTFGGG

TKLEIK3H10 VL Nucleotide Sequence in FASTA format
(SEQ ID NO: 78)
CAAATTATTCTCACCCAGTCTCCAGCAATCATGTCTGCATCTCCAGGGGA

GAAGGTCACCATGACCTGCAGTGCCAGCTCAAGTACAAGTTTCATGCACT

GGTACCAGCAGAAGCCAGGCACCTCCCCCAAAAGATGGATTTTTGACACA

TCCAAACTGGCTTCTGGAGTCCCTGGTCGCTTCATTGGTAGTGGGTCTGG

GACCTCTTATTCTCTCACAATCAGCACCATGGAGGCTGAAGATGCTGCCA

CTTATTACTGCCATCAGCGGAGTGCTTACCCATGGACGTTCGGTGGAGGC

ACCAAGCTGGAAATCAAA

3H10 VH Amino Acid Sequence in FASTA format
(SEQ ID NO: 17)
EVQLQQSGAELVRPGASVKLSCTASGFNIKDYYMHWVKERPEQGLEWIGR

IDPEDGDIEYDPKFQGKATMTADTSSNTAYLQFSSLTSEDTAVYYCVTDY

DYDGGWFAYWGQGTLVTVSA

3H10 VH Nucleotide Sequence in FASTA format
(SEQ ID NO: 89)
GAGGTTCAGCTGCAGCAGTCTGGGGCAGAGCTTGTGAGGCCAGGGGCCTC

AGTCAAGTTGTCCTGCACAGCTTCTGGCTTCAACATTAAAGACTACTATA

TGCACTGGGTGAAAGAGAGGCCTGAACAGGGCCTGGAGTGGATTGGAAGG

ATTGATCCTGAGGATGGTGATATTGAATATGACCCGAAGTTCCAGGGCAA

GGCCACTATGACTGCAGATACATCCTCCAACACAGCCTACCTGCAGTTCA

GCAGCCTGACATCTGAGGACACTGCCGTCTATTATTGTGTCACGGACTAT

GATTACGACGGAGGCTGGTTTGCTTACTGGGGCCAAGGGACTCTGGTCAC

TGTCTCTGCA

5G12 SEQUENCES:
5G12 VL Amino Acid Sequence in FASTA format
(SEQ ID NO: 7)
DIKMTQSPSSMYASLGERVTITCKASQDINSYLSWFQQKPGKSPKTLIYR

ANRLVDGVPSRFSGSGSGQDYSLTISSLEYEDMGIYYCLQYDEFPYTFGG

GTKLEIKR

5G12 VL Nucleotide Sequence in FASTA format
(SEQ ID NO: 79)
GACATCAAGATGACCCAGTCTCCATCTTCCATGTATGCATCTCTAGGAGA

GAGAGTCACTATCACTTGCAAGGCGAGTCAGGACATTAATAGCTATTTAA

GCTGGTTCCAGCAGAAACCAGGGAAATCTCCTAAGACCCTGATCTATCGT

GCAAACAGATTGGTAGATGGGGTCCCATCAAGGTTCAGTGGCAGTGGATC

TGGGCAAGATTATTCTCTCACCATCAGCAGCCTGGAGTATGAAGATATGG

GAATTTATTATTGTCTACAGTATGATGAGTTTCCGTACACGTTCGGAGGG

GGGACCAAGCTGGAAATAAAA

5G12 VH Amino Acid Sequence in FASTA format
(SEQ ID NO: 18)
QVQLQQPGAELVKPGASVKMSCKASGYTFTSYWITWVIQRPGQGLEWIGD

IYCGSDTMHYNEKFKNKATLTVDTSSSTAYMQLSSLTSEDSAVYYCARWW

DYGSSYDYFDYWGQGTTLTVSS

5G12 VH Nucleotide Sequence in FASTA format
(SEQ ID NO: 90)
CAGGTCCAACTGCAGCAGCCTGGGGCTGAGCTTGTGAAGCCTGGGGCTTC

AGTGAAGATGTCCTGCAAGGCTTCTGGCTACACCTTCACCAGCTACTGGA

TAACCTGGGTGATACAGAGGCCGGGACAAGGCCTTGAGTGGATTGGAGAT

ATTTATTGTGGTAGTGATACTATGCACTACAATGAGAAGTTCAAGAACAA

GGCCACACTGACTGTAGACACATCCTCCAGCACAGCCTACATGCAGCTCA

GCAGCCTGACATCTGAGGACTCTGCGGTCTATTACTGTGCAAGATGGTGG

GACTACGGTAGTAGCTACGACTACTTTGACTACTGGGGCCAAGGCACCAC

TCTCACAGTCTCCTCA

6F8 SEQUENCES:
6F8 VL Amino Acid Sequence in FASTA format
(SEQ ID NO: 8)
DIVMTQAAPSVPVTPGESVSISCRSSKSLLHSNGNTYLYWFLQRPGQSPQ

LLIYRMSNLASGVPDRFGGSGSGTAFTLRISRVEAEDVGVYYCMQHLEYP

YTFGGGTKLEIKR

6F8 VL Nucleotide Sequence in FASTA format
(SEQ ID NO: 80)
GATATTGTGATGACTCAGGCTGCACCCTCTGTACCTGTCACTCCTGGAGA

GTCAGTATCCATCTCCTGCAGGTCTAGTAAGAGTCTCCTGCATAGTAATG

GCAACACTTACTTGTATTGGTTCCTGCAGAGGCCAGGCCAGTCTCCTCAG

CTCCTGATATATCGGATGTCCAACCTTGCCTCAGGAGTCCCAGACAGGTT

```
6F8 VH Amino Acid Sequence in FASTA format
                                      (SEQ ID NO: 19)
QVQLKQSGPELVRPGASVKISCEASGYTFTDYYVNWVKQRPGRGLEWIGK

IGPGSVSIYYNEKFKDKATLTADKSSSTAYMQLSGLTSEDSAVYFCASYY

YGFAYWGQGTLVTVSA

6F8 VH Nucleotide Sequence in FASTA format
                                      (SEQ ID NO: 91)
CAGGTCCAGCTGAAGCAGTCTGGACCTGAACTGGTGAGGCCTGGGCTTC

AGTGAAGATATCCTGCGAGGCTTCTGGCTACACCTTCACTGACTATTATG

TAAACTGGGTGAAGCAGAGGCCTGGACGGGGCCTTGAGTGGATTGGAAAG

ATTGGTCCTGGAAGTGTTAGTATTTACTACAATGAGAAGTTCAAGGACAA

GGCCACACTGACTGCAGACAAATCCTCCAGCACAGCCTACATGCAGCTCA

GCGGCCTGACATCTGAGGACTCTGCAGTCTATTTCTGTGCAAGTTATTAC

TACGGTTTTGCTTACTGGGGCCAAGGGACTCTGGTCACTGTCTCTGCA

8C8 SEQUENCES:
8C8 VL Amino Acid Sequence in FASTA format
                                      (SEQ ID NO: 9)
DIVMTQAAPSVPVTPGESVSISCRSSKSLLHSNGNTYLYWFLQRPGQSPQ

LLIYRMSNLASGVPDRFGGSGSGTAFTLRISRVEAEDVGVYYCMQHLEYP

YTFGGGTKLEIK

8C8 VL Nucleotide Sequence in FASTA format
                                      (SEQ ID NO: 81)
GATATTGTGATGACTCAGGCTGCACCCTCTGTACCTGTCACTCCTGGAGA

GTCAGTATCCATCTCCTGCAGGTCTAGTAAGAGTCTCCTGCATAGTAATG

GCAACACTTACTTGTATTGGTTCCTGCAGAGGCCAGGCCAGTCTCCTCAG

CTCCTGATATATCGGATGTCCAACCTTGCCTCAGGAGTCCCAGACAGGTT

CGGTGGCAGTGGGTCAGGAACTGCTTTCACACTGAGAATCAGTAGAGTGG

AGGCTGAGGATGTGGGTGTTTATTACTGTATGCAACATCTAGAATATCCG

TACACGTTCGGAGGGGGGACCAAGCTGGAAATAAAA

8C8 VH Amino Acid Sequence in FASTA format
                                      (SEQ ID NO: 20)
QVQLKQSGAELVKPGASVKISCKASGYTFTDYYVNWVKQRPGQGLEWIGK

IGPESVSIYYSEKFKAKATLTADKSSSTAYMQLSSLTSEDSAVYFCASYY

YGFAYWGQGTLVTVSA

8C8 VH Nucleotide Sequence in FASTA format
                                      (SEQ ID NO: 92)
CAGGTCCAGCTGAAGCAGTCTGGAGCTGAGCTGGTGAAGCCTGGGCTTC

AGTGAAGATATCCTGCAAGGCTTCTGGCTACACCTTCACTGACTATTATG

TAAACTGGGTGAAGCAGAGGCCTGGACAGGGCCTTGAGTGGATTGGAAAG

ATTGGTCCTGAAAGTGTTAGTATTTATTACAGTGAGAAGTTCAAGGCCAA

GGCCACACTGACTGCAGACAAATCCTCCAGCACAGCCTACATGCAACTCA

GCAGCCTGACATCTGAGGACTCTGCAGTCTATTTCTGTGCAAGTTATTAC

TACGGGTTTGCTTACTGGGGCCAAGGGACTCTGGTCACTGTCTCTGCA

8H8 SEQUENCES:
8H8 VL Amino Acid Sequence in FASTA format
                                      (SEQ ID NO: 10)
QAVVTQESALTTSPGETVTLTCRSSSGAVTTGNFANWVQEKPDHLFTGLI

GGTNNRAPGVPARFSGSLIGDKAALTITGAQTEDEAIYFCALWYSNHWVF

GGGTKLTVL

8H8 VL Nucleotide Sequence in FASTA format
                                      (SEQ ID NO: 82)
CAGGCTGTTGTGACTCAGGAATCTGCACTCACCACATCACCTGGTGAAAC

AGTCACACTCACTTGTCGCTCAAGTTCTGGGGCTGTTACAACTGGTAACT

TTGCCAACTGGGTCCAAGAAAAACCAGATCATTTATTCACTGGTCTAATA

GGTGGTACCAACAACCGAGCTCCAGGTGTTCCTGCCAGATTCTCAGGCTC

CCTGATTGGAGACAAGGCTGCCCTCACCATCACAGGGGCACAGACTGAGG

ATGAGGCAATATATTTCTGTGCTCTATGGTACAGCAACCACTGGGTGTTC

GGTGGAGGAACCAAACTGACTGTCCTA

8H8 VH Amino Acid Sequence in FASTA format
                                      (SEQ ID NO: 21)
EVQLLETGGGLVQPGGSRGLSCEGSGFTFSGFWMSWVRQTPGKTLEWIGD

INSDGSAINYAPSIKDRFTIFRDNDKNTLYLQMNNVRSEDTATYFCVRYD

DYGYFDVWGTGTTVTSS

8H8 VH Nucleotide Sequence in FASTA format
                                      (SEQ ID NO: 93)
GAAGTGCAGCTGTTGGAGACTGGAGGAGGCTTGGTGCAACCGGGGGGGTC

ACGGGGACTCTCTTGTGAAGGCTCAGGGTTCACTTTTAGTGGCTTCTGGA

TGAGCTGGGTTCGACAGACACCTGGGAAGACCCTGGAGTGGATTGGAGAC

ATTAATTCTGATGGCAGTGCAATAAACTACGCACCATCCATAAAGGATCG

ATTCACTATCTTCAGAGACAATGACAAGAACACCCTGTACCTGCAGATGA

ACAATGTGCGATCGGAGGACACAGCCACGTATTTCTGTGTGAGATATGAT

GATTACGGGTACTTCGATGTCTGGGGCACAGGGACCACGGTCACCGTCTC

CTCA

9A5 SEQUENCES:
9A5 VL Amino Acid Sequence in FASTA format
                                      (SEQ ID NO: 11)
DVVMTQTPLTLSVTIGQSASISCKSSQSLLDSDGKTYLNWLLQRPGQSPK

RLIYLVSKLDSGVPDRFTGSGSGTDFTLKISRVEAEDLGVYYCWQGTHFP

FTFGSGTKLEIK

9A5 VL Nucleotide Sequence in FASTA format
                                      (SEQ ID NO: 83)
GATGTTGTGATGACCCAGACTCCACTCACTTTGTCGGTTACCATTGGACA

GTCAGCCTCCATCTCTTGCAAGTCAAGTCAGAGCCTCTTAGATAGTGATG

GAAAGACATATTTGAATTGGTTGTTACAGAGGCCAGGCCAGTCTCCAAAG

CGCCTAATCTATCTGGTGTCTAAACTGGACTCTGGAGTCCCTGACAGGTT

CACTGGCAGTGGATCAGGGACAGATTTCACACTGAAAATCAGCAGAGTGG

AGGCTGAGGATTTGGGAGTTTATTATTGCTGGCAAGGTACACATTTTCCA

TTCACGTTCGGCTCGGGGACAAAGTTGGAAATAAAA
```

9A5 VH Amino Acid Sequence in FASTA format
(SEQ ID NO: 22)
HVQLQQSGAELARPGASVKLSCKASGYTFTSYGLIWVKQRTGQGLEWIGE

IYPRSGNTYYNEKFKGKATLTADISSSTAYMELRSLTSEDSAVYFCASSS

PHGDYWGQGTTLTVSS

9A5 VH Nucleotide Sequence in FASTA format
(SEQ ID NO: 94)
CACGTTCAGCTGCAGCAGTCTGGAGCTGAGTTGGCGAGGCCTGGGGCTTC

AGTGAAGCTGTCCTGCAAGGCTTCTGGCTACACCTTCACAAGCTATGGTT

TAATCTGGGTGAAGCAGAGAACTGGACAGGGCCTTGAGTGGATTGGAGAG

ATTTATCCTAGAAGTGGTAATACTTACTACAATGAGAAGTTCAAGGGCAA

GGCCACACTGACTGCAGACATATCCTCCAGCACAGCGTACATGGAGCTCC

GCAGCCTGACATCTGAGGACTCTGCGGTCTATTTCTGTGCAAGTTCCTCT

CCTCACGGGGACTACTGGGGCCAAGGCACCACTCTCACAGTCTCCTCA

10G9 SEQUENCES:
10G9 VL Amino Acid Sequence in FASTA format
(SEQ ID NO: 12)
QAVVTQESALTTSPGETVTLTCRSSTGAVTTSNYANWVQEKPDHLFTGLI

GGTNNRAPGVPARFSGSLIGDKAALTITGAQTEDEAIYFCALWYSNHWVF

GGGTKLTVL

10G9 VL Nucleotide Sequence in FASTA format
(SEQ ID NO: 84)
CAGGCTGTTGTGACTCAGGAATCTGCACTCACCACATCACCTGGTGAAAC

AGTCACACTCACTTGTCGCTCAAGTACTGGGGCTGTTACAACTAGTAACT

ATGCCAACTGGGTCCAAGAAAAACCAGATCATTTATTCACTGGTCTAATA

GGTGGTACCAACAACCGAGCTCCAGGTGTTCCTGCCAGATTCTCAGGCTC

CCTGATTGGAGACAAGGCTGCCCTCACCATCACAGGGGCACAGACTGAGG

ATGAGGCAATATATTTCTGTGCTCTATGGTACAGCAACCACTGGGTGTTC

GGTGGAGGAACCAAACTGACTGTCCTA

10G9 VH Amino Acid Sequence in FASTA format
(SEQ ID NO: 23)
EVQLLETGGGLVQPGGSRGLSCEGSGFTFSDFWMSWVRQTPGKTLEWIGD

INSDGSAVNYAPSIKDQFTIFRDNDKRTLHLQMINVRSEDTATYFCVRYD

DYGYFDVWGTGTTVTVSS

10G9 VH Nucleotide Sequence in FASTA format
(SEQ ID NO: 95)
GAAGTGCAGCTGTTGGAGACTGGAGGAGGCTTAGTGCAACCTGGGGGGTC

ACGGGGACTCTCTTGTGAAGGCTCAGGGTTCACTTTTAGTGACTTCTGGA

TGAGCTGGGTTCGACAGACACCTGGGAAGACCCTGGAGTGGATTGGAGAC

ATTAATTCTGATGGCAGTGCAGTTAACTACGCACCATCCATAAAGGATCA

ATTCACTATCTTCAGAGACAATGACAAGAGGACCCTGCACCTGCAGATGA

TCAATGTTCGATCGGAGGACACAGCCACGTATTTCTGTGTGAGATATGAT

GATTACGGGTACTTCGATGTCTGGGGCACAGGGACCACGGTCACCGTCTC

CTCA

6A SEQUENCES:
6A VL Amino Acid Sequence in FASTA format
(SEQ ID NO: 96)
DVLMTQTPLSLPVSLGDQASISCRSSQSIVHSNGNTYLEWYLQKPGQSPK

LLIYKVSNRFSGVPDRFSGSGSGTDFTLRISRVEAEDLGVYYCFQGSHVP

LTFGAGTKLELK

6A VL Nucleotide Sequence in FASTA format
(SEQ ID NO: 120)
GATGTTTTGATGACCCAAACTCCACTCTCCCTGCCTGTCAGTCTTGGAGA

TCAAGCCTCCATCTCTTGCAGATCTAGTCAGAGTATTGTACATAGTAATG

GAAACACCTATTTAGAATGGTACCTGCAGAAGCCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAGGATCAGCAGAGTGG

AGGCTGAGGATCTGGGAGTTTATTACTGCTTTCAAGGTTCACATGTTCCG

CTCACGTTCGGTGCTGGGACCAAGCTGGAGCTGAAA

6A VH Amino Acid Sequence in FASTA format
(SEQ ID NO: 108)
EVQLQQSGAELVRPGASVKLSCTASGFNIKDDYMHWVKQRPEQGLEWIGC

TDPENGDTEYASKFQDKATITTDTSSNTAYLQLSSLTSEDTAVYYCTTYV

GFAYWGQGTLVTVST

6A VH Nucleotide Sequence in FASTA format
(SEQ ID NO: 133)
GAGGTTCAGCTGCAGCAGTCTGGGGCTGAACTTGTGAGGCCAGGGGCCTC

AGTCAAGTTGTCCTGCACAGCTTCTGGCTTTAACATTAAAGACGACTATA

TGCACTGGGTGAAACAGAGGCCTGAACAGGGCCTGGAGTGGATTGGATGC

ATTGATCCTGAGAATGGTGATACTGAATATGCCTCGAAATTCCAGGACAA

GGCCACTATAACAACAGACACATCCTCCAACACAGCCTACCTGCAGCTCA

GCAGCCTGACATCTGAGGACACTGCCGTCTATTACTGTACTACATACGTT

GGATTTGCTTACTGGGGCCAAGGGACTCTGGTCACTGTCTCTACA

28A SEQUENCES:
28A VL Amino Acid Sequence in FASTA format
(SEQ ID NO: 97)
DVVMTQTPLTLSIPIGQPASISCKSSQSLLDSDGKTYLNWLLQRPGQSPK

RLIYLVSELDSGVPDRFTGSGSGTDFTLKISRVEAEDLGVYYCWQGTHFP

FTFGSGTKLEIK

28A VL Nucleotide Sequence in FASTA format
(SEQ ID NO: 121)
GATGTTGTGATGACCCAGACTCCACTCACTTTGTCGATTCCCATTGGACA

ACCAGCCTCCATCTCTTGTAAGTCAAGTCAGAGCCTCTTAGATAGTGATG

GAAAGACATATTTGAATTGGTTGTTACAGAGGCCAGGCCAGTCTCCAAAG

CGCCTCATCTATCTGGTGTCTGAACTGGACTCTGGAGTCCCTGACAGGTT

CACTGGCAGTGGATCAGGGACAGATTTCACACTGAAAATCAGCAGAGTGG

AGGCTGAAGATTTGGGAGTTTATTATTGTTGGCAAGGTACACATTTTCCA

TTCACGTTCGGCTCGGGGACAAAGTTGGAAATAAAA

28A VH Amino Acid Sequence in FASTA format
(SEQ ID NO: 109)
QVQLQQSGAELARPGASVKLSCKASGYTFISYGITWVKQRTGQGLEWIGE

IHPRSGNTYYNENFKDRASLTADKSSSTAYMEVRSLTSEDSAVYFCARGG

PGDYWGQGTTLTVSS

28A VH Nucleotide Sequence in FASTA format
(SEQ ID NO: 134)
CAGGTTCAGCTGCAGCAGTCTGGAGCTGAGCTGGCGAGGCCTGGGGCTTC

AGTGAAGCTGTCCTGCAAGGCTTCTGGCTACACCTTCATAAGCTATGGTA

TAACCTGGGTGAAGCAGAGAACTGGACAGGGCCTTGAGTGGATTGGAGAG

ATTCATCCTAGAAGTGGTAATACTTACTACAATGAGAATTTCAAGGACAG

GGCCTCACTGACTGCAGACAAATCCTCCAGCACAGCGTACATGGAGGTCC

GCAGCCTGACATCTGAGGACTCTGCGGTCTATTTCTGTGCAAGGGGTGGG

CCGGGGGACTACTGGGGCCAAGGCACCACTCTCACAGTCTCCTCA

63A SEQUENCES:
63A VL Amino Acid Sequence in FASTA format
(SEQ ID NO: 98)
DVVMTQTPLTLSVTIGQPASISCKSSQSLLDSDGKTYLNWLLQRPGQSPK

RLIYLVSKLDSGVPDRFTGSGSGTDFTLKISRVEAEDLGVYYCWQGTHFP

FTFGSGTKLEIK

63A VL Nucleotide Sequence in FASTA format
(SEQ ID NO: 122)
GATGTTGTGATGACCCAGACTCCACTCACTTTGTCGGTTACCATTGGACA

ACCAGCCTCCATCTCTTGCAAGTCAAGTCAGAGCCTCTTAGATAGTGATG

GAAAGACATATTTGAATTGGTTGTTACAGAGGCCAGGCCAGTCTCCAAAG

CGCCTAATCTATCTGGTGTCTAAACTGGACTCTGGAGTCCCTGACAGGTT

CACTGGCAGTGGATCAGGGACAGATTTCACACTGAAAATCAGCAGAGTGG

AGGCTGAGGATTTGGGAGTTTATTATTGTTGGCAAGGTACACATTTTCCA

TTCACGTTCGGCTCGGGGACAAAGTTGGAAATAAAA

63A VH Amino Acid Sequence in FASTA format
(SEQ ID NO: 110)
QVQLQQSGAELARPGASVKLSCKASGYTFTSYGISWVKQRTGQGLEWIGQ

IYPRSDNTYYNERFKGKATLTADKSSSTAYMALRSLTSEDSAVYFCAREG

GPDYWGQGTTLTVSS

63A VH Nucleotide Sequence in FASTA format
(SEQ ID NO: 135)
CAGGTTCAGCTGCAGCAGTCTGGAGCTGAGCTGGCGAGGCCTGGGGCTTC

AGTGAAGCTGTCCTGCAAGGCTTCTGGCTACACCTTCACAAGCTATGGTA

TAAGCTGGGTGAAGCAGAGAACTGGACAGGGCCTTGAGTGGATTGGACAG

ATTTATCCTAGAAGTGACAATACTTACTACAATGAGAGGTTCAAGGGCAA

GGCCACACTGACTGCAGACAAATCCTCCAGCACAGCGTACATGGCGCTCC

GCAGCCTGACATCTGAGGACTCTGCGGTCTATTTCTGTGCAAGAGAGGGG

GGTCCCGACTACTGGGGCCAAGGCACCACTCTCACAGTCTCCTCA

71A SEQUENCES:
71A VL Amino Acid Sequence in FASTA format
(SEQ ID NO: 99)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

LTFGAGTKLELK

71A VL Nucleotide Sequence in FASTA format
(SEQ ID NO: 123)
GACGTTTTGATGACCCAAACTCCACTCTCCCTGCCTGTCAGTCTTGGAGA

TCAAGCCTCCATCTCTTGCAGATCTAGTCAGAGTATTGTACATAGTAATG

GAAACACCTATTTAGAATGGTACCTACAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

CTCACGTTCGGTGCTGGGACCAAGCTGGAGCTGAAA

71A VH Amino Acid Sequence in FASTA format
(SEQ ID NO: 111)
EVQLQQSGAELVRPGASVKLSCTASGFNIKDDYMHWVKQRPEQGLEWIGC

IDPENGDIEYASRFQGKATMTADTSSNTAYLQLTSLTSADTAVYYCTTYV

GFGYWGQGTLVTVSA

71A VH Nucleotide Sequence in FASTA format
(SEQ ID NO: 136)
GAGGTTCAGCTGCAGCAGTCTGGGGCTGAGCTTGTGAGGCCAGGGGCCTC

AGTCAAGTTGTCCTGCACAGCTTCTGGCTTTAACATTAAAGACGACTATA

TGCACTGGGTGAAACAGAGGCCTGAACAGGGCCTGGAGTGGATTGGATGC

ATTGATCCTGAGAATGGTGATATTGAATATGCCTCGAGGTTCCAGGGCAA

GGCCACTATGACAGCAGACACATCCTCCAACACAGCCTACCTGCAGCTCA

CCAGCCTGACATCTGCGGACACTGCCGTCTATTACTGTACTACATACGTT

GGATTTGGTTACTGGGGCCAAGGGACTCTGGTCACTGTCTCTGCA

77A SEQUENCES:
77A VL Amino Acid Sequence in FASTA format
(SEQ ID NO: 100)
DVLMTQSPLSLPVSLGDQASISCRSSQNIVHSNGNTYLEWLKKPGQSPK

LLIYKVSNRFSGVPDRFSGSGSGTDFTLKISRVEAEDLGMYYCFQGSHVP

LTFGAGTKLELK

77A VL Nucleotide Sequence in FASTA format
(SEQ ID NO: 124)
GATGTTTTGATGACCCAAAGTCCACTCTCCCTGCCTGTCAGTCTTGGAGA

TCAAGCCTCCATCTCTTGCAGATCTAGTCAGAACATAGTACATAGTAATG

GTAACACCTATTTAGAATGGTACCTGAAGAAACCAGGCCAGTCTCCAAAG

CTCCTGATCTACAAAGTCTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAATGTATTACTGCTTTCAAGGTTCACATGTTCCG

CTCACGTTCGGAGCTGGGACCAAGCTGGAGCTGAAA

77A VH Amino Acid Sequence in FASTA format
(SEQ ID NO: 112)
EVQLQQSGAELVRPGASVKLSCTASGFNIKDDYMHWVKQRPEQGLEWIGC

IDPENGDTEYASKFQGKATITADTSSNTVYLQLSSLTSEDTAVYYCTTYV

GFGYWGQGTLVTVSA

77A VH Nucleotide Sequence in FASTA format
(SEQ ID NO: 137)
GAGGTTCAGCTGCAGCAGTCTGGGGCTGAGCTTGTGAGGCCAGGGGCCTC

AGTCAAGTTGTCCTGCACAGCTTCTGGCTTTAACATTAAAGACGACTATA

TGCACTGGGTGAAACAGAGGCCTGAACAGGGCCTGGAGTGGATTGGATGT

ATTGATCCTGAGAATGGTGATACTGAATATGCCTCGAAGTTCCAGGGCAA

GGCCACTATAACAGCAGACACATCCTCCAACACAGTCTACCTGCAGCTCA

GCAGCCTGACATCTGAGGACACTGCCGTCTATTACTGTACTACATACGTT

GGATTTGGTTACTGGGGCCAGGGGACTCTGGTCACTGTCTCTGCA

80A SEQUENCES:
80A VL Amino Acid Sequence in FASTA format
(SEQ ID NO: 101)
DIVMTQSPSSLTVTAGEKVTMSCKSNQSLLNSGDQKNYLTWYQQKPGQPP

KLLIYWASTRESGVPDRFTGSGSGTDFTLTISSVQAEDLAIYYCQNDYSY

PLTFGAGTKLELK

80A VL Nucleotide Sequence in FASTA format
(SEQ ID NO: 125)
GACATTGTGATGACACAGTCTCCATCCTCCCTGACTGTGACAGCAGGAGA

GAAGGTCACTATGAGCTGCAAGTCCAATCAGAGTCTGTTAAACAGTGGAG

ATCAAAAGAACTACTTGACCTGGTACCAGCAGAAACCAGGGCAGCCTCCT

AAACTATTGATCTACTGGGCATCCACTAGGGAATCTGGGGTCCCTGATCG

CTTCACAGGCAGTGGATCTGGAACAGATTTCACTCTCACCATCAGCAGTG

TGCAGGCTGAAGACCTGGCAATTTATTACTGTCAGAATGATTATAGTTAT

CCACTCACGTTCGGTGCTGGGACCAAGCTGGAGCTGAAA

80A VH Amino Acid Sequence in FASTA format
(SEQ ID NO: 113)
QVQLKQSGAELVRPGASVKLSCRASGYTFTDFYINWVKQRPGQGLEWIAR

IYPGSDETYYNEKFKDKVTLTAEKSSSTAYMQLSSLTSEDSAVYFCALWF

FDVWGTGTTVTVSS

80A VH Nucleotide Sequence in FASTA format
(SEQ ID NO: 138)
CAGGTCCAACTGAAGCAGTCTGGGGCTGAACTGGTGAGGCCTGGGGCTTC

AGTGAAGCTGTCCTGCAGGGCTTCTGGCTACACTTTCACTGACTTCTACA

TAAACTGGGTGAAGCAGAGGCCTGGACAGGGACTTGAGTGGATTGCAAGG

ATTTATCCTGGAAGTGATGAGACTTACTACAATGAGAAGTTTAAGGACAA

GGTCACACTGACTGCAGAAAAATCCTCCAGCACTGCCTACATGCAGCTCA

GCAGCCTGACATCTGAGGACTCTGCTGTCTATTTCTGTGCCCTCTGGTTC

TTCGATGTCTGGGGCACAGGGACCACGGTCACCGTCTCCTCA

82B SEQUENCES:
82B VL Amino Acid Sequence in FASTA format
(SEQ ID NO: 102)
DVVMTQTPLTLSVTIGQSASISCKSSQSLLDSDGNTYLNWLLQRPGQSPK

RLIYLVSELDSGVPDRFTGSGSGTDFTLKISRVEAEDLGVYYCWQGTHFP

FTFGSGTKLEIK

82B VL Nucleotide Sequence in FASTA format
(SEQ ID NO: 126)
GATGTTGTGATGACCCAGACTCCACTCACTTTGTCGGTTACTATTGGACA

ATCAGCCTCCATCTCTTGCAAGTCAAGTCAGAGCCTCCTAGATAGTGATG

GAAACACATATTTGAATTGGTTGTTACAGAGGCCAGGCCAGTCTCCAAAG

CGCCTAATCTATTTGGTGTCTGAACTGGACTCTGGAGTCCCTGACAGGTT

CACTGGCAGTGGATCAGGGACAGATTTCACACTGAAAATCAGCAGAGTGG

AGGCTGAGGATTTGGGAGTTTATTATTGCTGGCAAGGTACACATTTTCCA

TTCACGTTCGGCTCGGGGACAAAGTTGGAAATAAAA

82B VH Amino Acid Sequence in FASTA format
(SEQ ID NO: 114)
QVQLQQSGAELARPGASVKLSCKASGYTFTSDGITWVKQRTGQGLEWIGQ

IHPRSGNTYYNGKFKGKATLTADRSSSTTYMELRSLTSEDSAVYFCAKTG

TGDYWGQGTTLTVSS

82B VH Nucleotide Sequence in FASTA format
(SEQ ID NO: 139)
CAGGTTCAGCTGCAGCAGTCTGGAGCTGAGTTGGCGAGGCCTGGGGCTTC

AGTGAAGCTGTCCTGCAAGGCTTCGGGCTACACCTTCACAAGCGATGGTA

TTACCTGGGTGAAGCAGAGAACTGGACAGGGCCTTGAGTGGATTGGACAG

ATTCATCCTAGAAGTGGTAATACCTACTACAATGGGAAGTTCAAGGGCAA

GGCCACACTGACTGCAGACAGATCCTCCAGCACAACGTACATGGAACTCC

GCAGCCTGACATCTGAGGACTCTGCGGTCTATTTCTGTGCAAAAACTGGG

ACGGGGGACTACTGGGGCCAAGGCACCACTCTCACAGTCTCCTCA

83B SEQUENCES:
83B VL Amino Acid Sequence in FASTA format
(SEQ ID NO: 103)
EIQMTQSPSSMSASLGDRITITCQATQDIVKNLNWYQQKPGKPPSFLIYY

ATELAEGVPSRFSGSGSGSDYSLTISNLESEDFADYYCLQFYEFPYTFGG

GTKLEIK

83B VL Nucleotide Sequence in FASTA format
(SEQ ID NO: 127)
GAAATCCAGATGACCCAGTCTCCATCCTCTATGTCTGCATCTCTGGGAGA

CAGAATAACCATCACTTGCCAGGCAACTCAAGACATTGTTAAGAATTTAA

ACTGGTATCAGCAGAAACCAGGGAAACCCCCTTCATTCCTGATCTATTAT

GCAACTGAACTGGCAGAAGGGGTCCCATCAAGGTTCAGTGGCAGTGGGTC

TGGGTCAGACTATTCTCTGACAATCAGCAACCTGGAGTCTGAAGATTTTG

CAGACTATTACTGTCTACAGTTTTATGAATTTCCGTACACGTTCGGAGGG

GGGACCAAGCTGGAAATAAAA

83B VH Amino Acid Sequence in FASTA format
(SEQ ID NO: 115)
EVQLQQSGPELVKPGASVKMSCKASGYTFTDYNMHWVKQSHGKSLEWIGY

INPNNGGTSYNQKFKDKATLTVNKSSSTAFMELRSLASEDSAVYYCARSD

WEDCWGQGTTLTVSS

82B VH Nucleotide Sequence in FASTA format
(SEQ ID NO: 140)
GAGGTCCAGCTGCAACAGTCTGGACCTGAGCTGGTGAAGCCTGGGGCTTC

AGTGAAGATGTCCTGCAAGGCTTCTGGATACACATTCACTGACTACAACA

TGCACTGGGTGAAGCAGAGCCATGGAAAGAGCCTTGAGTGGATTGGATAT

ATTAACCCTAACAATGGTGGTACTAGCTACAACCAGAAGTTCAAGGACAA

GGCCACATTGACTGTAAACAAGTCCTCCAGCACAGCCTTCATGGAGCTCC

GCAGCCTGGCATCGGAGGATTCTGCAGTCTATTACTGTGCAAGGTCTGAC

TGGGAAGACTGCTGGGGCCAAGGCACCACTCTCACAGTCTCCTCA

92A SEQUENCES:
92A VL Amino Acid Sequence in FASTA format
(SEQ ID NO: 104)
QIVLTQSPAIMSASLGEEITLICSASSSVSYMHWYQQKSGTSPKLLIYRT

SNLASGVPSRFSGSGSGTFYSLTISSVEAEDAADYYCHQWSSWTFGGGTQ

LEIK

92A VL Nucleotide Sequence in FASTA format
(SEQ ID NO: 128)
CAAATTGTTCTCACCCAGTCTCCAGCAATCATGTCTGCATCTCTAGGGGA
GGAGATCACCCTAATTTGCAGTGCCAGCTCGAGTGTAAGTTACATGCACT
GGTACCAGCAGAAGTCAGGCACTTCTCCCAAACTCTTGATTTATCGCACA
TCCAACCTGGCTTCTGGAGTCCCTTCTCGCTTCAGTGGCAGTGGGTCTGG
GACCTTTTATTCTCTTACAATCAGCAGTGTGGAGGCTGAAGATGCTGCCG
ATTATTACTGCCATCAGTGGAGTAGTTGGACGTTCGGTGGAGGCACCCAG
CTGGAAATCAAA 92A VH Amino Acid Sequence in FASTA format
(SEQ ID NO: 116)
DVQLQESGPGLVKFSQSLSLTCSVTGYSITSGYYWNWIRQFPGNKLEWMG
YIRHDGSNNYNPSLKNRISITRDTSKNQFFLKLNSVITEDTATYYCVREI
YDGSSGYFDVWGTGTTVTVSS 92A VH Nucleotide Sequence in FASTA format
(SEQ ID NO: 141)
GATGTACAGCTTCAGGAGTCAGGACCTGGCCTCGTGAAATTTTCTCAGTC
TCTGTCTCTCACCTGCTCTGTCACTGGCTACTCCATCACCAGTGGTTATT
ACTGGAACTGGATCCGGCAGTTTCCAGGAAACAAACTGGAATGGATGGGC
TACATAAGACACGATGGTAGCAATAACTACAACCCGTCTCTCAAAAATCG
AATCTCCATCACTCGTGACACATCTAAGAACCAGTTTTTCCTGAAGTTGA
ATTCTGTGATTACTGAGGACACAGCCACATATTACTGTGTAAGAGAGATC
TATGATGGTTCCTCCGGGTACTTCGATGTCTGGGGCACAGGGACCACGGT
CACCGTCTCCTCA 93B SEQUENCES:
93B VL Amino Acid Sequence in FASTA format
(SEQ ID NO: 105)
DIVMTQSPSSLTVTAGEKVTMSCKSSQSLLNSGNQKNYLTWYQQKPGQPP
KLLIYWASTRESGVPDRFTGSGSGTDFTLTISNVQPEDLAVYYCQNDYSF
PFTFGSGTELEMK 93B VL Nucleotide Sequence in FASTA format
(SEQ ID NO: 129)
GACATTGTGATGACACAGTCTCCATCCTCCCTGACTGTGACAGCAGGAGA
GAAGGTCACTATGAGCTGCAAGTCCAGTCAGAGTCTGTTAAACAGTGGAA
ATCAAAAGAATTACTTGACCTGGTACCAGCAGAAACCAGGACAGCCTCCT
AAACTGTTGATCTACTGGGCATCCACTAGGGAATCTGGGGTCCCTGATCG
CTTCACAGGCAGTGGATCTGGAACAGATTTCACTCTCACCATTAGCAATG
TGCAGCCTGAAGACCTGGCAGTTTATTACTGTCAGAATGATTATAGTTTT
CCATTCACGTTCGGCTCGGGGACAGAGTTGGAAATGAAA 93B VH Amino Acid Sequence in FASTA format
(SEQ ID NO: 117)
QVQLKQSGAELVRPGASVKLSCKASGYTFTDYYINWVKQRPGQGLEWIAR
IYPGNGNTDYNEKFKDKATLTAEKSSTTAYIQLSSLTSEDSAVYFCCLWY
FDVWGTGTTVTVSS 93B VH Nucleotide Sequence in FASTA format
(SEQ ID NO: 142)
CAGGTCCAGCTGAAGCAGTCTGGGGCTGAACTGGTGAGGCCTGGGGCTTC
AGTGAAGCTGTCCTGCAAGGCTTCTGGCTACACTTTCACTGACTACTATA TAAACTGGGTGAAGCAGAGGCCTGGACAGGGACTTGAGTGGATTGCAAGG
ATTTATCCTGGAAATGGTAATACTGACTACAATGAGAAGTTCAAGGACAA
GGCCACACTGACTGCAGAAAAATCCTCCACCACTGCCTACATACAACTCA
GCAGTCTGACATCTGAGGACTCTGCTGTCTATTTCTGTGCCTCTGGTAC
TTCGATGTCTGGGGCACAGGAACCACGGTCACCGTCTCCTCA 99B SEQUENCES:
99B VL Amino Acid Sequence in FASTA format
(SEQ ID NO: 106)
DVVMTQTPLTLSVTIGQPASISCKSSQSLLDSDGKTYLNWLLQRPGQSPK
RLIYLVSKLDSGVPDRFTGSGSGTDFTLKISRVEAEDLGIYYCWQGTHFP
FTFGSGTKLEIK 99B VL Nucleotide Sequence in FASTA format
(SEQ ID NO: 130)
GATGTTGTGATGACCCAGACTCCACTCACTTTGTCGGTTACCATTGGACA
ACCAGCCTCCATCTCTTGCAAGTCAAGTCAGAGCCTCTTAGATAGTGATG
GAAAGACATATTTGAATTGGTTGTTACAGAGGCCAGGCCAGTCTCCAAAG
CGCCTAATCTATCTGGTGTCTAAACTGGACTCTGGAGTCCCTGACAGGTT
CACTGGCAGTGGATCAGGGACAGATTTCACACTGAAAATCAGCAGAGTGG
AGGCTGAGGATTTGGGAATTTATTATTGCTGGCAAGGTACACATTTTCCA
TTCACGTTCGGCTCGGGGACAAAGTTGGAAATAAAA 99B VH Amino Acid Sequence in FASTA format
(SEQ ID NO: 118)
QVQLQQSGAELARPGASVKLSCKASGYTFTSDGITWLKQRTGQGLEWIGQ
IHPRSGNTYYNEKFKGKATLTADKSSSTAYMELRSLTSEDSAVYFCAKTG
TGDYWGQGTTLTVSS 99B VH Nucleotide Sequence in FASTA format
(SEQ ID NO: 143)
CAGGTTCAGCTGCAGCAGTCTGGAGCTGAGCTGGCGAGGCCTGGGGCTTC
AGTGAAGCTGTCCTGCAAGGCTTCGGGCTACACCTTCACAAGCGACGGTA
TAACCTGGCTGAAACAGAGAACTGGACAGGGCCTTGAGTGGATTGGACAG
ATTCATCCTAGAAGTGGTAATACCTACTACAATGAGAAGTTCAAGGGCAA
GGCCACACTGACTGCAGACAAATCCTCCAGCACAGCGTACATGGAACTCC
GCAGCCTGACATCTGAGGACTCTGCGGTCTATTTCTGTGCAAAAACTGGG
ACGGGGGACTACTGGGGCCAAGGCACCACTCTCACAGTCTCCTCA 104B SEQUENCES:
104B VL Amino Acid Sequence in FASTA format
(SEQ ID NO: 107)
DVVMTQTPLTLSVTIGQPASISCKSSLSLLDSDGKTYLNWLLQRPGQSPK
RLIYLVSKLDSGVPDRFTGSGSGTDFTLKIIRVEAEDLGIYYCWQGTHFP
FTFGSGTKLEVK 104B VL Nucleotide Sequence in FASTA format
(SEQ ID NO: 131)
GATGTTGTGATGACCCAGACTCCACTCACTTTGTCGGTTACCATTGGACA
ACCAGCCTCCATCTCTTGCAAGTCAAGTCTGAGCCTCTTAGATAGTGATG
GAAAGACATATTTGAATTGGTTGTTACAGAGGCCAGGCCAGTCTCCAAAG
CGCCTAATCTATCTGGTGTCTAAACTGGACTCTGGAGTCCCTGACAGGTT
CACTGGCAGTGGATCAGGGACAGATTTCACACTGAAAATCATCAGAGTGG -continued
AGGCTGAGGATTTGGGAATTTATTATTGCTGGCAAGGTACACATTTTCCA

TTCACGTTCGGCTCGGGGACAAAGTTGGAAGTAAAA

104B VH Amino Acid Sequence in FASTA format
(SEQ ID NO: 119)
QVQLQQSGPELARPGASVKLSCKASGYTFTSYGISWVKQRTGQGLEWIGQ

IHPRSGNTYYNENFKGKATLTAAKSSSTAYLELRSLTSEDSAVYFCAREG

GPDYWGQGTTLTVSS

104B VH Nucleotide Sequence in FASTA format
(SEQ ID NO: 144)
CAGGTTCAGCTGCAGCAGTCTGGGCCTGAGCTGGCGAGGCCTGGGGCCTC

AGTGAAGCTGTCCTGCAAGGCTTCTGGCTACACCTTCACAAGCTATGGTA

TAAGCTGGGTGAAGCAAAGAACTGGACAGGGCCTTGAGTGGATTGGACAG

ATTCATCCTAGAAGTGGTAATACTTACTACAATGAACTTCAAGGGCAA

GGCCACACTGACTGCAGCCAAATCCTCCAGCACAGCGTACCTGGAGCTCC

GCAGCCTGACATCTGAGGACTCTGCGGTCTATTTCTGTGCAAGAGAGGGG

GGTCCCGACTACTGGGGCCAAGGCACCACTCTCACAGTCTCCTCA

105A SEQUENCES:
105A VL Amino Acid Sequence in FASTA format
(SEQ ID NO: 99)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

LTFGAGTKLELK

105A VL Nucleotide Sequence in FASTA format
(SEQ ID NO: 132)
GATGTTTTGATGACCCAAACTCCACTCTCCCTGCCTGTCAGTCTTGGAGA

TCAAGCCTCCATCTCTTGCAGATCTAGTCAGAGTATTGTACATAGTAATG

GAAACACCTATTTAGAATGGTACCTACAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

CTCACGTTCGGTGCTGGGACCAAGCTGGAGCTGAAA

105A VH Amino Acid Sequence in FASTA format
(SEQ ID NO: 111)
EVQLQQSGAELVRPGASVKLSCTASGFNIKDDYMHWVKQRPEQGLEWIGC

IDPENGDIEYASRFQGKATMTADTSSNTAYLQLTSLTSADTAVYYCTTYV

GFGYWGQGTLVTVSA

105A VH Nucleotide Sequence in FASTA format
(SEQ ID NO: 145)
GAGGTTCAGCTGCAGCAGTCTGGGGCTGAGCTTGTGAGGCCAGGGGCCTC

AGTCAAGTTGTCCTGCACAGCTTCTGGCTTTAACATTAAAGACGACTATA

TGCACTGGGTGAAACAGAGGCCTGAACAGGGCCTGGAGTGGATTGGATGC

ATTGATCCTGAGAATGGTGATATTGAATATGCCTCGAGGTTCCAGGGCAA

GGCCACTATGACAGCAGACACATCCTCCAACACAGCCTACCTGCAGCTCA

CCAGCCTGACATCTGCGGACACTGCCGTCTATTACTGTACTACATACGTT

GGATTTGGTTACTGGGGCCAAGGGACTCTGGTCACTGTCTCTGCA

Example 2: Anti-huS15 Antibodies Bind to Cells
Expressing Human S15 or Mouse S15

Materials and Methods

Human 293T and mouse CRC MC38 tumor cell lines were transduced with lentivector carrying human Siglec 15 or mouse Siglec 15. Cells were sorted to establish human S15 and mouse S15 stable cell lines. 293T.hS15 and MC38.mS15 stable cells were resuspended in FACS buffer and Fc receptors were blocked prior to incubation with purified Siglec-15 mAbs. 1E05 cells in 100 µL FACS buffer were aliquoted to separate tubes and 1 µg of purified mAb was added. Cells were incubated at 4 degrees C. for 30 minutes, then washed twice with excess FACS buffer. Cells were resuspended in 100 µL FACS buffer and 0.005 µg of anti-mouse IgG-PE secondary antibody was added to samples, incubated for 30 minutes and washed twice with excess FACS buffer. Cells were fixed in fixation buffer and subsequently analyzed by flow cytometry.

Figure 4A:
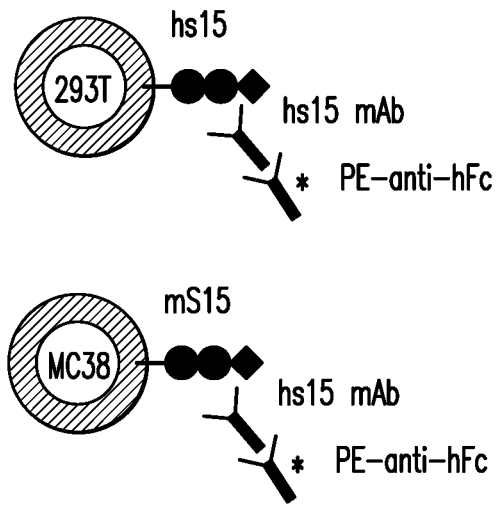
FIG. 4A is a diagram of an assay for measuring direct binding of anti-Siglec-15 antibodies to human or mouse Siglec-15-expressing cells.

The assay is illustrated in FIG. 4A.

Results

Figure 4B:
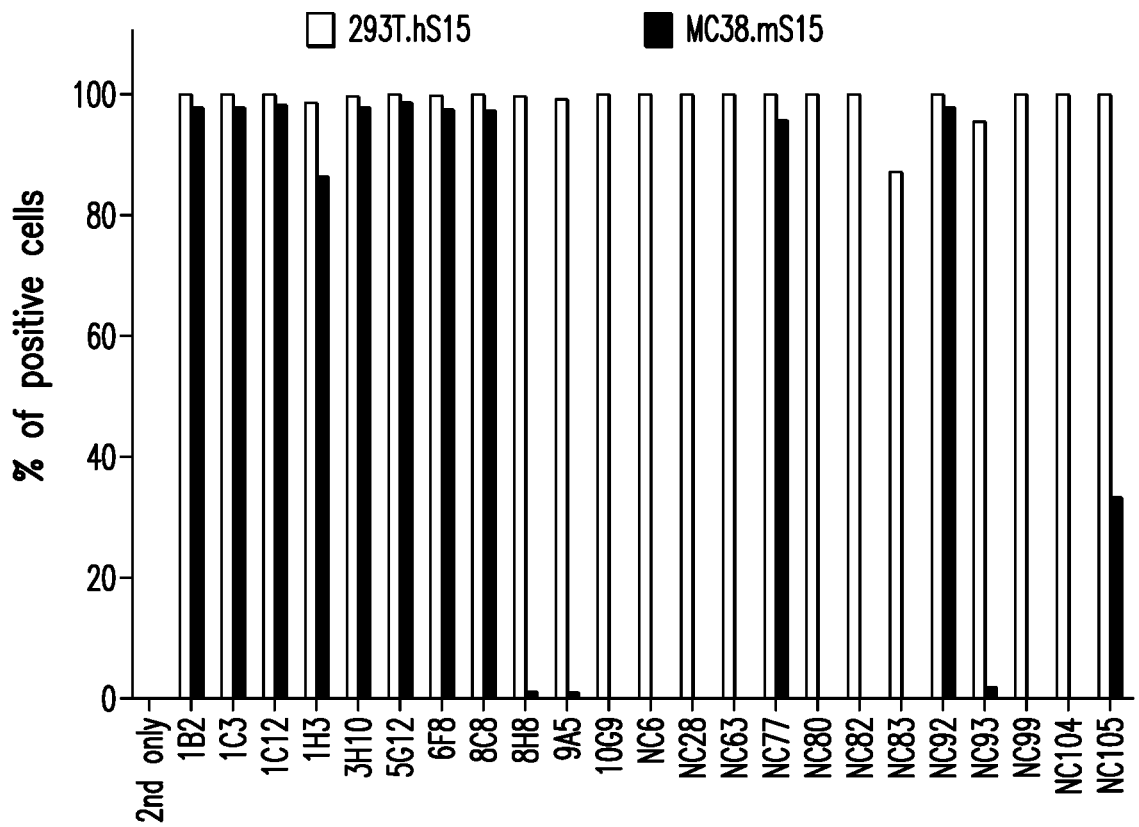
FIG. 4B (1B2, 1C3, 1C12, 1H3, 3H10, 5G12, 6F8, 8C8, 8H8, 9A5, and 10G9) and FIG. 8C (6A (NC6), 28A (NC28), 63A (NC63), 77A (NC77), 80A (NC80), 82B (NC82), 83B (NC83), 92A (NC92), 93B (NC93), 99B (NC99), 104B (NC104), and 105A (NC105)) are bar graphs showing binding of anti-Siglec-15 antibodies (% positive cells) to Siglec-15-expressing cells in the assay illustrated in FIG. 4A.
Figure 4C:
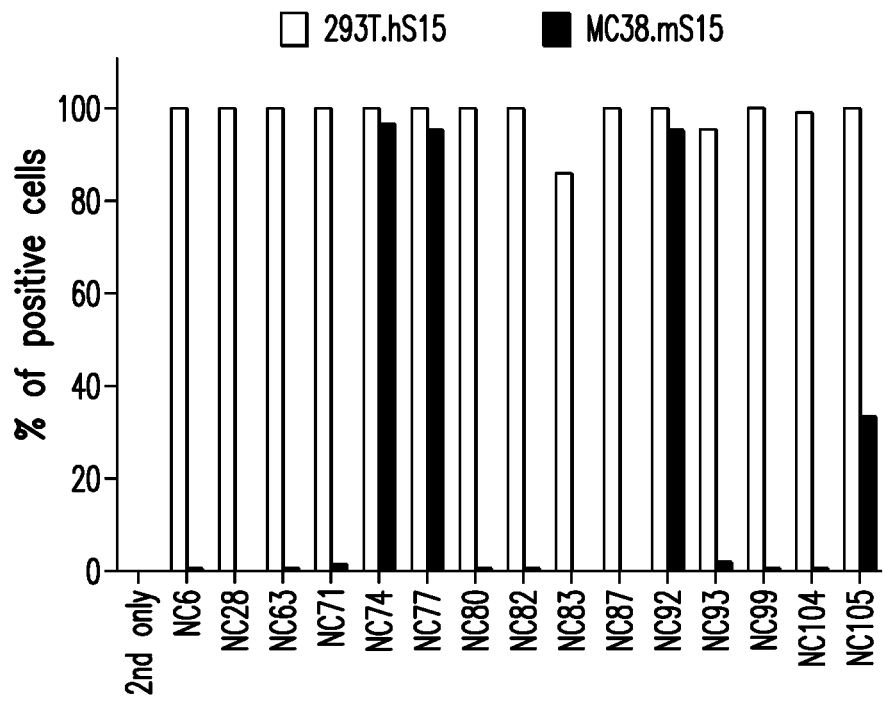
FIG. 4C is a bar graph showing binding of anti-Siglec-15 antibodies 6A (NC6), 28A (NC28), 63A (NC63), 71A (NC71), NC74, 77A (NC77), 80A (NC80), 82B (NC82), 83B (NC83), NC87, 92A (NC92), 93B (NC93), 99B (NC99), 104B (NC104), 105A (NC105) (% positive cells) to formalin-fixed Siglec-15-expressing cells.

Anti-huS15 antibodies including 1B2, 1C3, 1C12, 1H3, 3H10, 5G12, 6F8, 8C8, 8H8, 9A5, 10G9 (FIG. 4B), and 6A (NC6), 28A (NC28), 63A (NC63), 71A (NC71), NC74, 77A (NC77), 80A (NC80), 82B (NC82), 83B (NC83), NC87, 92A (NC92), 93B (NC93), 99B (NC99), 104B (NC104), 105A (NC105) (FIG. 4C) were tested for binding to cells expressing human S15 or mouse S15. The results are illustrated in FIGS. 4B-4C.

Figure 4D:
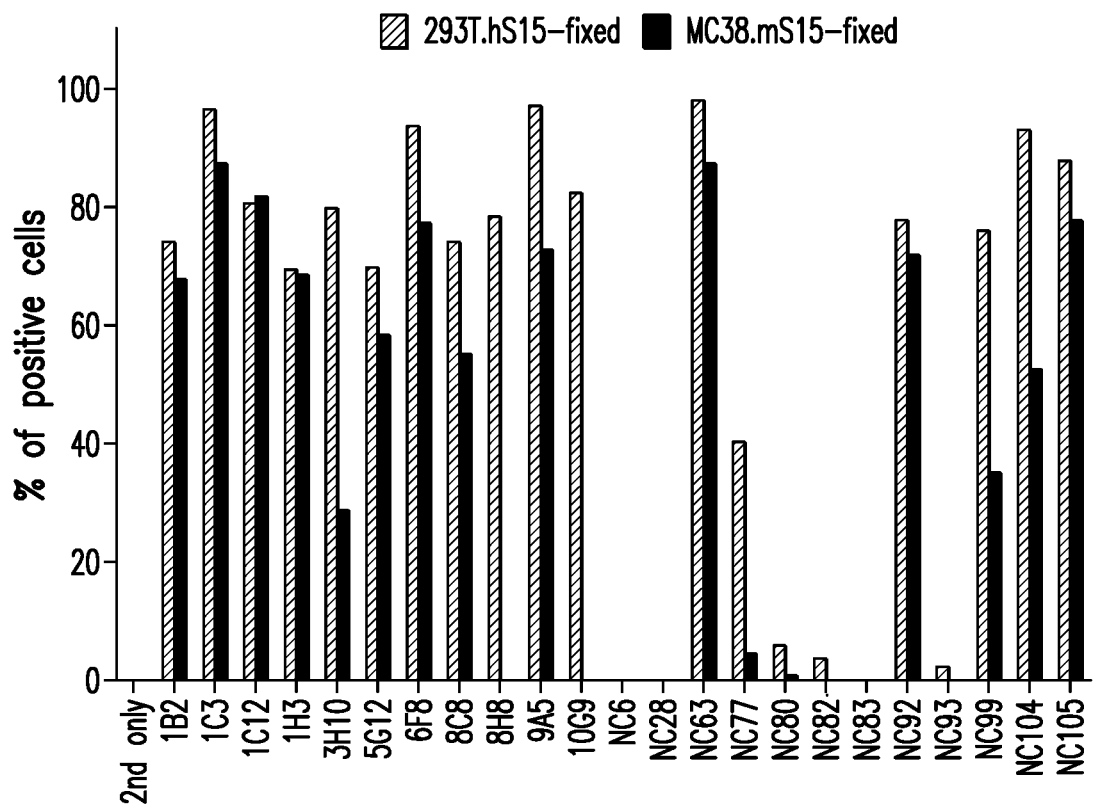
FIG. 4D is a bar graph showing binding of anti-Siglec-15 antibodies (1B2, 1C3, 1C12, 1H3, 3H10, 5G12, 6F8, 8C8, 8H8, 9A5, 10G9, 6A (NC6), 28A (NC28), 63A (NC63), 77A (NC77), 80A (NC80), 82B (NC82), 83B (NC83), 92A (NC92), 93B (NC93), 99B (NC99), 104B (NC104), and 105A (NC105)) (% positive cells) to formalin-fixed Siglec-15-expressing cells.

Anti-huS15 antibodies including 1B2, 1C3, 1C12, 1H3, 3H10, 5G12, 6F8, 8C8, 8H8, 9A5, 10G9, and 6A (NC6), 28A (NC28), 63A (NC63), 77A (NC77), 80A (NC80), 82B (NC82), 83B (NC83), 92A (NC92), 93B (NC93), 99B (NC99), 104B (NC104), or 105A (NC105), were also tested for binding to formalin-fixed cells. The results are shown in FIG. 4D.

Example 3: Purified Antibodies Bind to Mouse and Human Siglec-15

Materials and Methods

S15-TM transiently transfected 293T cells (Operetta)
S15-TM transiently transfected K562 cells (FACS)

293T cells were transiently transfected with murine Siglec-15 plasmid DNA using the Lipofectamine system, and K562 cells were transfected with human Siglec-15 plasmid DNA by electroporation. 1e5 transfected cells in 100 ul of FACS buffer (PBS containing 0.5% serum) were aliquoted to separate tubes and 1 ug of purified mAb was added. Cells were incubated at 4 degrees C. for 30 minutes, then washed twice with excess FACS buffer. Cells were resuspended in 100 ul FACS buffer and 0.005 ug of anti-mouse IgG-PE secondary antibody was added to samples, incubated for 30 minutes and washed twice with excess FACS buffer. Cells were fixed in fixation buffer (2% formaldehyde in PBS) and subsequently analyzed by flow cytometry.

U87 cells were resuspended in FACS buffer and Fc receptors were blocked prior to incubation with purified Siglec-15 mAbs. 1e5 cells in 100 ul FACS buffer were aliquoted to separate tubes and 1 ug of purified mAb was added. Cells were incubated at 4 degrees C. for 30 minutes, then washed twice with excess FACS buffer. Cells were resuspended in 100 ul FACS buffer and 0.005 ug of anti-mouse IgG-PE secondary antibody was added to samples, incubated for 30 minutes and washed twice with excess FACS buffer. Cells were fixed in fixation buffer and subsequently analyzed by flow cytometry.

Results

Figure 5A:
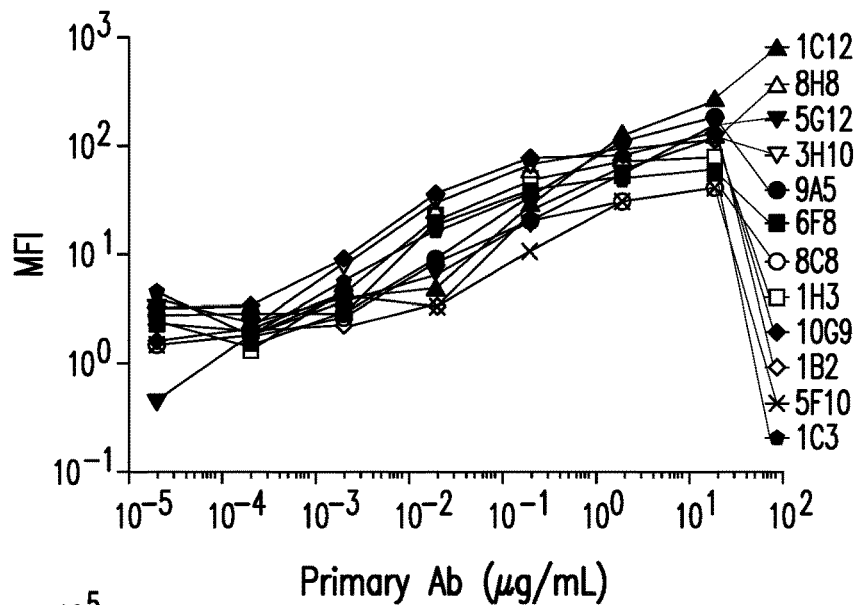
FIGS. 5A-5B are line graphs showing purified 1C12, 8H8, 5G12, 3H10, 9A5, 6F8, 8C8, 1H3, 10G9, 1B2, and 1C3 Ab binding to K562.hS15 cells (9A, background binding subtracted) and 293T.mS15 cells (9B) (Mean Fluorescence Intensity (MFI) as a function of primary antibody concentration (µg/ml)).
Figure 5B:
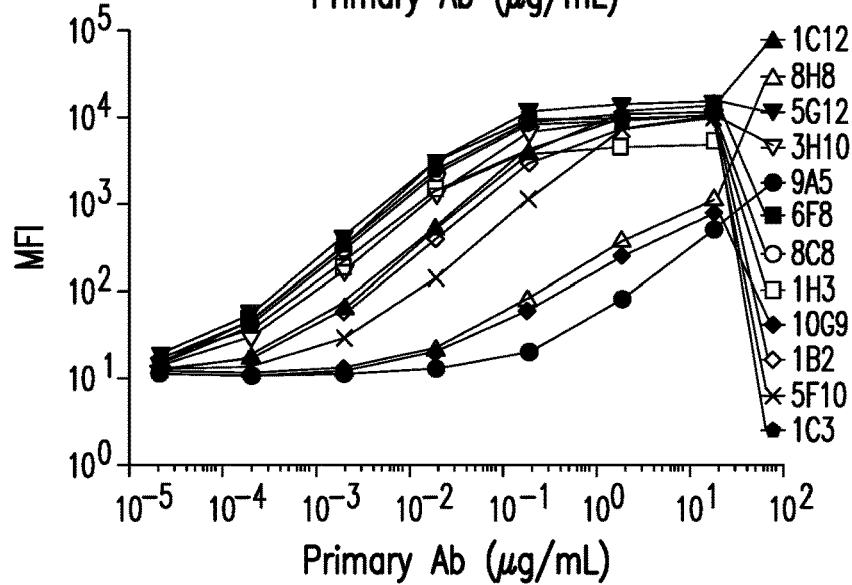
Figure 5C:
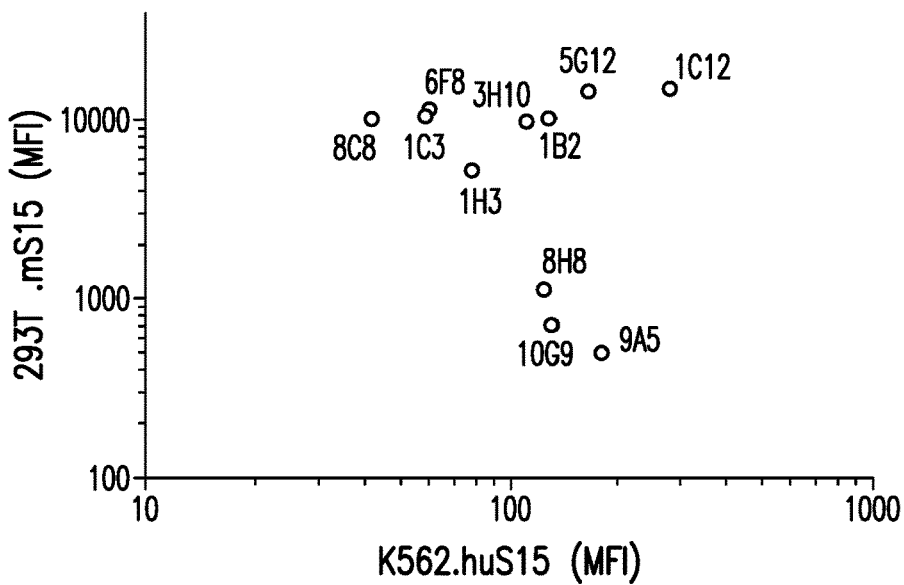
FIG. 5C is a dot plot binding (MFI) of purified 1B2, 1C3, 1H3, 1C12, 3H10, 5G12, 6F8, 8C8, 8H8, 9A5, and 10G9 Ab to K562.hS15 cells relative to 293T.mS15.

Purified antibodies 1B2, 1C3, 1H3, 1C12, 3H10, 5G12, 6F8, 8C8, 8H8, 9A5, and 10G9 were tested for binding to mouse Siglec-15 (mS15) expressed by 293T cells (a highly transfectable derivative of human embryonic kidney 293 cells) and to human Siglec-15 (hS15) expressed by K-562 cells (the pleural effusion of a 53-year-old female with chronic myelogenous leukemia in terminal blast crises). The results are illustrated in FIGS. 5A-5C.

Figure 6A:
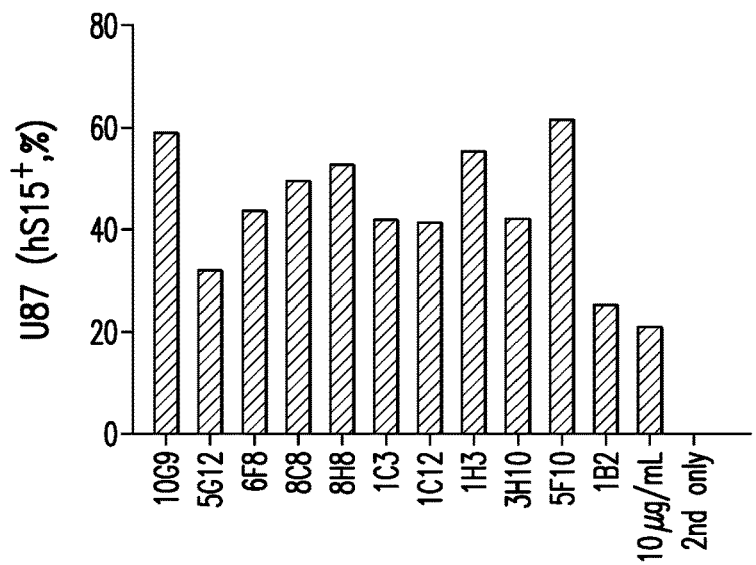
FIG. 6A is a bar graph showing the percentage of hS15+ U87 cells detected by each of 1B2, 1C3, 1H3, 1C12, 3H10, 5G12, 6F8, 8C8, 8H8, and 10G9 Ab.
Figure 6B:
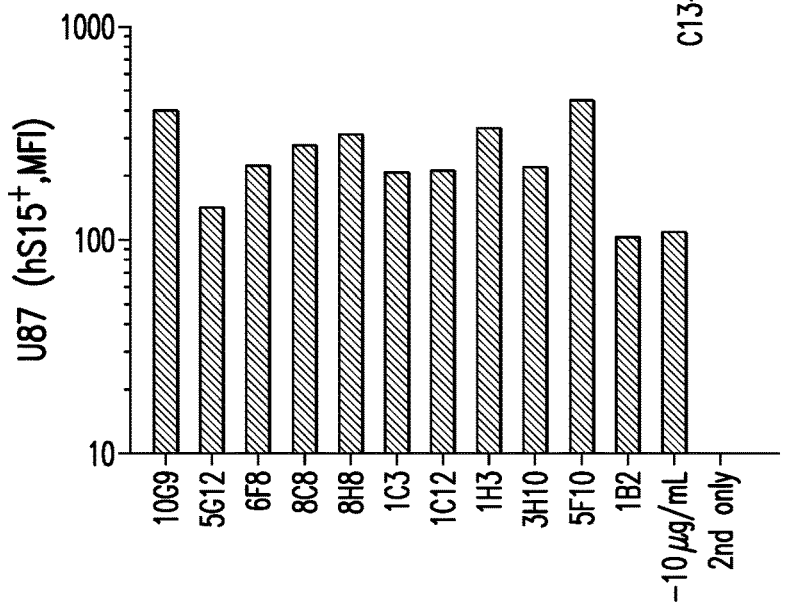
FIG. 6B is a bar graph showing the MFI of hS15+U87 cells detected by each of 1B2, 1C3, 1H3, 1C12, 3H10, 5G12, 6F8, 8C8, 8H8, and 10G9 Ab.
Figure 6C:
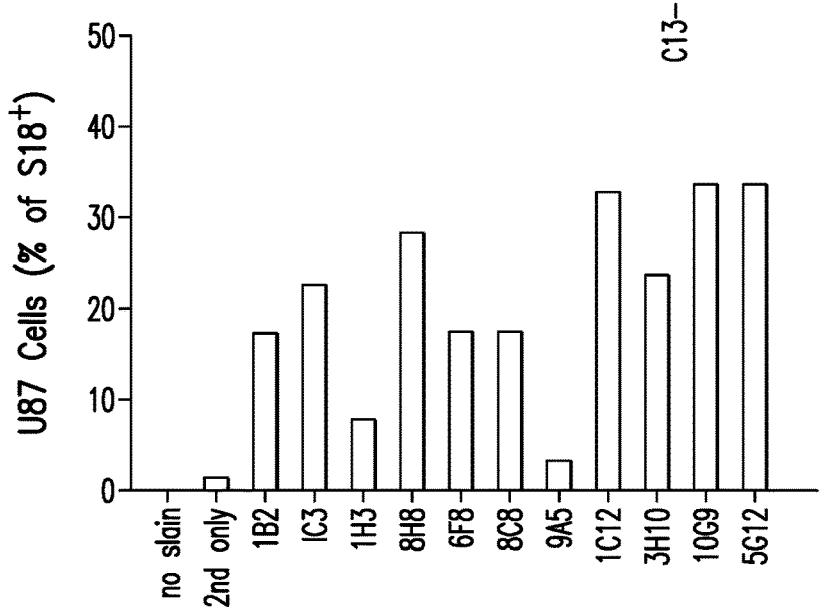
FIG. 6C is a bar graph showing the percent of S15+U87 cells detected by each of 1B2, 1C3, 1H3, 1C12, 3H10, 5G12, 6F8, 8C8, 8H8, 9A5, and 10G9 Ab.

Purified antibodies 1B2, 1C3, 1H3, 1C12, 3H10, 5G12, 6F8, 8C8, 8H8, 9A5, 10G9, and 5F10 were also tested for binding to human U87 glioma cells, which endogenously express human Siglec-15 (hS15). The results are illustrated in FIGS. 6A-6C, which show the percentage of hS15+ cells (FIGS. 6A and 6C) and mean fluorescence intensity (MFI) (FIG. 6B), respectively for each antibody.

Example 4: Anti-Siglec-15 Antibodies can Block Siglec-15 Function

Materials and Methods

Manufacture of hS15.hG1

A monomer S15 fusion protein including a full S15 extracellular domain fused to IgG backbone was prepared for affinity and competition analyses. A thrombin cleavable hS15.hFc cDNA was subcloned into pEE17.4 Fragmented fusion proteins are seen in transiently transfected CHO cells but not in 293 cells at 37° C. Intact fusion protein is expressed more efficiently at 31° C. The fusion protein has the sequence:

(SEQ ID NO:193)
MEWSWVFLFFLSVTTGVHS*FVRTKIDTTENLLNTEVHSSPAQRWSMQVPPEVS*

*AEAGDAAVLPCTFTHPHRHYDGPLTAIWRAGEPYAGPQVFRCAAARGSELCQT*

*ALSLHGRFRLLGNPRRNDLSLRVERLALADDRRYFCRVEFAGDVHDRYESRHG*

*VRLHVTAAPRIVNISVLPSPAHAFRALCTAEGEPPPALAWSGPALGNSLAAVR*

*SPREGHGHLVTAELPALTHDGRYTCTAANSLGRSEASVYLFRFHGASG*DKTHT

CPPCPAPEFEGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAS

IEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYT

QKSLSLSPG.

A mature fusion protein, with the signal sequence cleaved, is:

(SEQ ID NO:194)
*FVRTKIDTTENLLNTEVHSSPAQRWSMQVPPEVSAEAGDAAVLPCTFTHPHRH*

*YDGPLTAIWRAGEPYAGPQVFRCAAARGSELCQTALSLHGRFRLLGNPRRNDL*

*SLRVERLALADDRRYFCRVEFAGDVHDRYESRHGVRLHVTAAPRIVNISVLPS*

*PAHAFRALCTAEGEPPPALAWSGPALGNSLAAVRSPREGHGHLVTAELPALTH*

*DGRYTCTAANSLGRSEASVYLFRFHGASG*DKTHTCPPCPAPEFEGGPSVFLFP

PKPKDTLMISRTPEVTCVVVDVSHEDPEVKFNWYVDGVEVHNAKTKPREEQYN

STYRVVSVLHQDWLNGKEYKCKVSNKALPASIEKTISKAKGQPREPQVYT

LPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPG.

A Murine Leader Sequence is illustrated in underlined. A Siglec-15 extracellular domain (ECD)) is in italics. A Hinge Region is double underlined. The remaining sequence is derived from IgG1 Fc. L234F/L235E/P331S mutations in the IgG1 Fc domain bolded and dotted-underlined.

Blocking Analysis

293T.LRRC4C cells were established by 2 round of Lenti-LRRC4C transduction.

293T.LRRC4C stable cells were resuspended in FACS buffer and Fc receptors were blocked prior to incubation. 1E05 cells in 100 µL FACS buffer were aliquoted to separate tubes and 2 µg of purified mAb was added first, followed by the addition of 0.2 ug of hSiglec-15hFc. Cells were incubated at 4 degrees C. for 30 minutes, then washed twice with excess FACS buffer. Cells were resuspended in 100 µL FACS buffer and 0.005 µg of anti-human IgG-PE secondary antibody was added to samples, incubated for 30 minutes and washed twice with excess FACS buffer. Cells were fixed in fixation buffer and subsequently analyzed by flow cytometry to determine binding of Siglec-15 to LRRC4C.

1 µg/mL of hS15.hG1+100 µL of sup or 33 µg/mL of Cl #3, #1

Figure 7A:
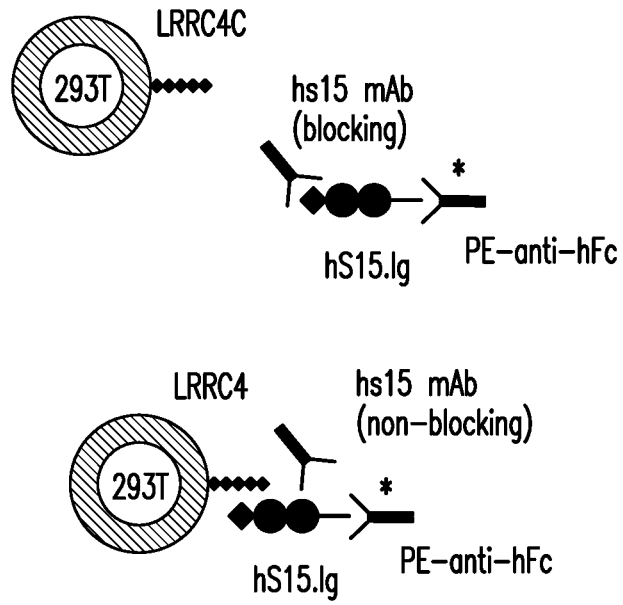
FIG. 7A is a cartoon illustrating an antibody blocking assay. 293T cells expressing ligand LRRC4C are treated with soluble receptor (hS15.hG1) and anti-S15 antibody, and subsequently bound receptor is detected with PE-anti-hFc antibody.
Figure 7B:
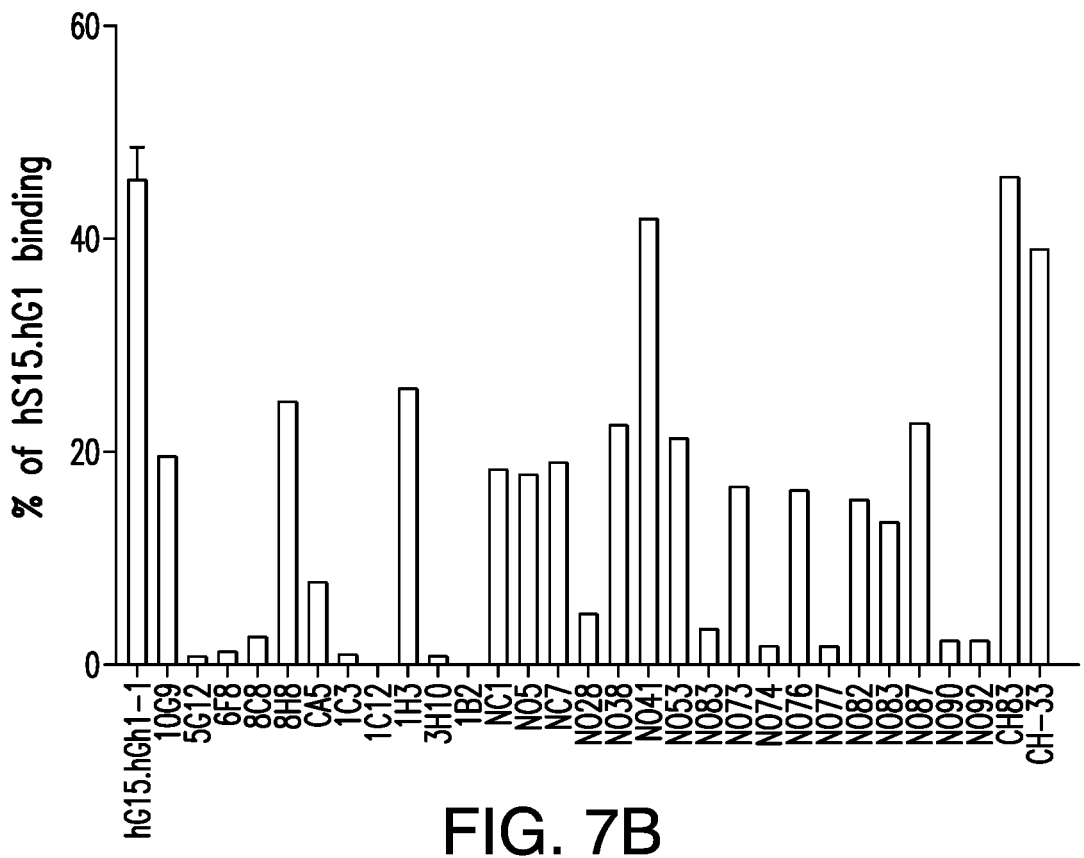
FIG. 7B is a bar graph showing the % of hS15.G1 binding for the hS15.hG1-1 and 10G9, 5G12, 6F8, 8C8, 8H8, 9A5, 1C3, 1C12, 1H3, 3H10, 1B2, NC1, NC5, NC7 28A (NC28), NC38, NC41, NC53, 63A (NC63), NC73, NC74, NC76, 77A (NC77), 82B (NC82), NC84, NC87, NC90, 92A (NC92), CI3-33, CI1-33) antibodies.
Figure 7C:
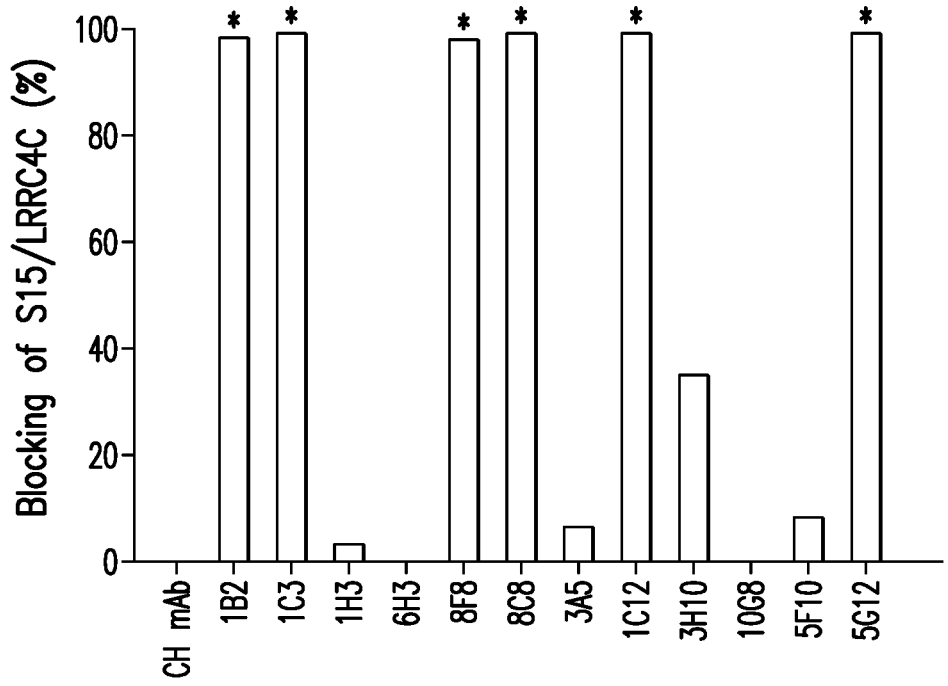
FIG. 7C is a bar graph showing blocking of S15/LRRC4C (%) for Control mAb, and 1B2, 1C3, 1H3, 8H8, 6F8, 8C8, 9A5, 1C12, 3H10, 10G9, and 5G12 antibodies.
Figure 7D:
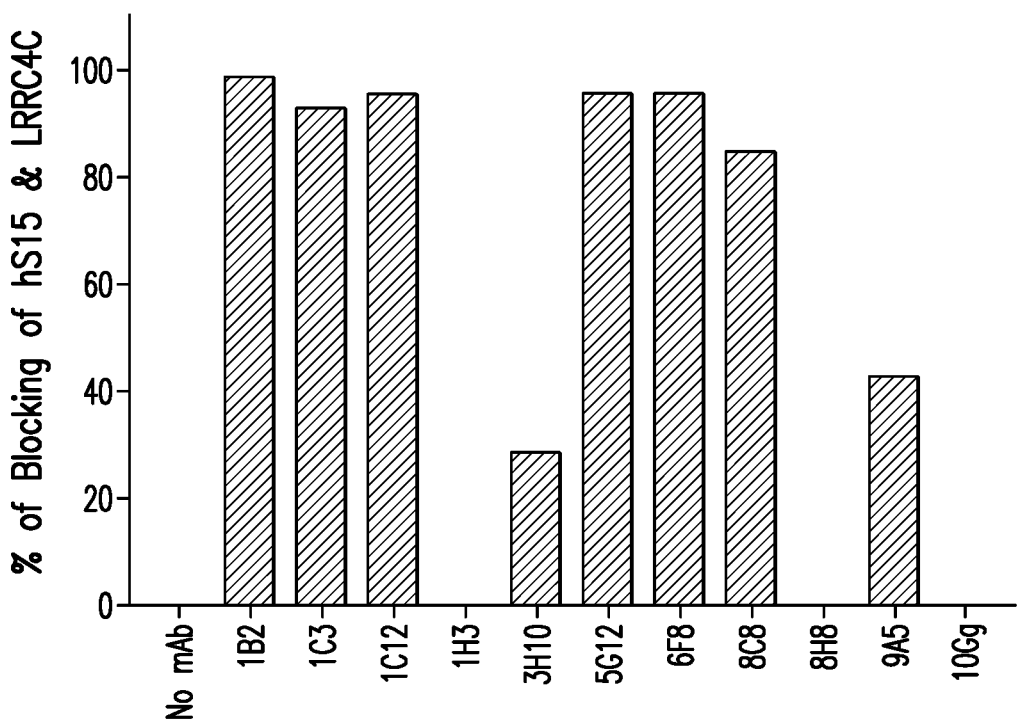
FIG. 7D is a bar graph showing blocking of S15/LRRC4C (%) for 1B2, 1C3, 1C12 1H3, 3H10, 5G12, 6F8, 8C8, 8H8, 9A5, and 10G9.
Figure 7E:
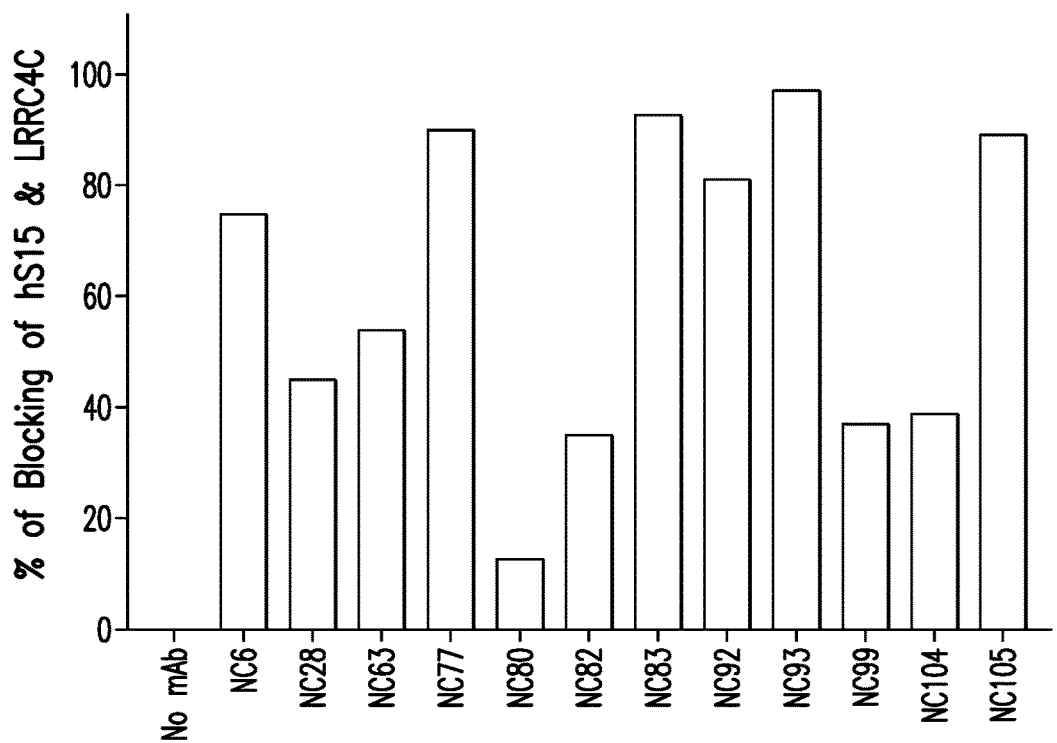
FIG. 7E is a bar graph showing blocking of S15/LRRC4C (%) for 6A (NC6), 28A (NC28), 63A (NC63), 77A (NC77), 80A (NC80), 82B (NC82), 83B (NC83), 92A (NC92), 93B (NC93), 99B (NC99), 104B (NC104), and 105A (NC105)).

The assay is illustrated in FIG. 7A.

Results

The results are illustrated in FIG. 7B-7E.

Full blockers of S15/LRRC4C interaction include, but are not limited to:
    5G12, 6F8, 8C8, 1C3, 1C12, 3H10, 1B2

Partial blockers include, but are not limited to:
    10G9, 8H8, 9A5

Example 5: S15 mAb Reverses hS15.hG1-Mediated Suppression of Human T Cells

Materials and Methods

PBMC Proliferation Assay

Anti-CD3 coated @ 0.05 µg/mL

Total humanPBMCs+/−5 µg/mL hS15.hFc and 12 µg/mL of Siglec-15 mAbs, or controls as indicated Anti-human CD3 (clone OKT3) was coated at 0.03 µg/mL in 100 µL of PBS per well of a 96-well flate-bottom tissue culture plate overnight at 4 degrees C. PBS and unbound CD3 was aspirated immediately prior to addition of components for assay. Total PBMCs from a healthy human donor were labeled with 5 µM CFSE for 10 minutes in RPMI-complete media (containing 10% FBS) at 37 degrees C. and washed 2× prior to resuspension for addition to wells at a concentration of 2.5E05 cells/well. Soluble hSiglec-15hFc or controls was added to wells at a final concentration of 5 µg/ml, while purified Siglec-15 mAbs or controls were added to wells at a final concentration of 12 µg/ml. Plates were incubated in a 37 degree C. $CO_2$ incubator for 72 hrs. Following removal of a small amount of supernatant for cytokine analysis, cells were transferred to a round-bottom plate, Fc receptors were blocked, and cells were stained with CD4 and CD8 fluorescent mAbs for 30 minutes at 4 degrees C. Cells were washed twice in FACS buffer, followed by fixation for analysis by flow cytometry. IFNgamma levels in the conditioned supernatant were assessed by MSD ELISA kit.

Figure 8A:
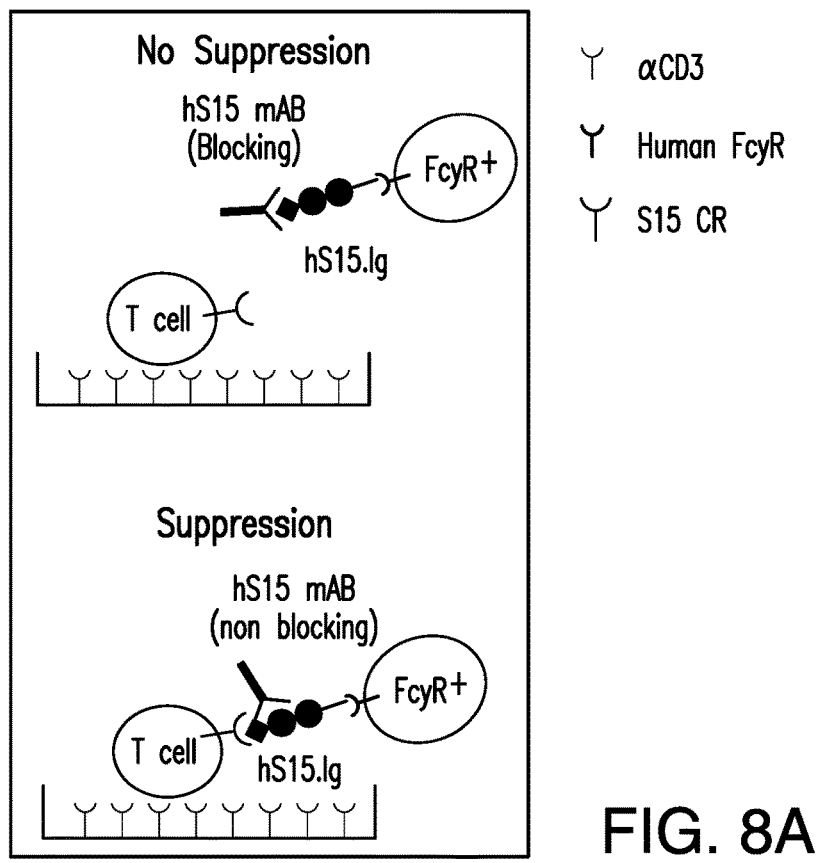
FIG. 8A is a diagram of a T cell suppression assay.
Figure 8B:
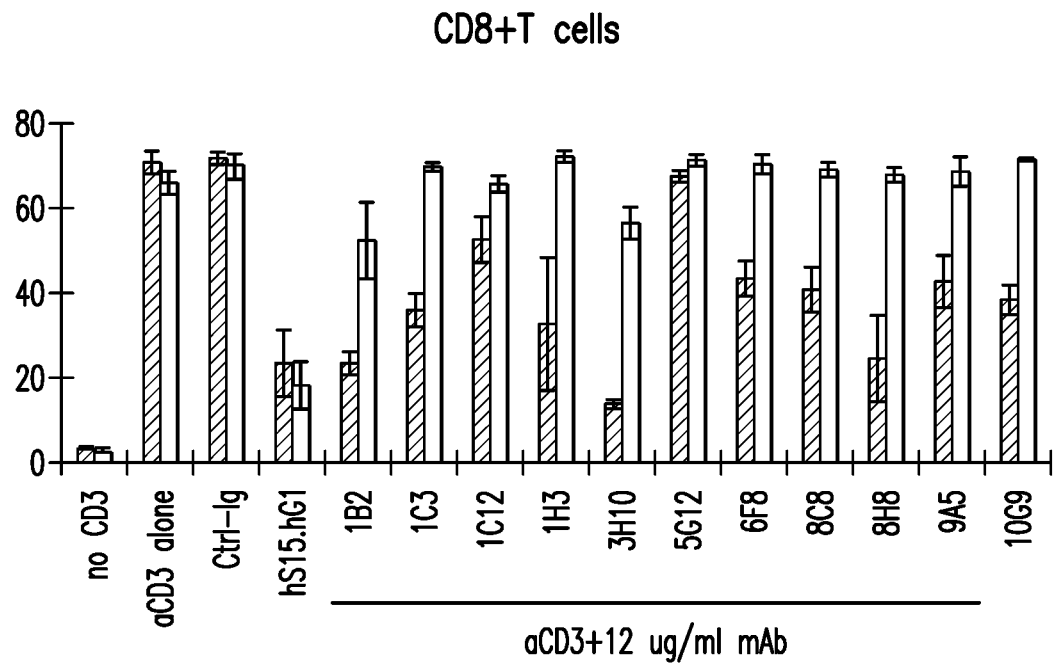
FIGS. 8B and 8C are bar graphs showing S15 mAb reversal of hS15.hG1-mediated suppression of Human T Cells as the % divided of CD8+ T cells (12B) and CD4+ T cells (12C) and comparing assays carried out with (e.g., +hS15.hG1) (left hand bar in each pair) and without (e.g., -hS15.hG1) (right hand bar in each pair) hS15.hG1 for antibodies 1B2, 1C3, 1C12 1H3, 3H10, 5G12, 6F8, 8C8, 8H8, 9A5, and 10G9.
Figure 8C:
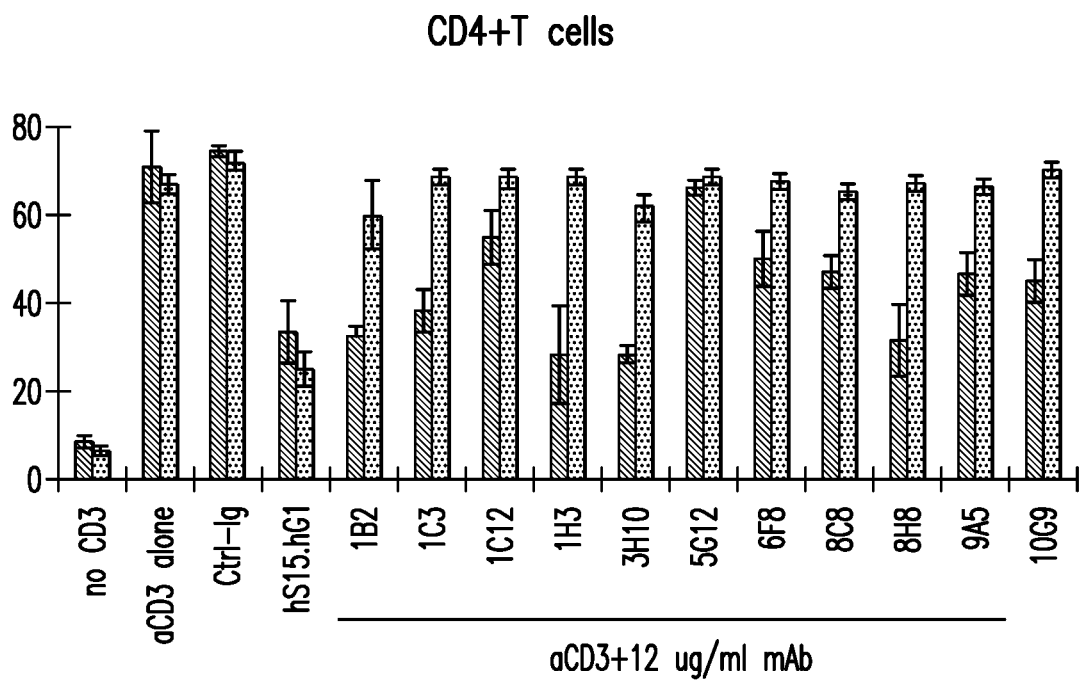
Figure 9A:
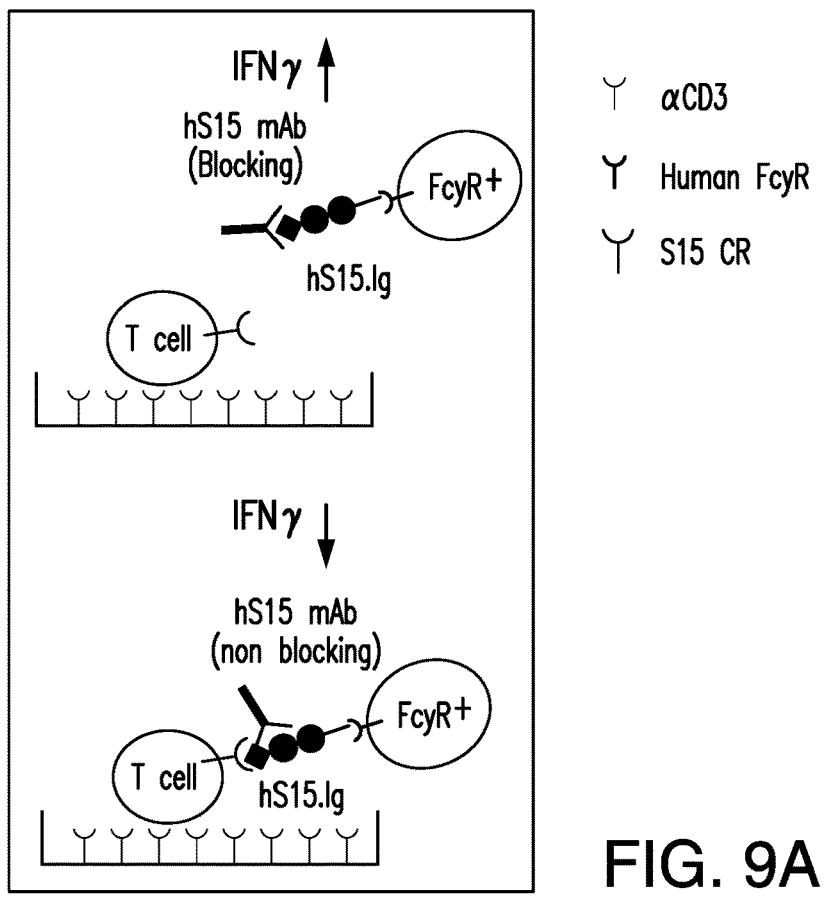
FIG. 9A is a diagram of an assay for measuring alteration in INFγ secretion.

The assays are illustrated in FIGS. 8A and 9A.

Results

Purified antibodies 1B2, 1C3, 1H3, 1C12, 3H10, 5G12, 6F8, 8C8, 8H8, 9A5, and 10G9 were tested in a PBMC proliferation assay (FIGS. 8B, 8C, 8D, and 8E), and 6A (NC6), 28A (NC28), 63A (NC63), 77A (NC77), 80A (NC80), 82B (NC82), 83B (NC83), 92A (NC92), 93B (NC93), 99B (NC99), 104B (NC104), 105A (NC105) (FIGS. 8F and 8G). CD4+ and CD8+ T cells were gated and analyzed for CFSE dilution as a measure of cell division (proliferation). Increased dilution indicated more cell proliferation. The results show that certain S15 mAb can reverse hS15.hG1-mediated suppression of human T cells.

Figure 8H:
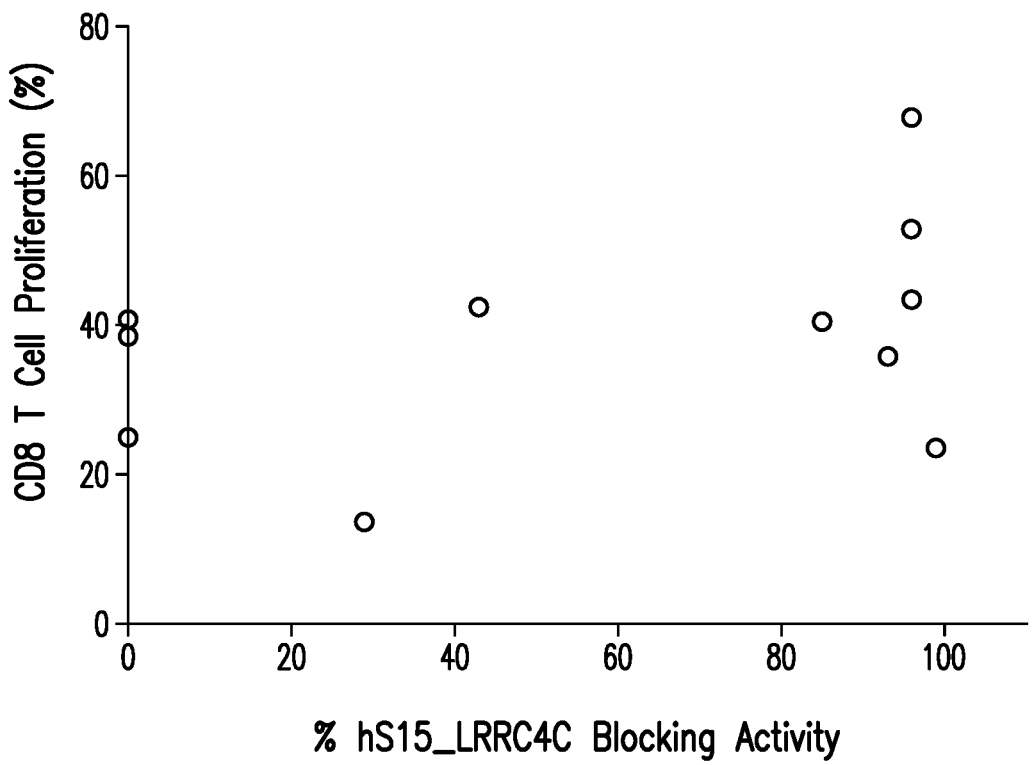
FIGS. 8H and 8I are dot plots showing CD8 T cell proliferation as a function of % hS15_LRRC4C blocking activity.
Figure 8I:
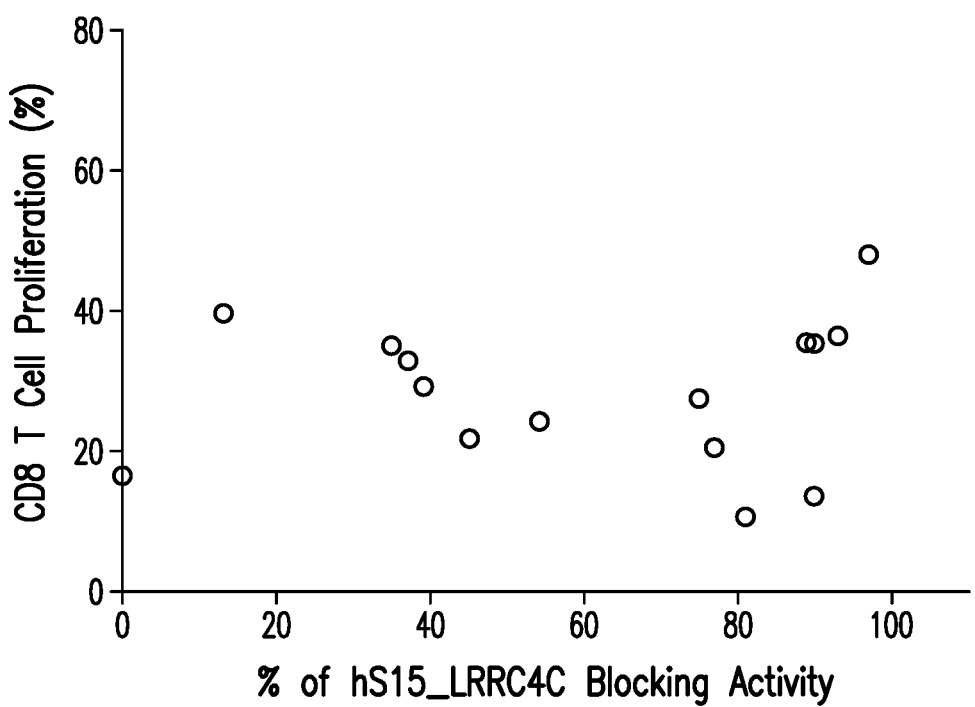

However, blocking of hS15 & LRRC4C interaction does not correlate with enhancement of T-cell function. The results are shown in FIGS. 8H and 8I.

Figure 9B:
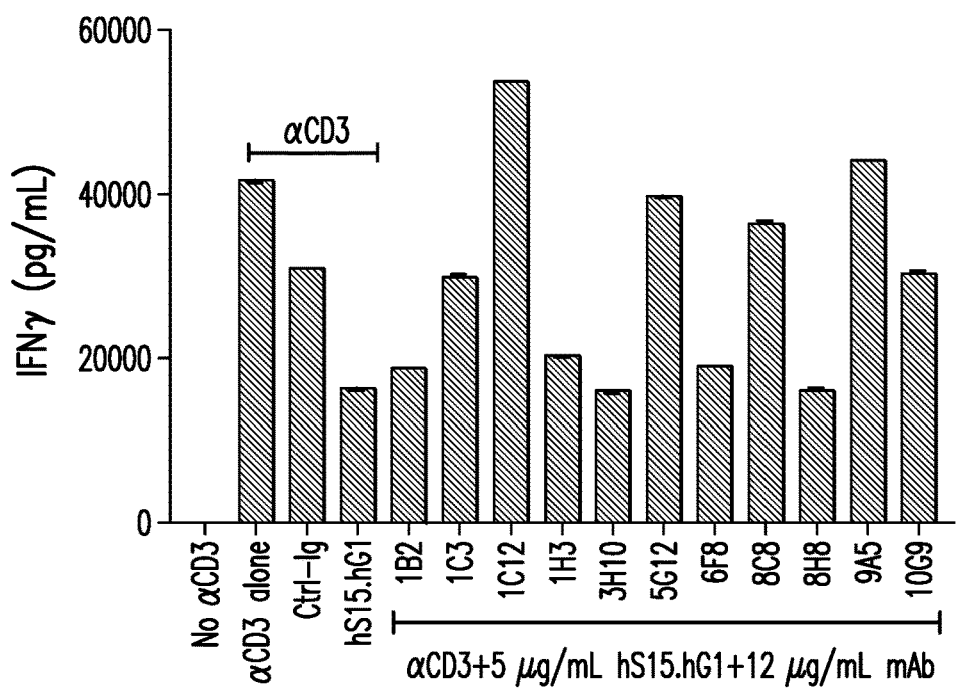
FIG. 9B is a bar graph showing the results of assay diagramed in FIG. 13A, for antibodies 1B2, 1C3, 1C12 1H3, 3H10, 5G12, 6F8, 8C8, 8H8, 9A5, and 10G9.

S15 mAbs were also identified that reverse hS15.hG1-mediated reduction of IFNγ Production in human T cells. The results are illustrated FIG. 9B.

Example 6: S15 mAbs can Block Osteoclast Formation

Materials and Methods

Figure 10:
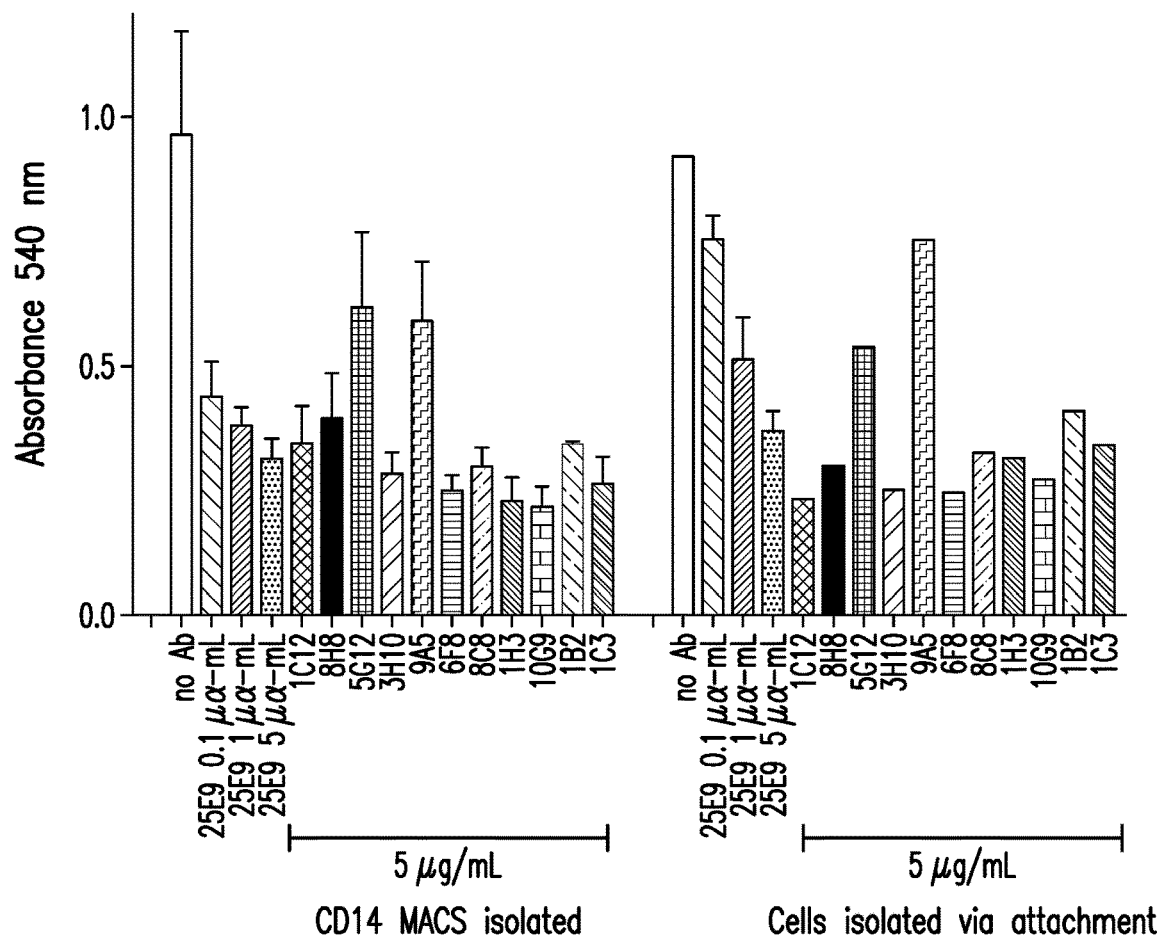
FIG. 10 is a bar graph showing TRAP (Tartrate-resistant acid phosphatase) (Abs 540 nm) in the presence of antibodies 1C12, 8H8, 5G12, 3H10, 9A5, 6F8, 8C8, 1H3, 10G9, 1B2, and 1C3 in an osteoclast formation assay of fresh PBMC's isolated and enriched for monocytes 2 ways.

Fresh PBMC's were isolated and enriched for monocytes 2 ways:
    MACS column sorting (FIG. 10, left panel); or
    Attachment to plastic in serum free media (FIG. 10, right panel).

Cells were cultured with M-CSF and RANKL for 8 days with 25E9 or S15 mAbs and assayed for TRAP (Tartrate-resistant acid phosphatase)

Results

The results, illustrated in FIG. 15, show that S15 mAbs can block osteoclast formation.

Example 7: Humanized 5G12 Antibodies

Clone 5G12 was humanized providing three humanized heavy chains and five humanized light chains (FIGS. 12A and 12B).

5G12 hVL1

(SEQ ID NO: 209)
DIQMTQSPSSLSASVGDRVTITCKASQDINSYLSWFQQKPGKAPKTLIYR

ANRLVDGVPSRFSGSGSGTDYTLTISSLQPEDFATYYCLQYDEFPYTFGG

GTKVEIK

CDR1 of 5G12 hVL1

(SEQ ID NO: 28)
KASQDINSYLS

CDR2 of 5G12 hVL1

(SEQ ID NO: 36)
RANRLVD

CDR3 of 5G12 hVL1

(SEQ ID NO: 43)
LQYDEFPYT

5G12 hVL2

(SEQ ID NO: 195)
DIQMTQSPSSLSASVGDRVTITCKASQDINTYLSWFQQKPGKAPKTLIYR

ANRLVDGVPSRFSGSGSGTDYTLTISSLQPEDFATYYCLQYDEFPYTFGG

GTKVEIK

CDR1 of 5G12 hVL2

(SEQ ID NO: 196)
KASQDINTYLS

CDR2 of 5G12 hVL2

(SEQ ID NO: 36)
RANRLVD

CDR3 of 5G12 hVL2

-continued

5G12 hVL3 (SEQ ID NO: 197)
DIQMTQSPSSLSASVGDRVTITCKASQDINVYLSWFQQKPGKAPKTLIYR
ANRLVDGVPSRFSGSGSGTDYTLTISSLQPEDFATYYCLQYDEFPYTFGG
GTKVEIK

CDR1 of 5G12 hVL3 (SEQ ID NO: 198)
KASQDINVYLS

CDR2 of 5G12 hVL3 (SEQ ID NO: 36)
RANRLVD

CDR3 of 5G12 hVL3 (SEQ ID NO: 43)
LQYDEFPYT

5G12 hVL4 (SEQ ID NO: 199)
DIQMTQSPSSLSASVGDRVTITCKASQDIQSYLSWFQQKPGKAPKTLIYR
ANRLVDGVPSRFSGSGSGTDYTLTISSLQPEDFATYYCLQYDEFPYTFGG
GTKVEIK

CDR1 of 5G12 hVL4 (SEQ ID NO: 200)
KASQDIQSYLS

CDR2 of 5G12 hVL4 (SEQ ID NO: 36)
RANRLVD

CDR3 of 5G12 hVL4 (SEQ ID NO: 43)
LQYDEFPYT

5G12 hVL5 (SEQ ID NO: 201)
DIQMTQSPSSLSASVGDRVTITCKASQDINVYLSWFQQKPGKAPKTLIYR
ANRLTSGVPSRFSGSGSGTDYTLTISSLQPEDFATYYCLQYDEFPYTFGG
GTKVEIK

CDR1 of 5G12 hVL5 (SEQ ID NO: 198)
KASQDINVYLS

CDR2 of 5G12 hVL5 (SEQ ID NO: 202)
RANRLTS

CDR3 of 5G12 hVL5 (SEQ ID NO: 43)
LQYDEFPYT

5G12 hVH1 (SEQ ID NO: 203)
QVQLVQSGAEVKKPGASVKVSCKASGYTFTSYWITWVRQAPGQGLEW
MGDIYSGSDTMHYAEKFQGRVTLTVDTSTSTAYMELSSLRSEDTAVYY
CARWWDYGSSYDYFDYWGQGTLVTVSS

CDR1 of 5G12 hVH1 (SEQ ID NO: 204)
SYWIT

CDR2 of 5G12 hVH1 (SEQ ID NO: 205)
DIYSGSDTMHYAEKFQG

CDR3 of 5G12 hVH1 (SEQ ID NO: 71)
WWDYGSSYDYFDY

5G12 hVH2 (SEQ ID NO: 206)
QVQLVQSGAEVKKPGASVKVSCKASGYTFTSYWITWVRQAPGQGLEW
MGDIYSGSDTTHYAEKFQGRVTLTVDTSTSTAYMELSSLRSEDTAVYYC
ARWWDYGSSYDYFDYWGQGTLVTVSS

CDR1 of hVH2 (SEQ ID NO: 204)
SYWIT

CDR2 of hVH2 (SEQ ID NO: 205)
DIYSGSDTTHYAEKFQG

CDR3 of hVH2 (SEQ ID NO: 71)
WWDYGSSYDYFDY

5G12 hVH3 (SEQ ID NO: 207)
QVQLVQSGAEVKKPGASVKVSCKASGYTFTSYWISWVRQAPGQGLEW
MGDIYSGSDTTHYAEKFQGRVTLTVDTSTSTAYMELSSLRSEDTAVYYC
ARWWDYGSSYDYFDYWGQGTLVTVSS

CDR1 of 5G12 hVH3 (SEQ ID NO: 208)
SYWIS

CDR2 of 5G12 hVH3 (SEQ ID NO: 205)
DIYSGSDTTHYAEKFQG

CDR3 of 5G12 hVH3 (SEQ ID NO: 71)
WWDYGSSYDYFDY

Example 8: Membrane Bound S15 is Immunosuppressive

Materials and Methods

Method for In Vitro PMBC T Cell Suppression Assay:

Peripheral blood mononuclear cells (PBMCs) from healthy donor's apheresis derived leukocyte-rich products (KeyBiologics, Memphis, Tenn.) were harvested using standard ficoll gradient procedure followed by cryopreservation. On the day of assay, the frozen PBMCs were thawed, washed with RPMI complete media (RPMI-C, RPMI [ThermoFisher]+10% FetalClone III serum [HyClone]) and counted. The cells were labeled with 5 μM CFSE (ThermoFisher) in RPMI-C for 10 minutes at 37° C., followed by two washes with RPMI-C. The total PMBCs (3E05 cells/well) were plated in 96-well flat-bottom Corning Costar plates that were pre-coated with anti-human CD3 (OKT3, 50 ng/mL; eBioScience) for overnight at 4° C. Siglec-15 hG1 Fc fusion protein was added to wells at final concentrations as indicated. Cells were cultured for 72 hours at 37° C. At 72 hours, 50 μL of supernatant was harvested from wells and immediately frozen for analysis of cytokines levels. Cells were then harvested from each well by pipetting, and transferred to a round-bottom plate for flow cytometry staining and analysis. Fc receptors were blocked with TruStain FcX (2 μL/well; Biolegend), followed by staining with antibodies against for CD4 APC-eFluor 780 (2 μL/well; ThermoFisher) and CD8 eFluor 450 (2 μL/well; ThermoFisher) for one hour at 4° C. After incubation, plates were washed twice with FACS buffer (PBS containing 1% Fetal- Clone III serum). Cells were resuspended in 150 μL fix buffer (3% formaldehyde in PBS) and analyzed with a YETI flow cytometer (Propel Labs). Data was analyzed with FlowJo. Data is displayed as percentage of cells that are divided based on CFSE dilution in comparison to unstimulated $CD4^+$ and $CD8^+$ T cells. Supernatants were analyzed with U-PLEX kit (Meso Scale Diagnostics [MSD)]) for IFN-γ, TNF-α and IL-6 according to instructions. U-PLEX was read using a Meso QuickPlex SQ 120 instrument.

Results

Membrane bound S15 is immunosuppressive. FIG. 14A is a line graph of % Proliferation of T cells versuse human S15 Fc (μg/mL) showing % proliferation of T cells is reduced as concentration of S15 Fc increases. Human PBMA were labeled with CFSE and added to anti0CD3 (OKT3) coated 96 well plates and cultured for 3 days with human S15 Fc fusion protein at the indicated concentrations. FIG. 14B is a bar graph of pg/ml of IFN-γ in conditioned supernatants from cells treated with 0 or 5 μg/mL of S15 Fc. FIG. 14C is a bar graph of pg/ml of TNF-α in conditioned supernatants from cells treated with 0 or 5 μg/mL of S15 Fc. FIG. 14D is a bar graph of pg/ml of IL-6 in conditioned supernatants from cells treated with 0 or 5 μg/mL of S15 Fc.

Example 9: Binding of s15 mAb Purified from Hybridoma to Cells Expressing Human S15 or Mouse s15

Materials and Methods 293T cells stably expressing human S15 (293T.hS15) and mouse MC38 cell stably expressing mouse S15 (MC38.mS15) were harvested from tissue culture. After one wash with PBS, the cells were seeded in 96-well U-bottom plate (5E04 cells/well) for staining. The cells were first mixed with 1 μg of indicated antibodies purified from mouse hybridomas in FACS staining buffer (PBS containing 1% FetalClone III serum) and incubated 30 min on ice. Cells were then washed 1 time with FACS buffer followed by incubation with PE conjugated anti mouse Ig antibody (eBioscience) for 30 min on ice. The cells were washed one time with FACS buffer and resuspended in 100 μL of FACS buffer prior to analyzed with a YETI flow cytometer (Propel Labs). Data was analyzed with FlowJo. Data is displayed as percentage of cells that are PE positive in a total cell population gated by forward scatter (FSC) & side scatter (SSC).

Results

FIGS. 15A and 15B show the percentage of positive cells for binding of S15 mAb purified from hybridoma to cells expressing human S15 or mouse S15. Binding was assessed by FACS analysis of cells incubated with indicated antibodies followed by incubation with PE conjugated anti-mouse Ig antibody. Cells were analyzed for $PE^+$ populations via FACS.

Example 10: Purified S15 mAbs from Hybridomas Reverse Membrane Bound S15 Mediated Suppression Materials and Methods Method for testing reversal of Siglec-15 Fc mediated suppression with Siglec-15 mAbs in total PBMC T cell proliferation assay:
Same as FIG. 14 Above, with Minor Changes:

Peripheral blood mononuclear cells (PBMCs) from healthy donor's apheresis derived leukocyte-rich products (KeyBiologics, Memphis, Tenn.) were harvested using standard ficoll gradient procedure followed by cryopreservation. On the day of assay, the frozen PBMCs were thawed, washed with RPMI complete media (RPMI-C, RPMI [ThermoFisher]+10% FetalClone III serum [HyClone]) and counted. The cells were labeled with 5 μM CFSE (ThermoFisher) in RPMI-C for 10 minutes at 37° C., followed by two washes with RPMI-C. The total PMBCs (3E05 cells/well) were plated in 96-well flat-bottom Corning Costar plates that were pre-coated with anti-human CD3 (OKT3, 50 ng/mL; eBioScience) for overnight at 4° C. Siglec-15 hG1 fusion protein was added to wells at 5 μg/ml (final concentration). Indicated Siglec-15 mAbs were then added to indicated wells at 12 μg/ml (final concentration). Cells were cultured for 72 hours at 37° C. At 72 hours, 50 μL of supernatant was harvested from wells and immediately frozen for analysis of cytokines levels. Cells were then harvested from each well by pipetting, and transferred to a round-bottom plate for flow cytometry staining and analysis. Fc receptors were blocked with TruStain FcX (2 μL/well; Biolegend), followed by staining with antibodies against for CD4 APC-eFluor 780 (2 μL/well; ThermoFisher) and CD8 eFluor 450 (2 μL/well; ThermoFisher) for one hour at 4° C. After incubation, plates were washed twice with FACS buffer (PBS containing 1% F4etalClone III serum). Cells were resuspended in 150 μL fix buffer (3% formaldehyde in PBS) and analyzed with a YETI flow cytometer (Propel Labs). Data was analyzed with FlowJo. Data is displayed as percentage of cells that are divided based on CFSE dilution in comparison to unstimulated $CD4^+$ and $CD8^+$ T cells. Supernatants were analyzed with U-PLEX kit (Meso Scale Diagnostics [MSD)]) for IFN-γ, TNF-α and IL-6 according to instructions. U-PLEX was read using a Meso QuickPlex SQ 120 instrument.

Results

FIGS. 16A and 16B are bar graphs of percent of Divided CD8+ T cells treated with the indicated antibodies. FIGS. 16C and 16D are bar graphs of the percentage of Divided CD4+ T cells treated with the indicated antibodies.

Example 11: In Vivo Bioactivity of Purified 5G12 in Three Tumor Models

Materials and Methods
Methods for In Vivo Tumor Models:
Colorectal Tumor Model

FIG. 17A: MC38 tumor cells (ATCC) transduced and sorted for Siglec-15 overexpression were subcutaneously injected at 2E05 cells in 100 μL into the shaved right flank of C57BL/6N mice (Charles River). Five mice/treatment group were administered 200 μg of control IgG (Innovative Research) or purified endotoxin-free anti-Siglec-15 clone 5G12 beginning six days after tumor injection. Treatments continued every four days for a total of four doses. Tumor were measured 3 times every week. Tumor volume was calculated as (length×width^2)*0.5. Mice were euthanized when tumor reached 2000 mm³.
Lymphoma Tumor Model FIG. 17B: EG7 tumor cells (ATCC) are EL4 tumor cells transfected to express chicken egg ovalbumin (OVA). Cells were cultured for 10 days prior to subcutaneous injection of 2E05 tumor cells into the shaved right flank of C57BL/6N mice (Charles River). Ten mice/treatment group were treated with 200 μg of control IgG or purified endotoxin-free anti-Siglec-15 clone 5G12. Treatments began eight days after EG7 injection and mice were treated every four days for a total of four doses. Tumor volume was calculated as (length×width^2)*0.5. Mice were euthanized when tumor reached 2000 mm³ or when tumors reached an average diameter of 15 cm.

Ovarian Cancer Model

FIG. 17C: ID8-OVA tumor cells are murine ID8 ovarian cancer cell line stably transfected to express chicken egg ovalbumin (OVA). Cells were cultured for 10 days prior to intraperitoneal injection of 5E06 cells. Three weeks later, mice were adoptively transferred by intraperitoneal injection with 5E05 OT-I Tg/Rag2$^{-/-}$ T cells that were isolated by CD8$^+$ T cell negative selection (Miltenyi Biotec). Treatment was initiated one day later (day 22; n=10/group). Mice received 200 µg every four days for a total of 5 doses of control IgG or purified endotoxin-free anti-Siglec-15 clone 5G12. Mice were weighed beginning 30 days after tumor injection, and tumor burden was analyzed by weight gain. Data displayed as percentage weight gain per mouse from initial weight at 30 days. Mice were euthanized when weight reached 150% weight gaining or greater than 30 grams.

Results

5G12 showed an increase in percent survival in the colorectal model (FIG. 17A) and lymphoma model (FIG. 17B). 5G12 also showed a reduction in tumor burden (FIG. 17C). FIG. 18 shows percent survival versus days post ID8/OVA inoculation.

Example 12: Affinity Assessment of Recombinant mAbs to S15 Monomer Protein

Optimized $K_D$ experiments were performed on a ForteBio Octet RED96 instrument using anti-human Fc capture (AHC, 18-5060; ForteBio) sensors. Assay buffer was PBS containing 0.05% Tween-20 and regeneration buffer was 10 mM glycine (pH 1.5). First the antibodies were loaded at 1 µg/mL for 600 seconds. This was followed by a 60 second baseline step, a 300 second association step in S15-extra cellular domain (ECD) monomer, and finally a 1200 second dissociation step. The monomer concentrations ranged from 100 nM to 1.56 nM in a two-fold dilution series and a blank well was included. Data was processed using ForteBio's Data Analysis Software 7.0; a global fit was used, along with reference well subtraction. Reported values are the average of at least three independent octet runs.

Results are in Table 1.

TABLE 1

Affinity assessment of recombinant mAbs to S15 monomer protein (n = 3-6 runs)

| | Affinity (nM) | $K_{on}$ (1E+5/Ms) | $K_{off}$ (1E−4/s) | Full X² | Full R² |
|---|---|---|---|---|---|
| 1H3 | 0.11 ± 0.02 | 3.59 | 0.39 | 0.1897 | 0.9971 |
| 5G12 | 0.30 ± 0.04 | 4.21 | 1.23 | 0.3913 | 0.9952 |
| 6F8 | 0.44 ± 0.08 | 3.04 | 1.34 | 0.2128 | 0.9977 |
| NC80 | 0.50 ± 0.02 | 3.48 | 1.75 | 0.1249 | 0.9987 |
| 10G9 | 0.55 ± 0.08 | 2.77 | 1.52 | 0.3085 | 0.998 |
| 1C3 | 0.58 ± 0.13 | 3.17 | 1.74 | 0.217 | 0.9979 |
| 3H10 | 0.60 ± 0.14 | 3.06 | 1.78 | 0.3725 | 0.9968 |
| NC93 | 0.88 ± 0.10 | 1.85 | 1.62 | 0.2795 | 0.9973 |
| 8C8 | 0.89 ± 0.25 | 2.92 | 2.3 | 0.1765 | 0.9976 |
| NC83 | 1.19 ± 0.09 | 3.53 | 4.15 | 0.4121 | 0.9927 |
| 8H8 | 1.30 ± 0.33 | 2.09 | 2.7 | 0.3012 | 0.9977 |
| NC105 | 1.39 ± 0.16 | 0.72 | 1.02 | 0.1331 | 0.9979 |
| NC92 | 1.42 ± 0.11 | 0.99 | 1.4 | 0.1138 | 0.9989 |
| NC77 | 1.93 ± 0.29 | 0.72 | 1.43 | 0.1377 | 0.9964 |
| NC6 | 2.94 ± 0.42 | 0.73 | 2.11 | 0.1085 | 0.9944 |
| NC104 | 3.08 ± 0.96 | 0.23 | 0.59 | 0.0489 | 0.998 |
| NC99 | 3.86 ± 1.40 | 0.32 | 1.02 | 0.0431 | 0.9952 |
| 1C12 | 4.01 ± 1.05 | 1.05 | 4.23 | 0.1694 | 0.993 |
| 1B2 | 4.33 ± 0.75 | 1.43 | 6.09 | 0.2432 | 0.9883 |
| NC82 | 4.84 ± 1.66 | 0.23 | 1.00 | 0.0494 | 0.9966 |

Example 13: S15 mAb Epitope Binning

The epitope binning experiments were performed on a ForteBio Octet RED96 instrument using streptavidin (SA, 18-5019; ForteBio) sensors. After a 30 second baseline step, biotin labeled S15-mG1 fusion protein was loaded on to the sensors at 10 µg/mL for 600 seconds. This was followed a 600 second association step in 1$^{st}$ antibody (30 µg/mL), a 30 second baseline, and a 400 second association step in the 2$^{nd}$ antibody (15 µg/mL). Assay buffer was PBS and regeneration was 10 mM glycine (pH3.0). Data was processed using ForteBio's Data Analysis Software 7.0 and the 2$^{nd}$ antibody curves were individually assessed for competitive binding. A curve during the second association step that is distinct from that of the first association step indicates binding to an unoccupied epitope. A lack of additional binding indicates epitope blocking.

Results are in Table 2.

TABLE 2

S15 epitope bins

| Bin 1 | 5G12, NC80, NC93 |
| Bin 2 | 6F8, 1C3, 3H10, NC92 |
| Bin 3 | 10G9, 8H8 |
| Bin 4 | 1H3 |
| Bin 5 | NC83, NC105 |

Example 14: Anti-Human S15 Clone 1H3 Inhibits Human Osteoclast Formation In Vitro Materials and Methods PBMC's were isolated from an apheresis derived leukocyte-rich product, purchased from Key Biologics, LLC. Leukocyte-rich product was layered on a cushion of Ficoll and centrifuged for 30 minutes at 400 RCF. Cells in the Ficoll interphase were removed, washed 3 times in PBS, and then frozen in FBS with 10% DMSO. On the day of the experiment, a vial of frozen PBMCs was removed from the liquid nitrogen storage and thawed. Monocytes were isolated using a MACS monocyte isolation kit (130-096-537; Miltenyi Biotec) per manufactures instructions. Isolated cells were 99% viable. Cells were plated in 96 well flat bottom tissue culture plates at a density of 3E05 cells/cm², 1E05 cells in 100 µL of assay media per well. Assay media consisted of α-MEM medium (Gibco 32571-036), supplemented with 10% FBS, 1 mM sodium pyruvate, 25 ng/ml of human macrophage colony-stimulating factor (Miltenyi, 103-096-491), and 30 ng/ml of human RANKL (Miltenyi, 130-093-988). Cells adhered to the plate for 3.5 hours before 10 µL of 50 µg/mL S15 antibody was added, final concentration 4.55 µg/mL. Triplicate wells were assessed for each antibody. After three days of incubation, the media was changed and fresh antibodies were added. On Day seven, the supernatants were transferred from the original plates to round bottom 96 well plates and centrifuged to remove cellular debris. The monocytes/osteoclasts were stained using the TRAP Staining Kit from B-Bridge International, Inc. (PMC-AK04F-COS) per manufactures instructions and images were taken using an Invitrogen EVOS FL Color. To assess the TRAP (Tartrate-resistant acid phosphatase) levels in the supernatant, 50 µL of the TRAP Staining Kit buffer was combined with 9 µL of supernatant and incubated at 37° C. for three hours. The absorbance of each well at 540 nM was recorded. The remaining supernatant was frozen at −80° C. for later cytokine analysis.

Results

FIG. 19A is a schematic diagram showing human CD14+ monocytes harvested from human PBMC using Mitenyi monocyte magnetic beads followed by seeding in 96-well plates in the presence of human M-CSF and human RANKL together with indicated antibodies. FIG. 19B is a micrograph showing osteoclasts. FIG. 19C is a bar graph of absorbance 540 nm of supernant collected after 7 days for Tartrate-resistance acid phosphatase analysis.

Example 15: 1H3 Reduces IL-6 and TNF-α Production Mediated by M-CSF and RANKL in Human Monocytes Materials and Methods Supernatants from the No-RANKL (M-CSF alone), control mAB (M-SCF+RANKL+Control mAb) and 1H3 (M-CSF+RANKL+1H3) wells from the experiment above were collected and tested for cytokine analysis.

Results

FIG. 20 is a bar graph showing cytokine (pg/mL) for INF-γ, IL-2, IL-4, IL-6, IL-10, IL-17A, and TNF-α.

Example 16: Anti Human S15 mAb 1H3 Prevents Mouse Osteoclast Formation In Vitro

Materials and Methods

Mouse RAW 264.7 macrophage cells were seeded in a flat bottom 96-well plate at a density of $1.5E04$ cells/cm$^2$, 4800 cells in 90 µL of media per well. Media consisted of DMEM with 10% FBS, 1 mM sodium pyruvate, and 50 ng/mL mouse RANKL (eBioscience, 14-8612-80). Cells were allowed to adhere for two hours before 10 µL of the indicated antibody (50 µg/mL) was added to wells, yielding a final concentration of 5 µg/mL; antibodies were assessed in triplicate wells. Cells differentiated for five days at which time the cells were stained and the supernatant was assessed for TRAP content as above.

Results

FIG. 21 is a bar graph of absorbance 540 nm mouse RAW 264.7 macrophage cells cultured in the presence of RANKL together with the indicated antibodies.

Example 17: Siglec-15 Expression is Upregulated in Human M2 Macrophages

Materials and Methods
Expression of Siglec-15

Human CD14+ monocytes were isolated from human PBMC via magnetic bead negative selection kit (Miltenyi Biotec) and treated with M-CSF for 3 days, then the cells were cultured in the presence of IL-10 (M2 macrophage polarization) or IFN-γ/LipiA (M1 macrophage polarization) for 3 more days. Cell surface expression of Siglec-15 was detected by anti-Siglec-15 antibody staining followed by FACS analysis.

Induction of Siglec-15 Expression

Mouse bone marrow cells were harvested from Balb/C mice. Adherent cells were removed by attachment to plastic culture dish. The floating mouse hematopoietic cells were harvested and treated with M-CSF for 3 days followed by straight M-CSF treatment or M-CSF+IL-10 treatment for another 4 days. The treated cells were harvested and stained with myeloid cell markers (CD11b and F4/80) and PE labeled anti-S15 followed by FACS analysis. Mean-fluorescence-intensity of PE is graphed in the lower panel. M-CSF slightly increased S15 expression.

Results

Siglec-15 expression is observed in human M2 macrophages (FIG. 25A) but not in human M1 macrophages (FIG. 25B).

M-CSF and IL-10 increase S15 expression in mouse bone marrow-derived myeloid cells (FIGS. 25C to 25E).

Example 18: Siglec-15 Promotes Human Myeloid Cell Survival and Increases Pro-Inflammatory Cytokine Production Materials and Methods Human CD14+ monocytes were first isolated from human PBMC (from 2 healthy donors) via magnetic bead negative selection kit (Miltenyi Biotec) and seeded to 96-well plate coated with Siglec-15 fusion protein (Siglec-15 coated) or without coating but with added Siglec-15 fusion protein in culture media (Siglec-15 soluble) at the concentration shown in the figure. Six days later, the conditioned supernatant was collected for cytokine analysis via MSD kit. Cell viability was assessed by adding XTT (ThermoFisher) to the plate. After 2 hour culture, cell metabolism/viability was measured by absorbance read at 450 nm.

Results

Higher absorbance was detected in wells with both plate coated Siglec-15 Fc and soluble Siglec-15 Fc. Cytokine analysis showed that S15 dose dependently increased TNF-α, IL-6 and IL-1β production in the treated wells (date from soluble S15 wells presented here).

Example 19: Siglec-15 Fc Treated Human Myeloid Cells Affect Human T Cell Function Material and Methods FIG. 27A is a schematic diagram for the following experiment. Human CD14+ monocytes were isolated from human PBMC (from 2 healthy donors) via magnetic bead negative selection kit (Miltenyi Biotec) and treated with Siglec-15 Fc for 6 days as described above or polarized to M2 or M1 macrophages, or treated with GM-CSF and IL-4 to differentiate the cells to immature dendritic cells (imDC). The cells were harvested by gently scraping from culture dish. After centrifugation, the cells were resuspended and cocultured with CFSE labeled negatively selected autologous pan-T cells at a cell ratio of 1 myeloid cell:2 T cell together with anti-CD3/CD28 beads (1 pan-T cell: 2 beads). Five days later, the conditioned supernatant was collected for cytokine analysis using MSD multiplex kit from MSD. The cells were harvested and stained with anti-CD4 and anti-CD8 antibodies. T cell proliferation was analyzed by FACS analysis to measure CFSE diluted cell population.

Results

Data showed that Siglec-15 Fc treated myeloid cells reduced anti-CD3/CD28 bead-mediated CD4 and CD8 T cell proliferation using cells from this particular donor (Donor #1707) and suppression was not as profound as M2 macrophages (FIGS. 27B-27G). Cytokine analysis revealed that S15 treated myeloid cells significantly impaired anti-CD3/CD28 bead-mediated IFN-γ, TNF-α, IL-6 and IL-10 production. Data from other tested donors showed S15 treated cells cost limited suppression on T cell proliferation, but in most of the cases, remarkable suppression on cytokine production.

Example 20: Siglec-15 mAb Dose Dependently Blocked S15-Mediated Survival Effect on Human Myeloid Cells Materials and Methods Human CD14+ monocytes were isolated from human PBMC (from 2 healthy donors) via magnetic bead negative selection kit (Miltenyi Biotec) and seeded to 96-well plate with 5 μg/mL of S15 Fc fusion protein together with a mAb for Siglec-15, 1:2 serially diluted down from 20 μg/mL. Cells were cultured for 7 days. Cell viability/metabolism was assessed by adding XTT (ThermoFisher) to the plate. After 2 hour culture, cell metabolism/viability was measured by absorbance read at 450 nm. High absorbance was detected in wells with S15 Fc fusion protein without any antibodies (no mAb). Low absorbance was obtained in wells without S15 Fc fusion protein (no S15 Fc).

Results

Siglec-15 mAb dose dependently decreased the absorbance (bottom line). Control antibody (top line) had no effect on cell survival and metabolism. FIGS. 28A (donor 1709) and 28B (donor 1713) show that anti-S15 mAb dose dependently blocked S15-mediated survival effect on human myeloid cells.

Example 21: Siglec-15 Plays a Critical Role in Osteoclast Formation

M-CSF expressed on osteoblast and stromal cells induces Siglec-15 expression on myeloid cells, which interacts with a Siglec-15 binding partner either in cis or in trans and stimulates myeloid cells producing pro-inflammatory cytokines such as TNF-α, IL-6 and IL-1β and up regulating $α_vβ_3$ integrin expression. Together with RANKL signaling, the osteoclast precursor cells fuse and form multinucleated osteoclasts (FIG. 29).

Example 22: Siglec-15 Induces $α_vβ3$ Integrin Expression in Human CD14+ Monocytes Materials and Methods Human CD14+ monocytes were isolated from human PBMC via magnetic bead negative selection kit (Miltenyi Biotec) and treated with 5 μg/mL of S15 Fc fusion protein for 6 days. Six days later, S15 Fc treated myeloid cells were harvested and stained with anti-$α_vβ_3$ integrin (clone 23C6).

Results

Compared to isotype control antibody staining and also staining of cells prior to S15 Fc treatment on Day 0, $α_vβ_3$ integrin expression was upregulated in the S15 Fc treatment myeloid cells (FIGS. 30A and 30B).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

We claim:

1. A monoclonal antibody or antigen-binding fragment thereof that binds specifically to SIGLEC-15, wherein the antibody comprises the three heavy chain CDRs (HCDR1, HCDR2 and HCDR3) having the amino acid sequences of SEQ ID NOs:208, 374 and 71, respectively; and the three light chain CDRs (LCDR1, LCDR2 and LCDR3) having the amino acid sequences of SEQ ID NOs: 198, 202 and 43, respectively.

2. The monoclonal antibody or antigen-binding fragment thereof of claim 1, comprising:
   (a) heavy chain variable region having the amino acid sequence of SEQ ID NO:207; and
   (b) a light chain variable region having the amino acid sequence of SEQ ID NO:201.

3. A pharmaceutical composition comprising the monoclonal antibody or antigen binding fragment thereof of claim 1 in combination with an excipient.

* * * * *